US012707889B2

(12) United States Patent
Ma et al.

(10) Patent No.: US 12,707,889 B2
(45) Date of Patent: Aug. 11, 2026

(54) ORGANIC ELECTROLUMINESCENT MATERIALS AND DEVICES

(71) Applicant: UNIVERSAL DISPLAY CORPORATION, Ewing, NJ (US)

(72) Inventors: Bin Ma, Plainsboro, NJ (US); Bert Alleyne, Newtown, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 1187 days.

(21) Appl. No.: 17/452,684

(22) Filed: Oct. 28, 2021

(65) Prior Publication Data

US 2022/0140256 A1 May 5, 2022

Related U.S. Application Data

(60) Provisional application No. 63/108,490, filed on Nov. 2, 2020.

(51) Int. Cl.

| | |
|---|---|
| ***H01L 51/54*** | (2006.01) |
| ***C07D 471/04*** | (2006.01) |
| ***C09K 11/06*** | (2006.01) |
| ***H10K 85/60*** | (2023.01) |
| *H10K 50/11* | (2023.01) |
| *H10K 101/10* | (2023.01) |
| *H10K 102/00* | (2023.01) |

(52) U.S. Cl.

CPC ....... *H10K 85/6572* (2023.02); *C07D 471/04* (2013.01); *C09K 11/06* (2013.01); *C09K 2211/1018* (2013.01); *H10K 50/11* (2023.02); *H10K 2101/10* (2023.02); *H10K 2102/351* (2023.02)

(58) Field of Classification Search

None

See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,639,914 | A | 6/1997 | Tomiyama et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,413,656 | B1 | 7/2002 | Thompson |
| 6,468,819 | B1 | 10/2002 | Kim et al. |
| 6,517,957 | B1 | 2/2003 | Senoo et al. |
| 6,653,654 | B1 | 11/2003 | Che |
| 6,656,612 | B2 | 12/2003 | Okada et al. |
| 6,670,645 | B2 | 12/2003 | Grushin et al. |
| 6,687,266 | B1 | 2/2004 | Ma et al. |
| 6,699,599 | B2 | 3/2004 | Li et al. |
| 6,835,469 | B2 | 12/2004 | Kwong et al. |
| 6,916,554 | B2 | 7/2005 | Ma et al. |
| 6,921,915 | B2 | 7/2005 | Takiguchi et al. |
| 7,154,114 | B2 | 12/2006 | Brooks et al. |
| 7,279,704 | B2 | 10/2007 | Walters et al. |
| 7,332,232 | B2 | 2/2008 | Ma et al. |
| 7,345,301 | B2 | 3/2008 | Gerhard et al. |
| 7,378,162 | B2 | 5/2008 | Jeong et al. |
| 7,431,968 | B1 | 10/2008 | Shtein et al. |
| 7,534,505 | B2 | 5/2009 | Lin et al. |
| 7,605,277 | B2 | 10/2009 | Kai et al. |
| 7,675,228 | B2 | 3/2010 | Ionkin et al. |
| 7,728,137 | B2 | 6/2010 | Stössel et al. |
| 7,740,957 | B2 | 6/2010 | Kim et al. |
| 7,749,615 | B2 | 7/2010 | Fukumatsu et al. |
| 7,759,489 | B2 | 7/2010 | Watanabe et al. |
| 7,846,763 | B2 | 12/2010 | Bold et al. |
| 7,951,947 | B2 | 5/2011 | Igarashi et al. |
| 7,968,146 | B2 | 6/2011 | Wagner et al. |
| 7,993,760 | B2 | 8/2011 | Komori et al. |
| 8,044,222 | B2 | 10/2011 | Yabunouchi et al. |

(Continued)

FOREIGN PATENT DOCUMENTS

| | | | |
|---|---|---|---|
| CN | 1696137 | A | 11/2005 |
| CN | 102702075 | A | 10/2012 |

(Continued)

OTHER PUBLICATIONS

Machine translation of KR2010-0113204. (Year: 2010).*
Machine translation of KR2012-0083243. (Year: 2012).*
Ming Yan, et al., Tetrahedron 2015, 71, 1425-30 and Atzrodt et al., Angew. Chem. Int. Ed. (Reviews) 2007, 46, 7744-65.
Baldo et al., "Highly Efficient Phosphorescent Emission from Organic Electroluminescent Devices," Nature, vol. 395, 151-154, 1998.
Baldo et al., "Very high-efficiency green organic light-emitting devices based on electrophosphorescence," Appl. Phys. Lett., vol. 75, No. 3, 4-6 (1999).
Atzrodt et al., Angew. Chem. Int. Ed. (Reviews) 2007, 46, 7744-65.
Fink, R.; Heischkel, Y.; Thelakkat, M.; Schmidt, H.-W. Chem. Mater. 1998, 10, 3620-3625.

(Continued)

*Primary Examiner* — Andrew K Bohaty
(74) *Attorney, Agent, or Firm* — LNK Law, PLLC

(57) ABSTRACT

Provided are fused-indole containing compounds which contain as a further structural unit at least one of pyrimidine, triazine, quinazoline, benzene, biphenyl, terphenyl, naphthalene, phenanthrene, anthracene, triphenylene, pyridine, pyrazine, fluorene, dibenzofuran, dibenzothiophene, carbazole, quinoline, isoquinoline, triarylboryl or quinoxaline, which may be further substituted. Also provided are formulations comprising these compounds. Further provided are OLEDs and related consumer products that utilize these compounds.

20 Claims, 2 Drawing Sheets

(56) References Cited

U.S. PATENT DOCUMENTS 8,062,769 B2 11/2011 Kai et al.
8,067,099 B2 11/2011 Watanabe et al.
8,129,083 B2 3/2012 Yabunouchi et al.
8,222,637 B2 7/2012 Kawamura et al.
8,231,983 B2 7/2012 Sugita et al.
8,258,297 B2 9/2012 Molt et al.
8,263,770 B2 9/2012 Mat-Suo et al.
8,288,013 B2 10/2012 Morishita
8,372,527 B2 2/2013 Morishita et al.
8,373,159 B2 2/2013 Langer et al.
8,383,828 B2 2/2013 Molt et al.
8,415,031 B2 4/2013 Xia et al.
8,557,400 B2 10/2013 Xia et al.
8,574,725 B2 11/2013 Nishimura et al.
8,592,586 B2 11/2013 Molt et al.
8,597,798 B2 12/2013 Parham et al.
8,608,986 B2 12/2013 Akino et al.
8,614,010 B2 12/2013 Yabunouchi
8,703,304 B2 4/2014 Yabunouchi et al.
8,759,819 B2 6/2014 Nishimura et al.
8,871,361 B2 10/2014 Xia et al.
9,093,652 B2 7/2015 Jung et al.
9,169,282 B2 10/2015 Stoessel et al.
9,181,289 B2 11/2015 Stoessel et al.
9,196,842 B2 11/2015 Kato et al.
9,296,944 B2 3/2016 Toshihiro et al.
9,466,803 B1 10/2016 Park et al.
9,472,762 B2 10/2016 Murer et al.
9,490,432 B2 11/2016 Zeika et al.
9,564,595 B2 2/2017 Kato et al.
9,595,681 B2 3/2017 Mujica-Fernaud et al.
9,604,972 B2 3/2017 Yoshida et al.
9,634,255 B2 4/2017 Kato et al.
9,799,835 B2 10/2017 Kim et al.
9,837,622 B2 12/2017 Stoessel et al.
9,882,142 B2 1/2018 Mujica-Fernaud et al.
9,882,149 B2 1/2018 Kim et al.
9,978,975 B2 5/2018 Kambe et al.
10,008,672 B2 6/2018 Stoessel et al.
10,103,340 B2 10/2018 Stoessel et al.
10,347,850 B2 7/2019 Ono et al.
10,385,263 B2 8/2019 Fuchs et al.
10,522,768 B2 12/2019 Egen et al.
2001/0019782 A1 9/2001 Igarashi et al.
2002/0034656 A1 3/2002 Thompson et al.
2002/0158242 A1 10/2002 Son et al.
2003/0068526 A1 4/2003 Kamatani et al.
2003/0072964 A1 4/2003 Kwong et al.
2003/0138657 A1 7/2003 Li et al.
2003/0162053 A1 8/2003 Marks et al.
2003/0175553 A1 9/2003 Thompson et al.
2003/0230980 A1 12/2003 Forrest et al.
2004/0036077 A1 2/2004 Ise
2004/0174116 A1 9/2004 Lu et al.
2005/0123751 A1 6/2005 Tsutsui et al.
2005/0123788 A1 6/2005 Huo et al.
2005/0123791 A1 6/2005 Deaton et al.
2005/0139810 A1 6/2005 Kuehl et al.
2005/0238919 A1 10/2005 Ogasawara
2005/0244673 A1 11/2005 Satoh et al.
2005/0260449 A1 11/2005 Walters et al.
2006/0008670 A1 1/2006 Lin et al.
2006/0065890 A1 3/2006 Stossel et al.
2006/0127696 A1 6/2006 Stossel et al.
2006/0134459 A1 6/2006 Huo et al.
2006/0134462 A1 6/2006 Yeh et al.
2006/0182993 A1 8/2006 Ogata et al.
2006/0202194 A1 9/2006 Jeong et al.
2006/0240279 A1 10/2006 Adamovich et al.
2006/0251923 A1 11/2006 Lin et al.
2006/0280965 A1 12/2006 Kwong et al.
2007/0018155 A1 1/2007 Bae et al.
2007/0034863 A1 2/2007 Fortte et al.
2007/0087321 A1 4/2007 Pribenszky et al.
2007/0103060 A1 5/2007 Itoh et al.
2007/0104977 A1 5/2007 Arakane et al.
2007/0104979 A1 5/2007 Kim et al.
2007/0104980 A1 5/2007 Kim et al.
2007/0111026 A1 5/2007 Deaton et al.
2007/0138437 A1 6/2007 Haga et al.
2007/0145888 A1 6/2007 Yabonouchi et al.
2007/0160905 A1 7/2007 Morishita et al.
2007/0181874 A1 8/2007 Prakash et al.
2007/0190359 A1 8/2007 Knowles et al.
2007/0224450 A1 9/2007 Kim et al.
2007/0231600 A1 10/2007 Kamatani et al.
2007/0252140 A1 11/2007 Limmert et al.
2007/0278936 A1 12/2007 Herron et al.
2007/0278938 A1 12/2007 Yabunouchi et al.
2008/0005851 A1 1/2008 Perez-Prat Vinuesa et al.
2008/0014464 A1 1/2008 Kawamura et al.
2008/0018237 A1 1/2008 Yamamoto et al.
2008/0020237 A1 1/2008 Ren et al.
2008/0091025 A1 4/2008 Morishita et al.
2008/0106190 A1 5/2008 Yabunouchi et al.
2008/0107919 A1 5/2008 Hwang et al.
2008/0124572 A1 5/2008 Mizuki et al.
2008/0145707 A1 6/2008 Yabunouchi et al.
2008/0161567 A1 7/2008 Stoessel et al.
2008/0210930 A1 9/2008 Kamatani et al.
2008/0220265 A1 9/2008 Xia et al.
2008/0233410 A1 9/2008 Mashima et al.
2008/0233434 A1 9/2008 Kawamura et al.
2008/0261076 A1 10/2008 Kwong et al.
2008/0297033 A1 12/2008 Knowles et al.
2008/0303417 A1 12/2008 Yabunouchi et al.
2009/0017330 A1 1/2009 Toshihiro et al.
2009/0030202 A1 1/2009 Toshihiro et al.
2009/0039776 A1 2/2009 Yamada et al.
2009/0066235 A1 3/2009 Yabunouchi et al.
2009/0085476 A1 4/2009 Park et al.
2009/0091253 A1 4/2009 Yasukawa et al.
2009/0101870 A1 4/2009 Prakash et al.
2009/0104472 A1 4/2009 Je et al.
2009/0108737 A1 4/2009 Kwong et al.
2009/0115316 A1 5/2009 Zheng et al.
2009/0115320 A1 5/2009 Kawamura et al.
2009/0115322 A1 5/2009 Walters et al.
2009/0140637 A1 6/2009 Hosokawa et al.
2009/0167161 A1 7/2009 Yabunouchi et al.
2009/0167162 A1 7/2009 Chun et al.
2009/0167167 A1 7/2009 Aoyama et al.
2009/0179554 A1 7/2009 Kuma et al.
2009/0179555 A1 7/2009 Kim et al.
2009/0218940 A1 9/2009 Okajima et al.
2009/0302743 A1 12/2009 Kato et al.
2009/0309488 A1 12/2009 Kato et al.
2010/0012931 A1 1/2010 Kato et al.
2010/0084966 A1 4/2010 Shinya et al.
2010/0090591 A1 4/2010 Alleyne et al.
2010/0102716 A1 4/2010 Kim et al.
2010/0105902 A1 4/2010 Inoue et al.
2010/0108990 A1 5/2010 Hosokawa et al.
2010/0148663 A1 6/2010 Tsai et al.
2010/0187984 A1 7/2010 Chun et al.
2010/0219397 A1 9/2010 Watanabe et al.
2010/0244004 A1 9/2010 Xia et al.
2010/0270916 A1 10/2010 Xia et al.
2010/0288362 A1 11/2010 Hatwar et al.
2010/0295032 A1 11/2010 Kwong et al.
2011/0007385 A1 1/2011 Yamanashi et al.
2011/0037057 A1 2/2011 LeCloux et al.
2011/0057559 A1 3/2011 Xia et al.
2011/0108822 A1 5/2011 Parham et al.
2011/0156017 A1 6/2011 Lee et al.
2011/0163302 A1 7/2011 Lin et al.
2011/0204333 A1 8/2011 Xia et al.
2011/0210320 A1 9/2011 Shin et al.
2011/0215710 A1 9/2011 Xia et al.
2011/0227049 A1 9/2011 Xia et al.
2011/0240968 A1 10/2011 Kim et al.
2011/0278551 A1 11/2011 Yabunouchi et al.
2011/0285275 A1 11/2011 Huang et al.
2012/0075273 A1 3/2012 Shigemoto et al.

(56) References Cited

U.S. PATENT DOCUMENTS

| | | | |
|---|---|---|---|
| 2012/0126221 A1 | 5/2012 | Tetsu et al. | |
| 2012/0146012 A1 | 6/2012 | Limmert et al. | |
| 2012/0193612 A1 | 8/2012 | Chun et al. | |
| 2012/0205642 A1 | 8/2012 | Yokoyama et al. | |
| 2012/0205645 A1 | 8/2012 | Fuchs et al. | |
| 2012/0214993 A1 | 8/2012 | Aihara et al. | |
| 2012/0292601 A1 | 11/2012 | Kottas et al. | |
| 2012/0319091 A1 | 12/2012 | Tomoki et al. | |
| 2013/0009543 A1 | 1/2013 | Hiroshi et al. | |
| 2013/0033172 A1 | 2/2013 | Huang et al. | |
| 2013/0105787 A1 | 5/2013 | Daisaku et al. | |
| 2013/0146848 A1 | 6/2013 | Ma et al. | |
| 2013/0165653 A1 | 6/2013 | Inoue et al. | |
| 2013/0175519 A1 | 7/2013 | Naoki et al. | |
| 2013/0181190 A1 | 7/2013 | Ma et al. | |
| 2013/0241401 A1 | 9/2013 | Kwong et al. | |
| 2013/0248830 A1 | 9/2013 | Welsh et al. | |
| 2013/0334521 A1 | 12/2013 | Lee et al. | |
| 2014/0001446 A1 | 1/2014 | Mizuki et al. | |
| 2014/0014925 A1 | 1/2014 | Jung et al. | |
| 2014/0014927 A1 | 1/2014 | Kim et al. | |
| 2014/0034914 A1 | 2/2014 | Takada et al. | |
| 2014/0103305 A1 | 4/2014 | Ma et al. | |
| 2014/0117329 A1 | 5/2014 | Lee et al. | |
| 2014/0183503 A1 | 7/2014 | Hiroshi et al. | |
| 2014/0183517 A1 | 7/2014 | Huh et al. | |
| 2014/0191225 A1 | 7/2014 | Inoue et al. | |
| 2014/0225088 A1 | 8/2014 | Hwang et al. | |
| 2014/0246656 A1 | 9/2014 | Inoue et al. | |
| 2014/0284580 A1 | 9/2014 | Balaganesan et al. | |
| 2015/0060804 A1 | 3/2015 | Kanitz et al. | |
| 2015/0123047 A1 | 5/2015 | Maltenberger et al. | |
| 2015/0171348 A1 | 6/2015 | Stoessel et al. | |
| 2015/0221874 A1 | 8/2015 | Kim et al. | |
| 2015/0228899 A1 | 8/2015 | Tomoki et al. | |
| 2015/0263294 A1 | 9/2015 | Kim et al. | |
| 2015/0280136 A1 | 10/2015 | Ryu et al. | |
| 2016/0163995 A1 | 6/2016 | Kang et al. | |
| 2017/0263869 A1 | 9/2017 | Tada et al. | |
| 2019/0081248 A1 | 3/2019 | Lin et al. | |
| 2019/0237683 A1* | 8/2019 | Boudreault | H10K 85/361 |

FOREIGN PATENT DOCUMENTS

| | | | | |
|---|---|---|---|---|
| CN | 103508940 A | | 1/2014 | |
| CN | 103694277 A | | 4/2014 | |
| DE | 102012005215 B3 | | 4/2013 | |
| EP | 0650955 A1 | | 5/1995 | |
| EP | 1238981 A2 | | 9/2002 | |
| EP | 1239526 A2 | | 9/2002 | |
| EP | 1244155 A2 | | 9/2002 | |
| EP | 01602648 A1 | | 12/2005 | |
| EP | 1617493 A2 | | 1/2006 | |
| EP | 1624500 A1 | | 2/2006 | |
| EP | 1642951 A2 | | 4/2006 | |
| EP | 1647554 A2 | | 4/2006 | |
| EP | 1698613 A1 | | 9/2006 | |
| EP | 1725079 A1 | | 11/2006 | |
| EP | 01734038 A1 | | 12/2006 | |
| EP | 1806334 A1 | | 7/2007 | |
| EP | 1841834 A1 | | 10/2007 | |
| EP | 1930964 A1 | | 6/2008 | |
| EP | 01956007 A1 | | 8/2008 | |
| EP | 1961743 A | | 8/2008 | |
| EP | 1968131 A1 | | 9/2008 | |
| EP | 1972613 A1 | | 9/2008 | |
| EP | 1997799 A1 | | 12/2008 | |
| EP | 2011790 A1 | | 1/2009 | |
| EP | 2020694 A1 | | 2/2009 | |
| EP | 2034538 A1 | | 3/2009 | |
| EP | 1841834 B1 | | 5/2009 | |
| EP | 2055700 A1 | | 5/2009 | |
| EP | 2055701 A1 | | 5/2009 | |
| EP | 2062907 A2 | | 5/2009 | |
| EP | 2085382 A1 | | 8/2009 | |
| EP | 2660300 A2 | | 11/2013 | |
| EP | 2684932 A1 | | 1/2014 | |
| EP | 2730583 A1 | | 5/2014 | |
| EP | 2757608 A1 | | 7/2014 | |
| JP | 2004022334 A | | 1/2004 | |
| JP | 2005112765 A | | 4/2005 | |
| JP | 2005149918 A | | 6/2005 | |
| JP | 2005268199 A | | 9/2005 | |
| JP | 2007073529 A | | 3/2007 | |
| JP | 2007091719 A | | 4/2007 | |
| JP | 2007254297 A | | 10/2007 | |
| JP | 2008021687 A | | 1/2008 | |
| JP | 4478555 B2 | | 3/2010 | |
| JP | 2012074444 A | | 4/2012 | |
| JP | 2013110263 A | | 6/2013 | |
| JP | 2014009196 A | | 1/2014 | |
| KR | 0117693 | | 4/1998 | |
| KR | 20100079458 A | | 7/2010 | |
| KR | 2010113204 A | * | 10/2010 | |
| KR | 1020100113204 A | | 10/2010 | |
| KR | 20110077173 A | | 7/2011 | |
| KR | 20110088898 A | | 8/2011 | |
| KR | 20120032054 A | | 4/2012 | |
| KR | 2012083243 A | * | 7/2012 | H01L 51/0052 |
| KR | 1020120083243 A | | 7/2012 | |
| KR | 20120088644 A | | 8/2012 | |
| KR | 20120129733 A | | 11/2012 | |
| KR | 20130043460 A | | 4/2013 | |
| KR | 20130077473 A | | 7/2013 | |
| KR | 20130108183 | | 10/2013 | |
| KR | 20130115564 A | | 10/2013 | |
| KR | 1020150027659 A | | 3/2015 | |
| TW | 201139402 A | | 1/2011 | |
| TW | 201329200 A1 | | 7/2013 | |
| TW | 201332980 A | | 8/2013 | |
| WO | 2001039234 A2 | | 5/2001 | |
| WO | 2002015645 A1 | | 2/2002 | |
| WO | 2003040257 A1 | | 5/2003 | |
| WO | 2003060956 A1 | | 7/2003 | |
| WO | 2004093207 A2 | | 10/2004 | |
| WO | 2005014551 A1 | | 2/2005 | |
| WO | 2005019373 A2 | | 3/2005 | |
| WO | 2005075451 A1 | | 8/2005 | |
| WO | 2005089025 A1 | | 9/2005 | |
| WO | 2006056418 A2 | | 6/2006 | |
| WO | 2006072002 A2 | | 7/2006 | |
| WO | 2006081780 A1 | | 8/2006 | |
| WO | 2006081973 A1 | | 8/2006 | |
| WO | 2006095951 A1 | | 9/2006 | |
| WO | 2006114966 A1 | | 11/2006 | |
| WO | 2006121811 A1 | | 11/2006 | |
| WO | 2007018067 A1 | | 2/2007 | |
| WO | 2007063754 A1 | | 6/2007 | |
| WO | 2007108362 A1 | | 9/2007 | |
| WO | 2007111263 A1 | | 10/2007 | |
| WO | 2007115970 A1 | | 10/2007 | |
| WO | 2007115981 A1 | | 10/2007 | |
| WO | 2007125714 A1 | | 11/2007 | |
| WO | 2008023550 A1 | | 2/2008 | |
| WO | 2008023759 A1 | | 2/2008 | |
| WO | 2008035571 A1 | | 3/2008 | |
| WO | 2008054584 A1 | | 5/2008 | |
| WO | 2008056746 A1 | | 5/2008 | |
| WO | 2008057394 A1 | | 5/2008 | |
| WO | 2008078800 A1 | | 7/2008 | |
| WO | 2008096609 A1 | | 8/2008 | |
| WO | 2008101842 A | | 8/2008 | |
| WO | 2009000673 A2 | | 12/2008 | |
| WO | 2009003455 A1 | | 1/2009 | |
| WO | 2009003898 A1 | | 1/2009 | |
| WO | 2009008277 A1 | | 1/2009 | |
| WO | 2009011327 A1 | | 1/2009 | |
| WO | 2009021126 A2 | | 2/2009 | |
| WO | 2009050281 A1 | | 4/2009 | |
| WO | 2009063833 A1 | | 5/2009 | |
| WO | 2009066778 A1 | | 5/2009 | |
| WO | 2009066779 A1 | | 5/2009 | |
| WO | 2009086028 A2 | | 7/2009 | |
| WO | 2009100991 A1 | | 8/2009 | |

(56) References Cited

FOREIGN PATENT DOCUMENTS

| | | | |
|---|---|---|---|
| WO | 2009145016 | A1 | 12/2009 |
| WO | 2009148269 | A1 | 12/2009 |
| WO | 2010011390 | A2 | 1/2010 |
| WO | 2010028151 | A1 | 3/2010 |
| WO | 2010054731 | A1 | 5/2010 |
| WO | 2010056066 | A1 | 5/2010 |
| WO | 2010061824 | A1 | 6/2010 |
| WO | 2010067894 | A1 | 6/2010 |
| WO | 2010072300 | A1 | 7/2010 |
| WO | 2010086089 | A1 | 8/2010 |
| WO | 2010107244 | A2 | 9/2010 |
| WO | 2010118029 | A1 | 10/2010 |
| WO | 2011044988 | A1 | 4/2011 |
| WO | 2011051404 | A1 | 5/2011 |
| WO | 2011074770 | A1 | 6/2011 |
| WO | 2011074770 | A2 | 6/2011 |
| WO | 2011075644 | A2 | 6/2011 |
| WO | 2011081423 | A2 | 7/2011 |
| WO | 2011081431 | A2 | 7/2011 |
| WO | 2011086863 | A1 | 7/2011 |
| WO | 2011105373 | A1 | 9/2011 |
| WO | 2011107491 | A1 | 9/2011 |
| WO | 2012020327 | A1 | 2/2012 |
| WO | 2012128298 | A1 | 9/2012 |
| WO | 2012133644 | A1 | 10/2012 |
| WO | 2012133649 | A1 | 10/2012 |
| WO | 2012163471 | A1 | 12/2012 |
| WO | 2012177006 | A2 | 12/2012 |
| WO | 2013018530 | A1 | 2/2013 |
| WO | 2013024872 | A1 | 2/2013 |
| WO | 2013035275 | A1 | 3/2013 |
| WO | 2013039073 | A1 | 3/2013 |
| WO | 2013079217 | A1 | 6/2013 |
| WO | 2013081315 | A1 | 6/2013 |
| WO | 2013087142 | A1 | 6/2013 |
| WO | 2013094620 | A1 | 6/2013 |
| WO | 2013107487 | A1 | 7/2013 |
| WO | 2013118812 | A1 | 8/2013 |
| WO | 2013120577 | A1 | 8/2013 |
| WO | 2013145667 | A1 | 10/2013 |
| WO | 2013157367 | A1 | 10/2013 |
| WO | 2013174471 | A1 | 11/2013 |
| WO | 2013175747 | A1 | 11/2013 |
| WO | 2013180376 | A1 | 12/2013 |
| WO | 2013191404 | A1 | 12/2013 |
| WO | 2014002873 | A1 | 1/2014 |
| WO | 2014007565 | A1 | 1/2014 |
| WO | 2014008982 | A1 | 1/2014 |
| WO | 2014009310 | A1 | 1/2014 |
| WO | 2014015935 | A2 | 1/2014 |
| WO | 2014015937 | A1 | 1/2014 |
| WO | 2014023377 | A2 | 2/2014 |
| WO | 2014024131 | A1 | 2/2014 |
| WO | 2014030872 | A2 | 2/2014 |
| WO | 2014030921 | A1 | 2/2014 |
| WO | 2014031977 | A1 | 2/2014 |
| WO | 2014034791 | A1 | 3/2014 |
| WO | 2014038456 | A1 | 3/2014 |
| WO | 2014104499 | A1 | 7/2014 |
| WO | 2014104514 | A1 | 7/2014 |
| WO | 2014104535 | A1 | 7/2014 |
| WO | 2014112450 | A1 | 7/2014 |
| WO | 2014142472 | A1 | 9/2014 |
| WO | 2014157018 | A1 | 10/2014 |

OTHER PUBLICATIONS

Pommerehne, J.; Vestweber, H.; Guss, W.; Mahrt, R. F.; Bassler, H.; Porsch, M.; Daub, J. Adv. Mater. 1995, 7, 551.

Hong et al., Chem. Mater. 2016, 28, 5791-98, 5792-93.

Tavasli et al., J. Mater. Chem. 2012, 22, 6419-29, 6422.

Morello, G.R., J. Mol. Model. 2017, 23:174.

* cited by examiner

ORGANIC ELECTROLUMINESCENT MATERIALS AND DEVICES

This application claims priority under 35 U.S.C. § 119(e) to U.S. Provisional Application No. 63/108,490, filed on Nov. 2, 2020, the entire contents of which are incorporated herein by reference.

FIELD

The present disclosure generally relates to organometallic compounds and formulations and their various uses including as hosts or emitters in devices such as organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

In one aspect, the present disclosure provides a compound of Formula I:

Formula I

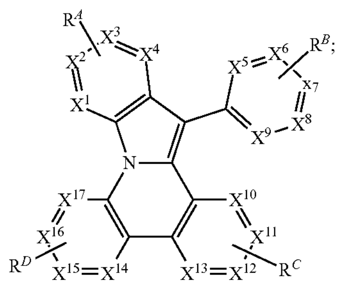

wherein each $X^1$-$X^{17}$ is independently C or N;

$R^A$, $R^B$, $R^C$, and $R^D$ each independently represent mono to the maximum allowable substitution, or no substitution;

each $R^A$, $R^B$, $R^C$, and $R^D$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, germyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof; at least one of $R^A$, $R^B$, $R^C$, and $R^D$ is joined to its respective ring by a single bond and comprises pyrimidine, triazine, quinazoline, benzene, biphenyl, terphenyl, naphthalene, phenanthrene, anthracene, triphenylene, pyridine, pyrazine, fluorene, dibenzofuran, dibenzothiophene, carbazole, quinoline, isoquinoline, triarylboryl or quinoxaline, which may be further substituted.

In another aspect, the present disclosure provides a formulation comprising the compound in accordance with the invention as described herein.

In yet another aspect, the present disclosure provides an organic light emitting device (OLED) comprising an anode; a cathode; and an organic layer disposed between the anode and the cathode, wherein the organic layer comprises the compound in accordance with the invention as described herein.

In yet another aspect, the present disclosure provides a consumer product comprising: an anode; a cathode; and an organic layer disposed between the anode and the cathode, wherein the organic layer comprises the compound in accordance with the invention as described herein.

In yet another aspect, the present disclosure provides a chemical structure selected from the group consisting of an isomer, a regioisomer, a stereoisomer, a monomer, a polymer, a macromolecule, and a supramolecule, wherein the chemical structure comprises the compound in accordance with the invention as described herein or a monovalent or polyvalent variant thereof.

DETAILED DESCRIPTION

A. Terminology

Figure 1:
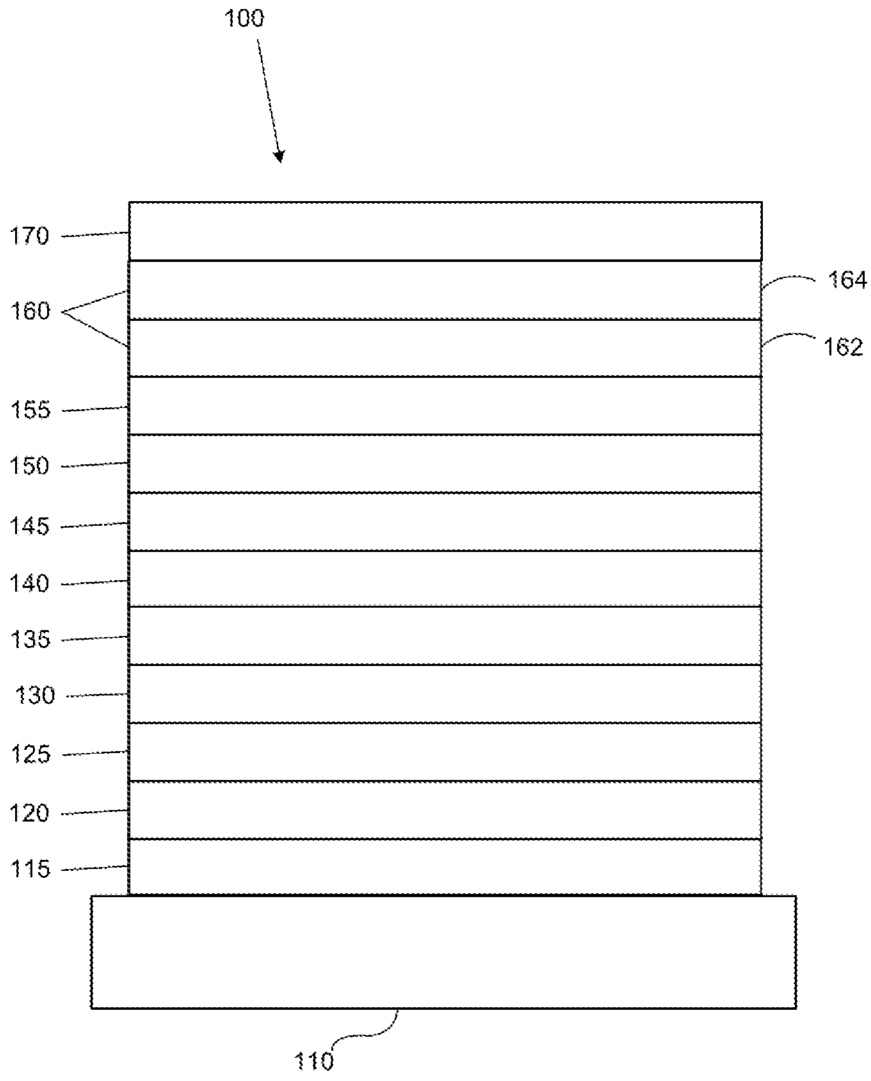
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical ($C(O)—R_s$).

The term "ester" refers to a substituted oxycarbonyl ($—O—C(O)—R_s$ or $—C(O)—O—R_s$) radical.

The term "ether" refers to an $—OR_s$ radical.

The terms "sulfanyl" or "thio-ether" are used interchangeably and refer to a $—SR_s$ radical.

The term "selenyl" refers to a $—SeR_s$ radical.

The term "sulfinyl" refers to a $—S(O)—R_s$ radical.

The term "sulfonyl" refers to a $—SO_2—R_s$ radical.

The term "phosphino" refers to a $—P(R_s)_3$ radical, wherein each $R_s$ can be same or different.

The term "silyl" refers to a $—Si(R_s)_3$ radical, wherein each $R_s$ can be same or different.

The term "germyl" refers to a $—Ge(R_s)_3$ radical, wherein each $R_s$ can be same or different.

The term "boryl" refers to a $—B(R_s)_2$ radical or its Lewis adduct $—B(R_s)_3$ radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo [3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group may be optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group may be optionally substituted.

The term "alkynyl" refers to and includes both straight and branched chain alkyne radicals. Alkynyl groups are essentially alkyl groups that include at least one carbon-carbon triple bond in the alkyl chain. Preferred alkynyl groups are those containing two to fifteen carbon atoms. Additionally, the alkynyl group may be optionally substituted.

The terms "aralkyl" or "arylalkyl" are used interchangeably and refer to an alkyl group that is substituted with an aryl group. Additionally, the aralkyl group may be optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term “aryl” refers to and includes both single-ring aromatic hydrocarbyl groups and polycyclic aromatic ring systems. The polycyclic rings may have two or more rings in which two carbons are common to two adjoining rings (the rings are “fused”) wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term “heteroaryl” refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are “fused”) wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, germyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, boryl, selenyl, and combinations thereof.

In some instances, the preferred general substituents are selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, boryl, and combinations thereof.

In some instances, the more preferred general substituents are selected from the group consisting of deuterium, fluorine, alkyl, cycloalkyl, alkoxy, aryloxy, amino, silyl, boryl, aryl, heteroaryl, sulfanyl, and combinations thereof.

In yet other instances, the most preferred general substituents are selected from the group consisting of deuterium, fluorine, alkyl, cycloalkyl, aryl, heteroaryl, and combinations thereof.

The terms “substituted” and “substitution” refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, “combinations thereof” indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The “aza” designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (*Reviews*) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

B. The Compounds of the Present Disclosure

In one aspect, the present disclosure provides a compound of Formula I:

Formula I

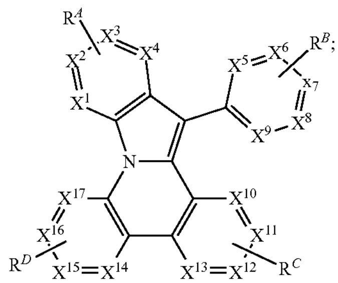

wherein each $X^1$-$X^{17}$ is independently C or N;

$R^A$, $R^B$, $R^C$, and $R^D$ each independently represent mono to the maximum allowable substitution, or no substitution;

each $R^A$, $R^B$, $R^C$, and $R^D$ is independently a hydrogen or a substituent selected from the list of general substituents disclosed above;

at least one of $R^A$, $R^B$, $R^C$, and $R^D$ is joined to its respective ring by a single bond and comprises pyrimidine, triazine, quinazoline, benzene, biphenyl, terphenyl, naphthalene, phenanthrene, anthracene, triphenylene, pyridine, pyrazine, fluorene, dibenzofuran, dibenzothiophene, carbazole, quinoline, isoquinoline, triarylboryl or quinoxaline, which may be further substituted.

In one embodiment, each $R^A$, $R^B$, $R^C$, and $R^D$ is independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

In one embodiment, one or two of $R^A$, $R^B$, $R^C$, and $R^D$ in the above Formula I comprise pyrimidine, triazine, quinazoline, carbazole, benzene, biphenyl, naphthalene, or triphenyl.

Further embodiments relate to the meaning of X in Formula I: In one embodiment, the maximum number of nitrogen can connect to each other within a ring is two. According to further embodiments, one or more of the following is true: exact one of $X^1$-$X^{17}$ is N; at least one of $X^1$-$X^4$ is N; at least one of $X^5$-$X^9$ is N; at least one of $X^{10}$-$X^{13}$ is N; or at least one of $X^{14}$-$X^{17}$ is N.

In a further embodiment, at least one of $R^A$, $R^B$, $R^C$ and $R^D$ is selected from the group consisting of any one of $R^{A1}$ to $R^{A16}$ as following:

$R^{A1}$ $R^{A2}$ $R^{A3}$ $R^{A4}$ $R^{A5}$ $R^{A6}$

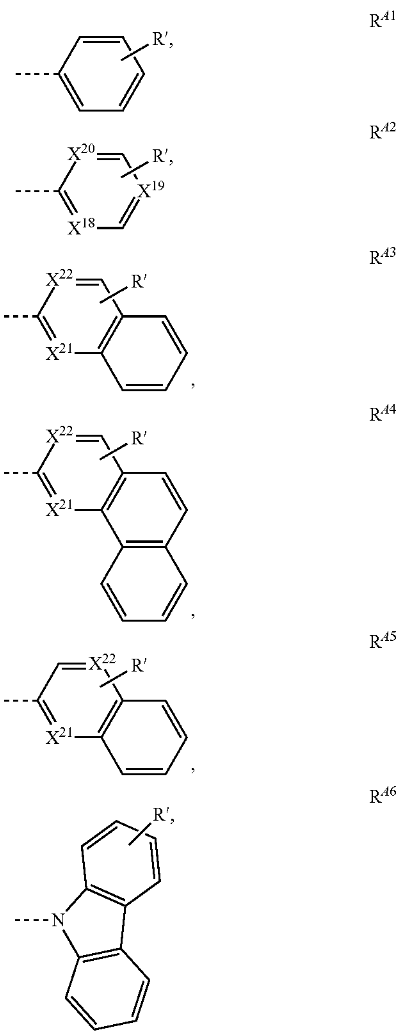

-continued $R^{A7}$

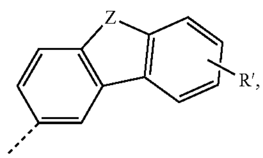

$R^{A8}$

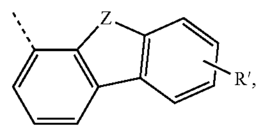

$R^{A9}$

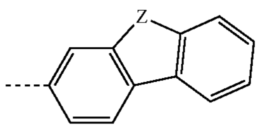

, $R^{A10}$

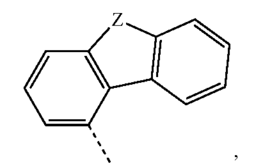

, $R^{A11}$

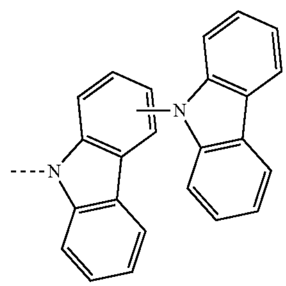

, $R^{A12}$

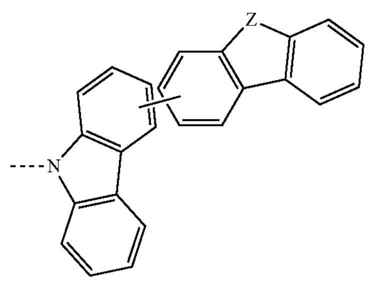

, $R^{A13}$

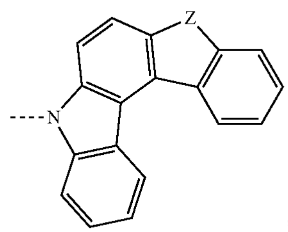

,

-continued $R^{A14}$

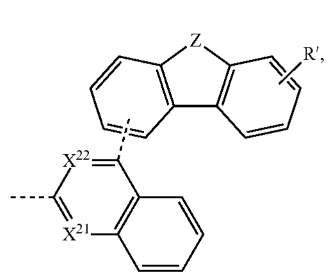

$R^{A15}$

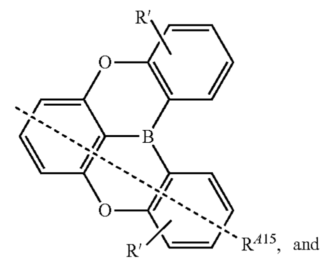

and $R^{A16}$

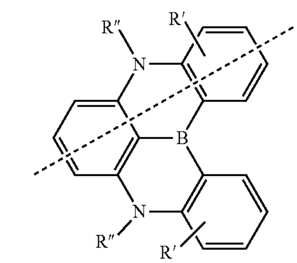

;

wherein R' and R" is independently a hydrogen or a substituent selected from the group consisting of aryl, phenyl, biphenyl, naphthyl, carbazolyl, triazinyl, pyrimidinyl, quinazolinyl and triphenylenyl; $X^{18}$-$X^{22}$ is C or N; and Z represents NR", O, or S, with R" being aryl or heteroaryl. In particular, at least one of $R^A$, $R^B$, $R^C$ and $R^D$ may be selected from the group consisting of $R^1$

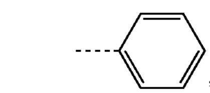

, $R^2$

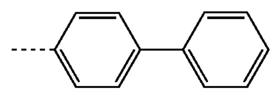

, $R^3$

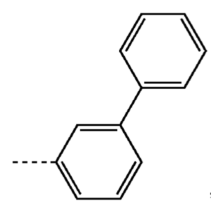

,

-continued
$R^4$
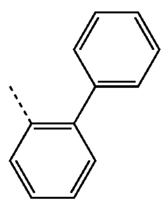
,
$R^5$
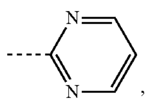
,
$R^6$
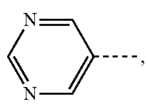
,
$R^7$
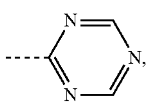
,
$R^8$
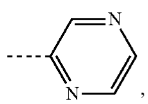
,
$R^9$
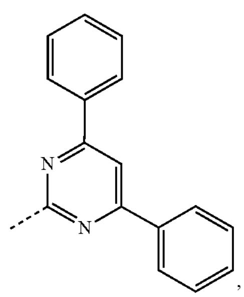
,
$R^{10}$
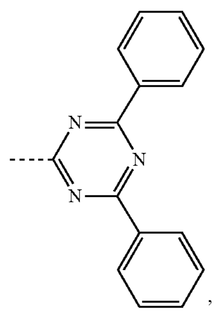
,
-continued
$R^{11}$
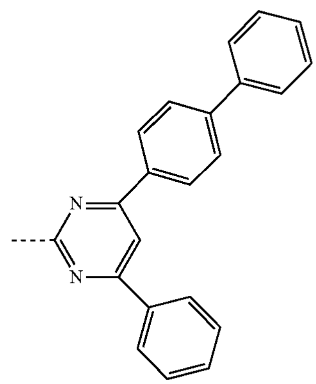
,
$R^{12}$
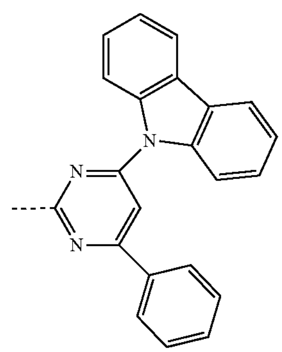
,
$R^{13}$
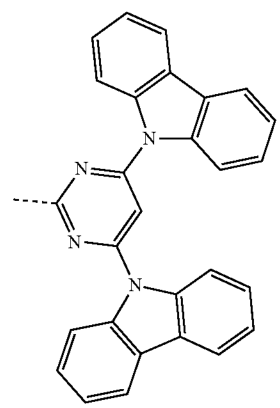
,
$R^{14}$
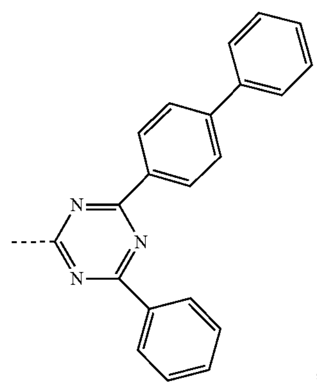
, -continued
R[15]
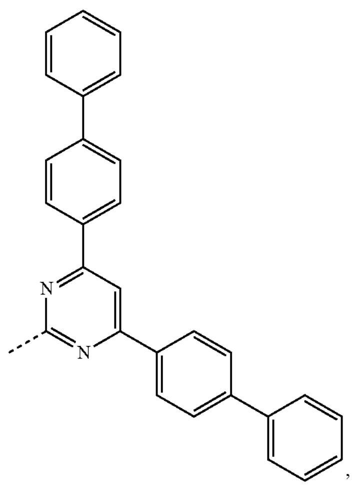
,
R[16]
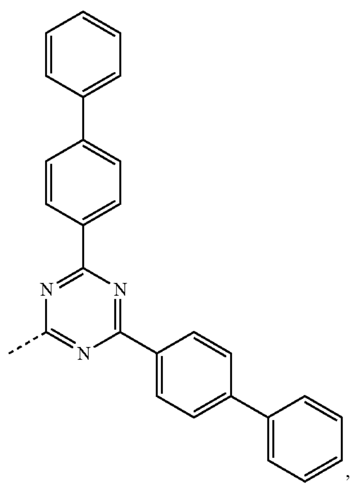
,
R[17]
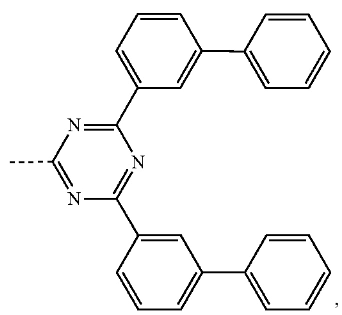
,
R[18]
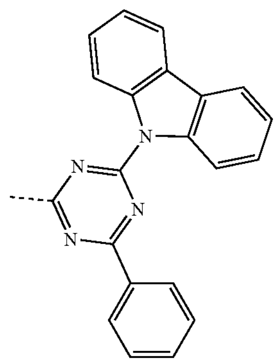
,
-continued
R[19]
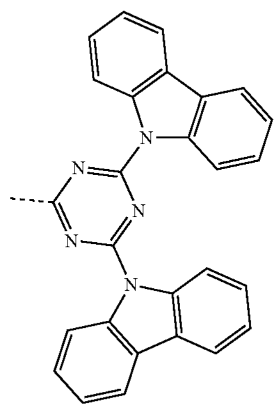
,
R[20]
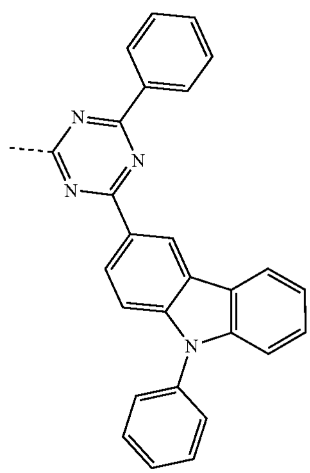
,
R[21]
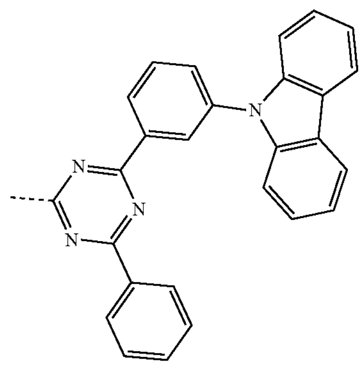
,
R[22]
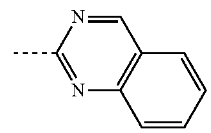
,
R[23]
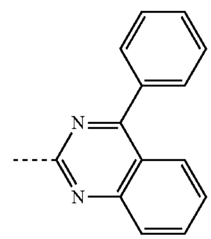
, -continued
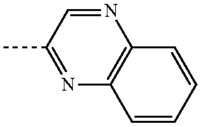
,
$R^{24}$
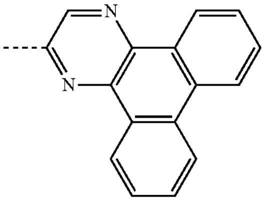
,
$R^{25}$
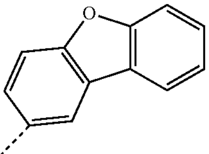
,
$R^{26}$
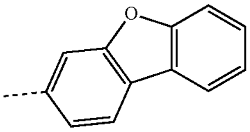
,
$R^{27}$
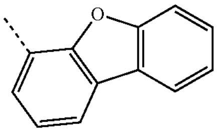
,
$R^{28}$
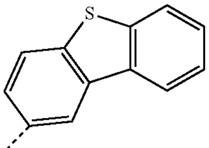
,
$R^{29}$
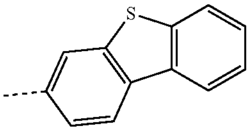
,
$R^{30}$
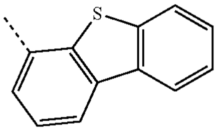
,
$R^{31}$
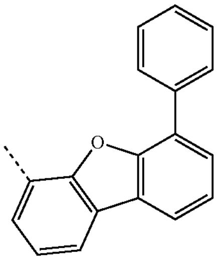
,
$R^{32}$
-continued
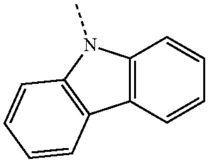
,
$R^{33}$
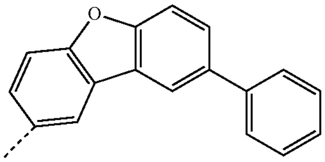
,
$R^{34}$
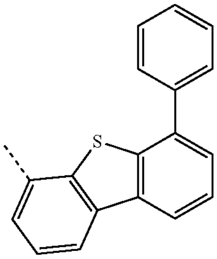
,
$R^{35}$
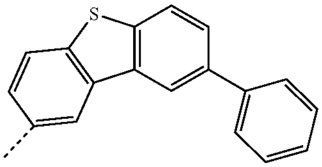
,
$R^{36}$
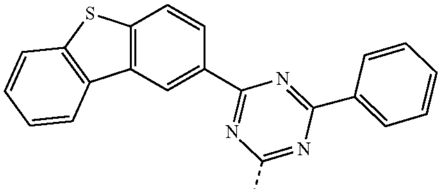
,
$R^{37}$
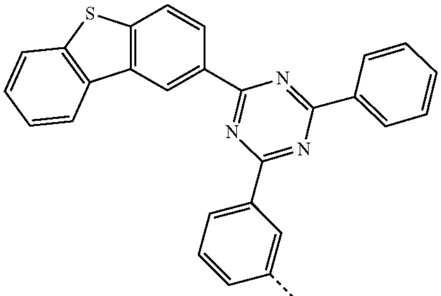
,
$R^{38}$ -continued
R39
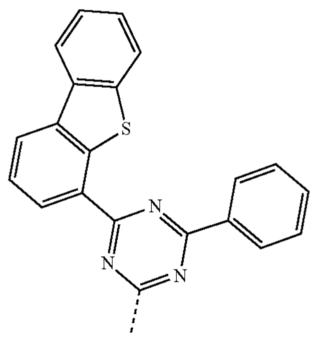
,
R40
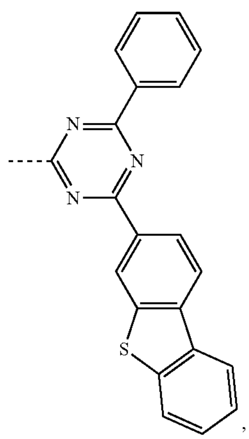
,
R41
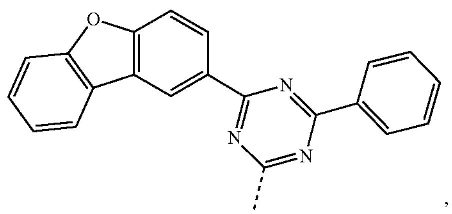
,
R42
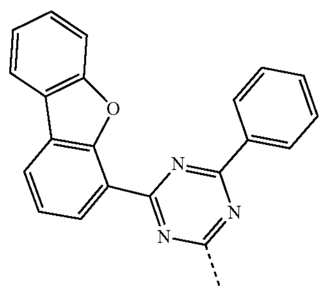
,
-continued
R43
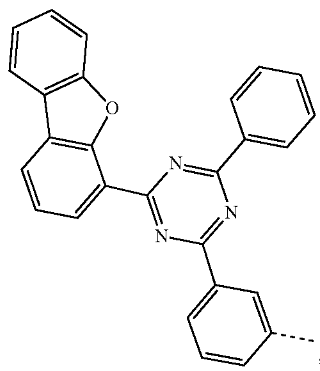
,
R44
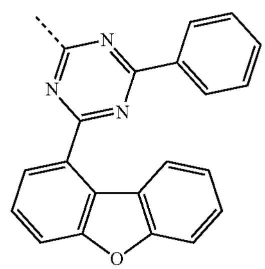
,
R45
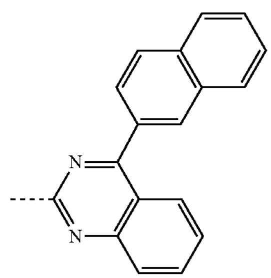
,
R46
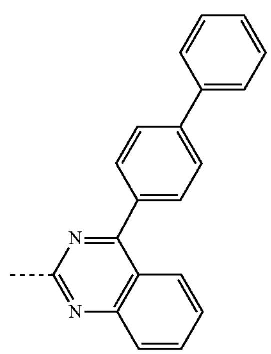
,
R47
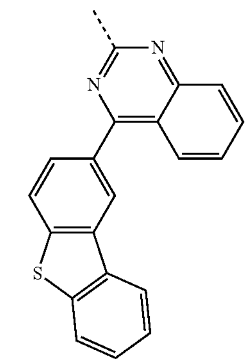
, -continued
R48
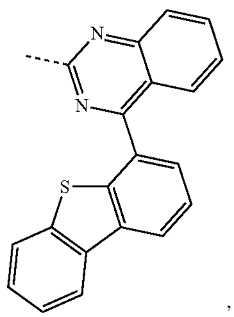
,
R49
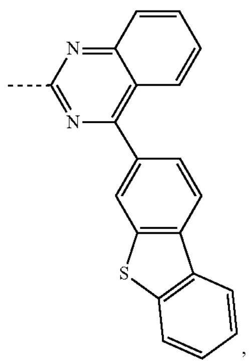
,
R50
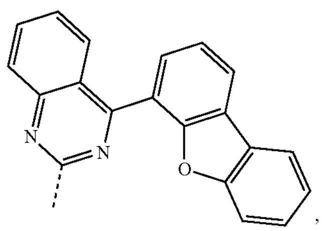
,
R51
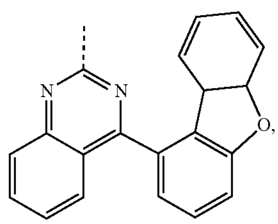
R52
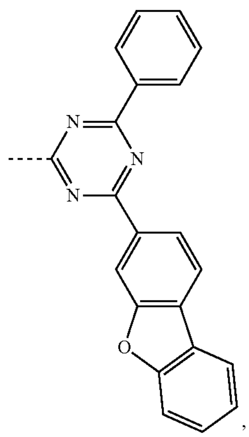
,
-continued
R53
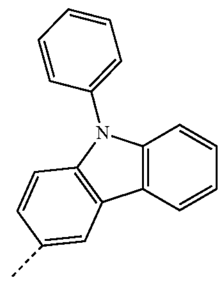
,
R54
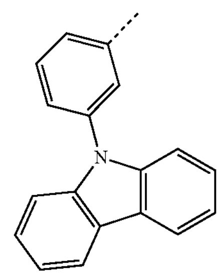
,
R55
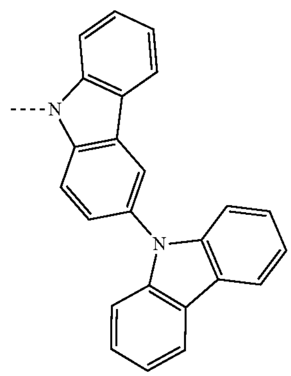
,
R56
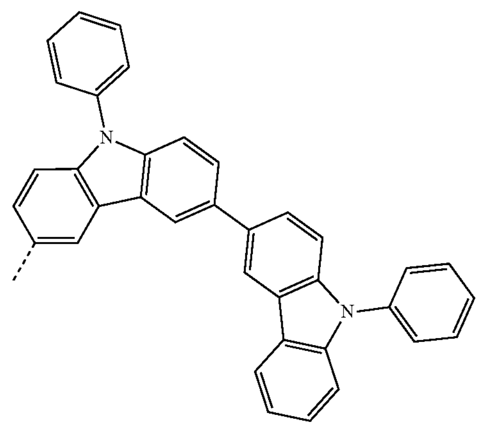
, -continued
$R^{57}$
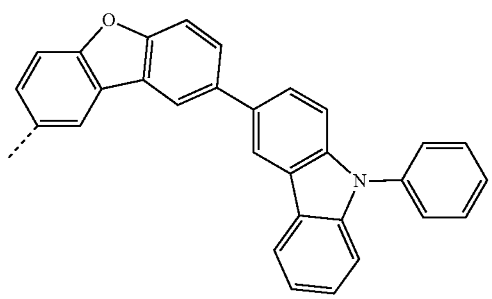
,
$R^{58}$
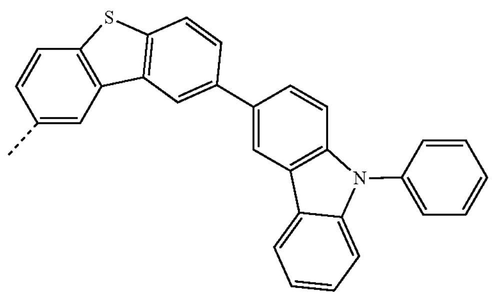
,
$R^{59}$
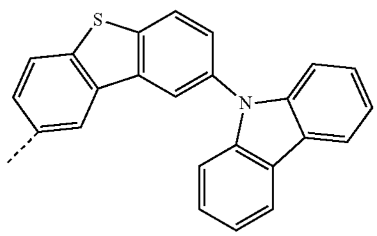
,
$R^{60}$
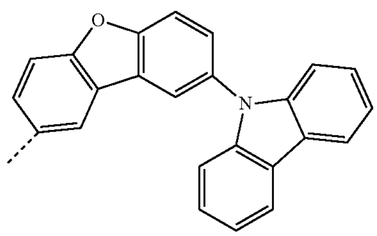
,
$R^{61}$
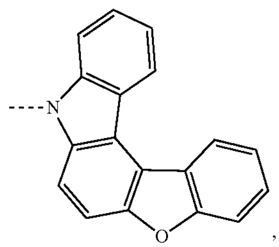
,
$R^{62}$
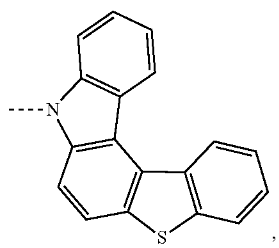
,
-continued
$R^{63}$
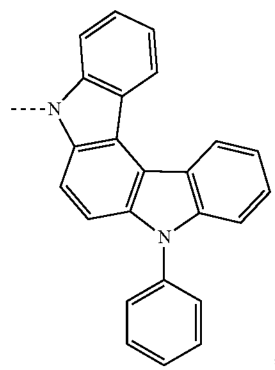
,
$R^{64}$
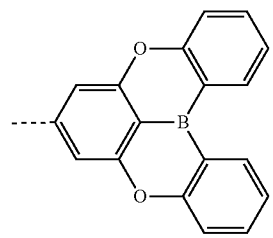
,
$R^{65}$
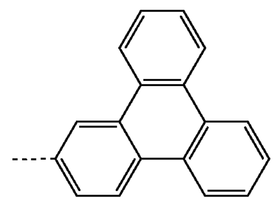
,
$R^{66}$
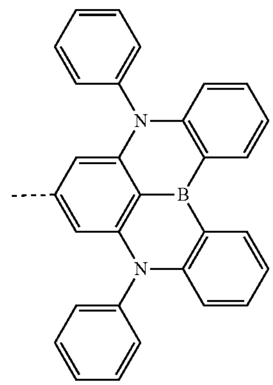
,
$R^{67}$
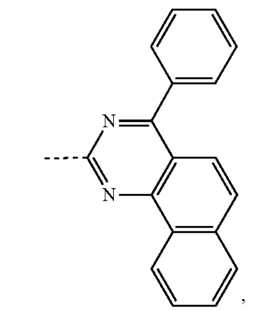
, -continued
$R^{68}$
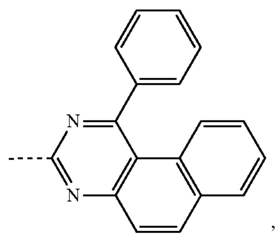
,
$R^{69}$
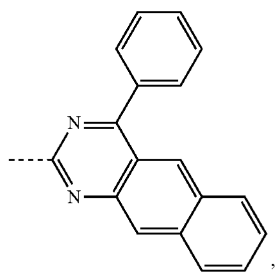
,
$R^{70}$
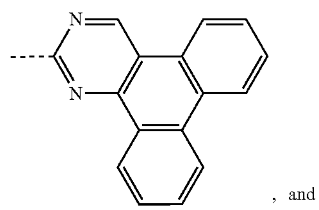
, and
$R^{71}$
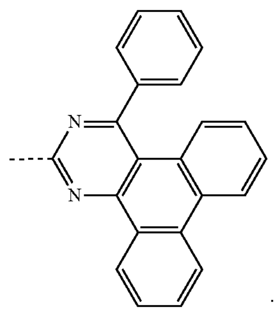
.
According to further embodiments of the invention, the compound may be selected from the group consisting of:
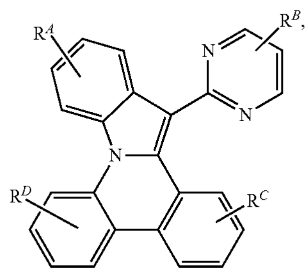
-continued
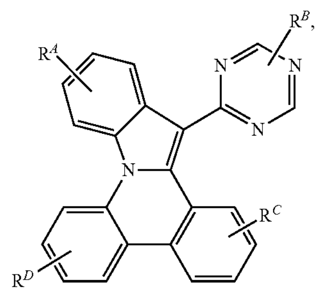
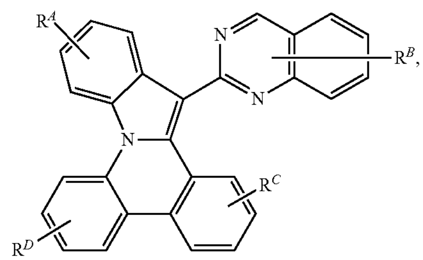
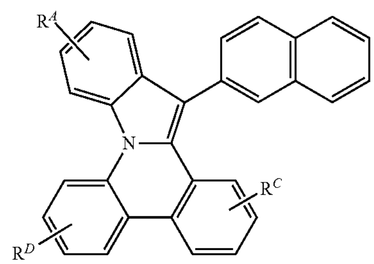
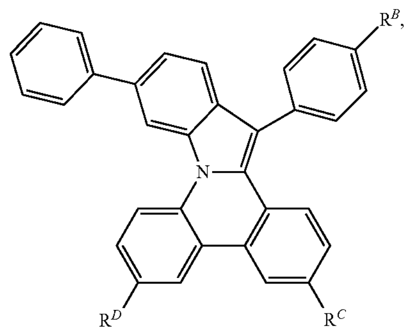
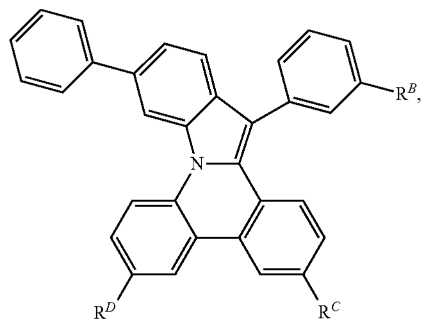

-continued
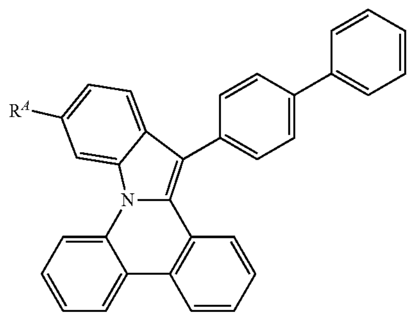
,
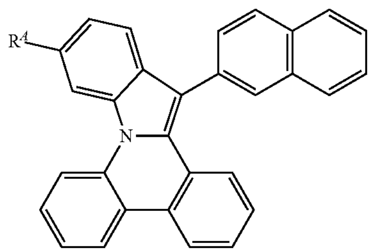
,
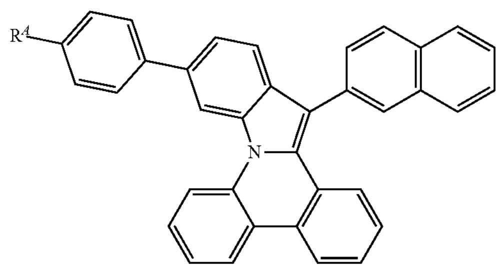
,
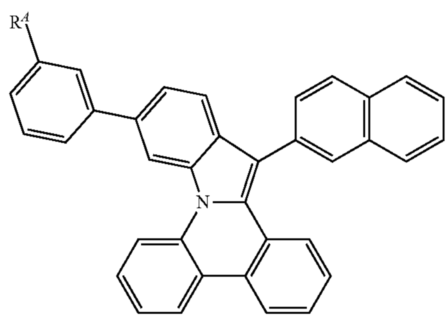
,
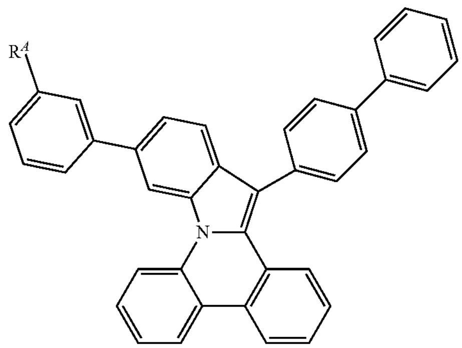
, and
-continued
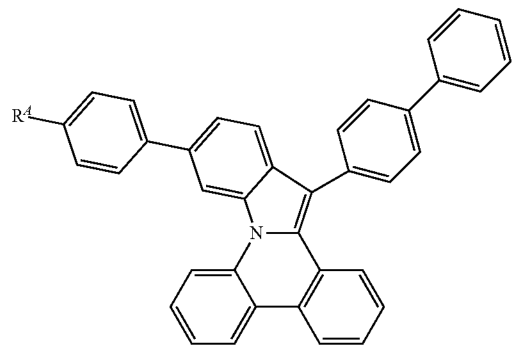
.
In particular, the compound may be selected from the group consisting of:
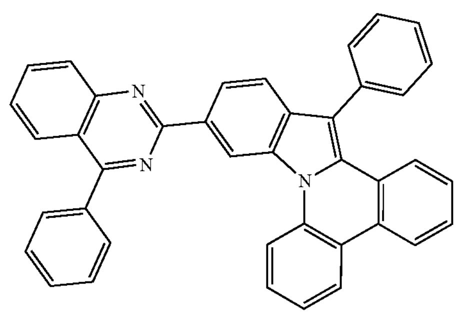
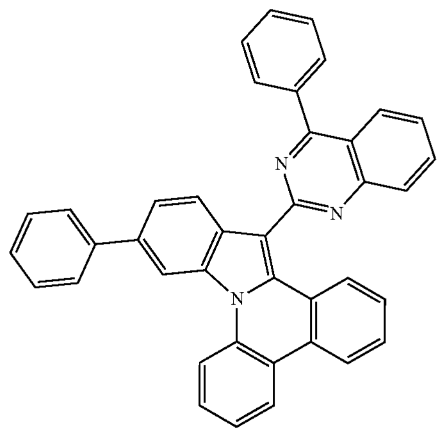
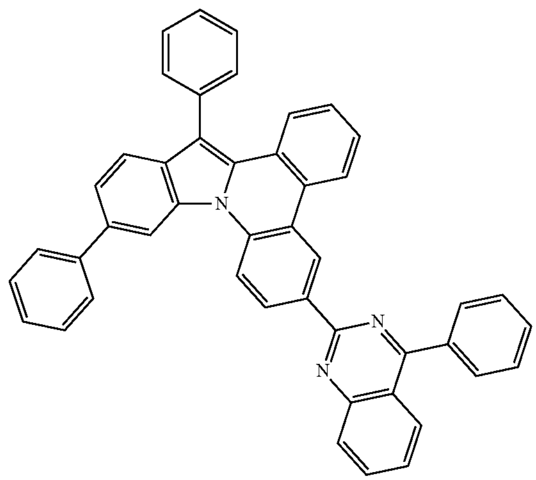

-continued
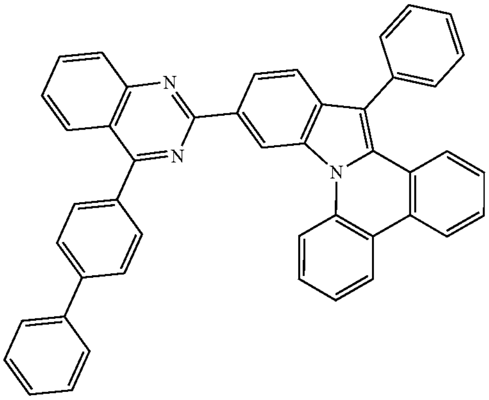
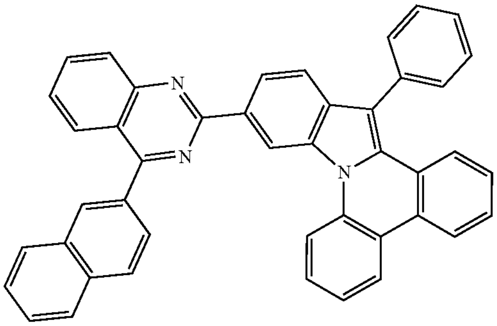
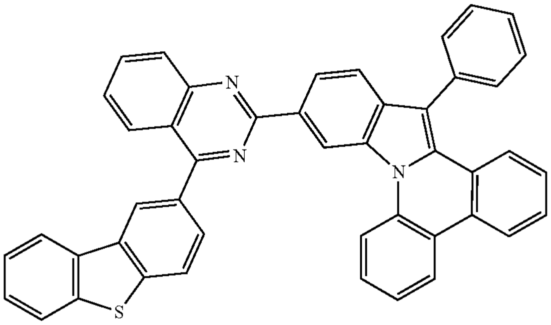
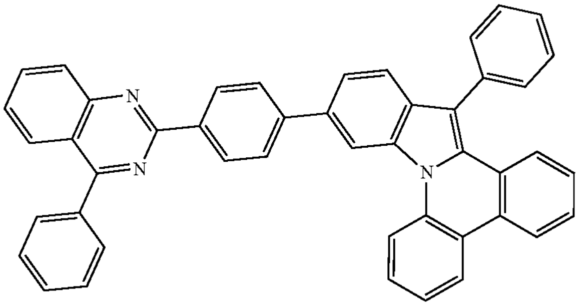
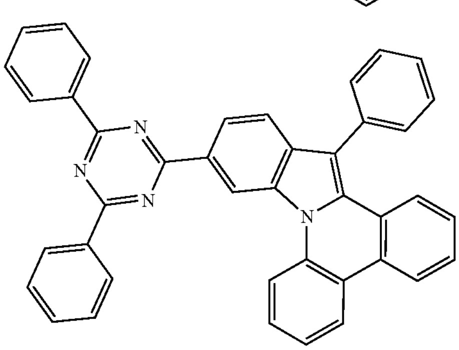
-continued
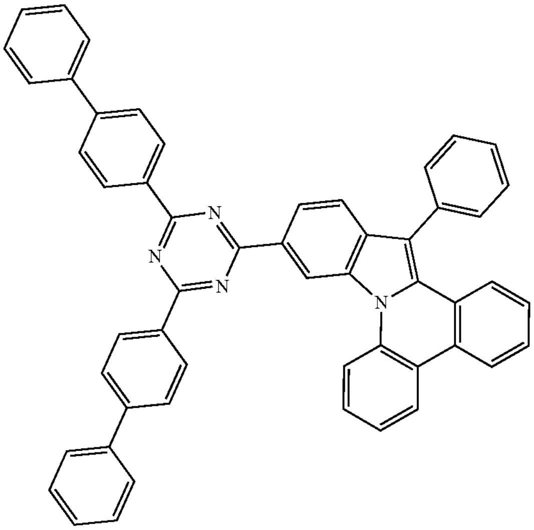
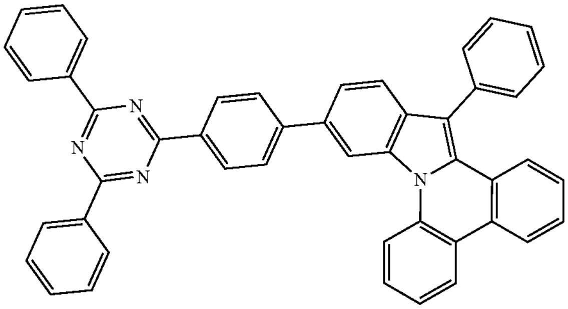
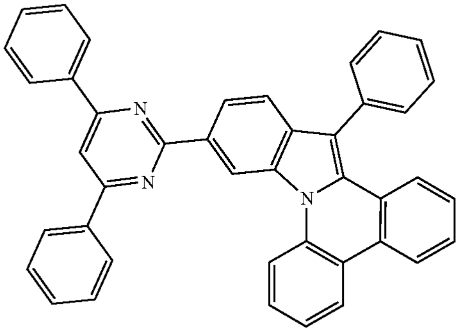
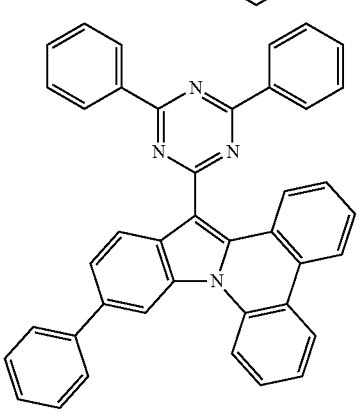

-continued
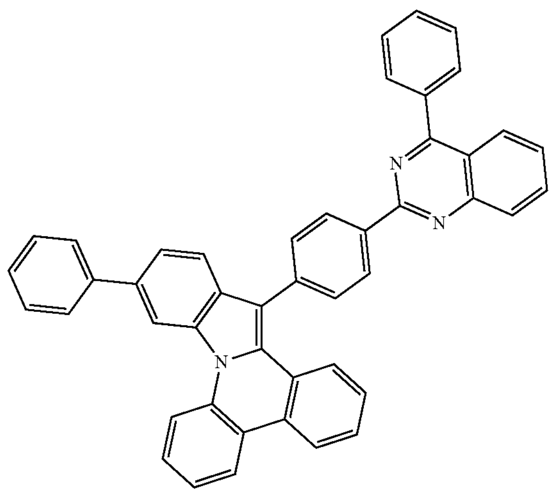
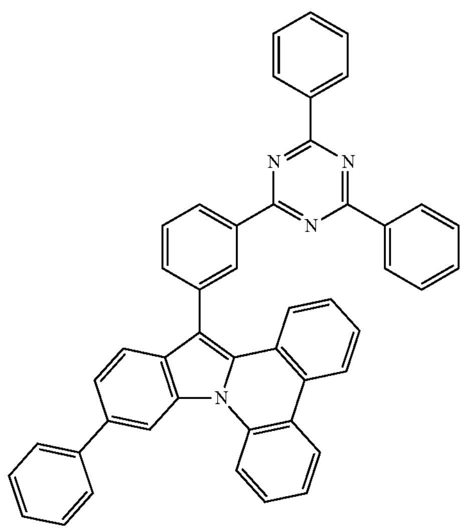
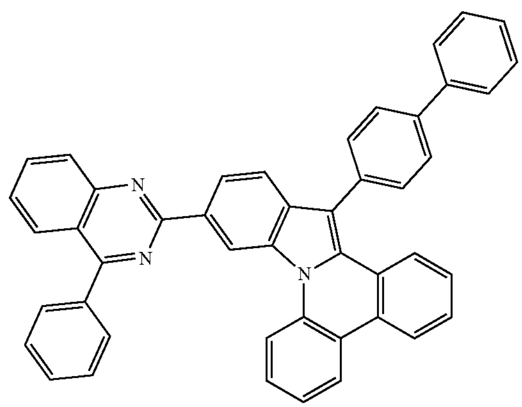
-continued
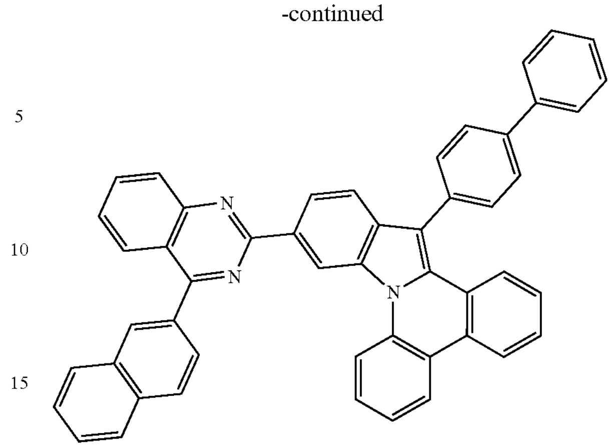
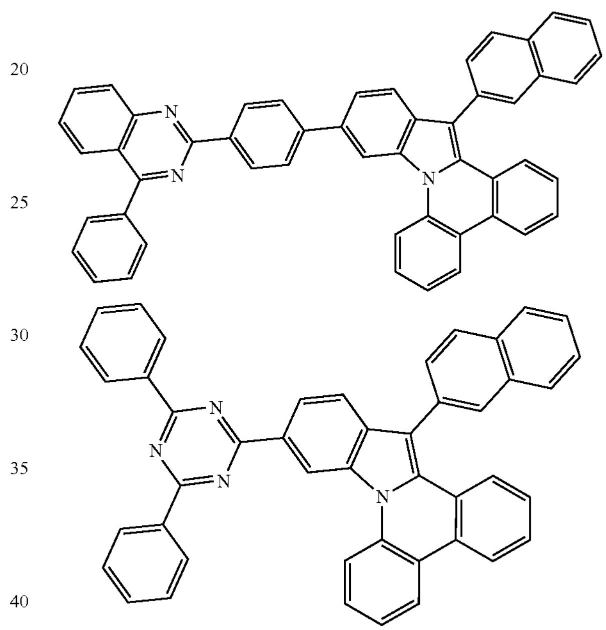
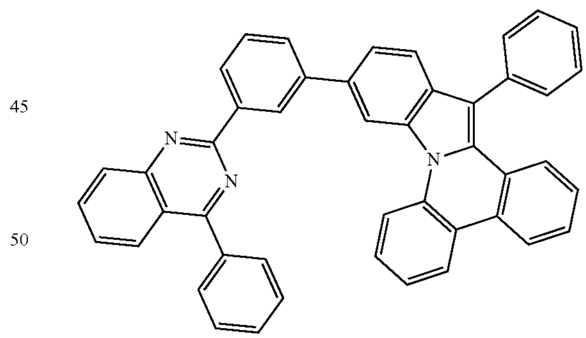
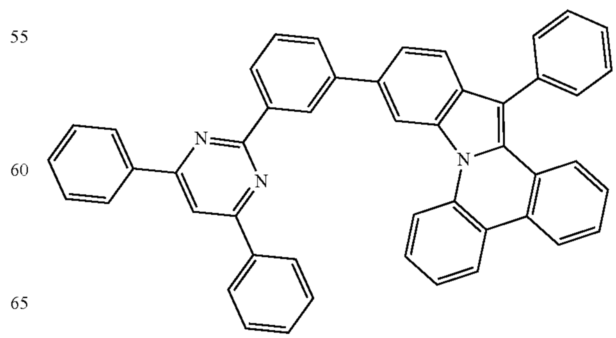

-continued
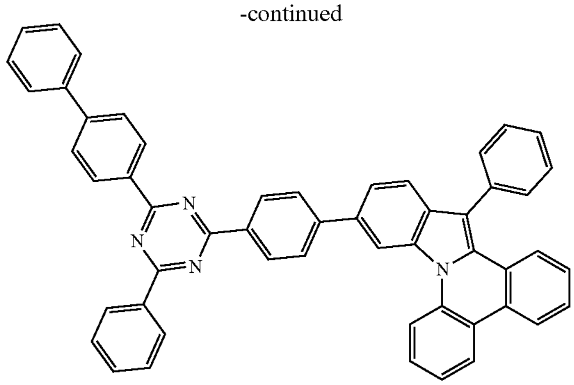
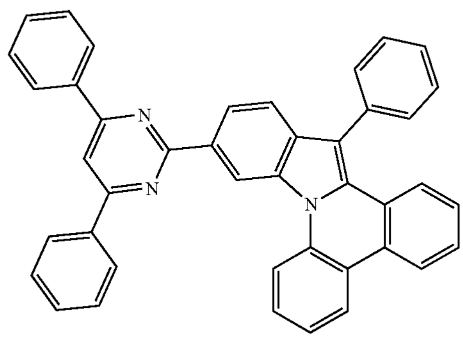
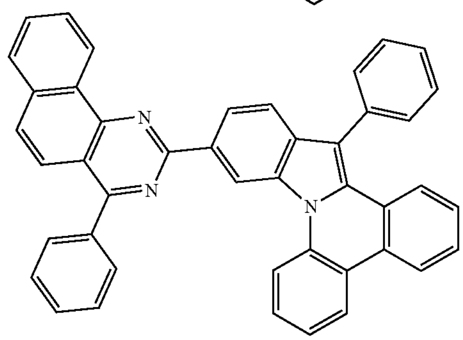
,
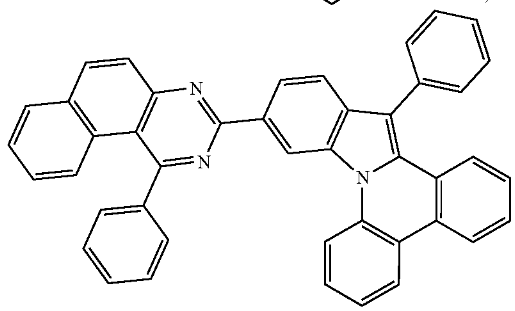
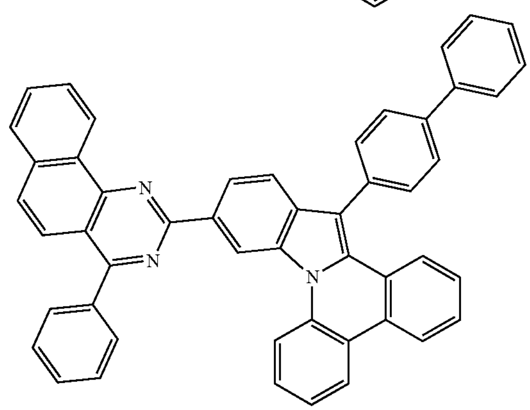
,
-continued
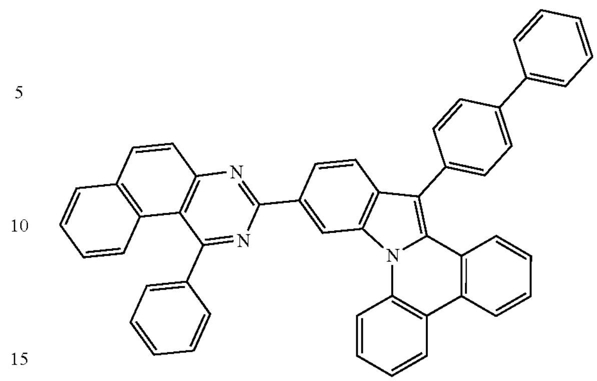
,
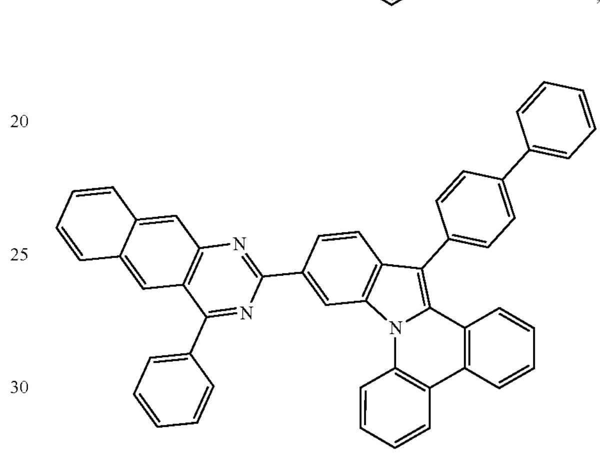
,
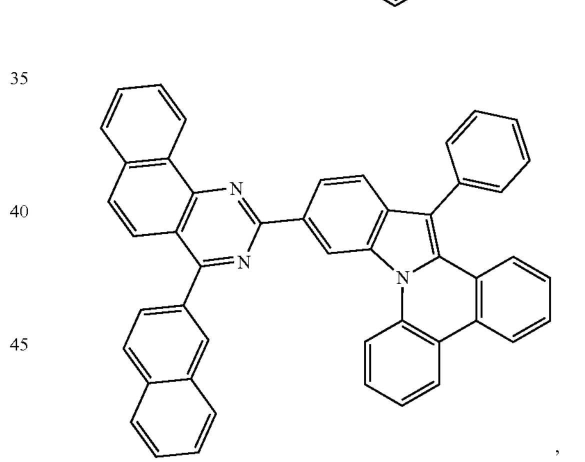
,
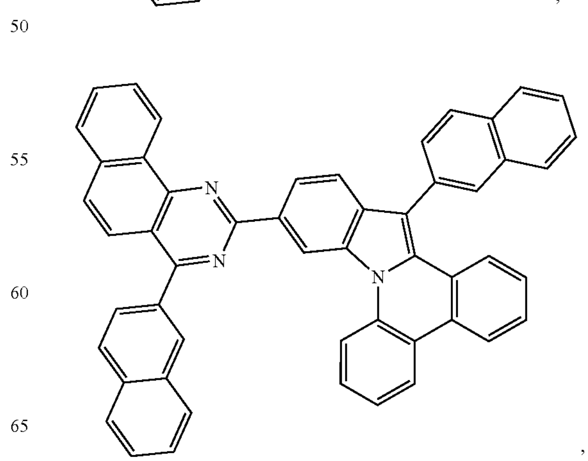
, -continued
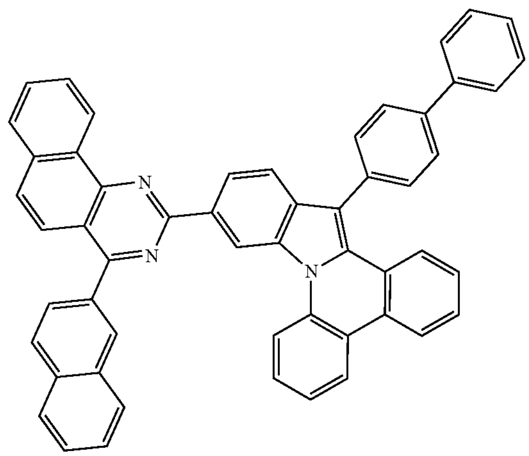
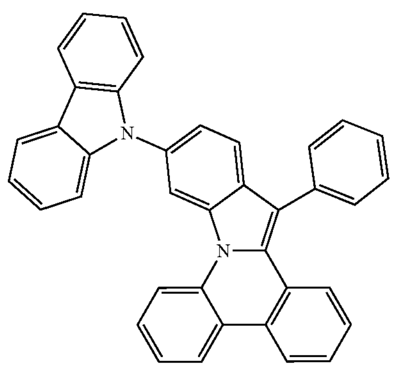
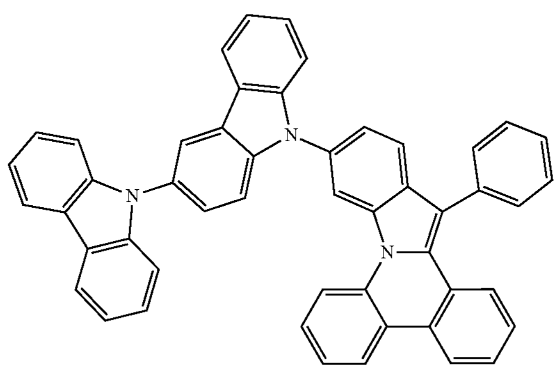
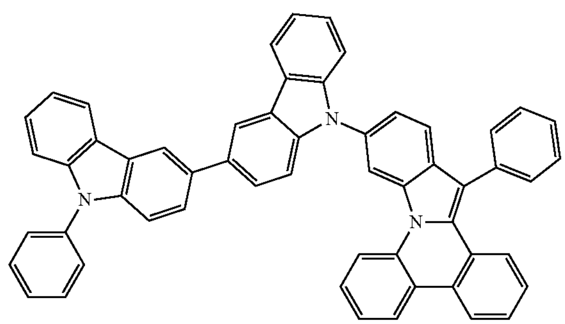
-continued
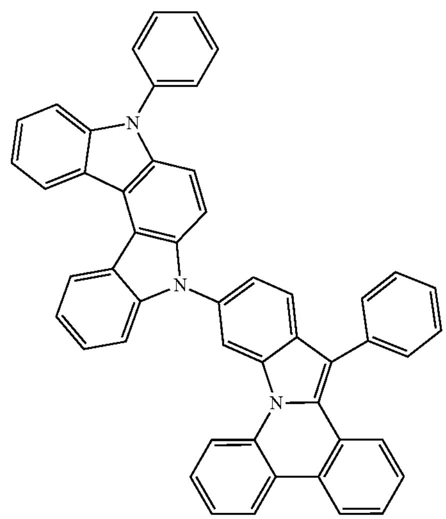
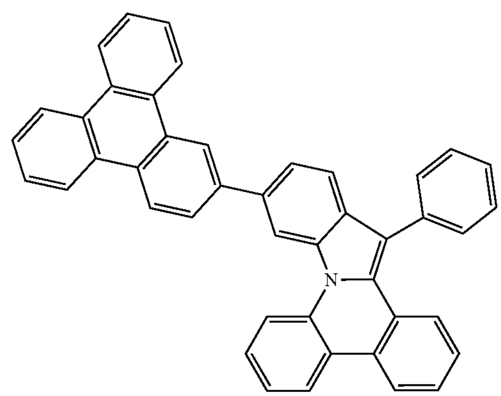
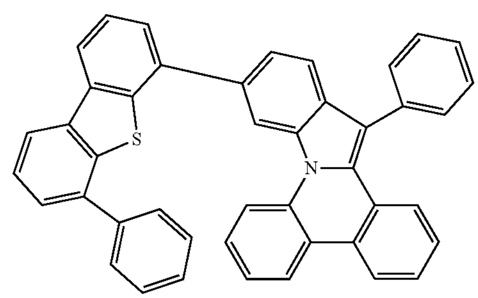
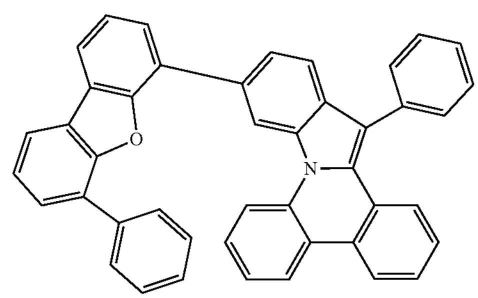

-continued
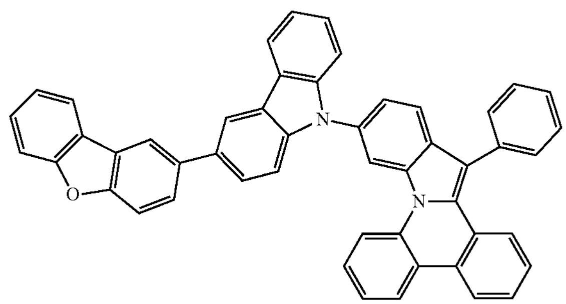
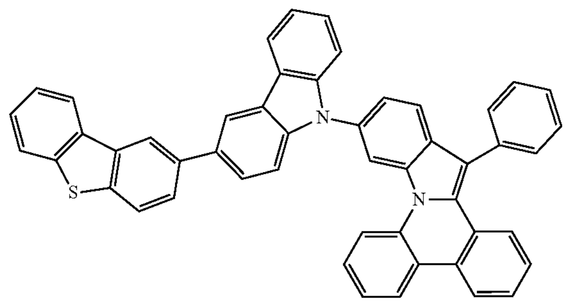
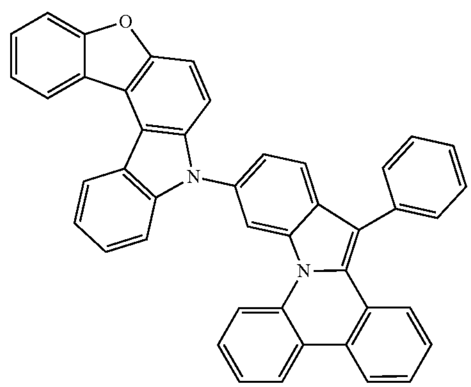
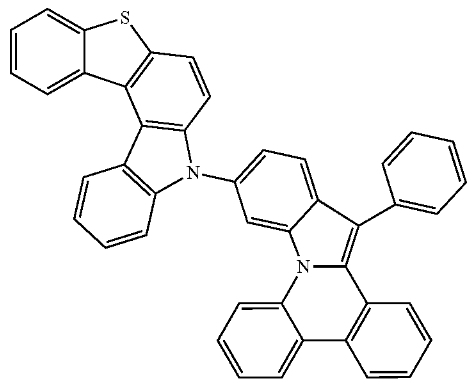
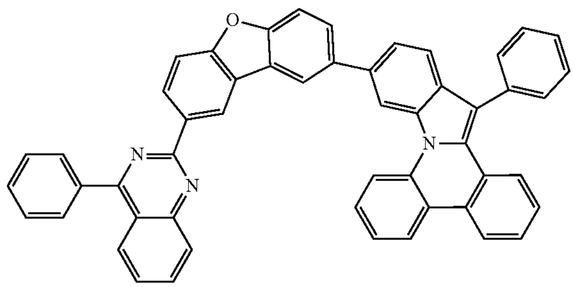
-continued
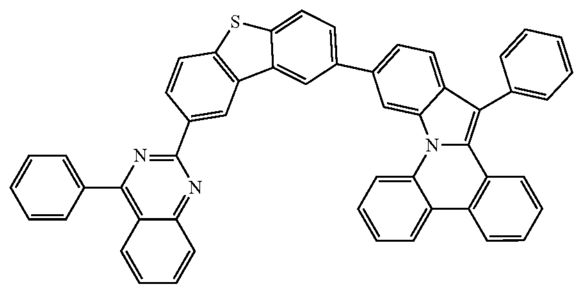
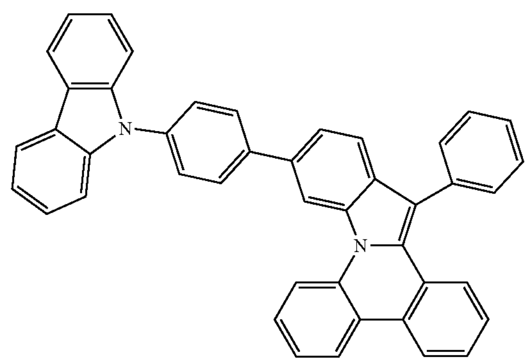
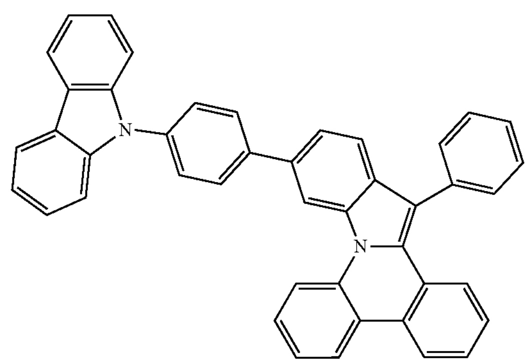
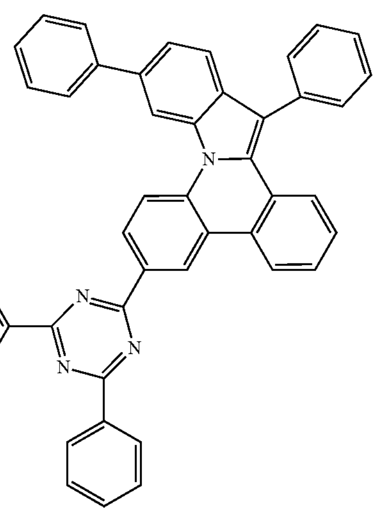

-continued
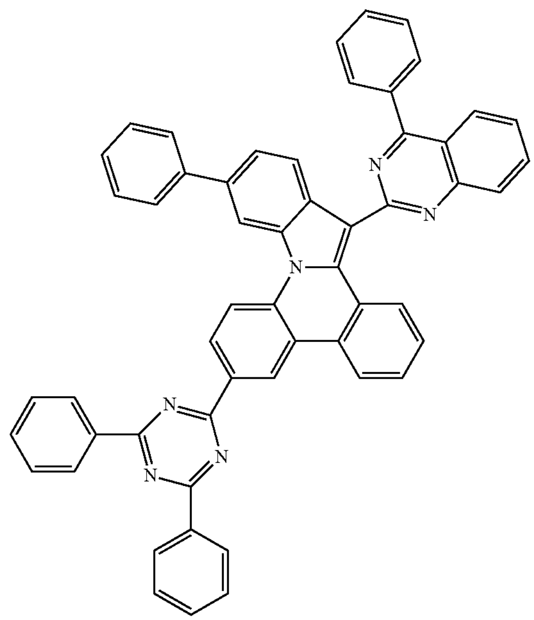
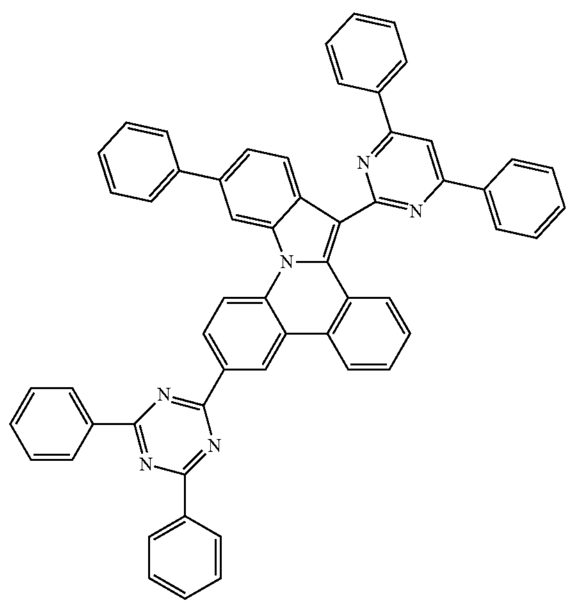
-continued
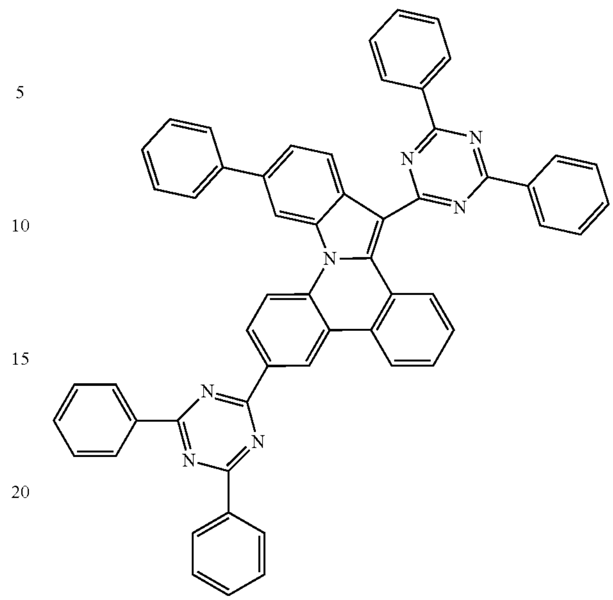
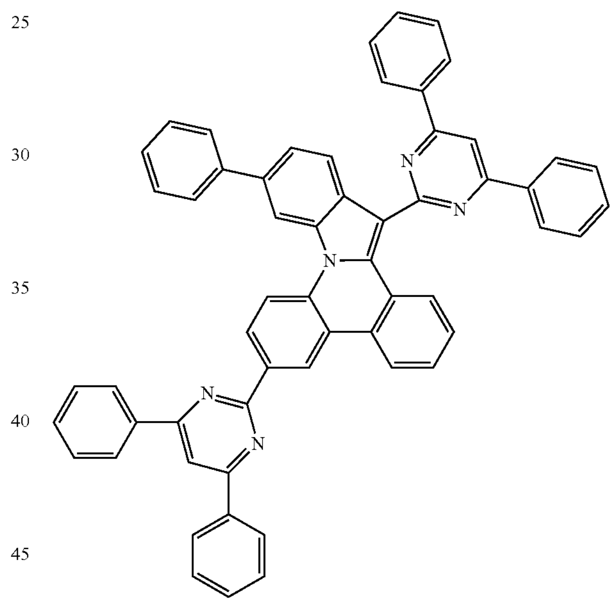
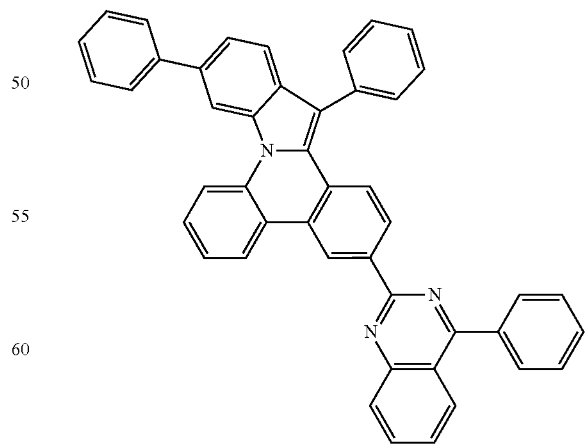

-continued
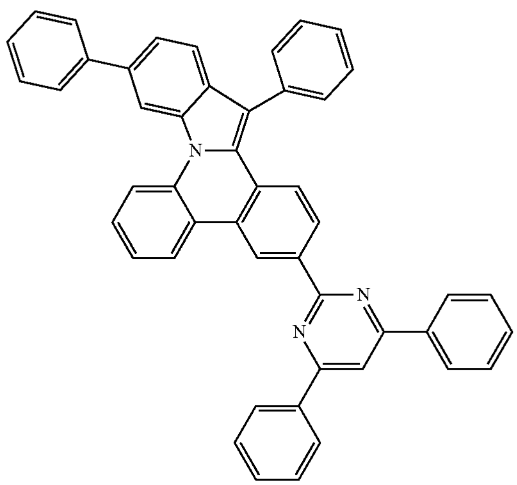
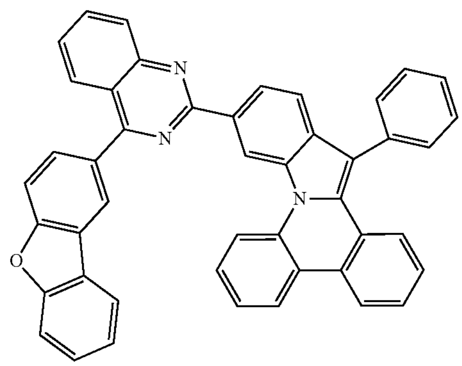
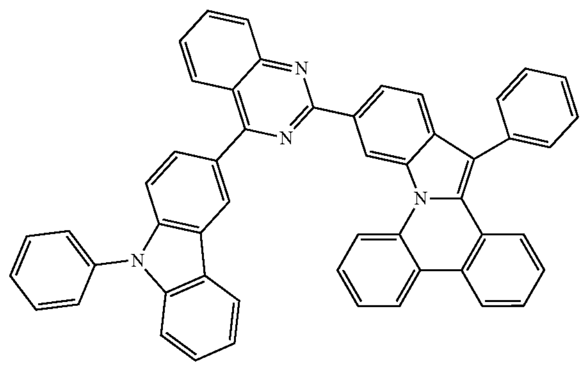
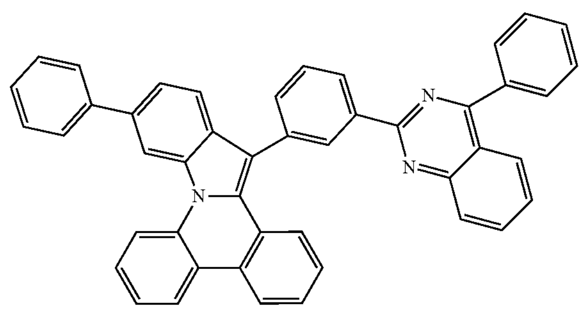
-continued
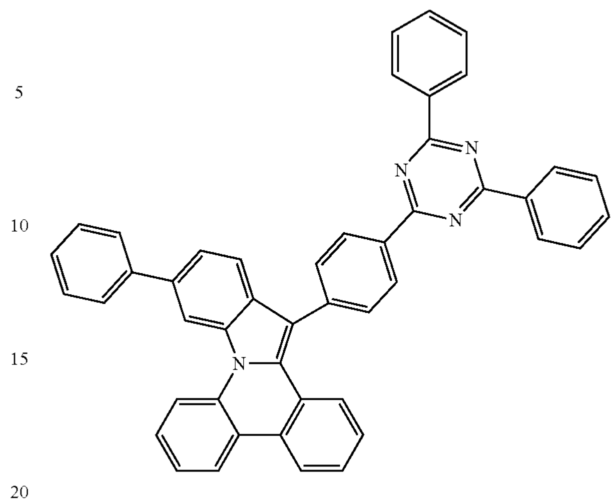
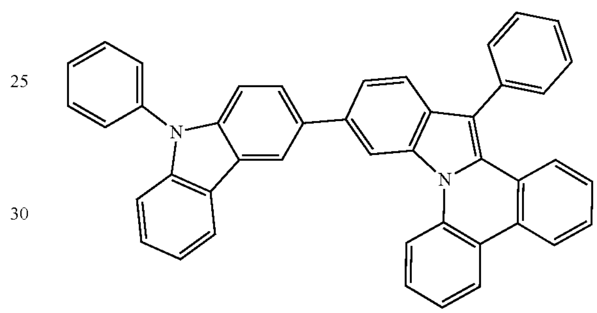
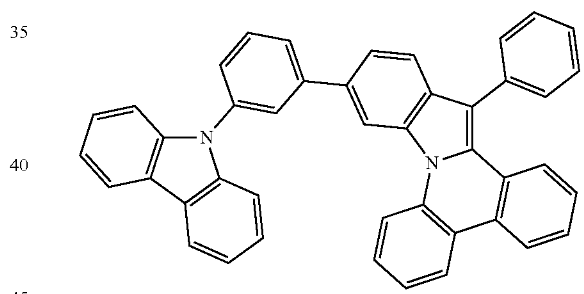
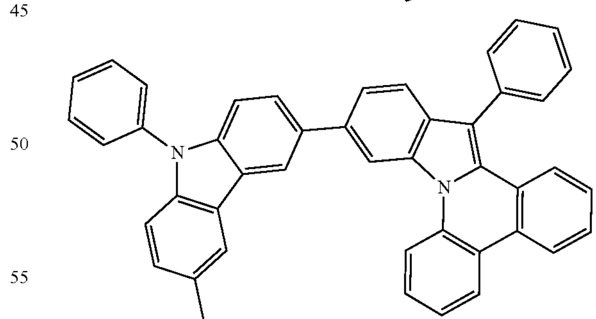
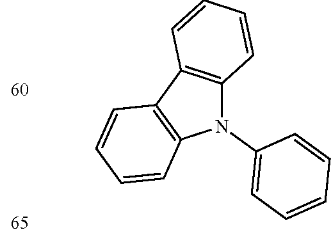

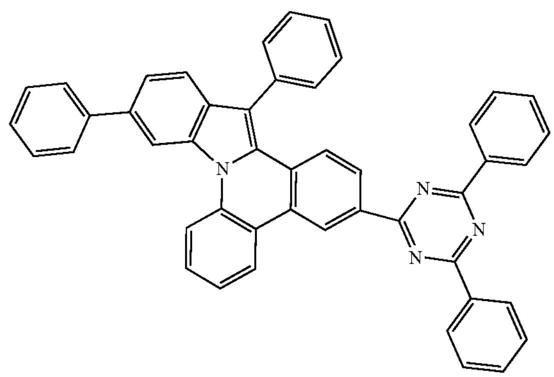
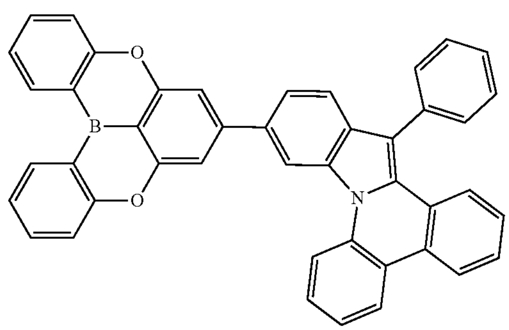
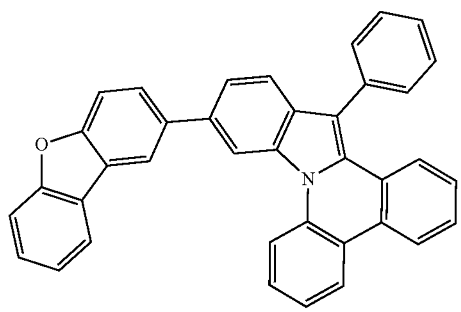
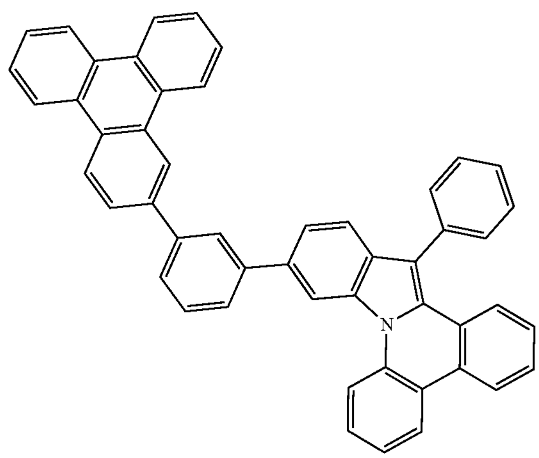
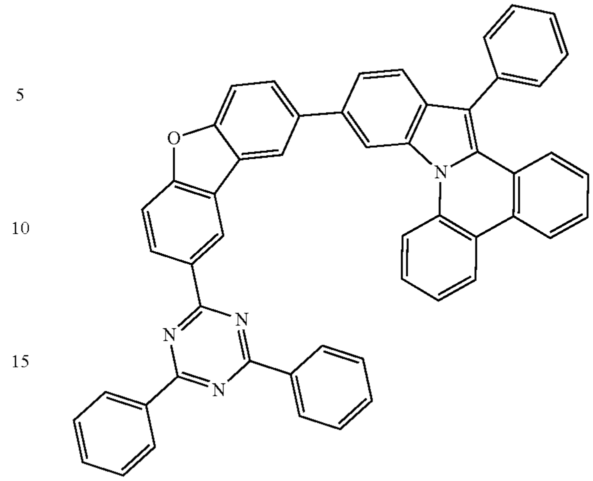
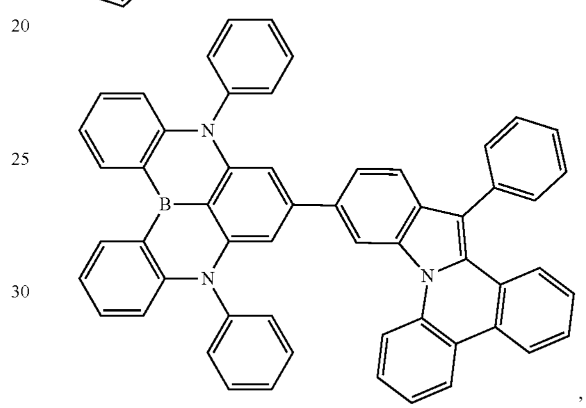
,
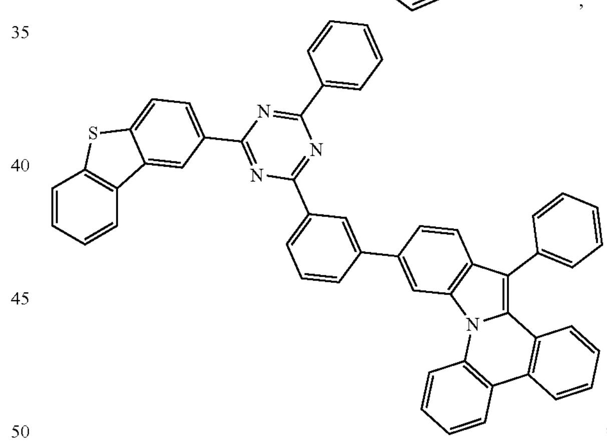
,
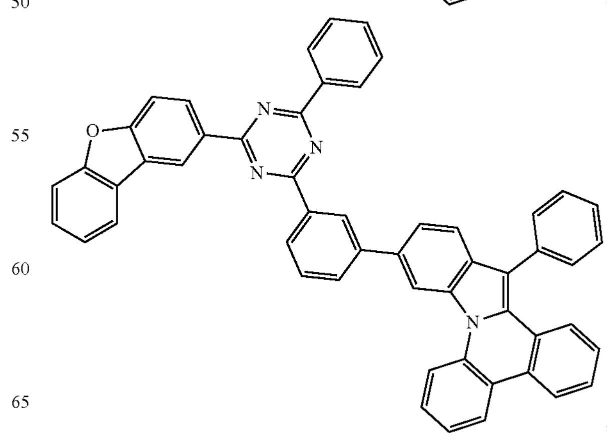
, -continued
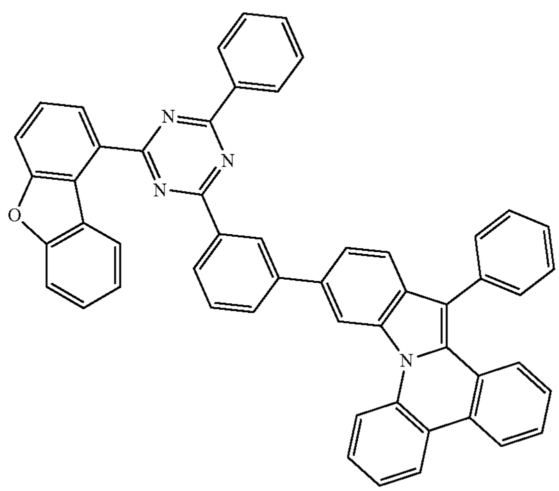
,
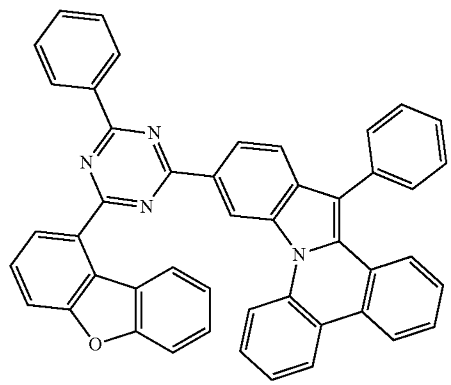
,
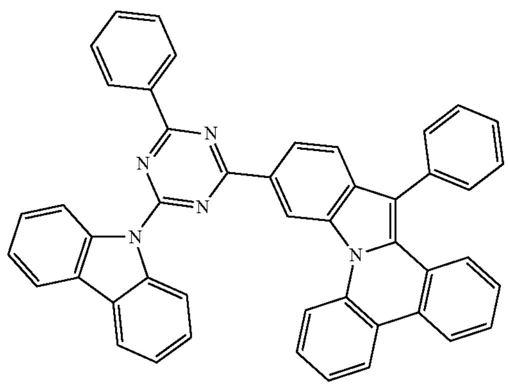
,
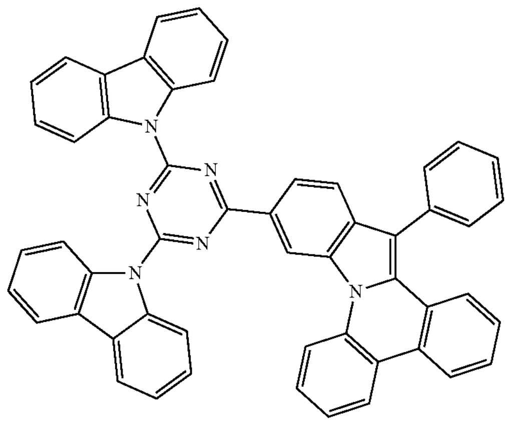
,
-continued
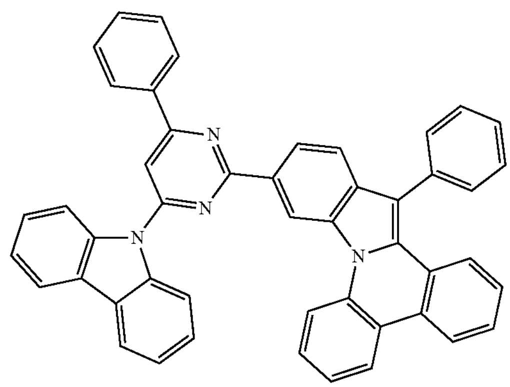
,
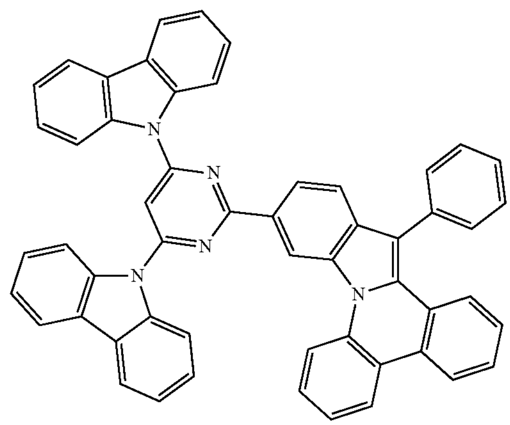
,
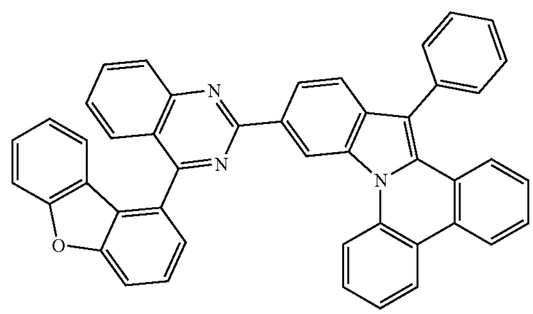
,
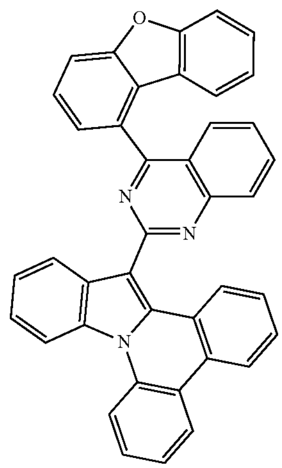
, -continued
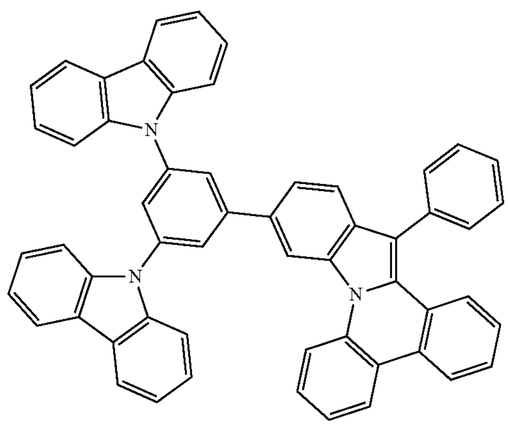
,
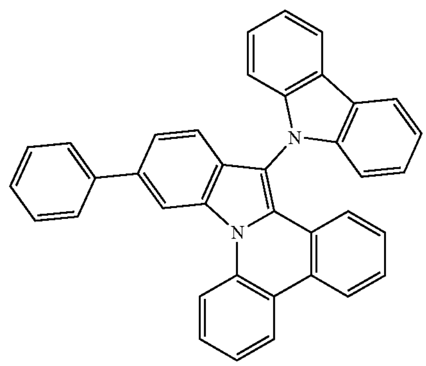
,
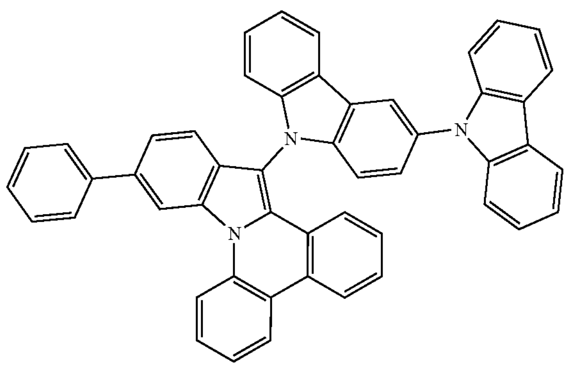
,
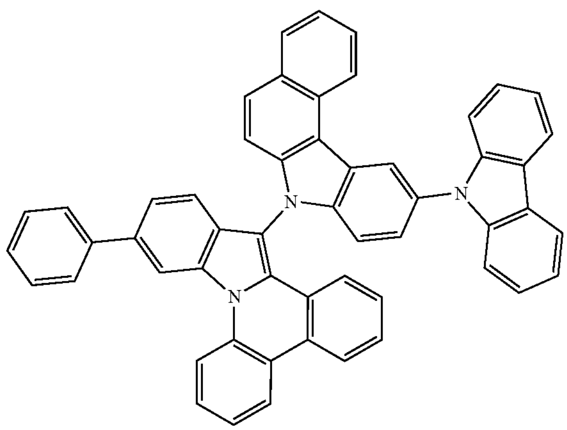
,
-continued
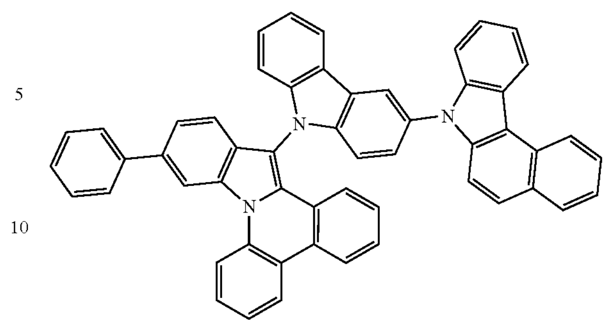
,
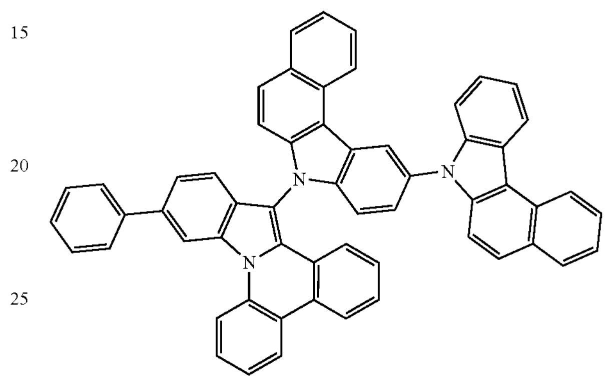
,
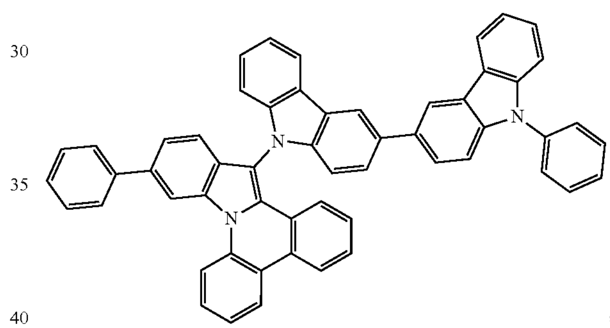
,
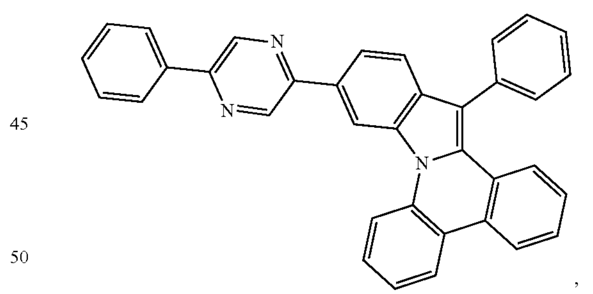
,
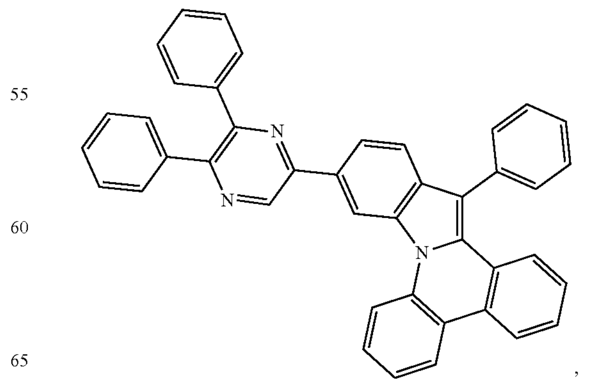
, -continued
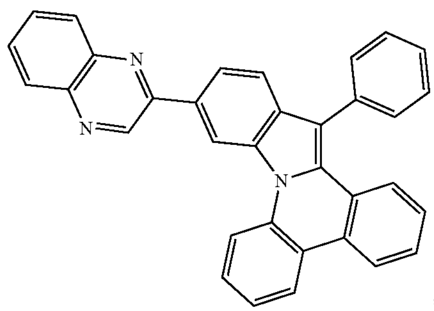
,
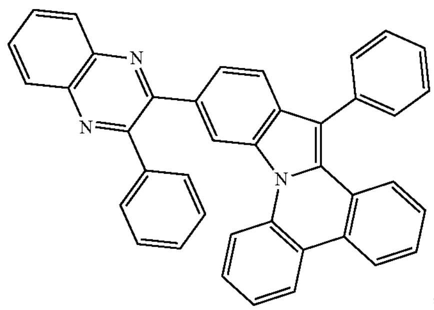
,
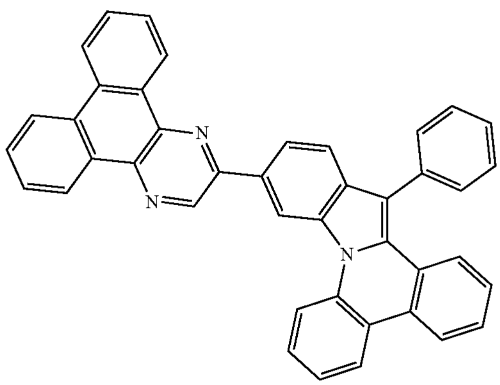
,
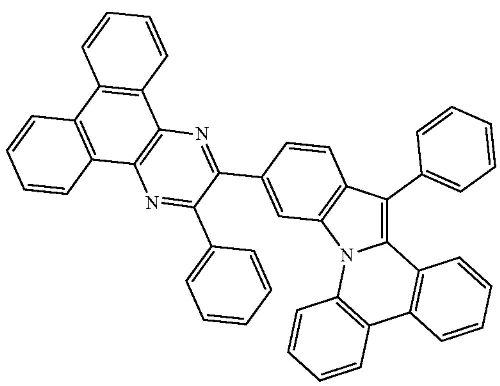
,
-continued
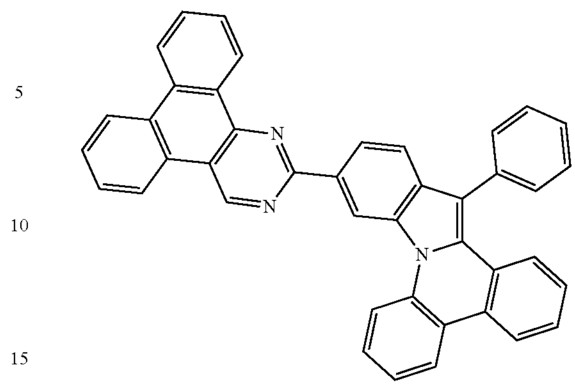
,
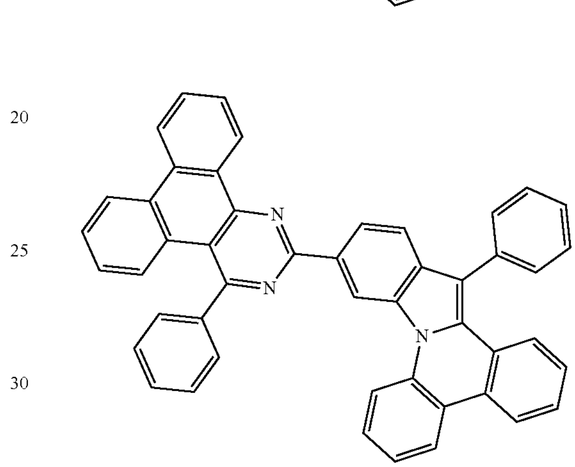
,
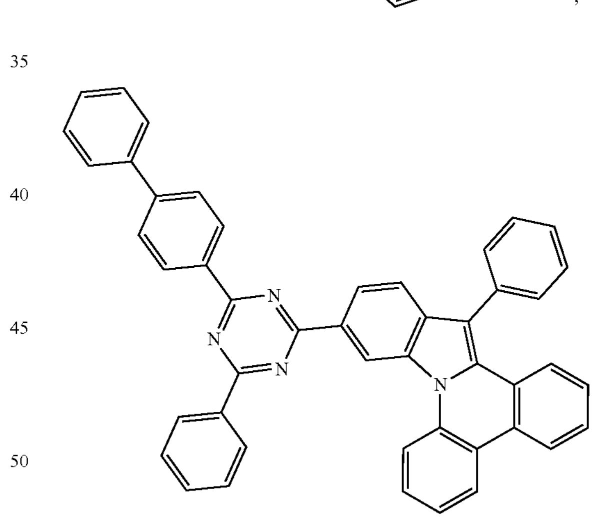
,
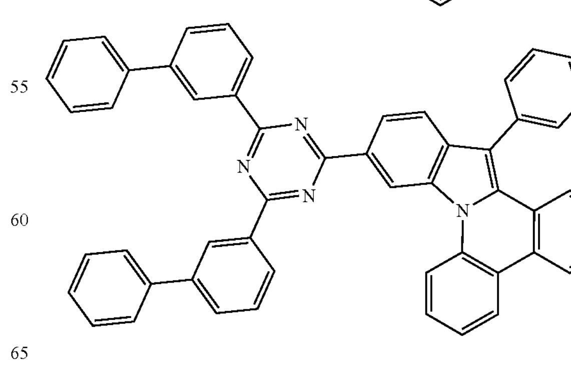
, -continued
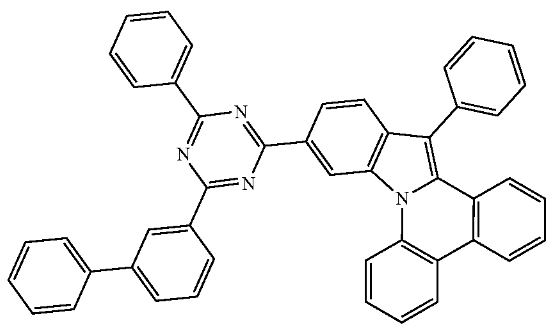
,
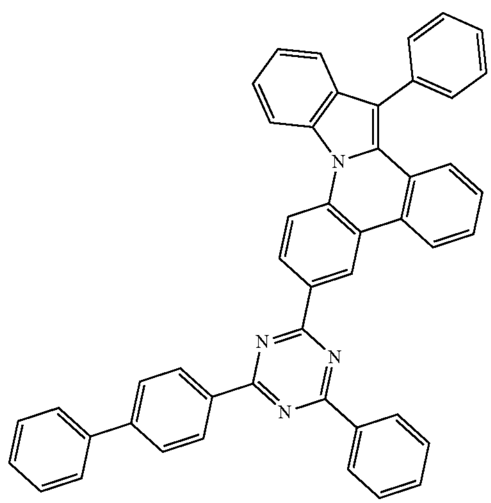
,
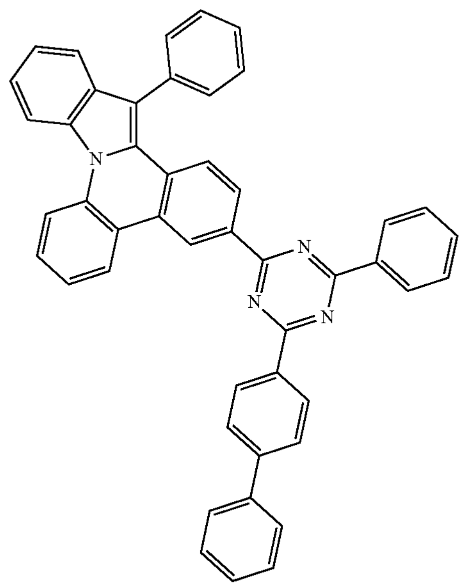
,
-continued
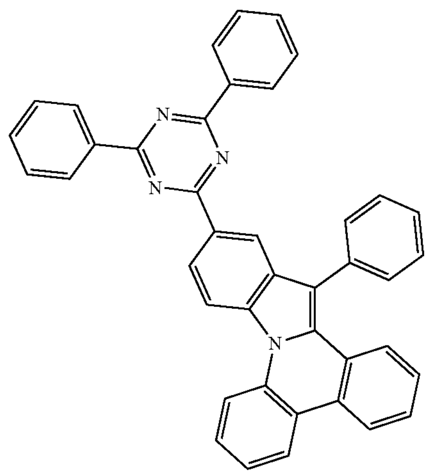
,
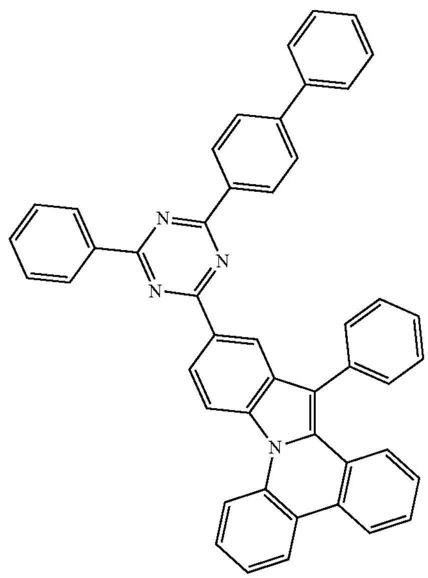
,
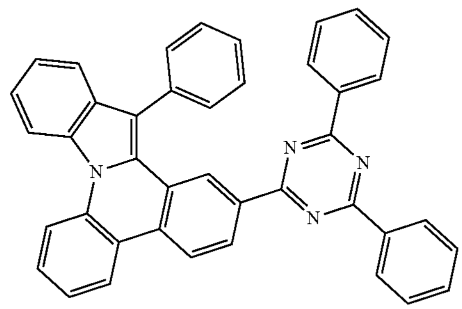
, -continued
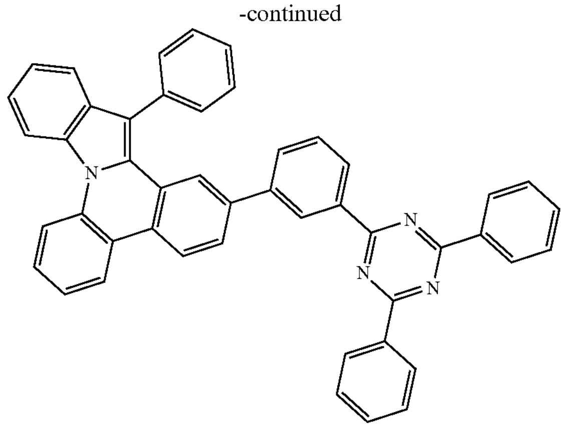
,
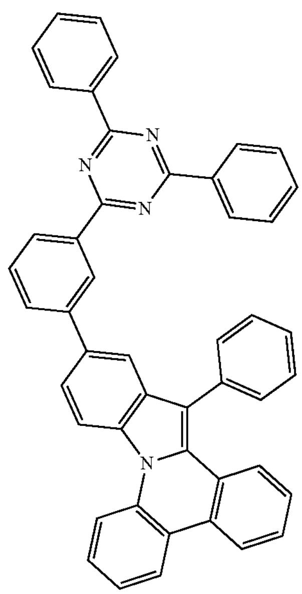
,
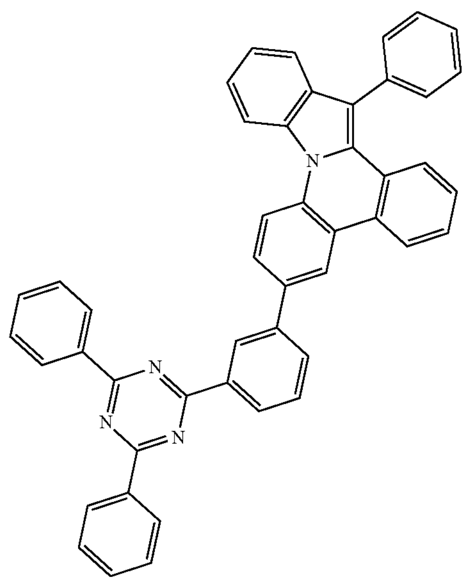
,
-continued
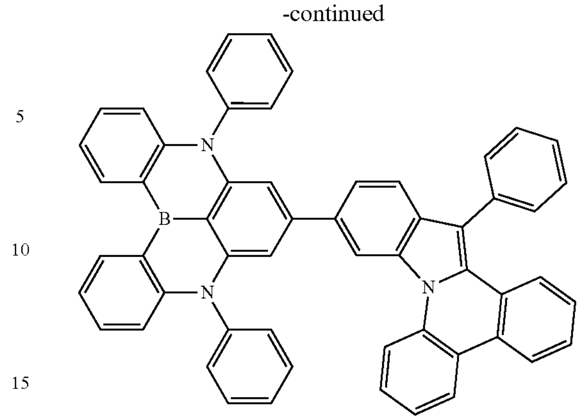
,
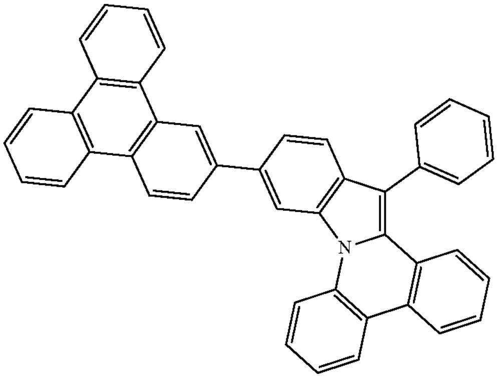
,
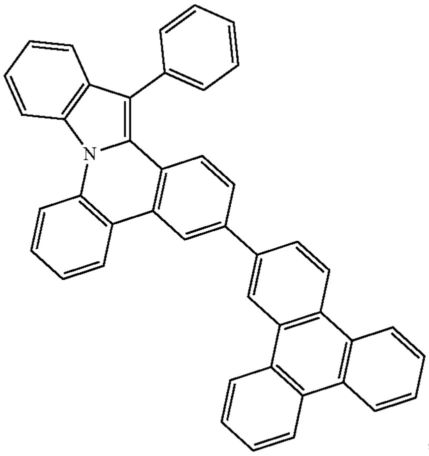
,
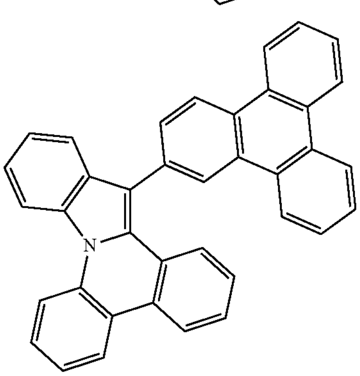
, -continued

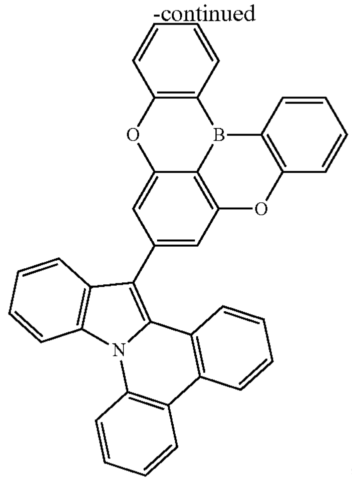

, and

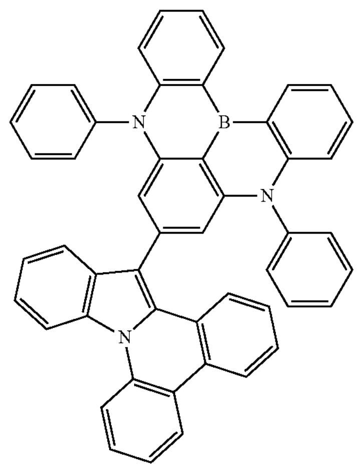

.

C. The OLEDs and the Devices of the Present Disclosure

In another aspect, the present disclosure also provides an OLED device comprising a first organic layer that contains a compound as disclosed in the above compounds section of the present disclosure.

In some embodiments, the first organic layer may comprise a compound as disclosed herein in the above compound section of the present disclosure.

In some embodiments, the compound may be a host, and the first organic layer may be an emissive layer that comprises a phosphorescent emitter.

In some embodiments, the phosphorescent emitter may be a transition metal complex having at least one ligand or part of the ligand if the ligand is more than bidentate selected from the group consisting of:

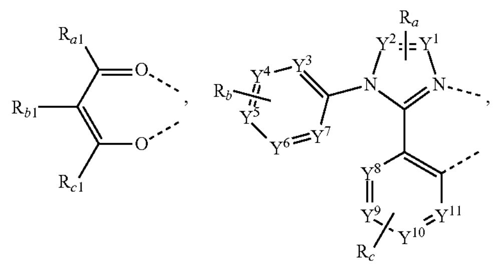

-continued

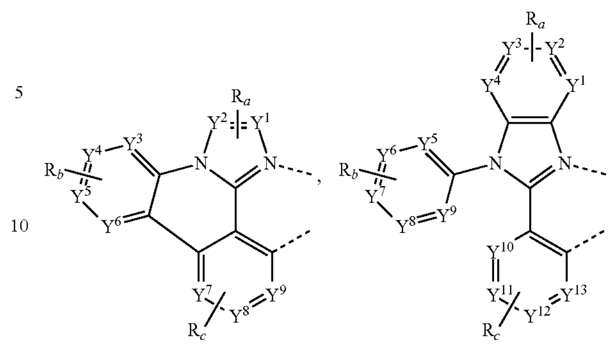

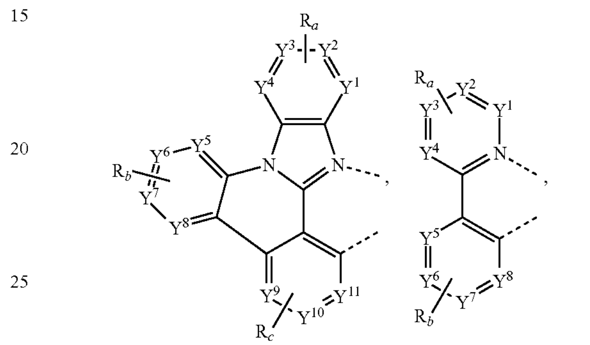

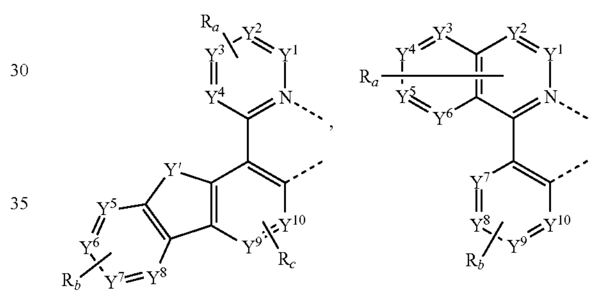

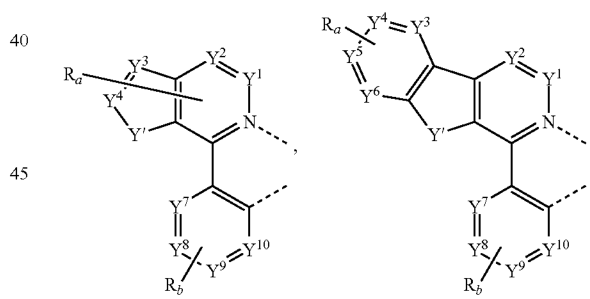

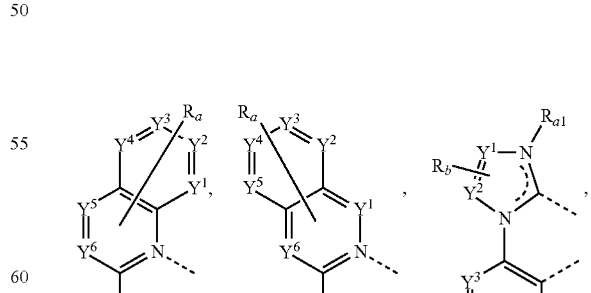

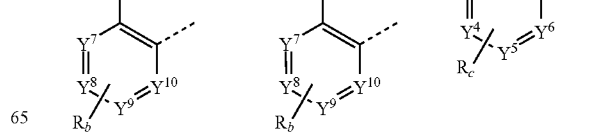

-continued

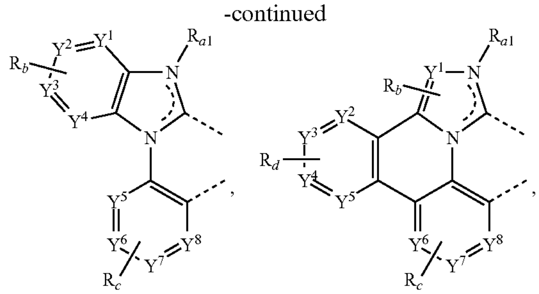

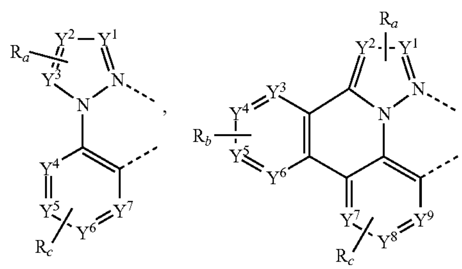

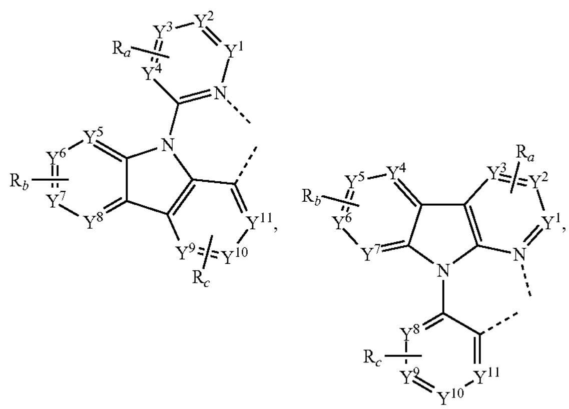

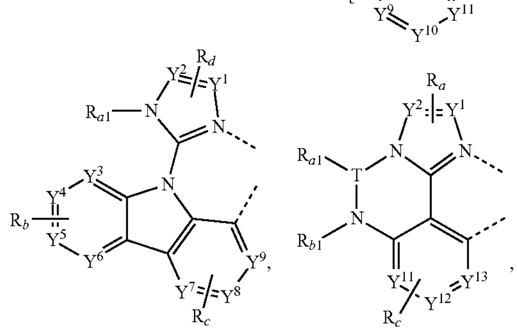

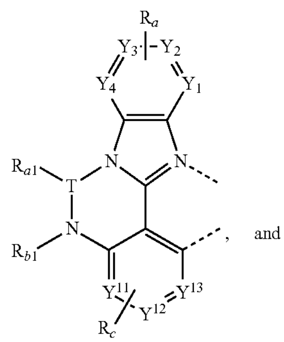

and

-continued

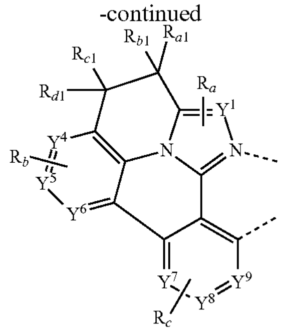

wherein:

T is selected from the group consisting of B, Al, Ga, and In;

each of $Y^1$ to $Y^{13}$ is independently selected from the group consisting of carbon and nitrogen;

Y' is selected from the group consisting of $BR_e$, $NR_e$, $PR_e$, O, S, Se, C═O, S═O, $SO_2$, $CR_eR_f$, $SiR_eR_f$, and $GeR_eR_f$;

$R_e$ and $R_f$ can be fused or joined to form a ring;

each $R_a$, $R_b$, $R_c$, and $R_d$ independently represent zero, mono, or up to a maximum allowed number of substitutions to its associated ring;

each of $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of deuterium, halide, alkyl, cycloalkyl, heteroalkyl, arylalkyl, alkoxy, aryloxy, amino, silyl, boryl, germyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, selenyl, and combinations thereof; and and any two adjacent substituents of $R_a$, $R_b$, $R_c$, $R_d$, $R_e$ and $R_f$ can be fused or joined to form a ring or form a multidentate ligand.

In some embodiments, the compound may be an acceptor, and the OLED may further comprise a sensitizer selected from the group consisting of a delayed fluorescence emitter, a phosphorescent emitter, and combination thereof.

In some embodiments, the compound may be a fluorescent emitter, a delayed fluorescence emitter, or a component of an exciplex that is a fluorescent emitter or a delayed fluorescence emitter.

In yet another aspect, the OLED of the present disclosure may also comprise an emissive region containing a compound as disclosed in the above compounds section of the present disclosure.

In some embodiments, the emissive region may comprise a compound of Formula I:

Formula I

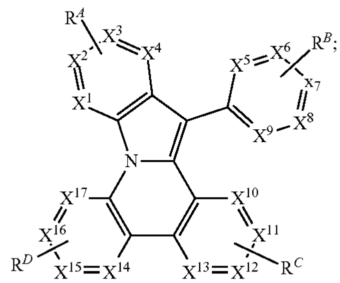

wherein each $X^1$-$X^{17}$ is independently C or N;

$R^A$, $R^B$, $R^C$, and $R^D$ each independently represent mono to the maximum allowable substitution, or no substitution;

each $R^A$, $R^B$, $R^C$, and $R^D$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, germyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof; at least one of $R^A$, $R^B$, $R^C$, and $R^D$ is joined to its respective ring by a single bond and comprises pyrimidine, triazine, quinazoline, benzene, biphenyl, terphenyl, naphthalene, phenanthrene, anthracene, triphenylene, pyridine, pyrazine, fluorene, dibenzofuran, dibenzothiophene, carbazole, quinoline, isoquinoline, triarylboryl or quinoxaline, which may be further substituted.

In some embodiments, at least one of the anode, the cathode, or a new layer disposed over the organic emissive layer functions as an enhancement layer. The enhancement layer comprises a plasmonic material exhibiting surface plasmon resonance that non-radiatively couples to the emitter material and transfers excited state energy from the emitter material to non-radiative mode of surface plasmon polariton. The enhancement layer is provided no more than a threshold distance away from the organic emissive layer, wherein the emitter material has a total non-radiative decay rate constant and a total radiative decay rate constant due to the presence of the enhancement layer and the threshold distance is where the total non-radiative decay rate constant is equal to the total radiative decay rate constant. In some embodiments, the OLED further comprises an outcoupling layer. In some embodiments, the outcoupling layer is disposed over the enhancement layer on the opposite side of the organic emissive layer. In some embodiments, the outcoupling layer is disposed on opposite side of the emissive layer from the enhancement layer but still outcouples energy from the surface plasmon mode of the enhancement layer. The outcoupling layer scatters the energy from the surface plasmon polaritons. In some embodiments this energy is scattered as photons to free space. In other embodiments, the energy is scattered from the surface plasmon mode into other modes of the device such as but not limited to the organic waveguide mode, the substrate mode, or another waveguiding mode. If energy is scattered to the non-free space mode of the OLED other outcoupling schemes could be incorporated to extract that energy to free space. In some embodiments, one or more intervening layer can be disposed between the enhancement layer and the outcoupling layer. The examples for intervening layer(s) can be dielectric materials, including organic, inorganic, perovskites, oxides, and may include stacks and/or mixtures of these materials.

The enhancement layer modifies the effective properties of the medium in which the emitter material resides resulting in any or all of the following: a decreased rate of emission, a modification of emission line-shape, a change in emission intensity with angle, a change in the stability of the emitter material, a change in the efficiency of the OLED, and reduced efficiency roll-off of the OLED device. Placement of the enhancement layer on the cathode side, anode side, or on both sides results in OLED devices which take advantage of any of the above-mentioned effects. In addition to the specific functional layers mentioned herein and illustrated in the various OLED examples shown in the figures, the OLEDs according to the present disclosure may include any of the other functional layers often found in OLEDs.

The enhancement layer can be comprised of plasmonic materials, optically active metamaterials, or hyperbolic metamaterials. As used herein, a plasmonic material is a material in which the real part of the dielectric constant crosses zero in the visible or ultraviolet region of the electromagnetic spectrum. In some embodiments, the plasmonic material includes at least one metal. In such embodiments the metal may include at least one of Ag, Al, Au, Ir, Pt, Ni, Cu, W, Ta, Fe, Cr, Mg, Ga, Rh, Ti, Ru, Pd, In, Bi, Ca alloys or mixtures of these materials, and stacks of these materials. In general, a metamaterial is a medium composed of different materials where the medium as a whole acts differently than the sum of its material parts. In particular, we define optically active metamaterials as materials which have both negative permittivity and negative permeability. Hyperbolic metamaterials, on the other hand, are anisotropic media in which the permittivity or permeability are of different sign for different spatial directions. Optically active metamaterials and hyperbolic metamaterials are strictly distinguished from many other photonic structures such as Distributed Bragg Reflectors ("DBRs") in that the medium should appear uniform in the direction of propagation on the length scale of the wavelength of light. Using terminology that one skilled in the art can understand: the dielectric constant of the metamaterials in the direction of propagation can be described with the effective medium approximation. Plasmonic materials and metamaterials provide methods for controlling the propagation of light that can enhance OLED performance in a number of ways.

In some embodiments, the enhancement layer is provided as a planar layer. In other embodiments, the enhancement layer has wavelength-sized features that are arranged periodically, quasi-periodically, or randomly, or sub-wavelength-sized features that are arranged periodically, quasi-periodically, or randomly. In some embodiments, the wavelength-sized features and the sub-wavelength-sized features have sharp edges.

In some embodiments, the outcoupling layer has wavelength-sized features that are arranged periodically, quasi-periodically, or randomly, or sub-wavelength-sized features that are arranged periodically, quasi-periodically, or randomly. In some embodiments, the outcoupling layer may be composed of a plurality of nanoparticles and in other embodiments the outcoupling layer is composed of a plurality of nanoparticles disposed over a material. In these embodiments the outcoupling may be tunable by at least one of varying a size of the plurality of nanoparticles, varying a shape of the plurality of nanoparticles, changing a material of the plurality of nanoparticles, adjusting a thickness of the material, changing the refractive index of the material or an additional layer disposed on the plurality of nanoparticles, varying a thickness of the enhancement layer, and/or varying the material of the enhancement layer. The plurality of nanoparticles of the device may be formed from at least one of metal, dielectric material, semiconductor materials, an alloy of metal, a mixture of dielectric materials, a stack or layering of one or more materials, and/or a core of one type of material and that is coated with a shell of a different type of material. In some embodiments, the outcoupling layer is composed of at least metal nanoparticles wherein the metal is selected from the group consisting of Ag, Al, Au, Ir, Pt, Ni, Cu, W, Ta, Fe, Cr, Mg, Ga, Rh, Ti, Ru, Pd, In, Bi, Ca, alloys or mixtures of these materials, and stacks of these materials. The plurality of nanoparticles may have additional layer disposed over them. In some embodiments, the polarization of the emission can be tuned using the outcoupling layer. Varying the dimensionality and periodicity of the outcoupling layer can select a type of polarization that is preferentially outcoupled to air. In some embodiments the outcoupling layer also acts as an electrode of the device.

In yet another aspect, the present disclosure also provides a consumer product comprising an organic light-emitting device (OLED) having an anode; a cathode; and an organic layer disposed between the anode and the cathode, wherein the organic layer may comprise a compound as disclosed in the above compounds section of the present disclosure.

In some embodiments, the consumer product comprises an organic light-emitting device (OLED) having an anode; a cathode; and an organic layer disposed between the anode and the cathode, wherein the organic layer may comprise the compound of Formula I as described herein.

In some embodiments, the consumer product can be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
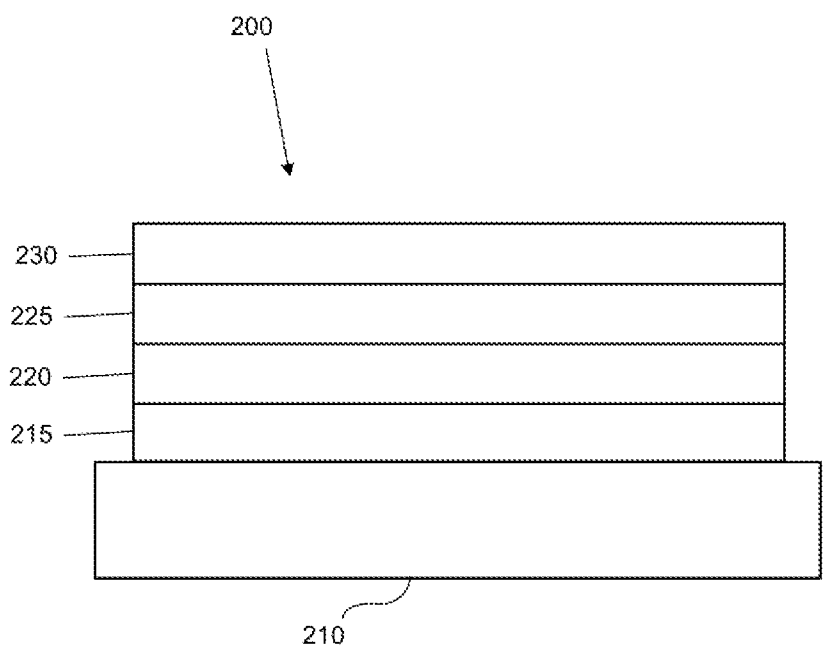
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18° C. to 30° C., and more preferably at room temperature (20-25° C.), but could be used outside this temperature range, for example, from −40° C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiments, the compound can be used as one component of an exciplex to be used as a sensitizer.

In some embodiments, the sensitizer is a single component, or one of the components to form an exciplex.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a “monovalent variant of a compound” refers to a moiety that is identical to the compound except that one hydrogen has been removed and replaced with a bond to the rest of the chemical structure. As used herein, a “polyvalent variant of a compound” refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

D. Combination of the Compounds of the Present Disclosure with Other Materials The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

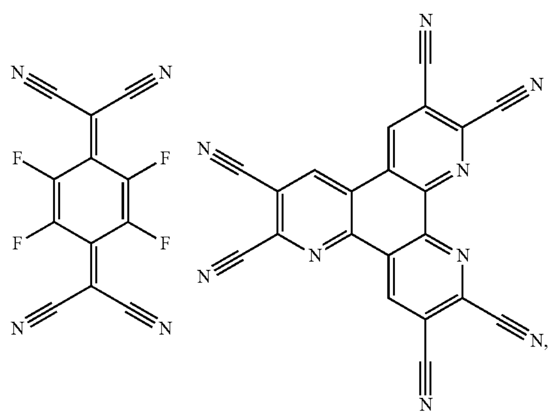
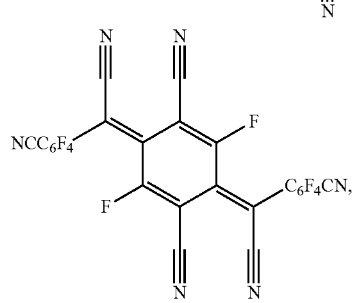
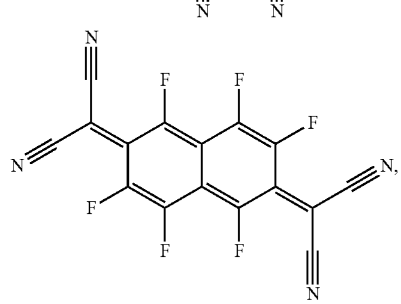
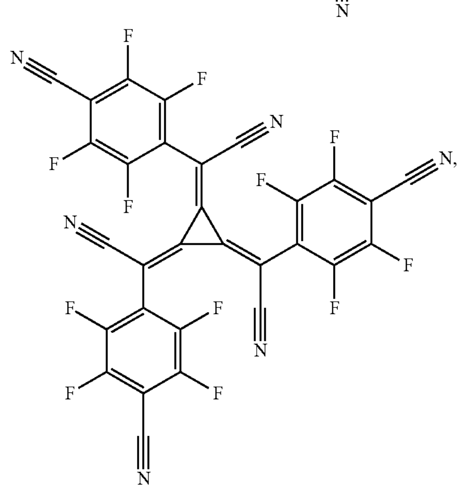
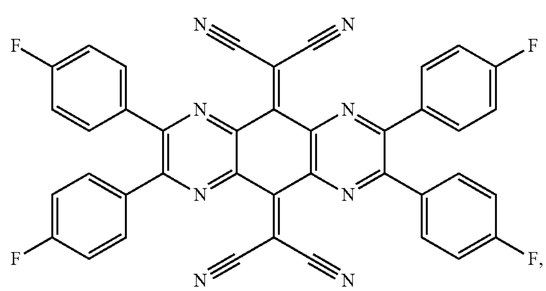
-continued
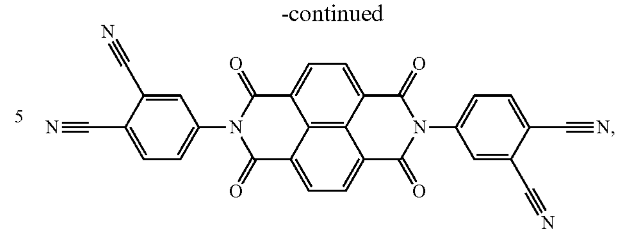
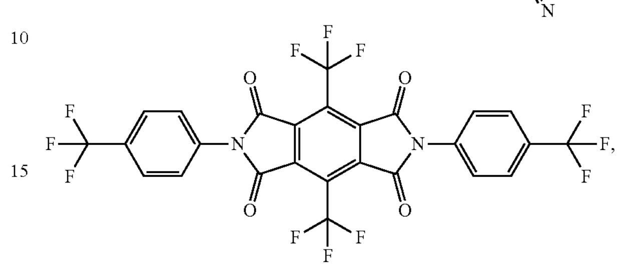
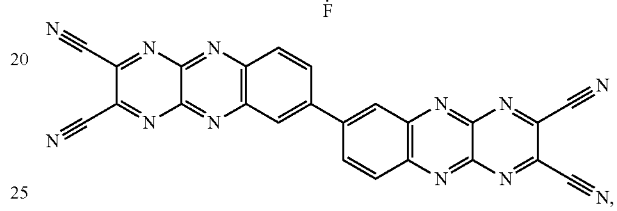
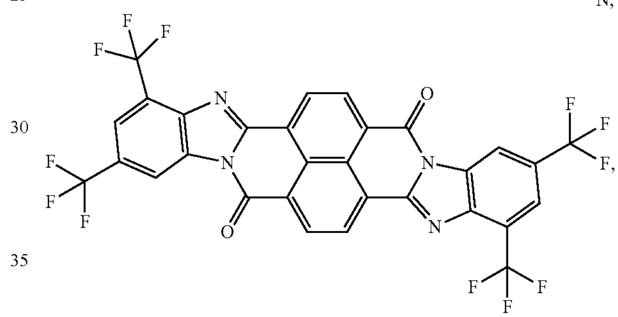
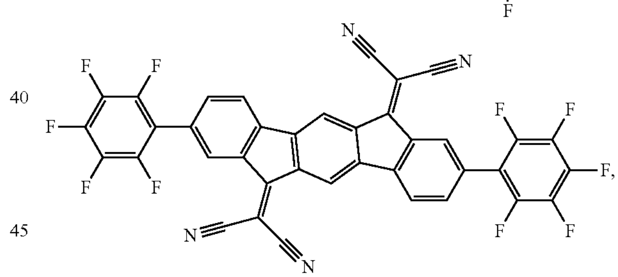
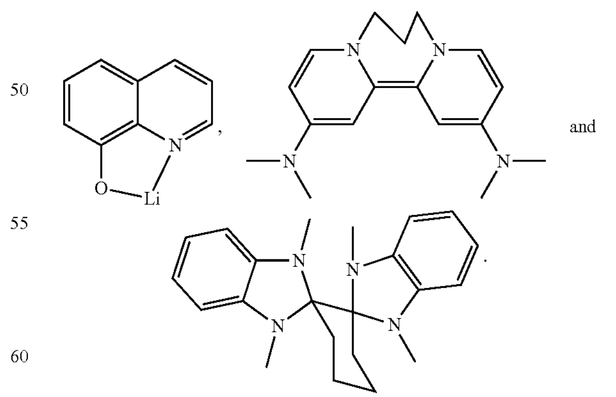
and
b) HIL/HTL:
A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

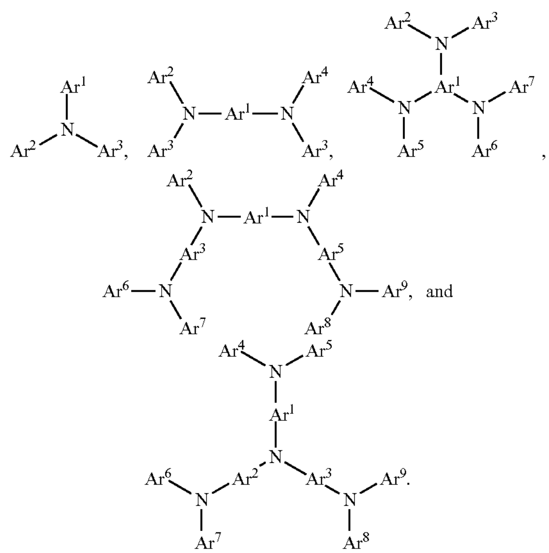

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

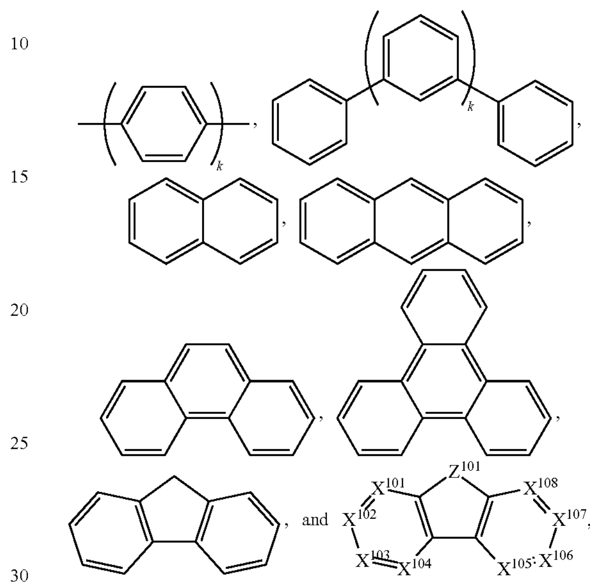

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

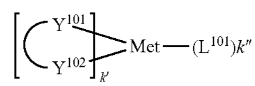

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.
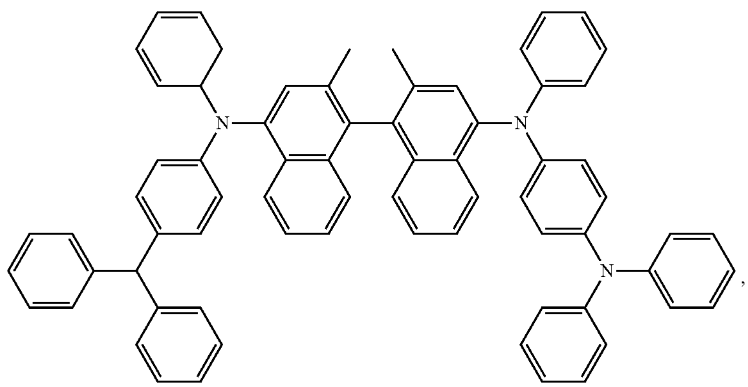
,
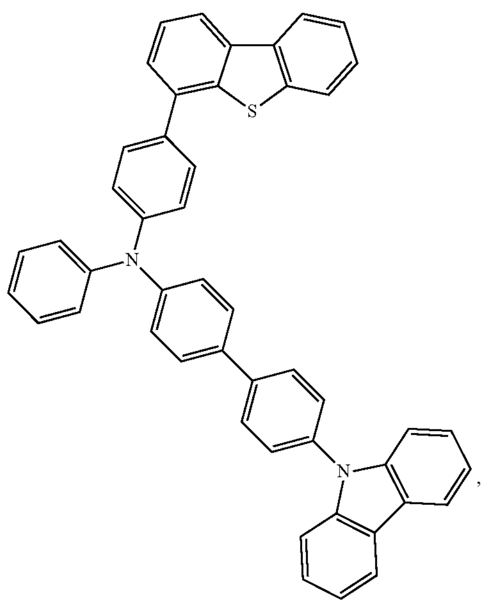
, -continued
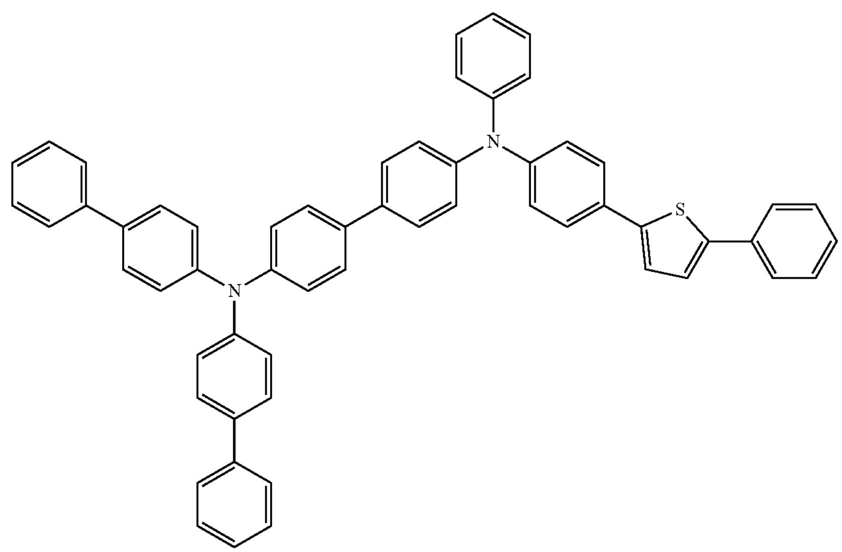
,
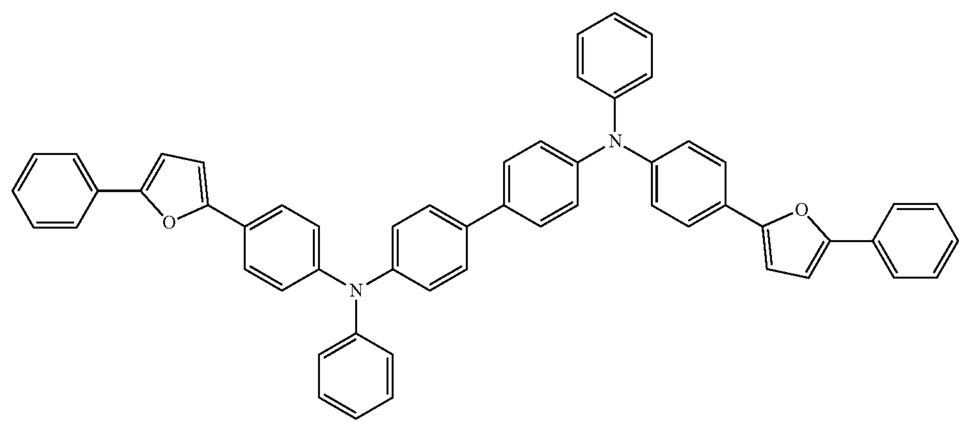
,
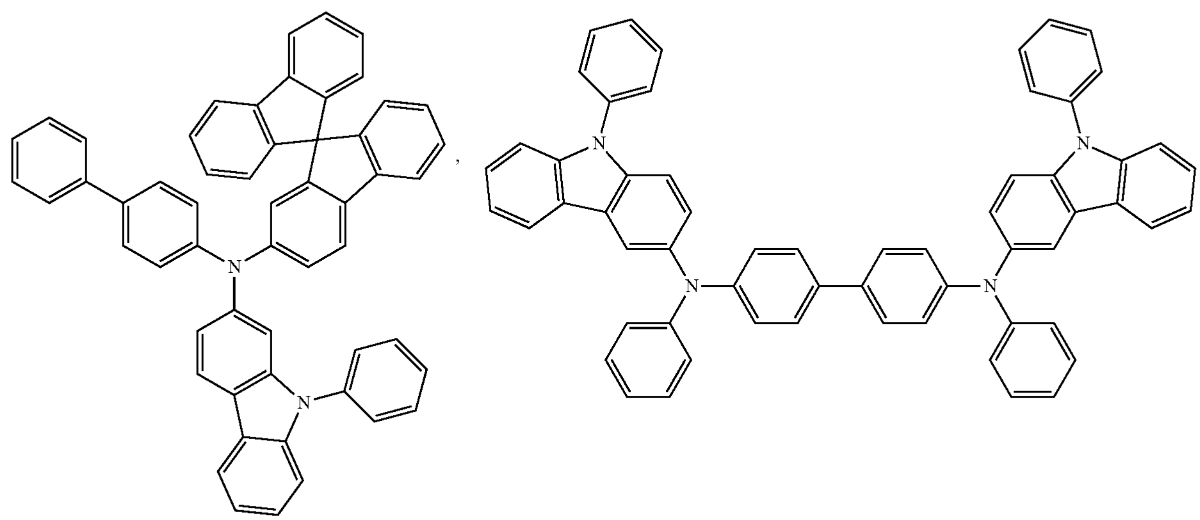
, , -continued
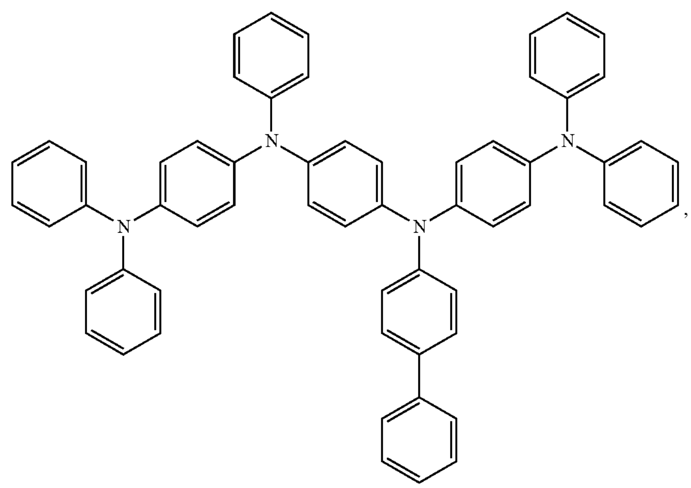
,
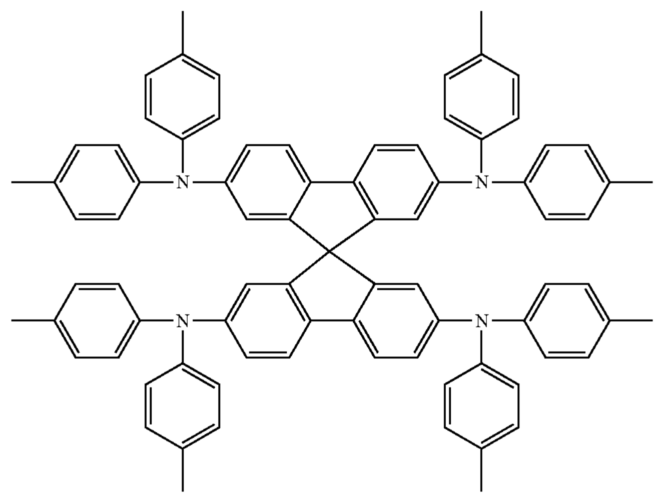
,
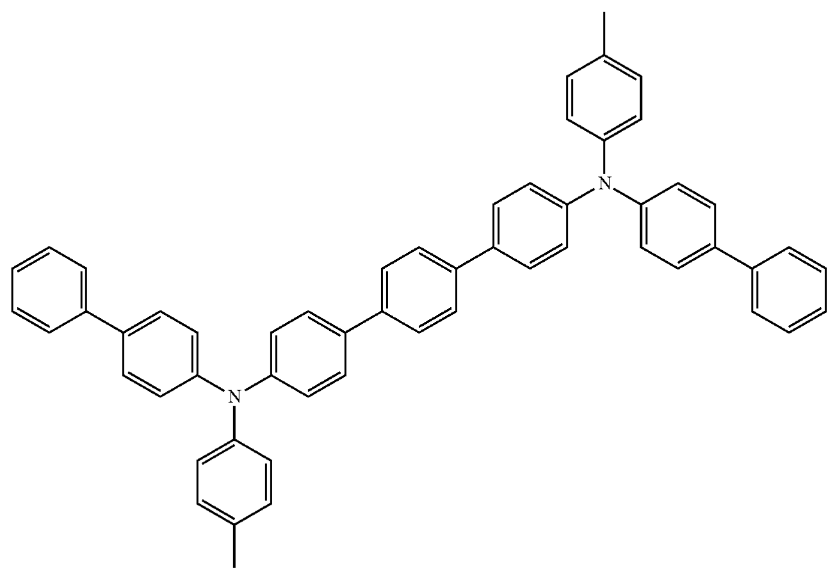
, -continued
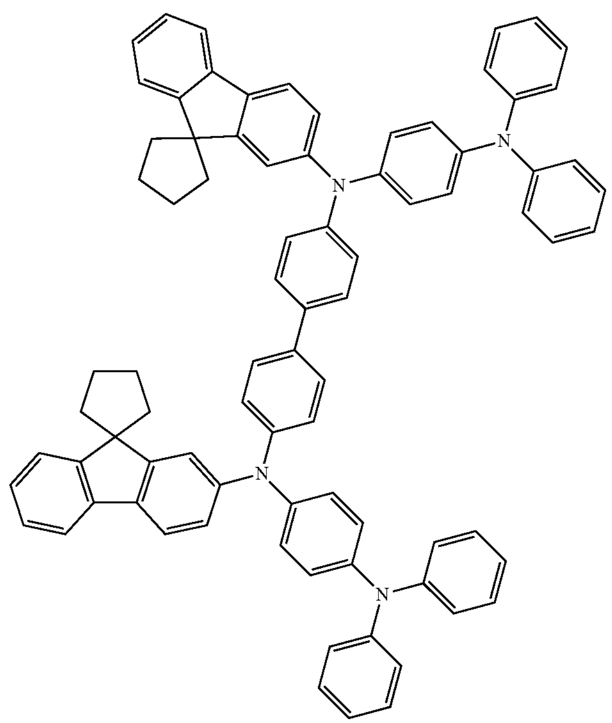
,
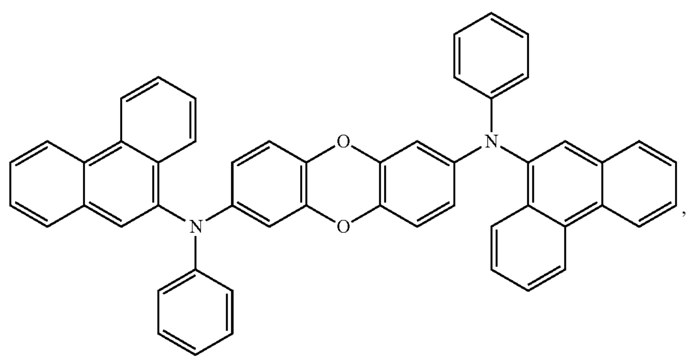
,
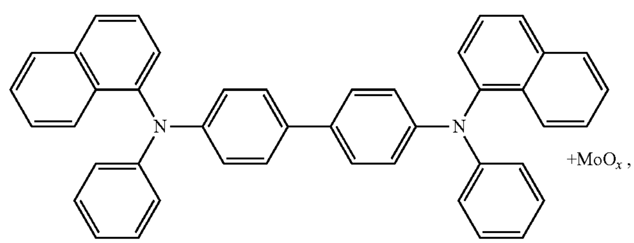
$+MoO_x$, -continued
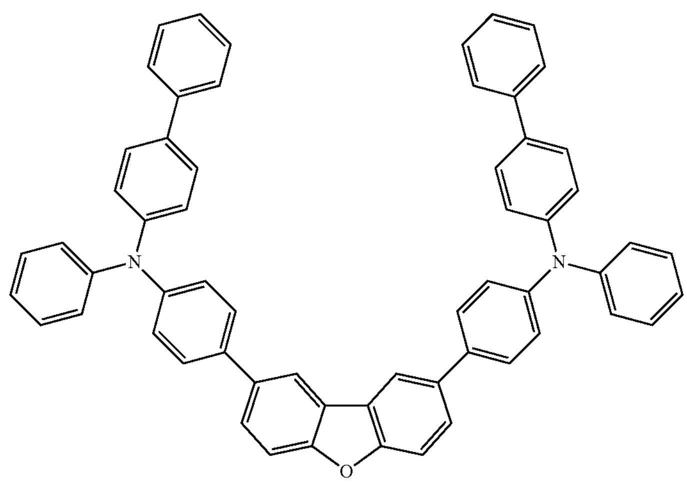
,
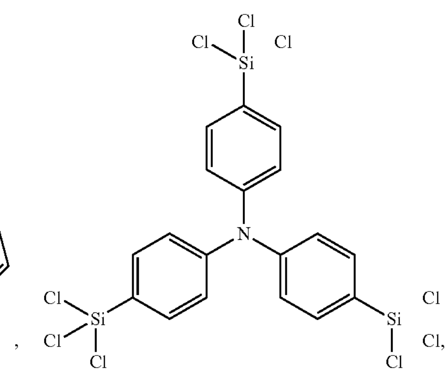
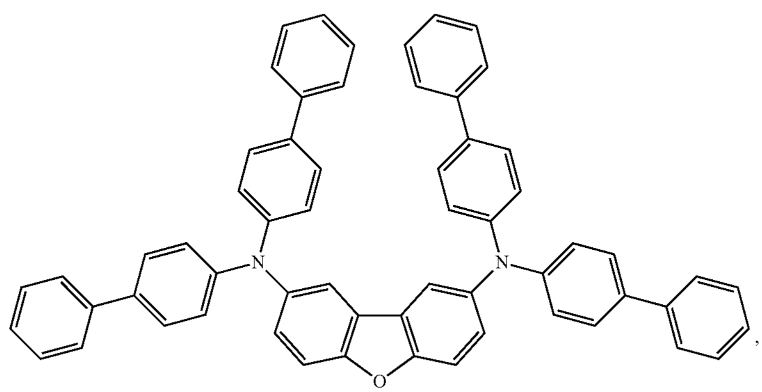
,
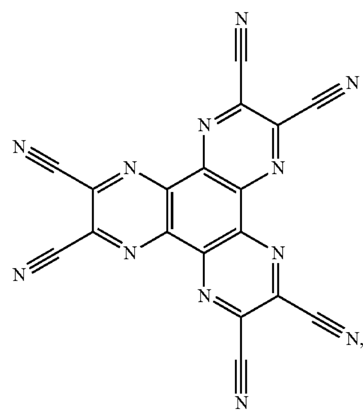
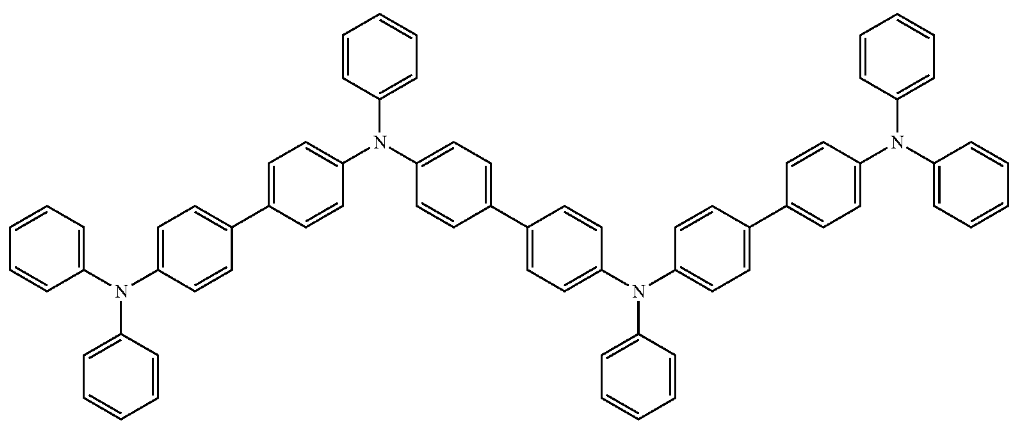

-continued
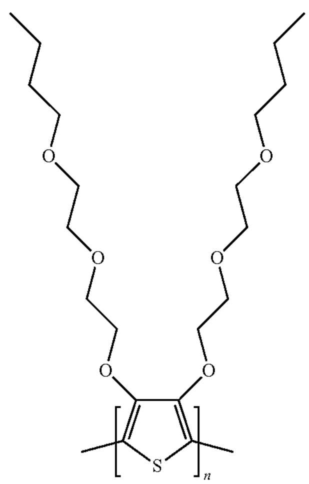
,
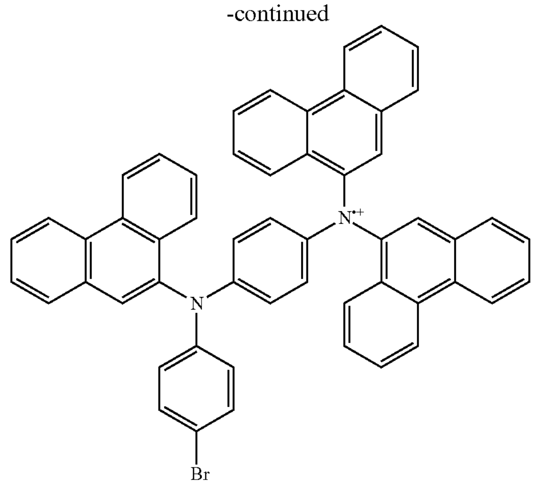
,
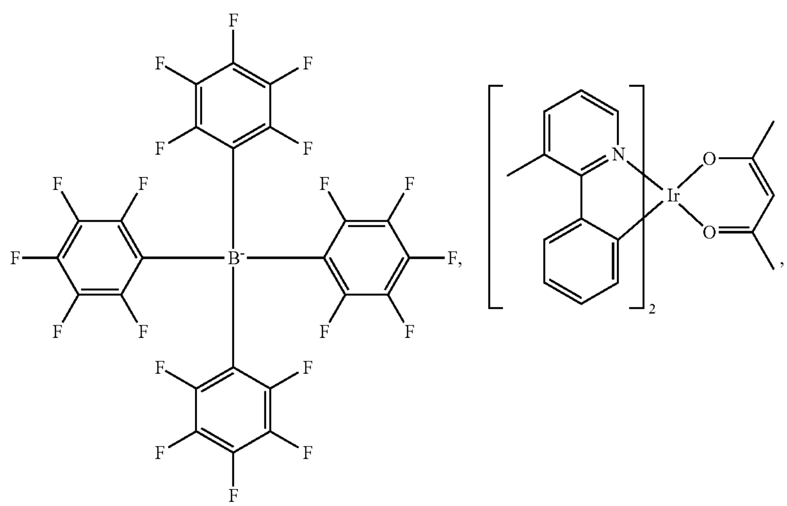
,
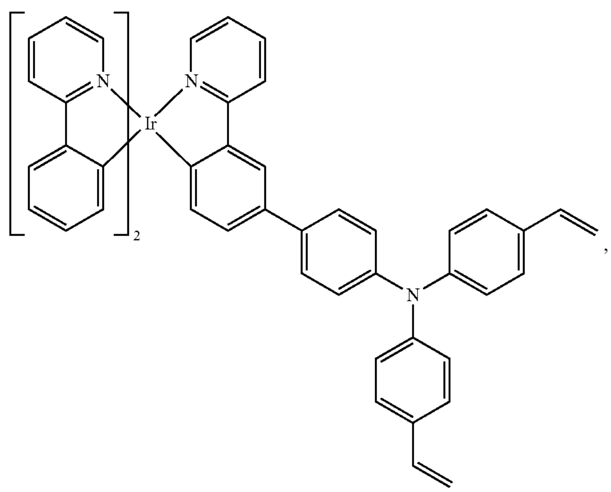
,

-continued
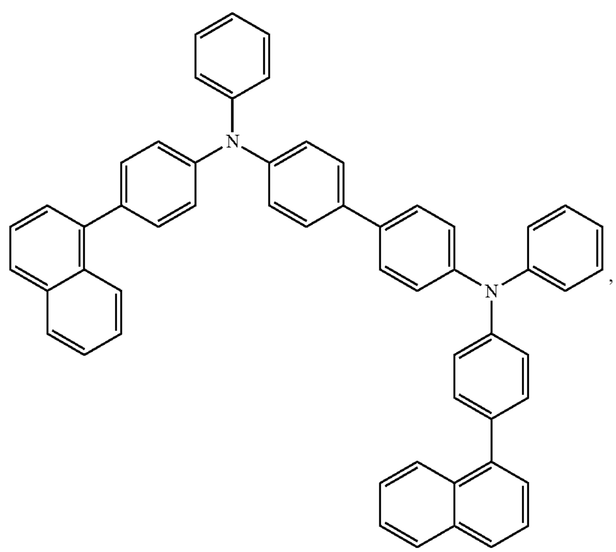,
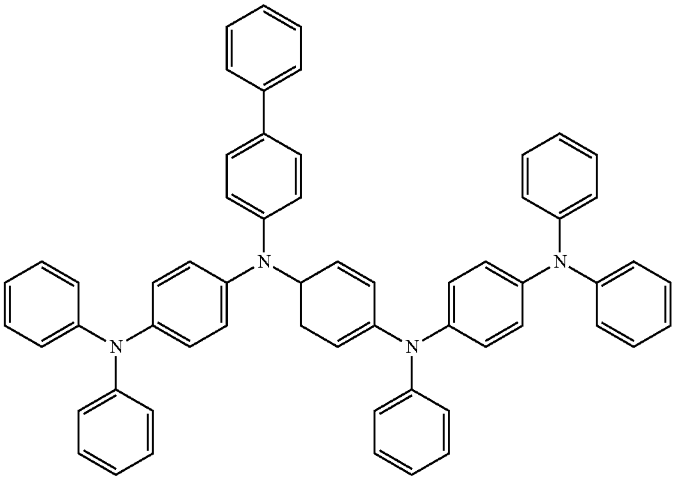,
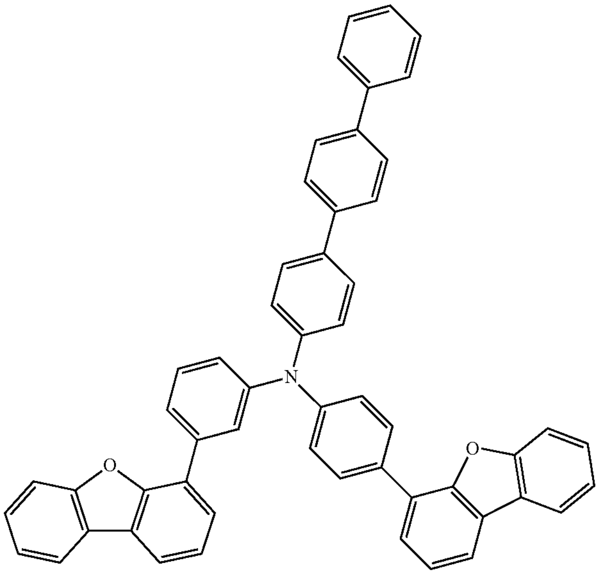,

-continued
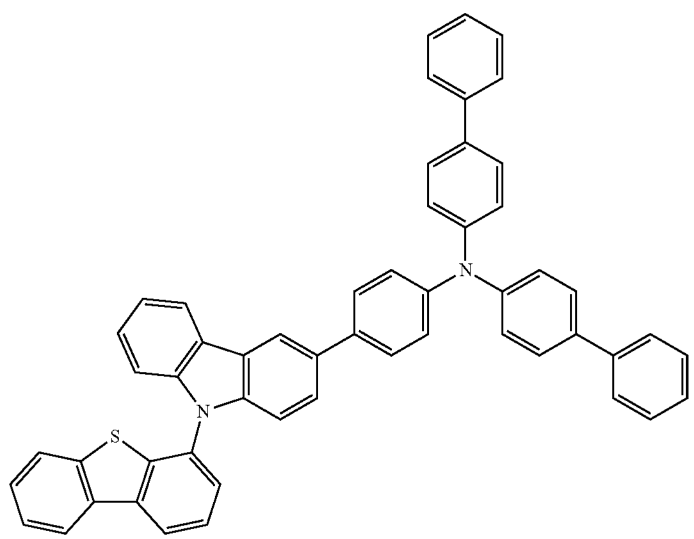
,
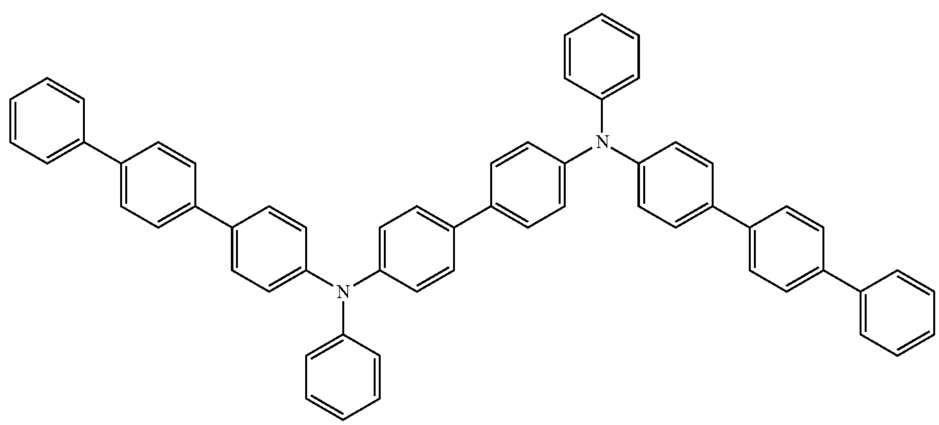
,
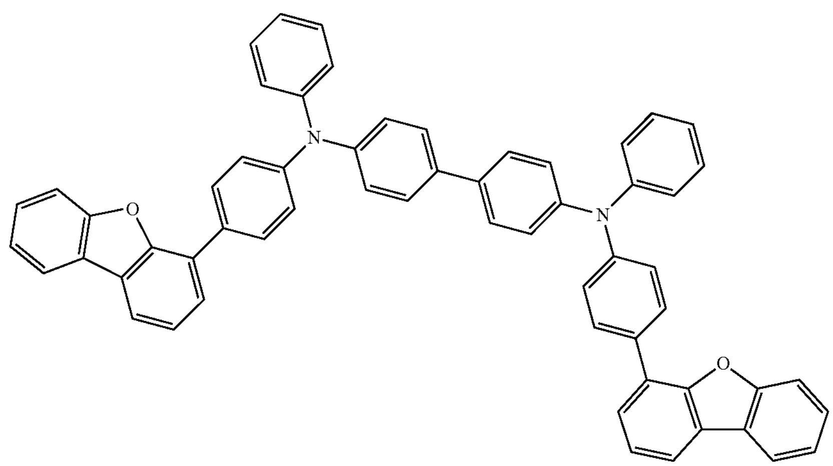
,

-continued
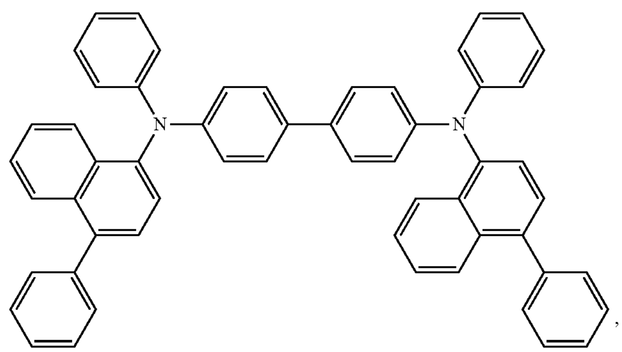
,
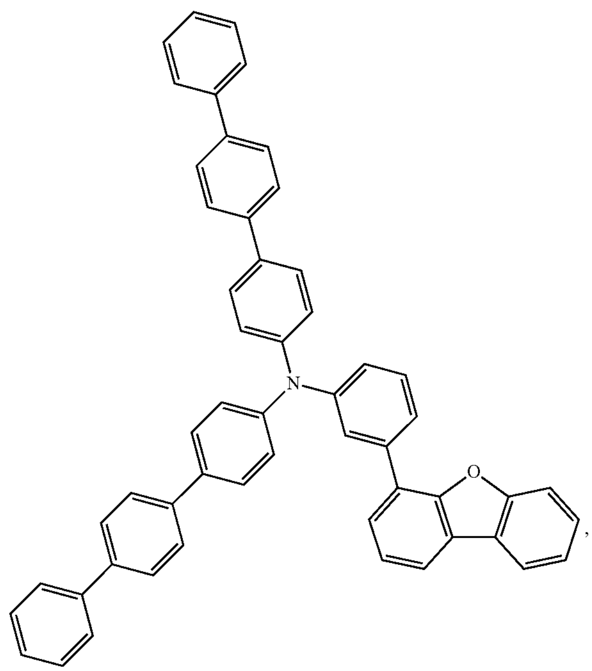
,
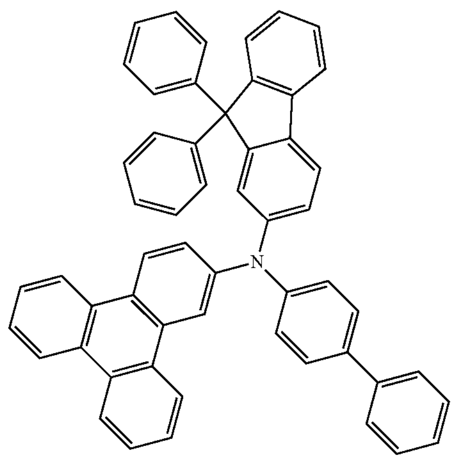
,
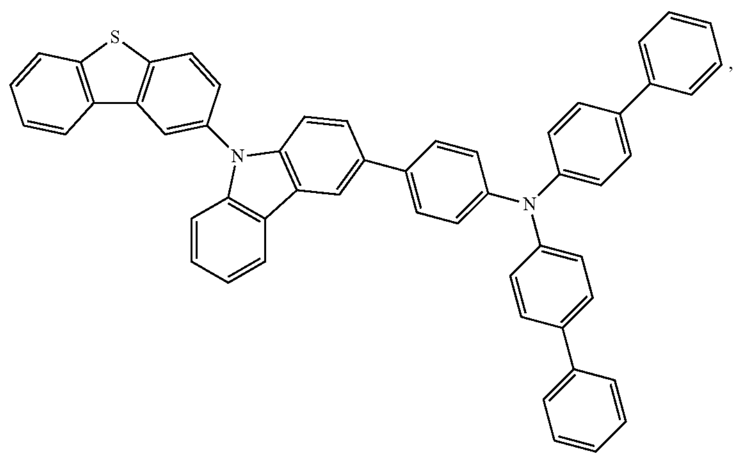
,

-continued
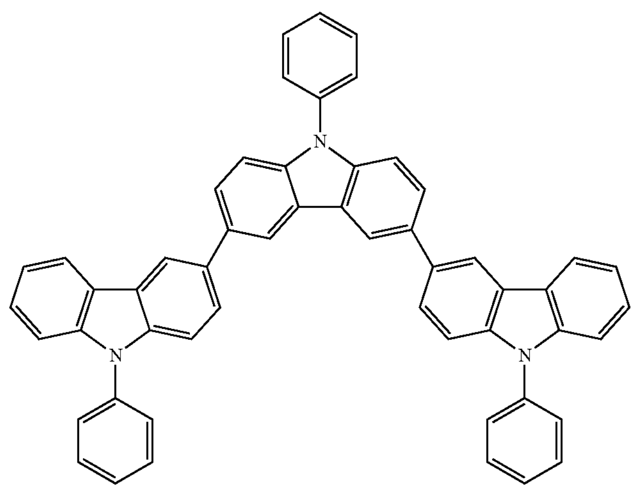
,
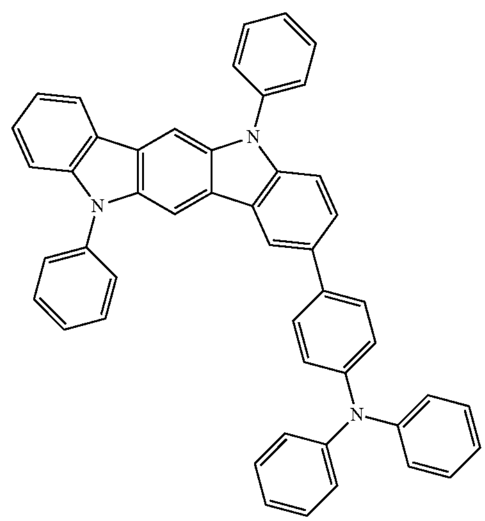
,
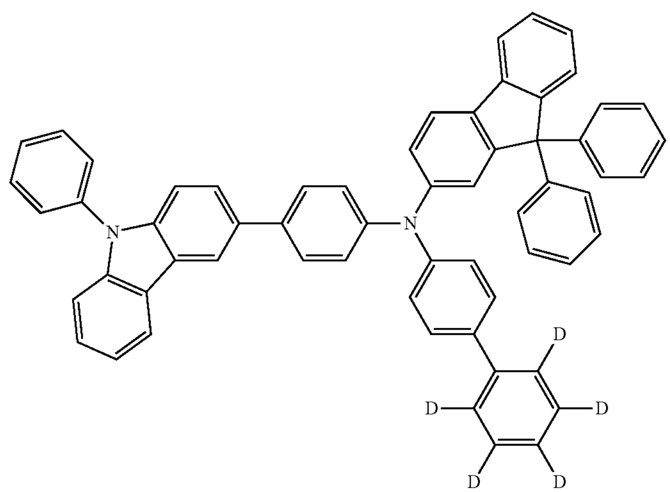
,
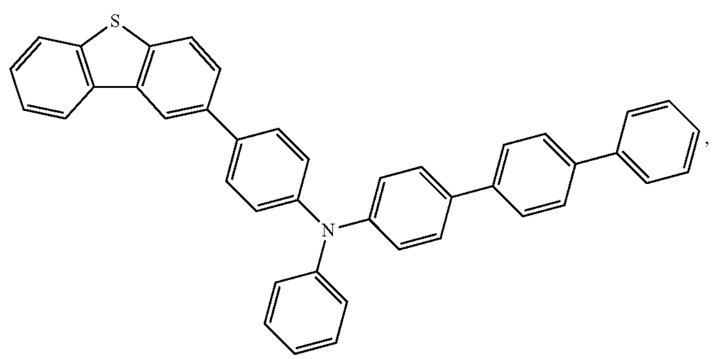
,

-continued
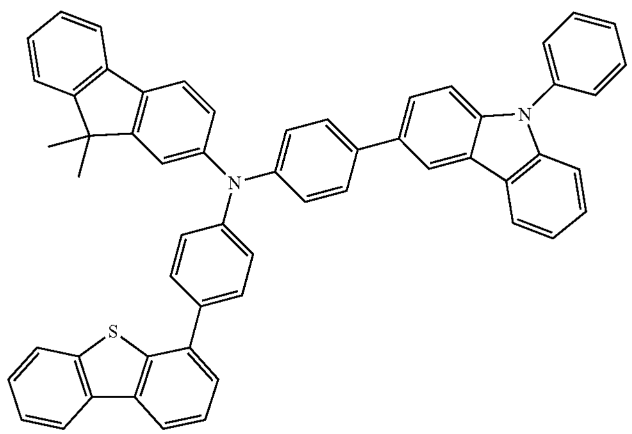
,
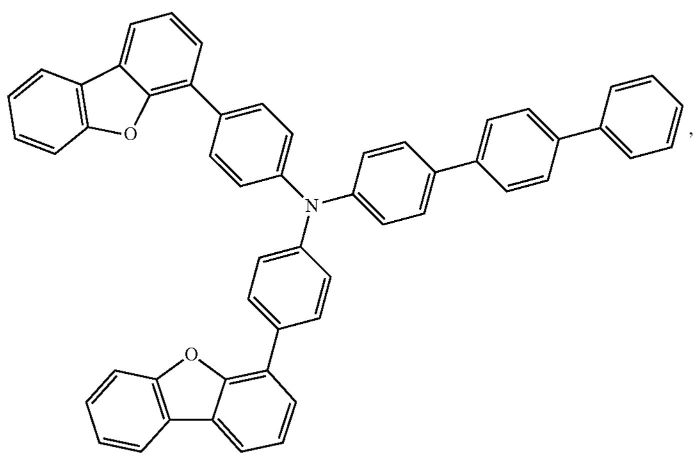
,
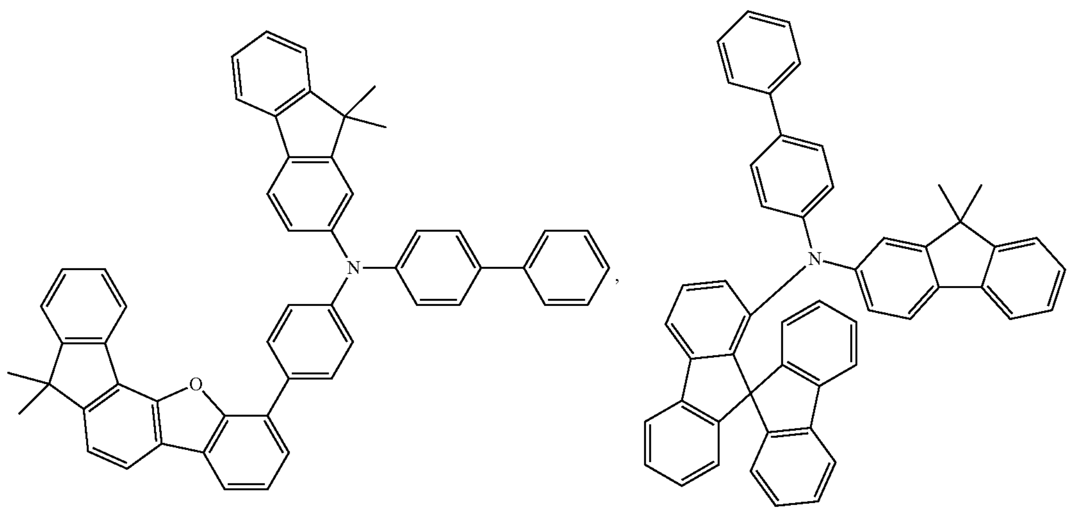
, ,

-continued
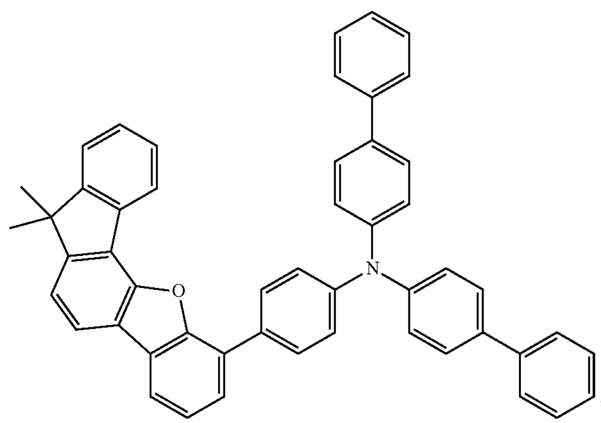
,
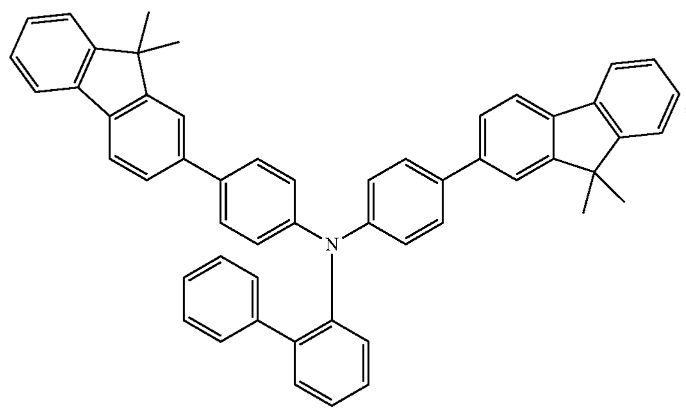
,
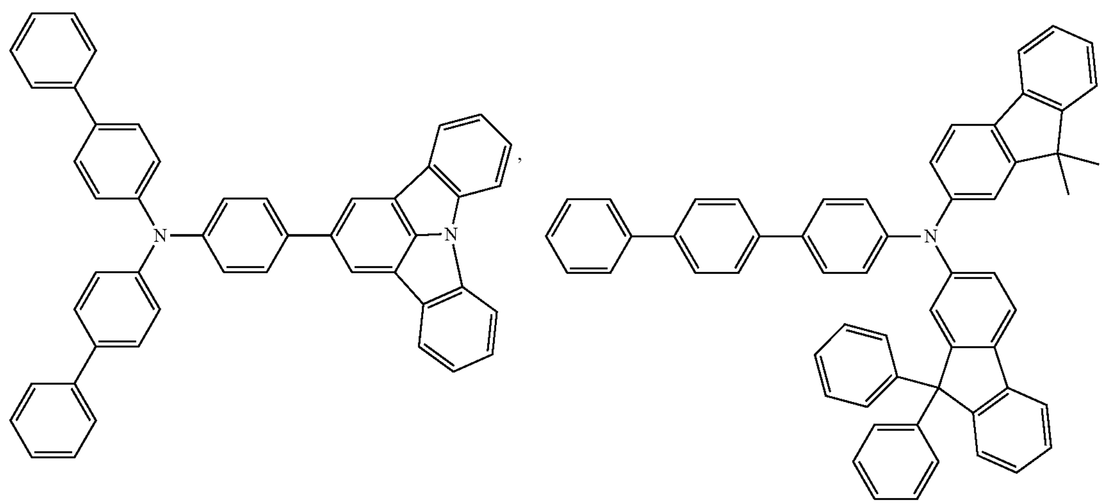
, ,

-continued
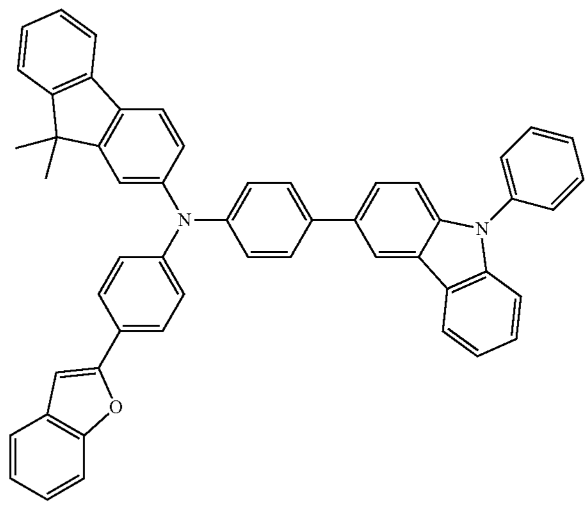
,
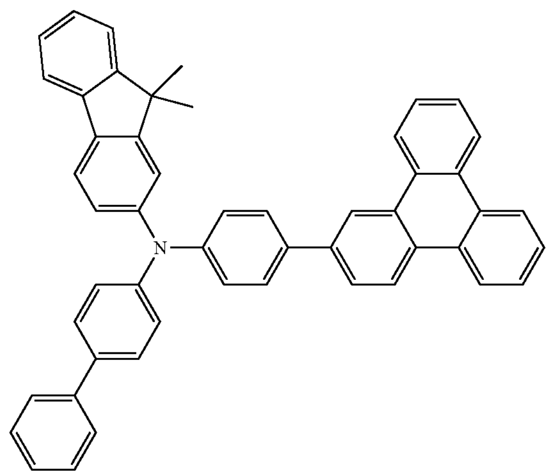
,
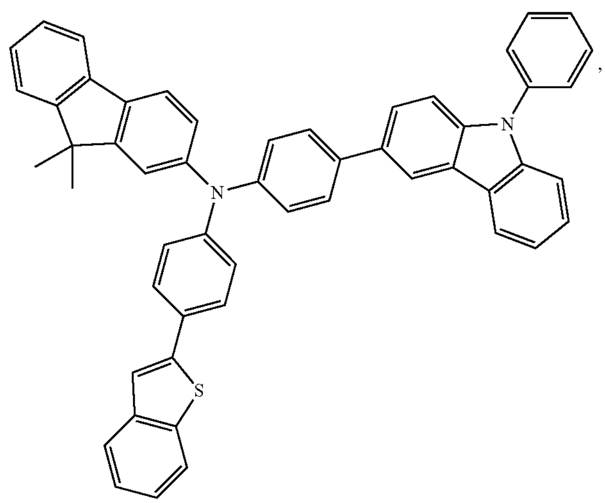
,
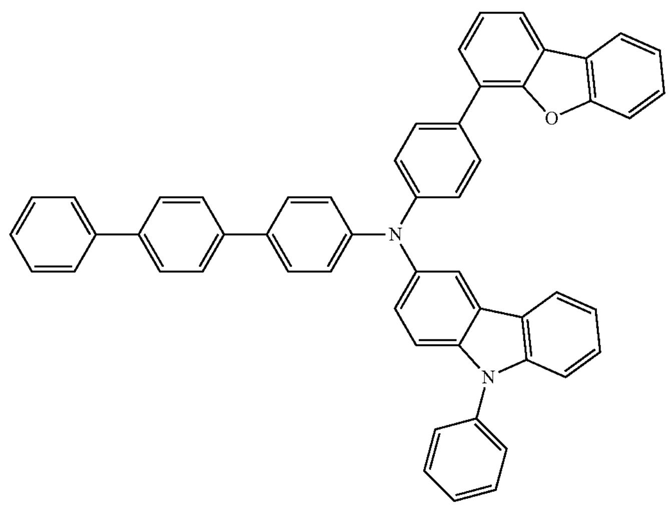
,

-continued
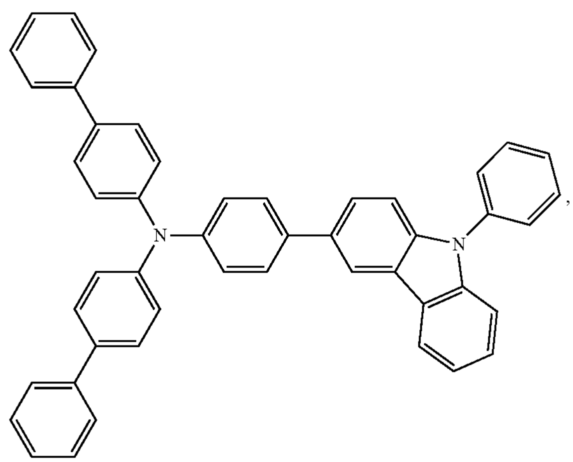,
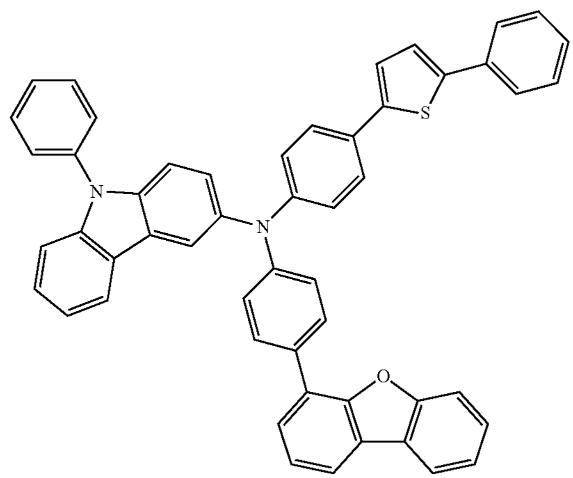,
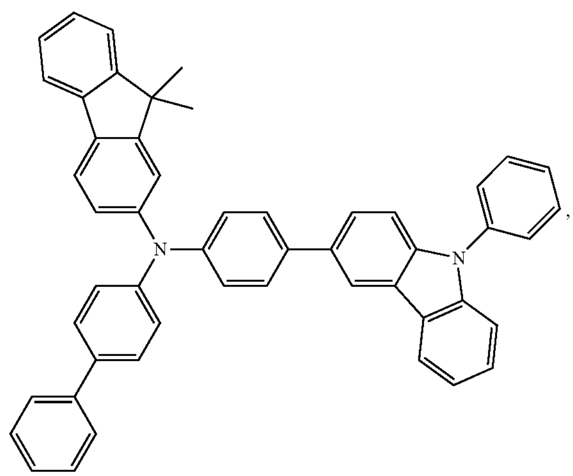,
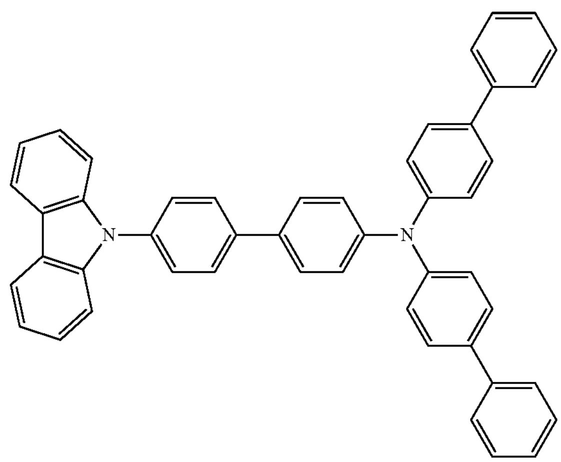,
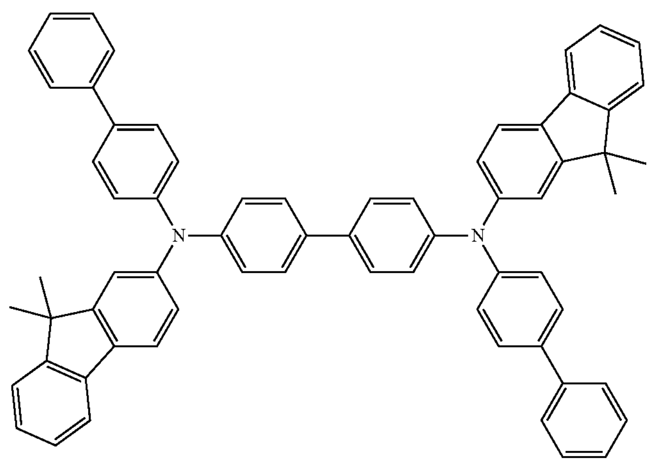,

-continued
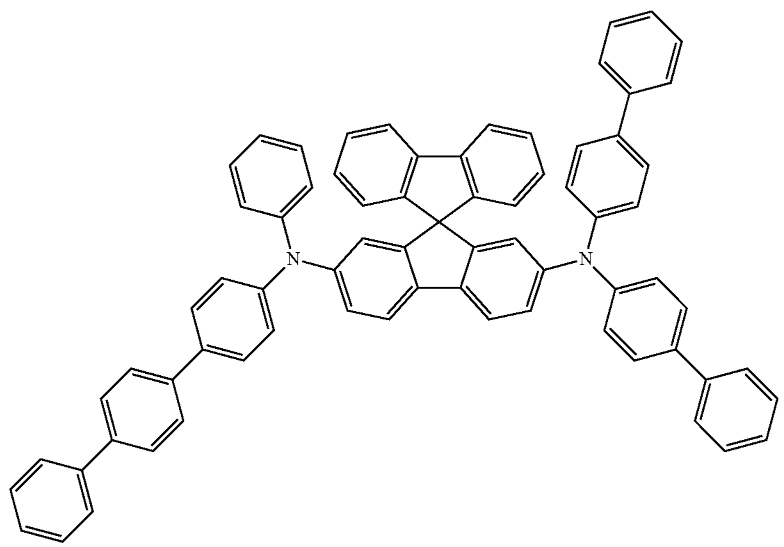
,
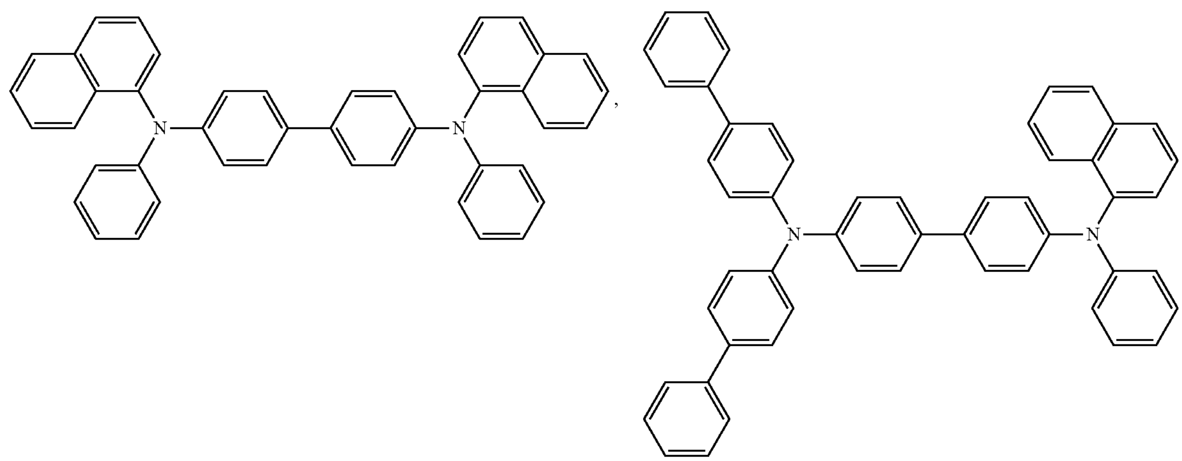
, ,
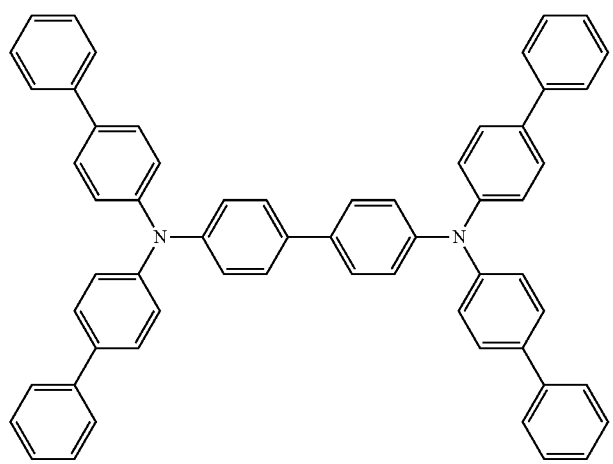
,

-continued
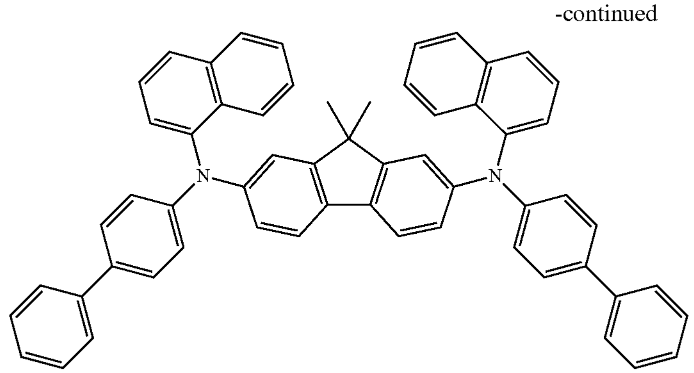
,
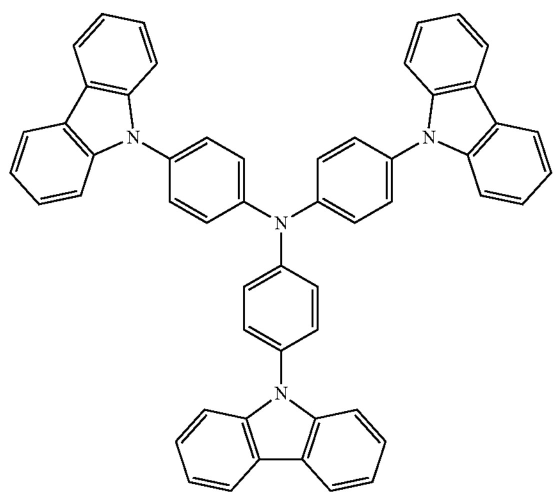
,
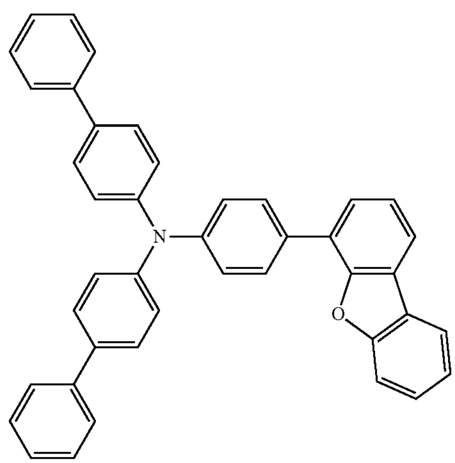
,
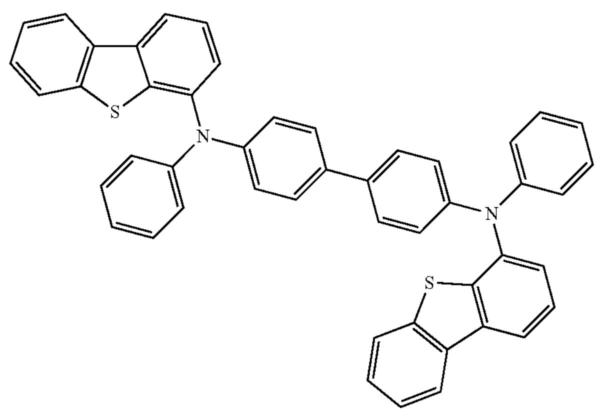
,
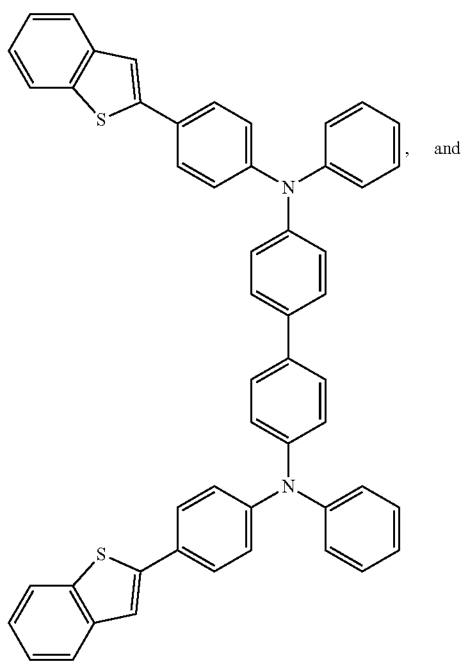
, and -continued

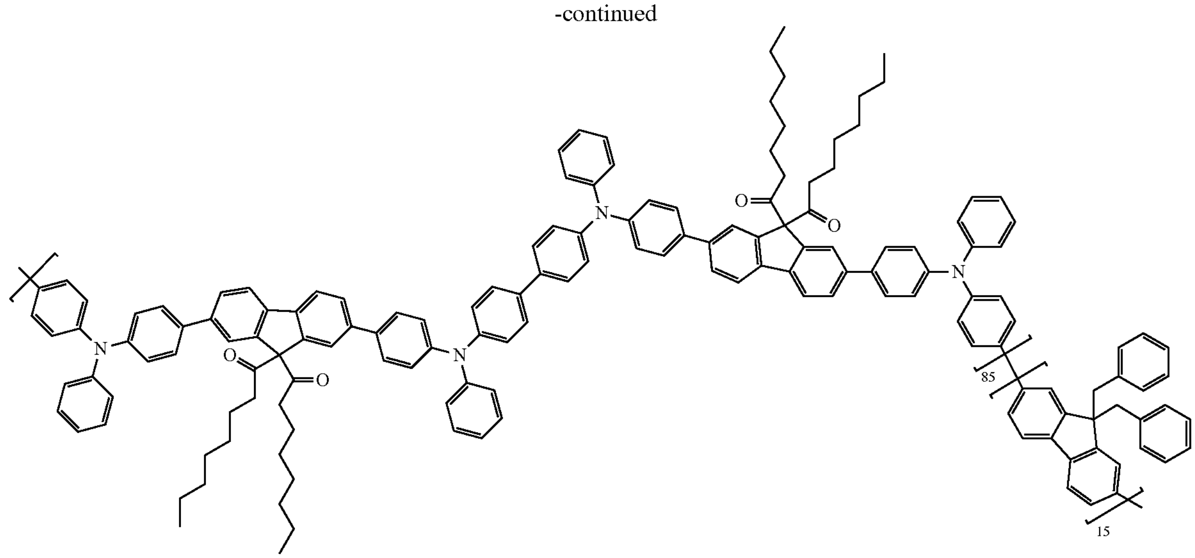

c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Hosts:

The light emitting layer of the organic EL device of the present disclosure preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

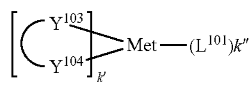

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

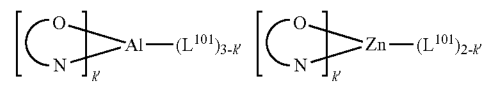

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

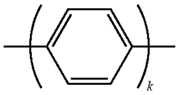,
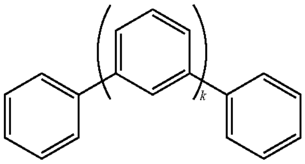,
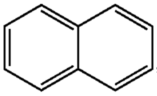,
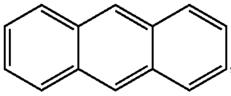,
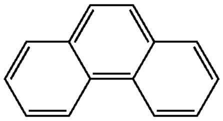,
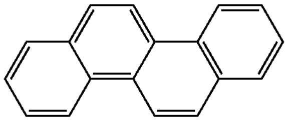,
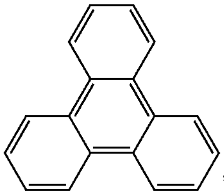,
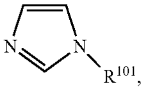,
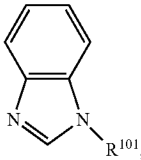,
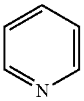,
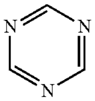,
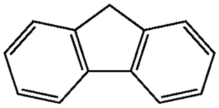,
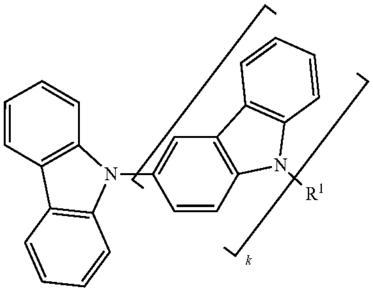,
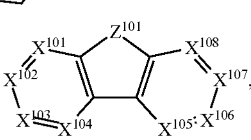,
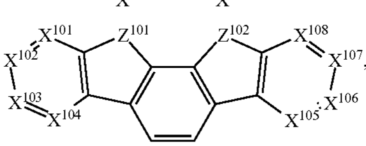,
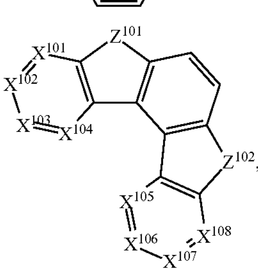, -continued

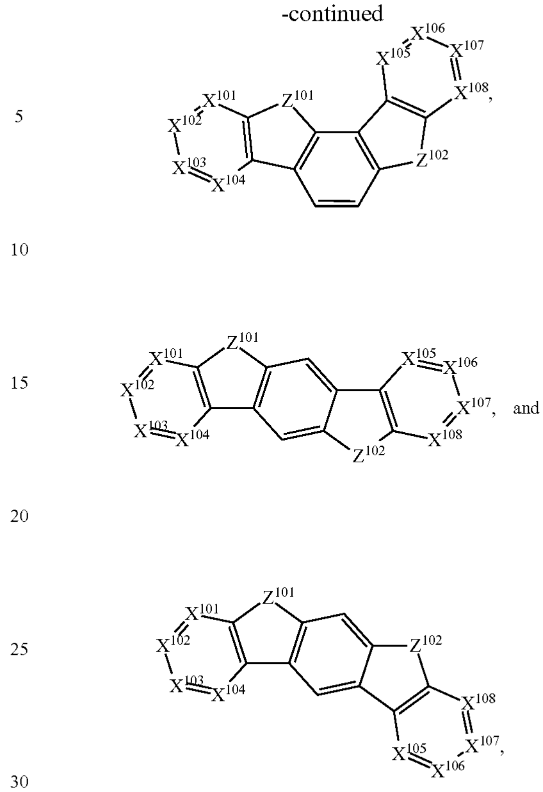

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803, -continued
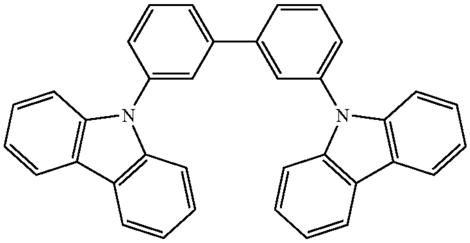
,
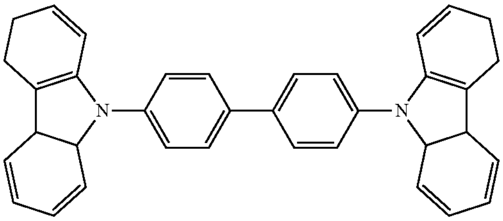
,
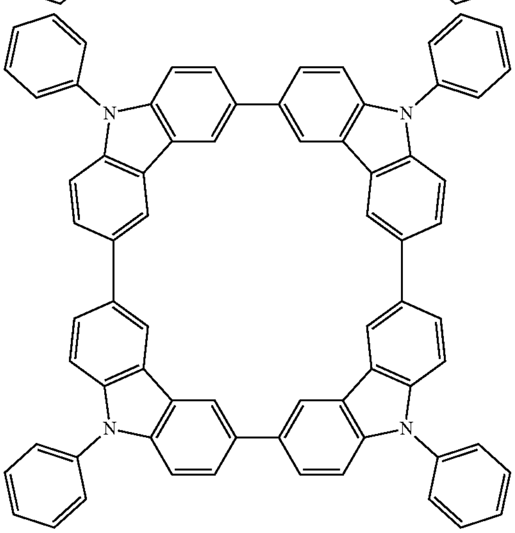
,
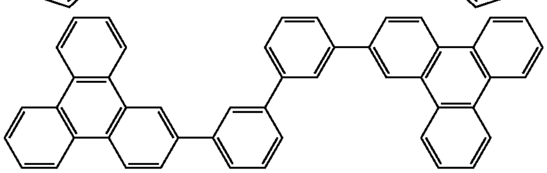
,
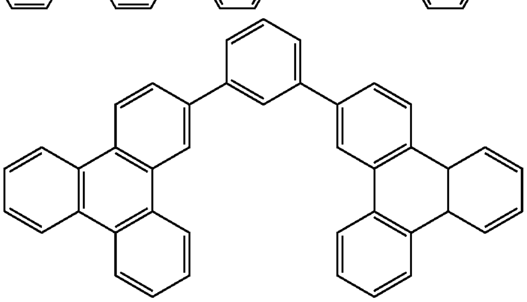
,
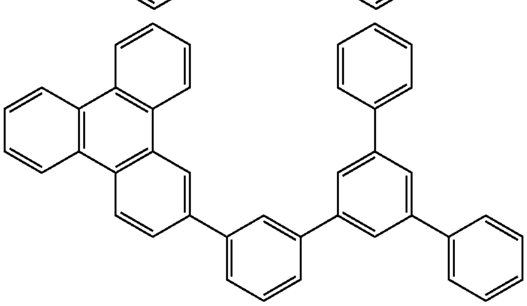
,
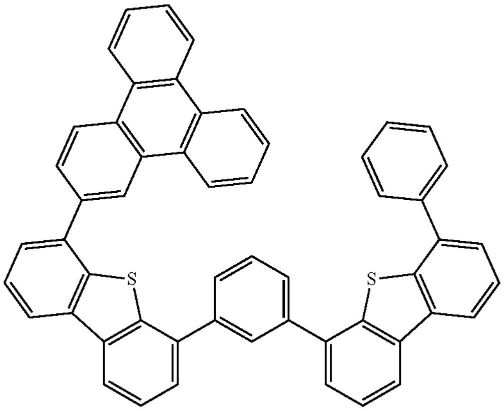
,
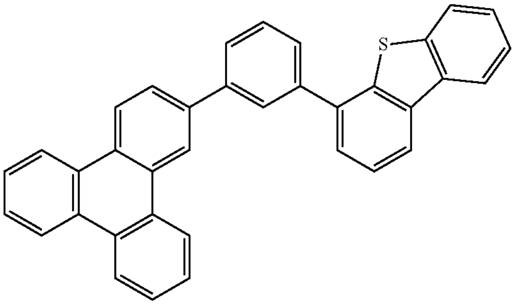
,
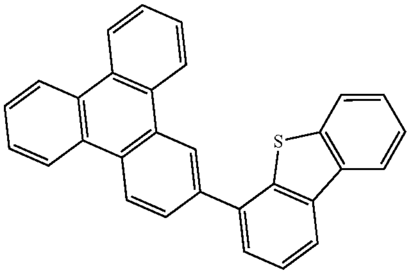
,
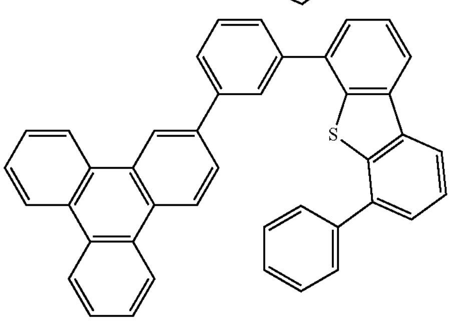
,
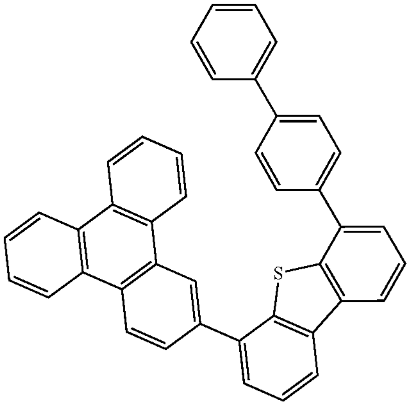
, -continued
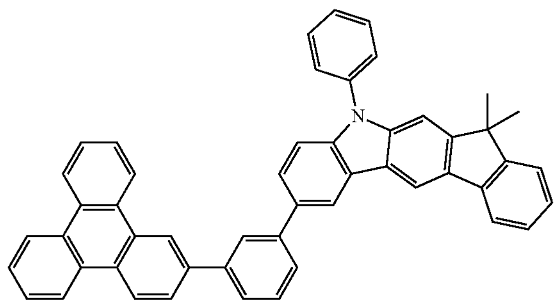
,
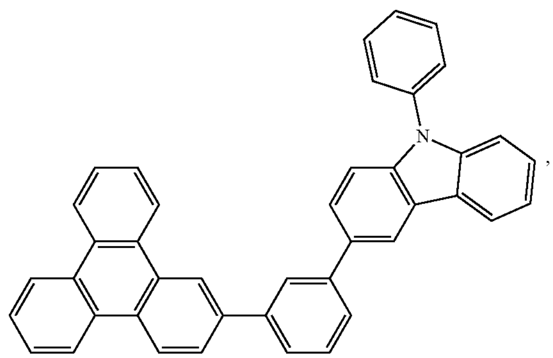
,
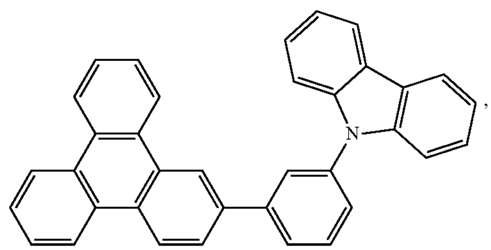
,
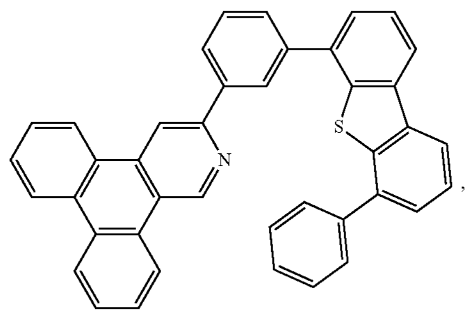
,
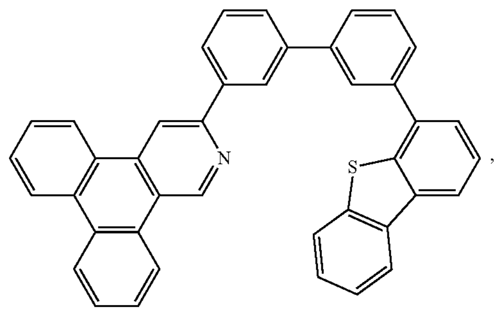
,
-continued
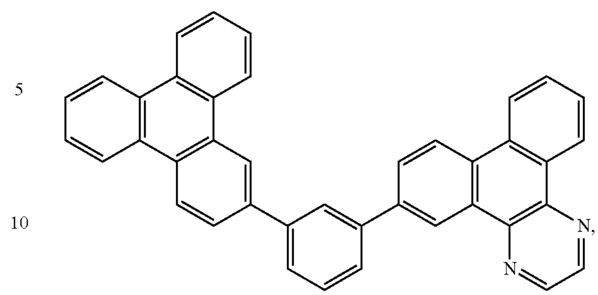
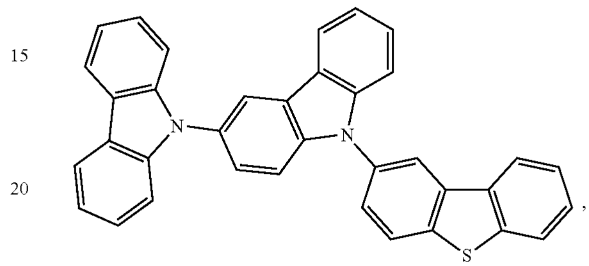
,
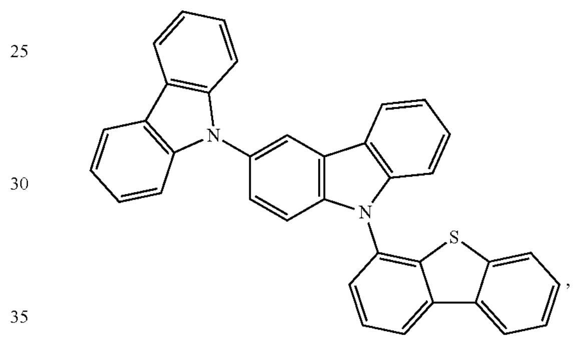
,
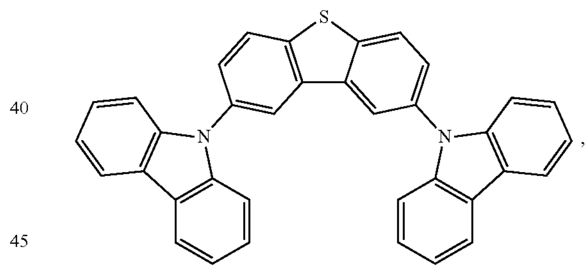
,
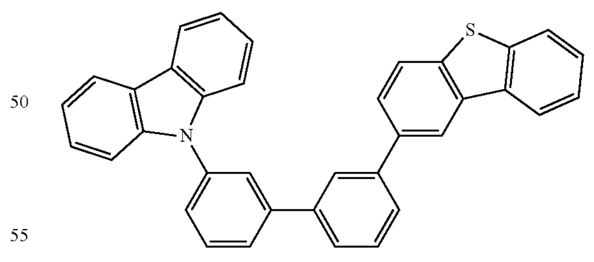
,
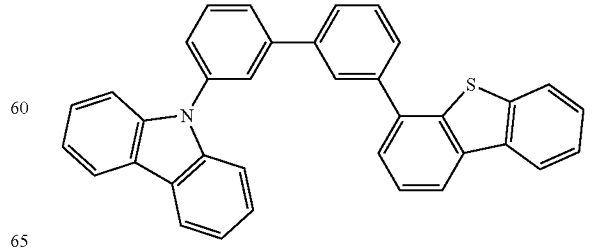
, -continued
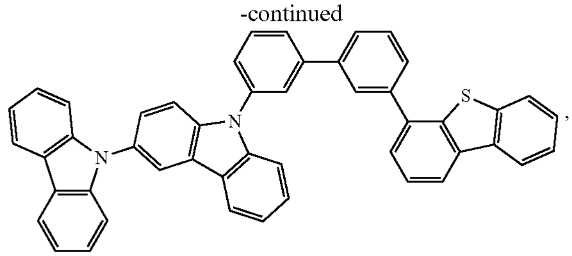
,
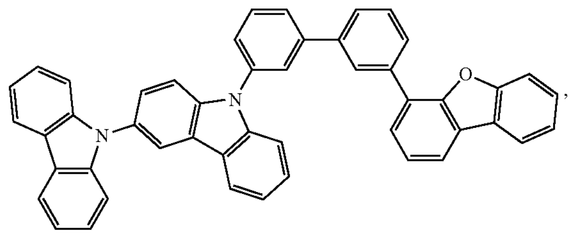
,
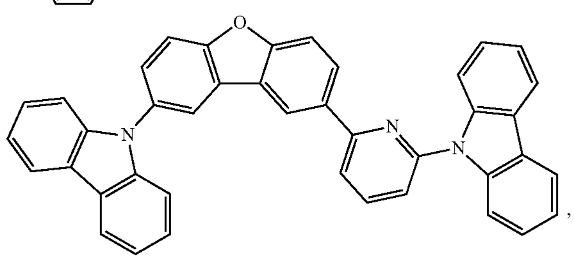
,
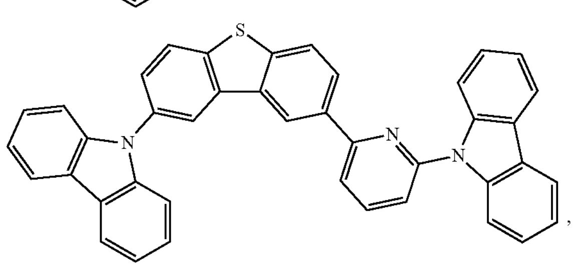
,
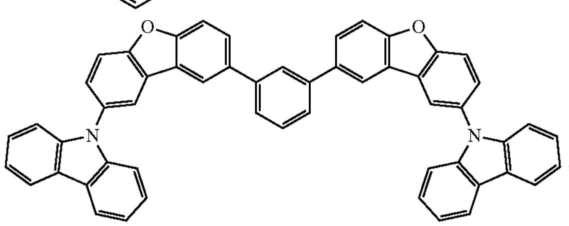
,
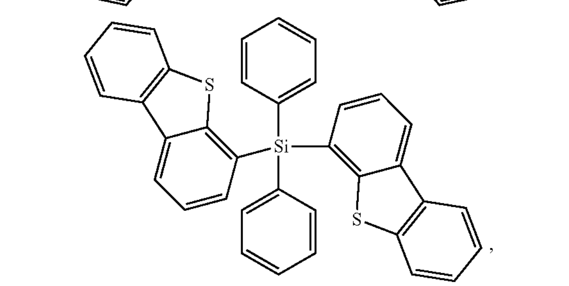
,
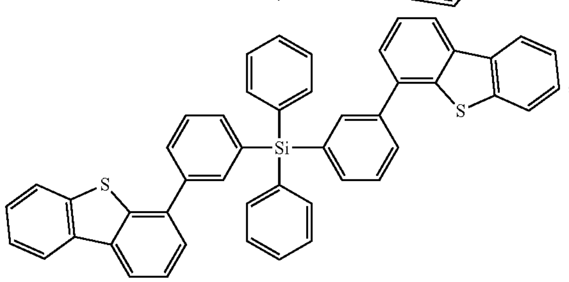
,
-continued
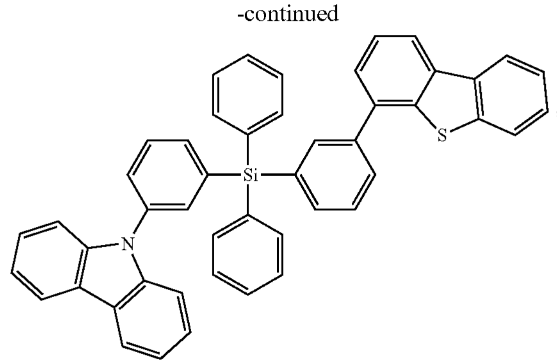
,
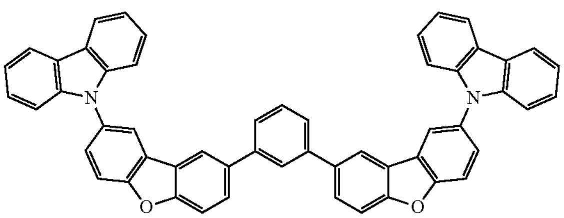
,
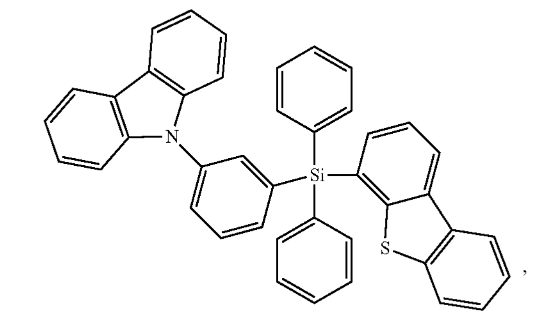
,
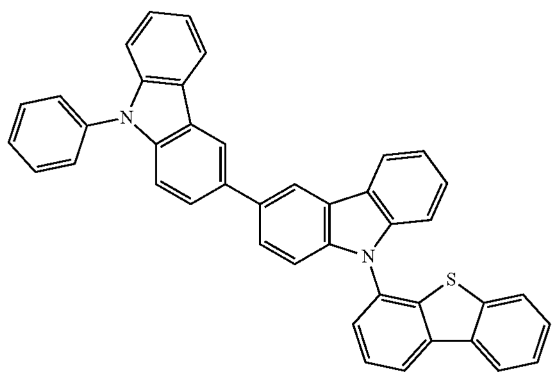
,
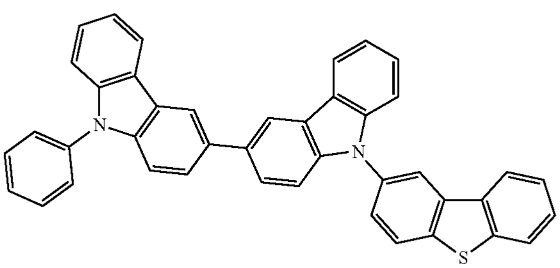
, -continued
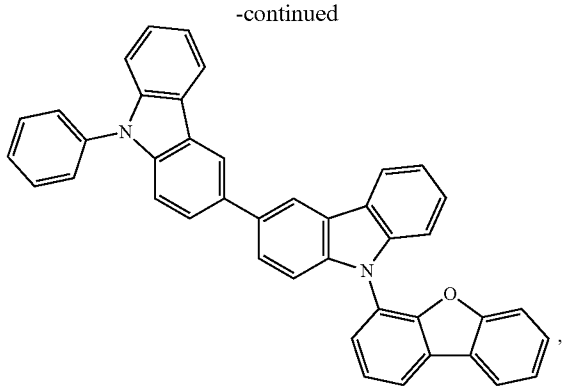
,
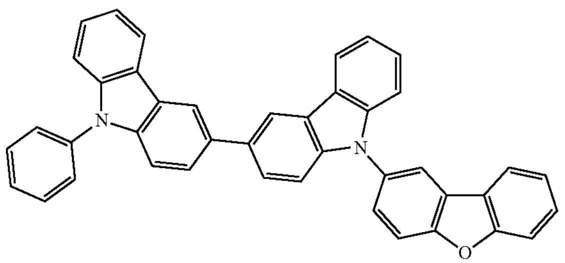
,
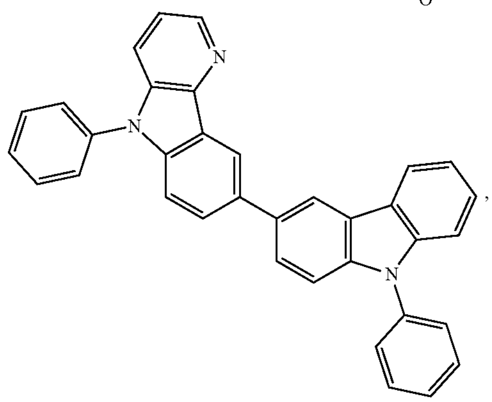
,
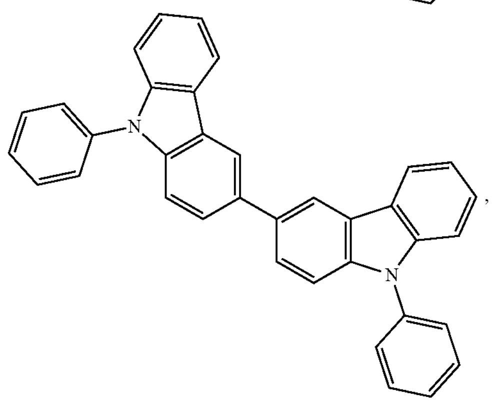
,
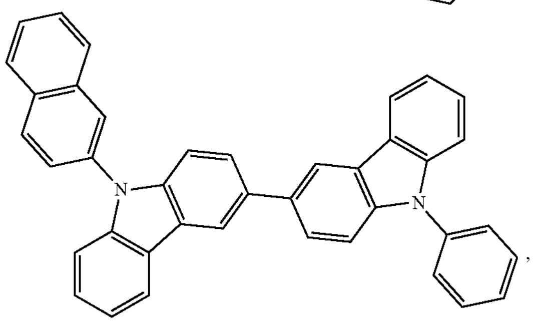
,
-continued
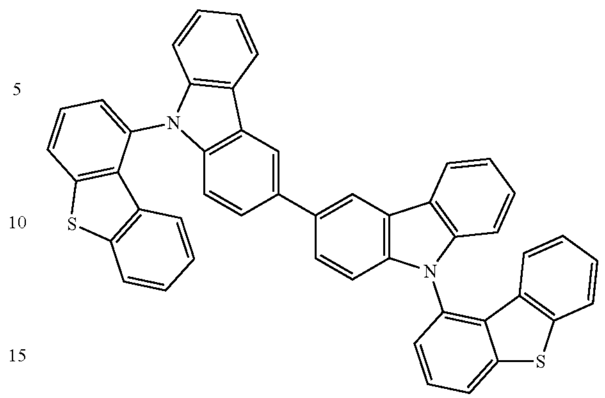
,
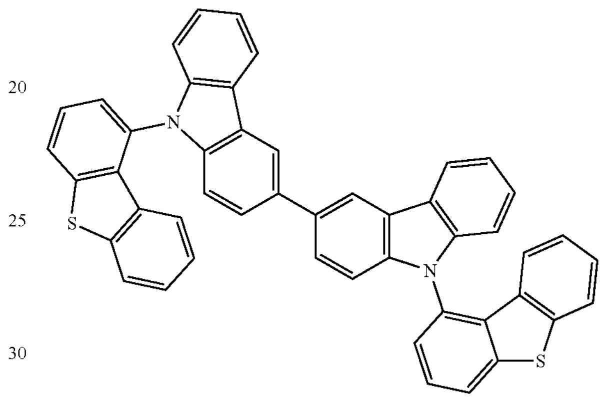
,
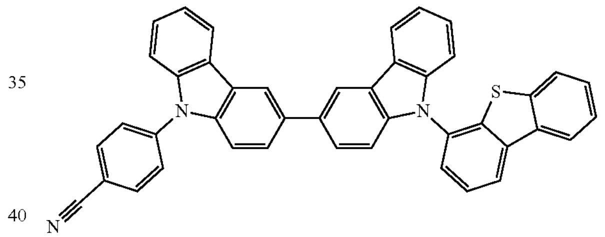
,
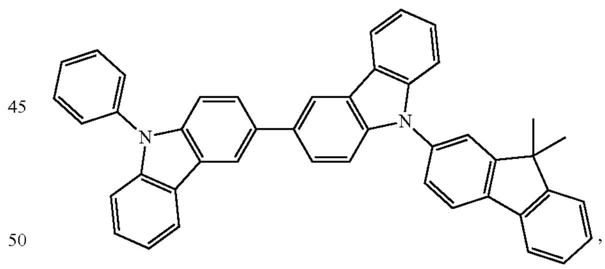
,
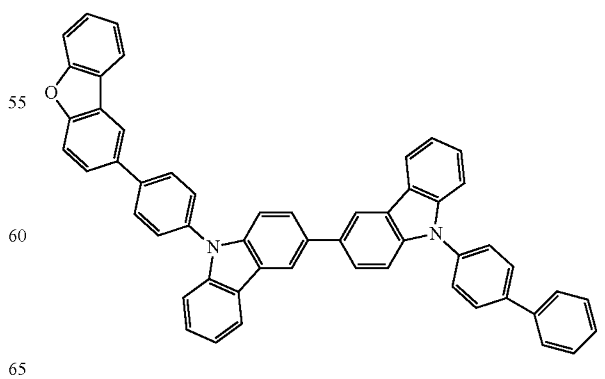
, -continued
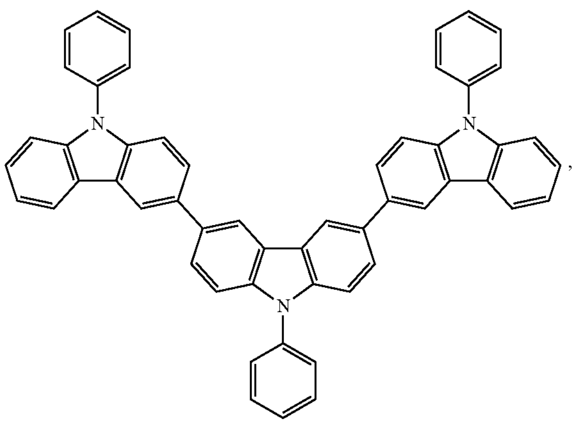
,
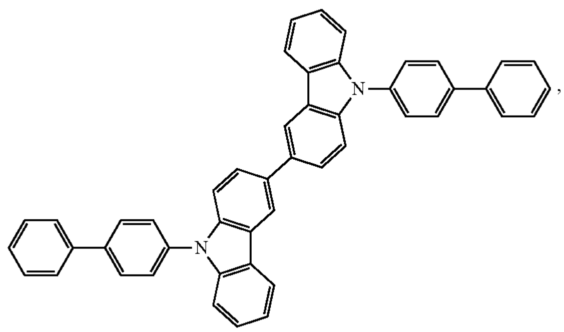
,
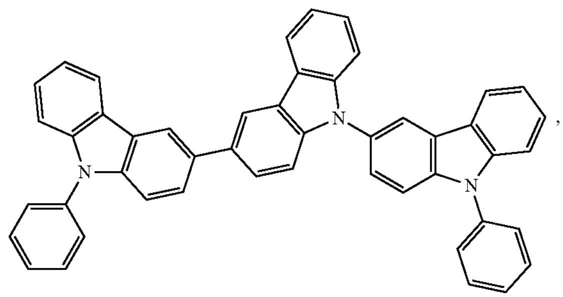
,
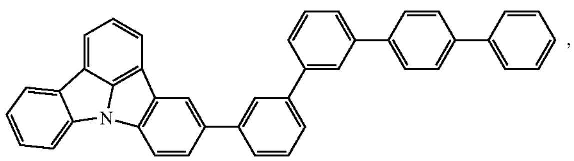
,
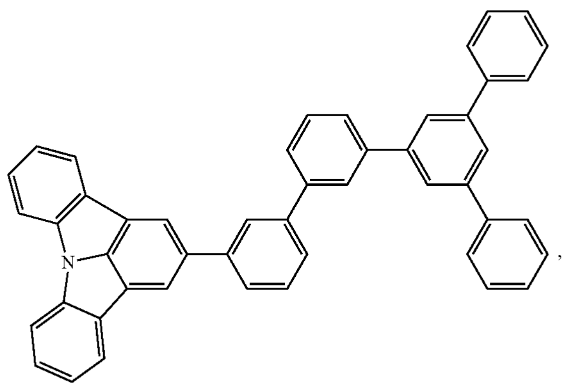
,
-continued
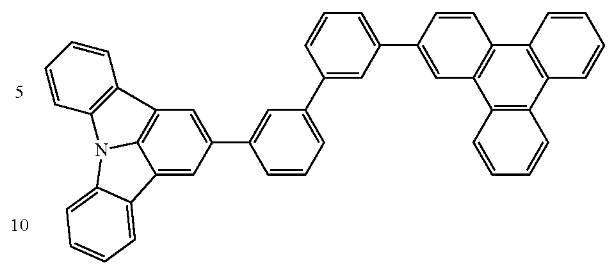
,
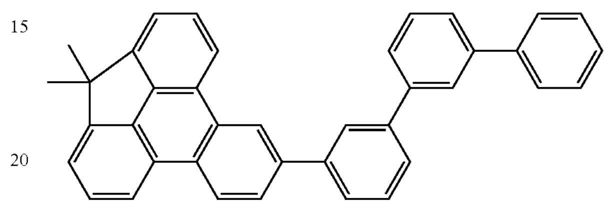
,
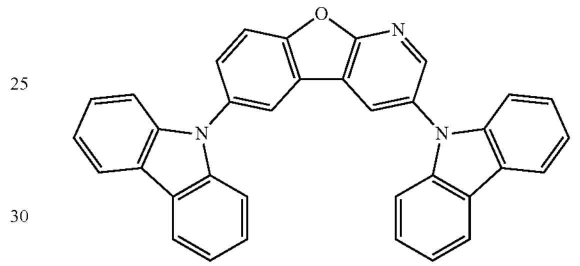
,
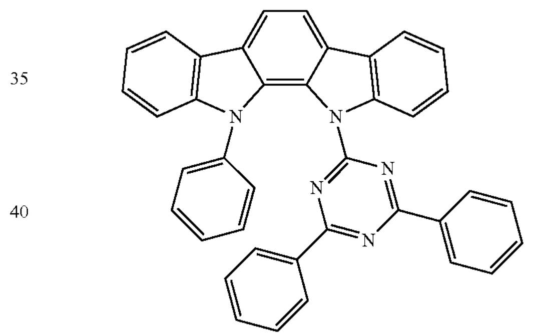
,
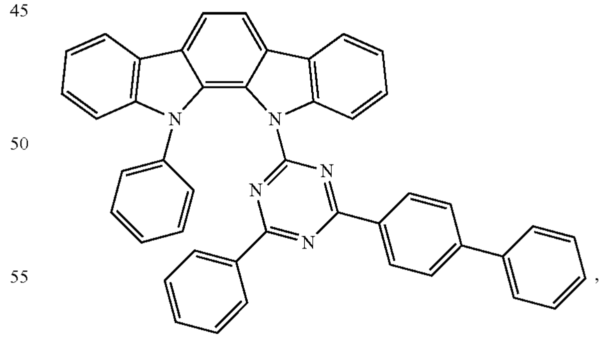
,
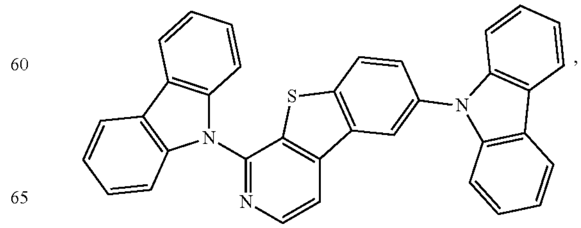
, -continued
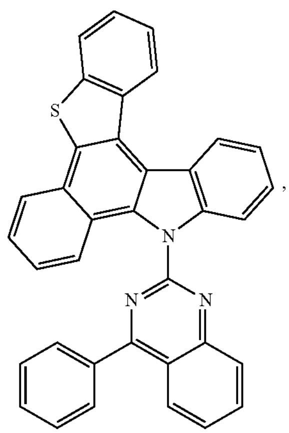
,
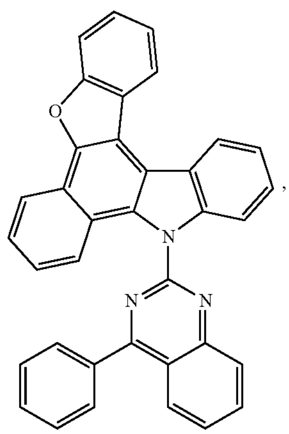
,
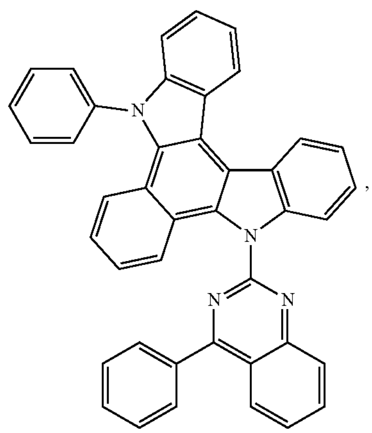
,
-continued
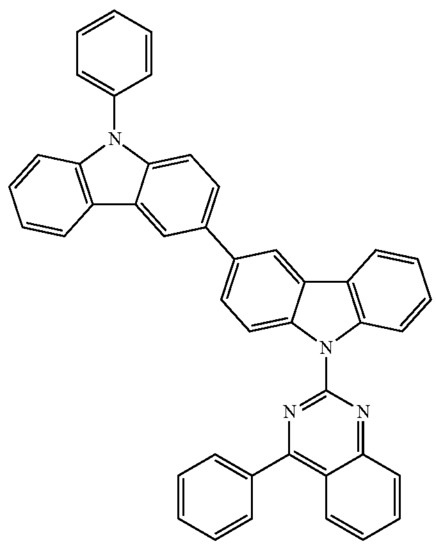
,
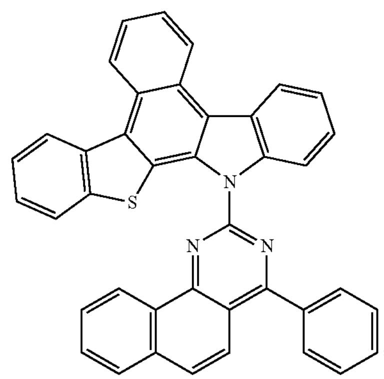
,
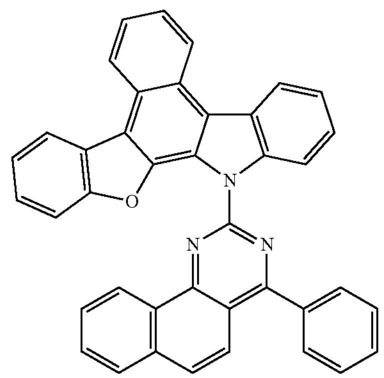
,
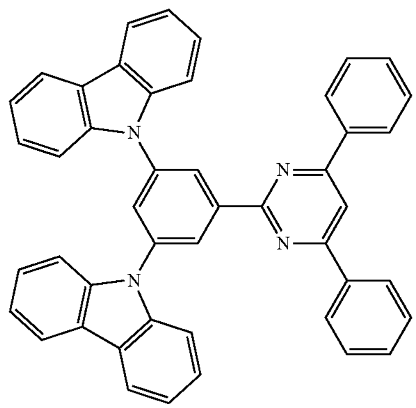
, -continued
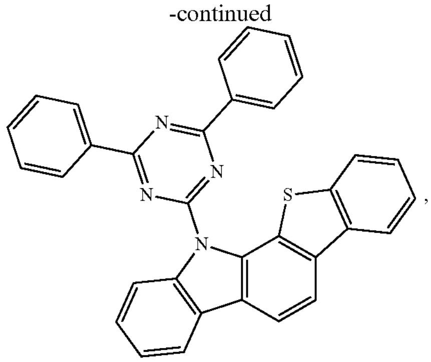
,
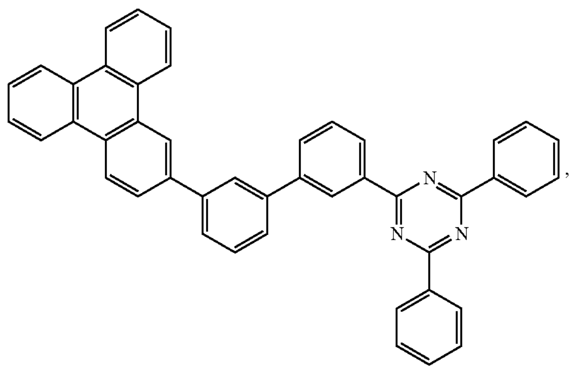
,
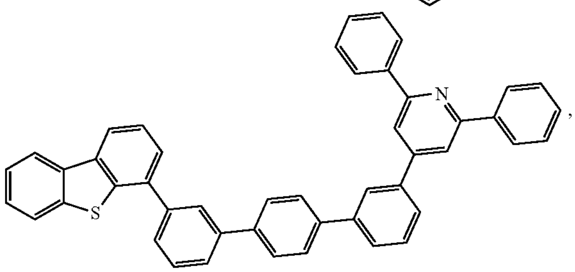
,
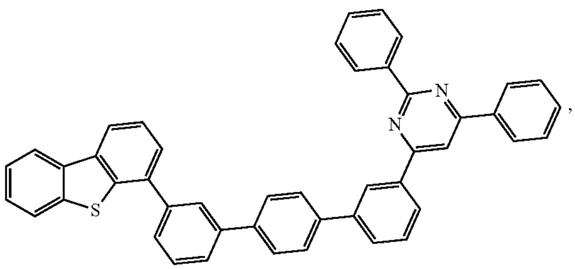
,
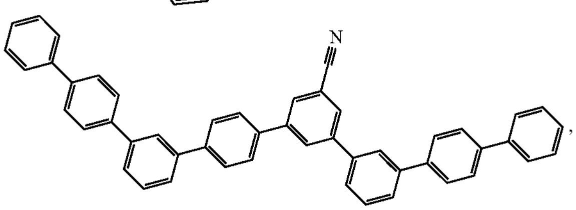
,
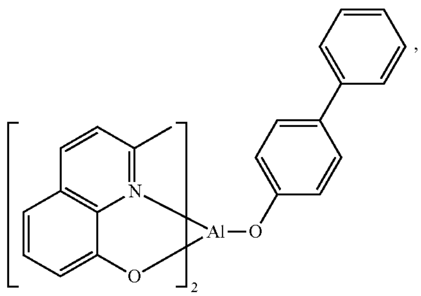
,
-continued
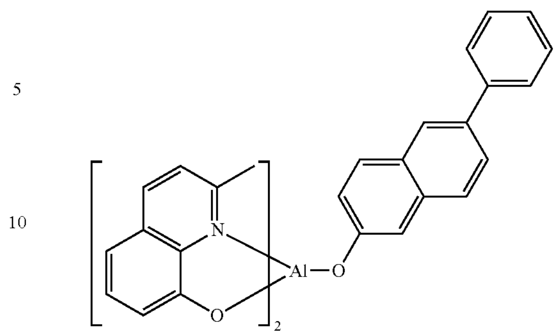
,
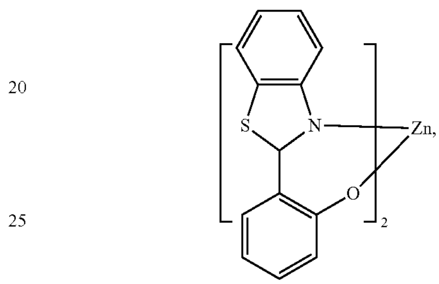
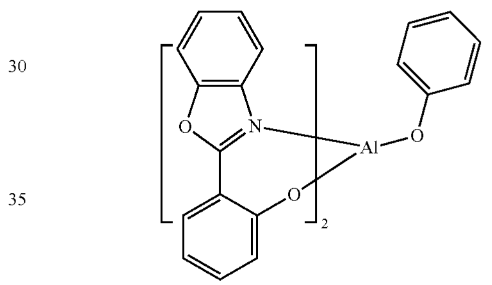
,
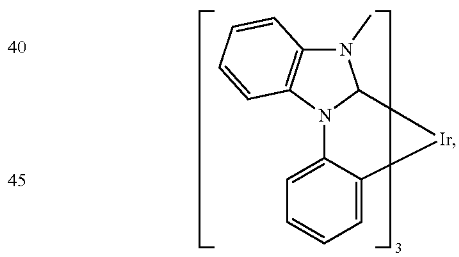
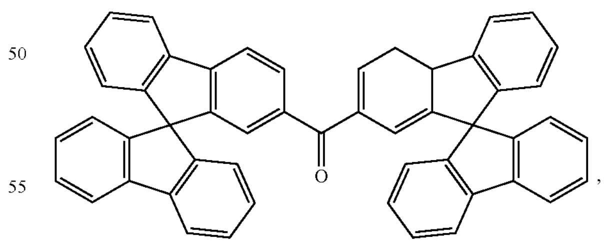
,
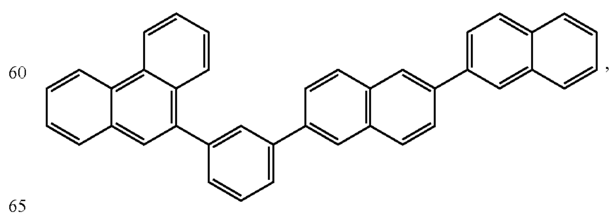
, -continued

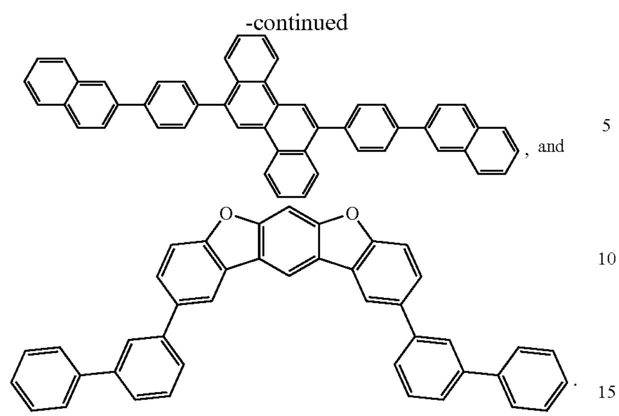

, and

.

e) Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

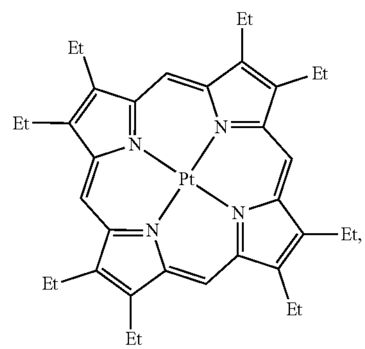

,

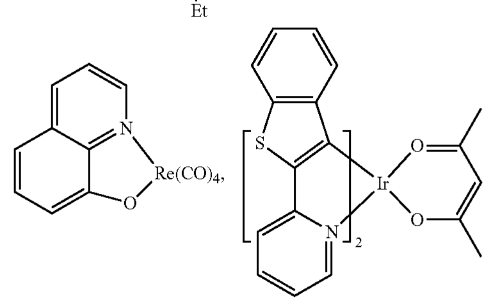

,

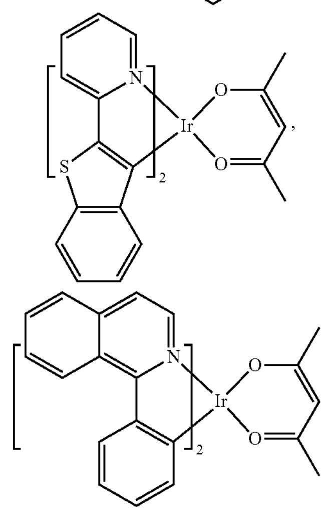

,

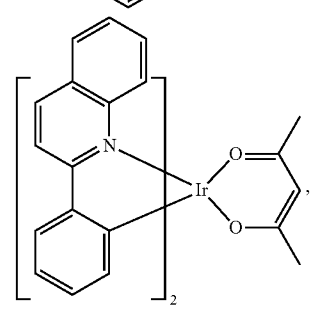

,

-continued
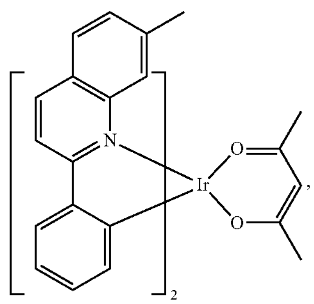
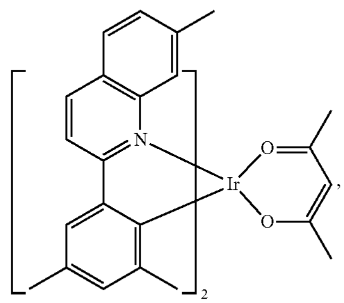
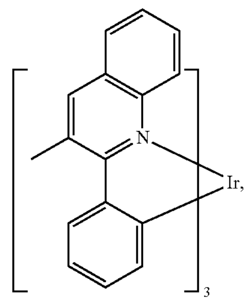
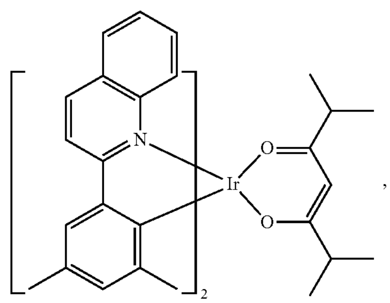
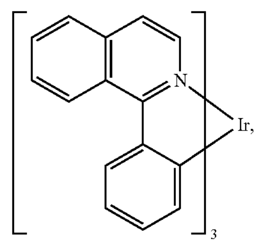
-continued
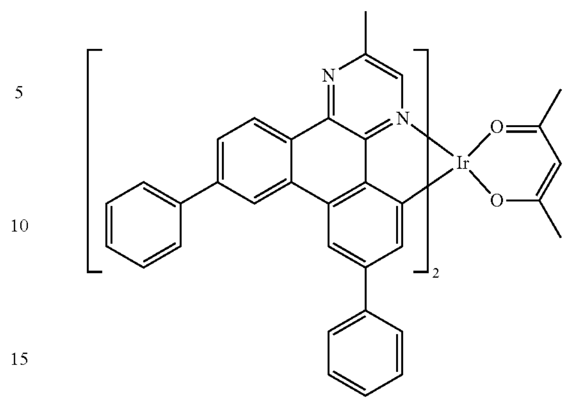
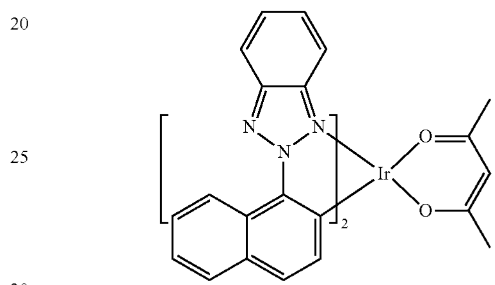
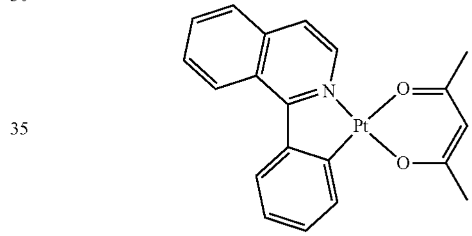
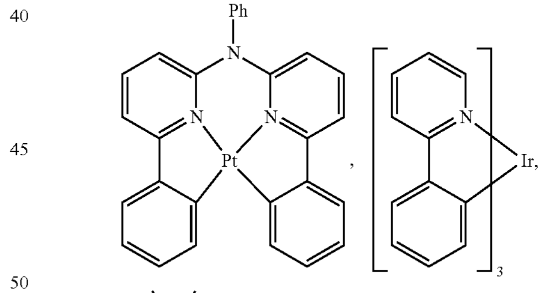
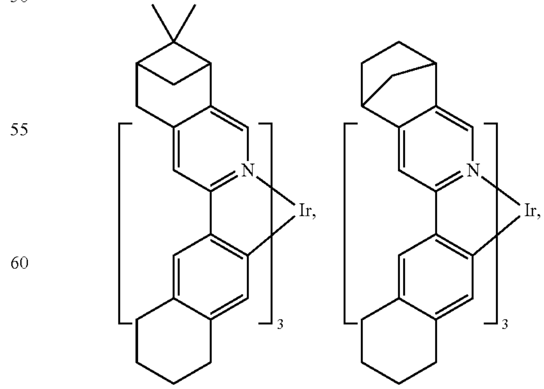

-continued
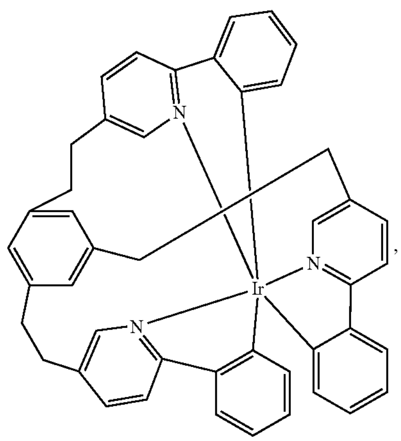
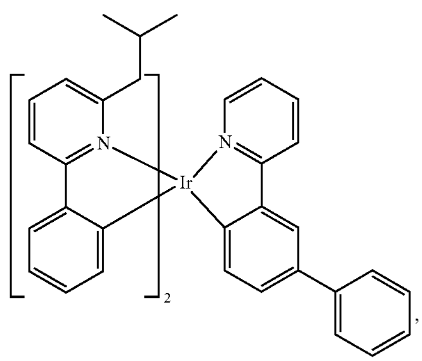
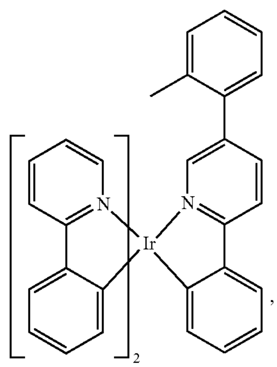
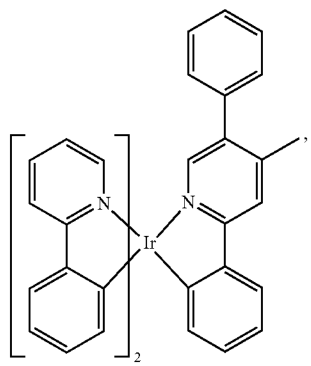
-continued
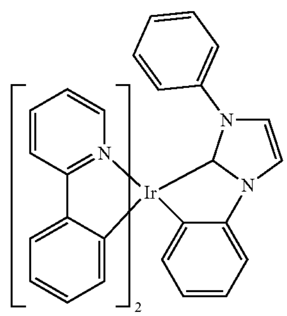
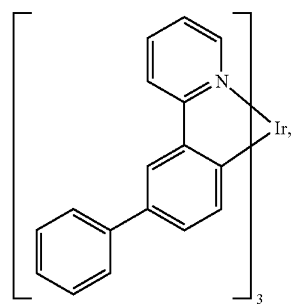
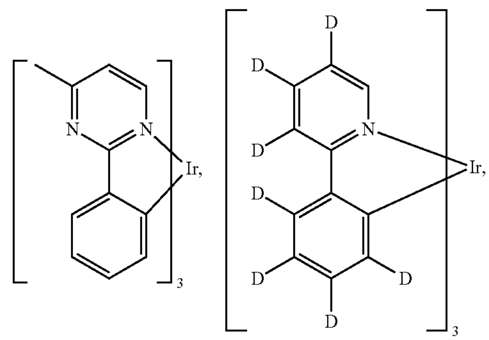
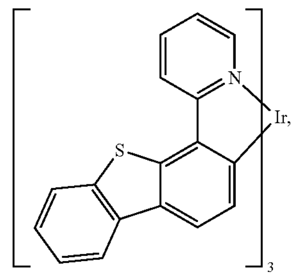
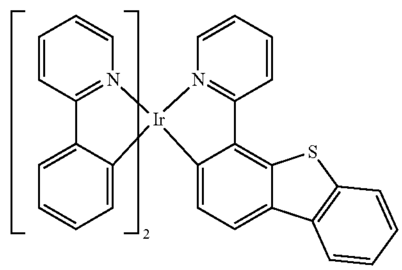

-continued
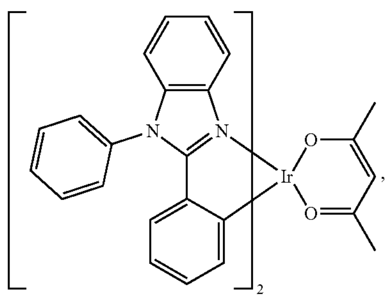
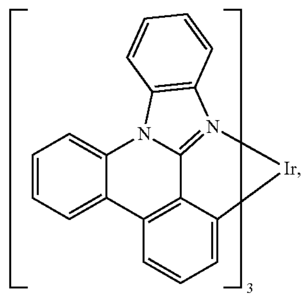
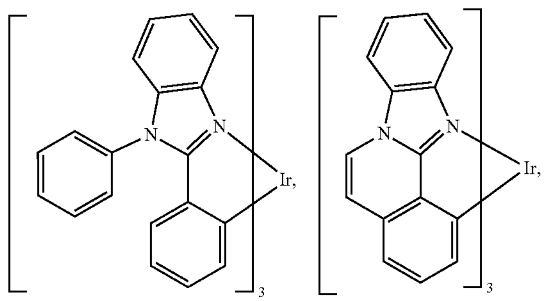
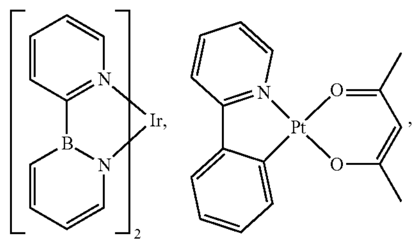
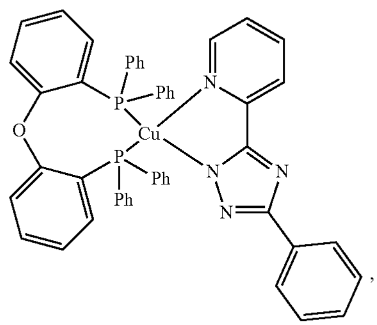
-continued
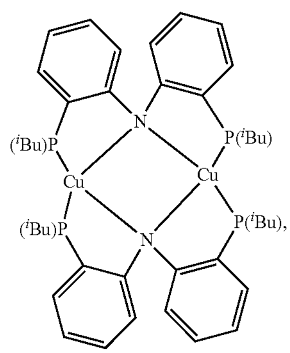
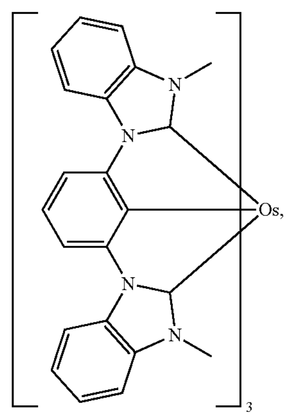
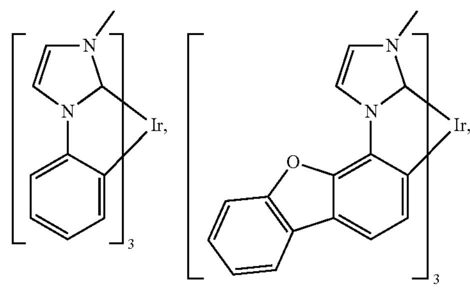
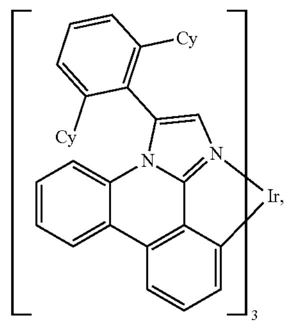
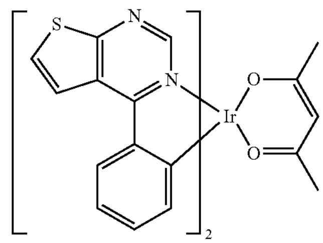

-continued
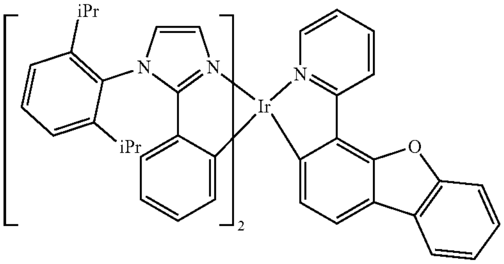
,
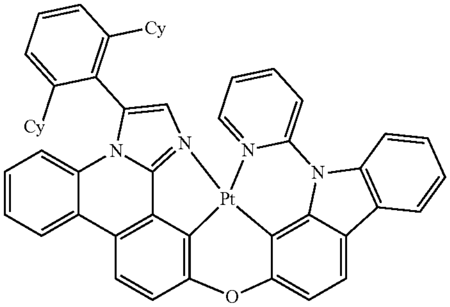
,
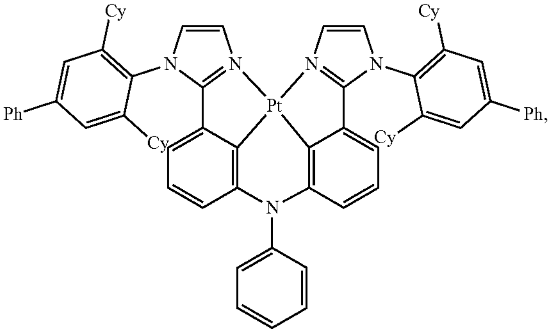
,
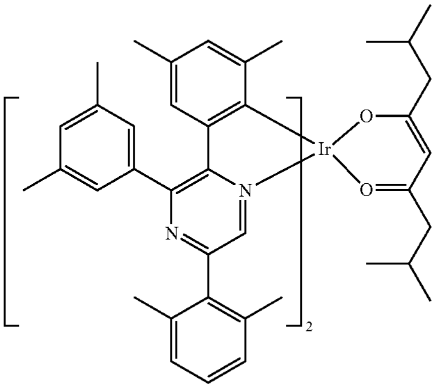
,
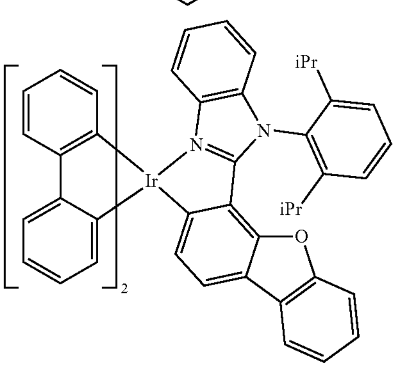
,
-continued
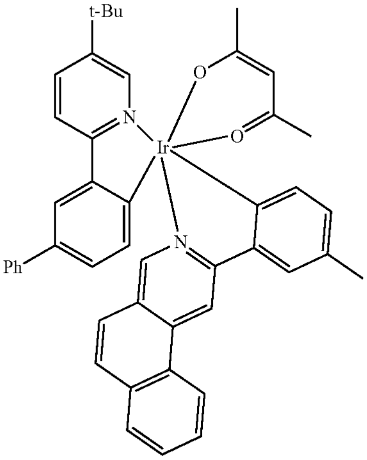
,
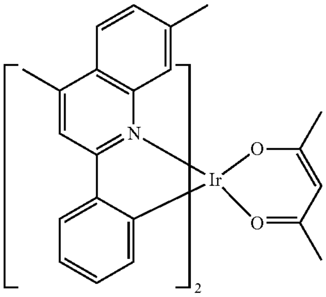
,
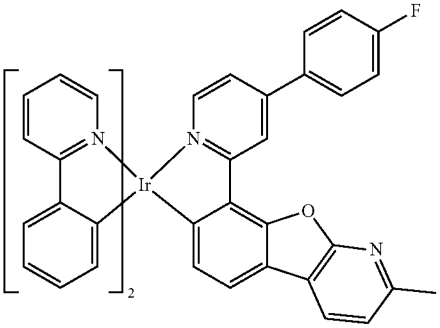
,
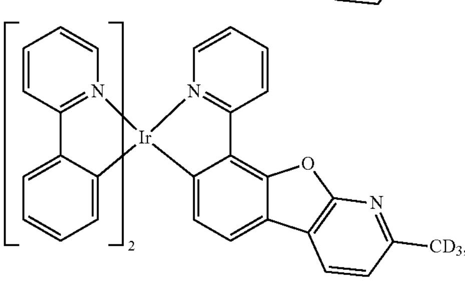
,
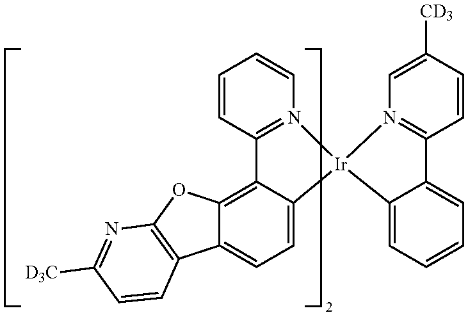

-continued
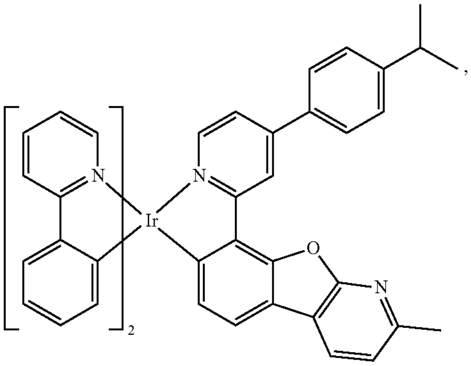
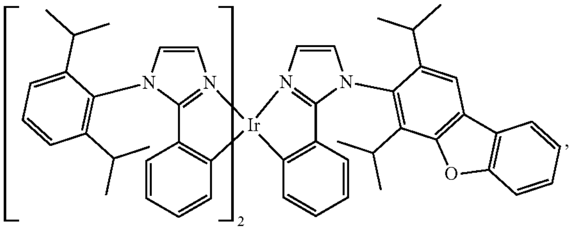
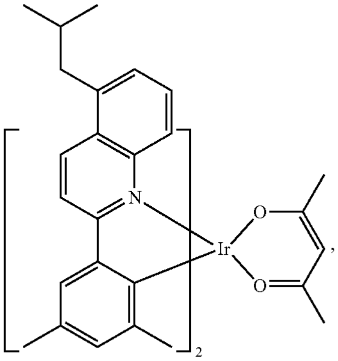
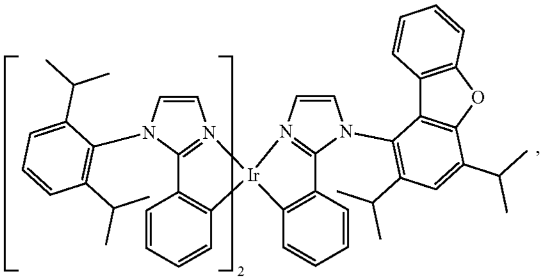
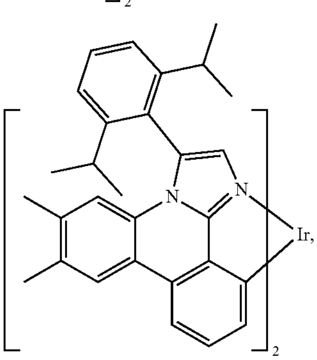
-continued
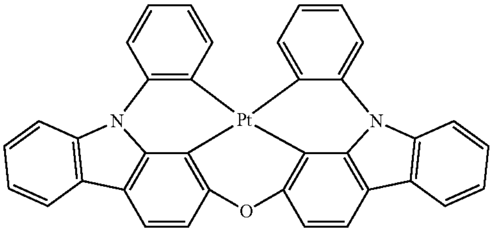
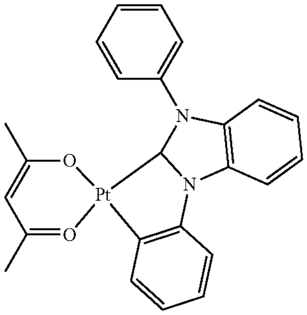
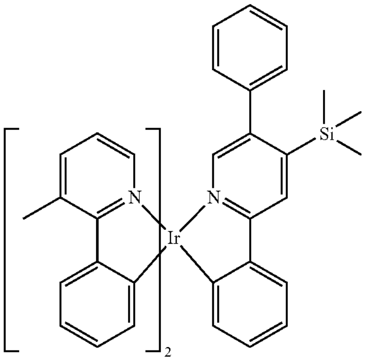
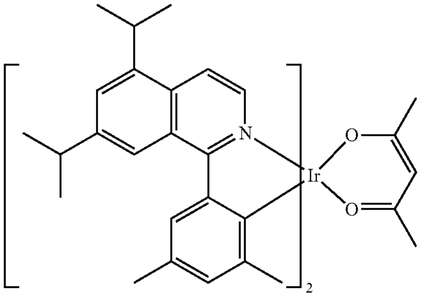
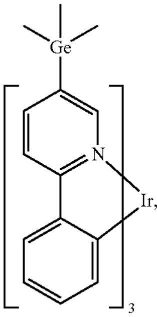
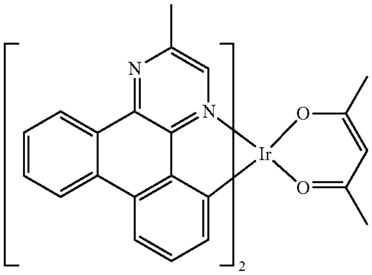

-continued
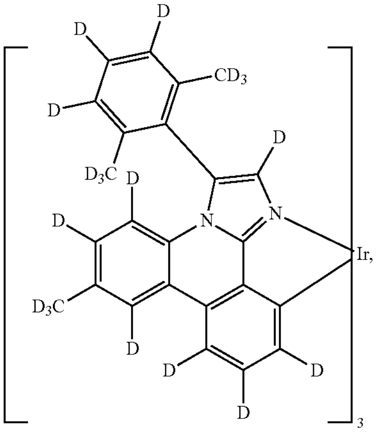
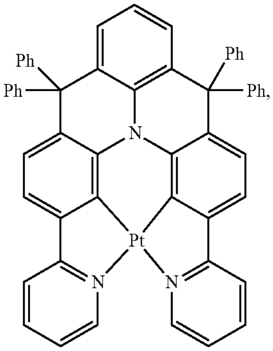
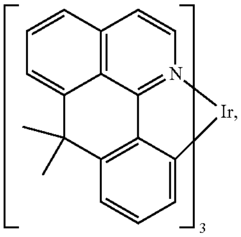
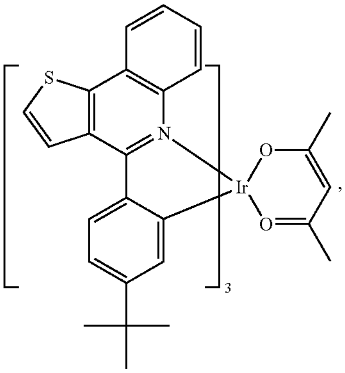
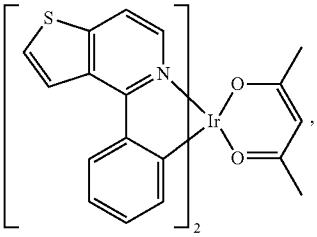
-continued
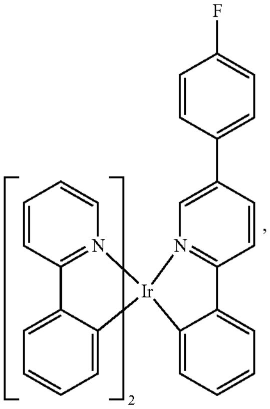
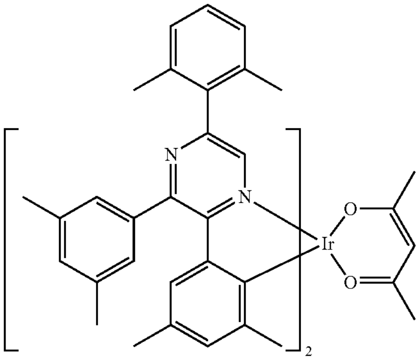
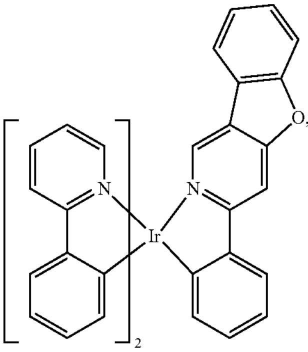
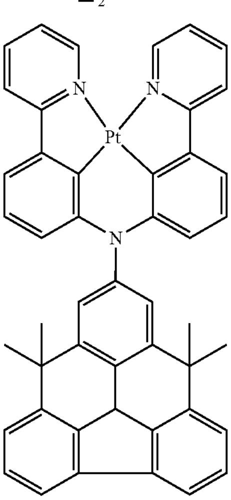

-continued
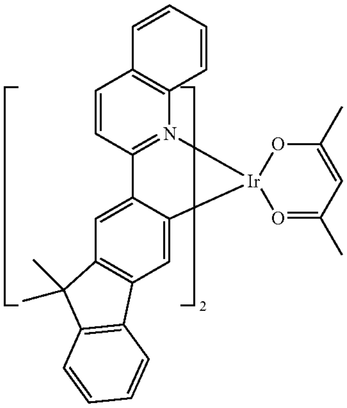
,
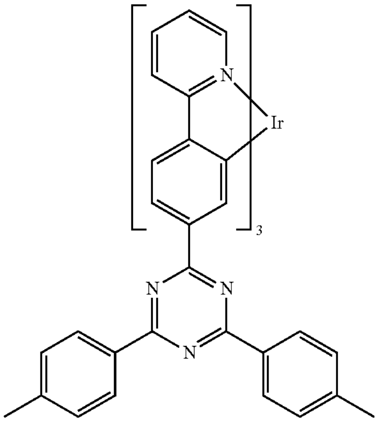
,
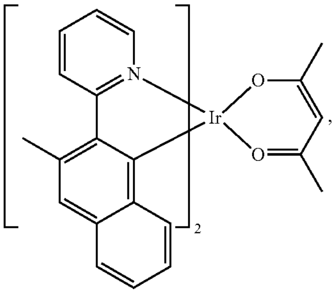
,
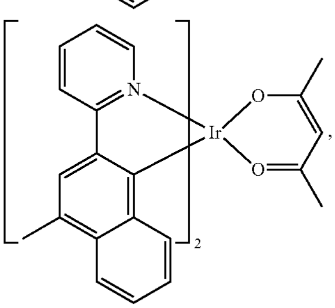
,
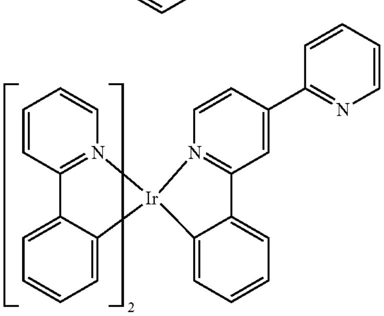
,
-continued
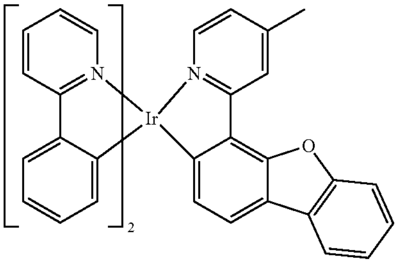
,
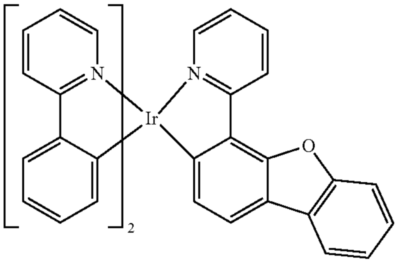
,
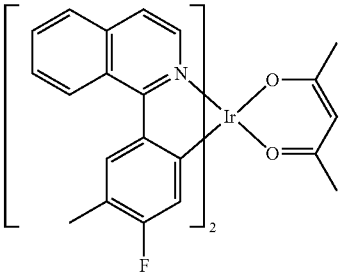
,
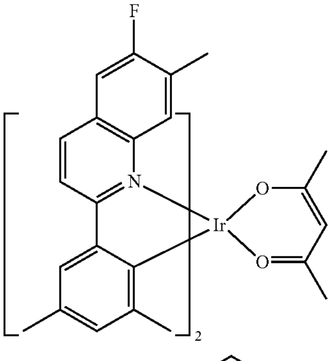
,
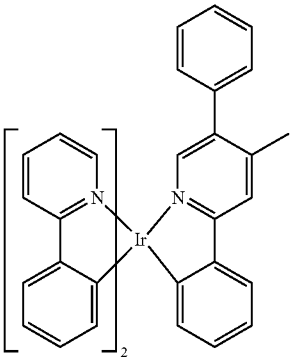
, -continued
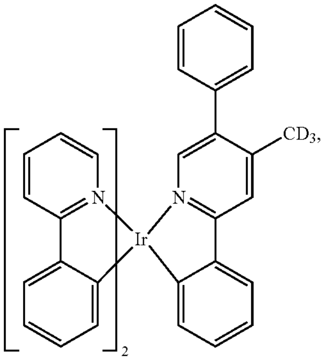
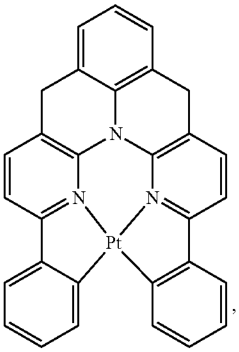
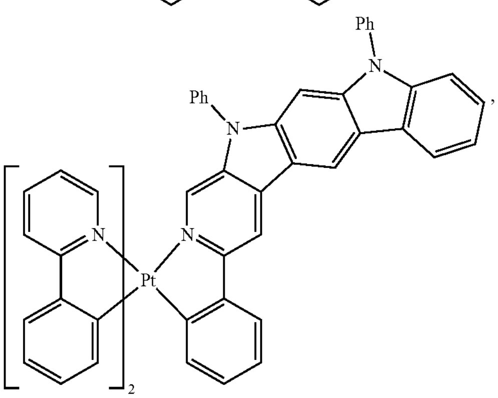
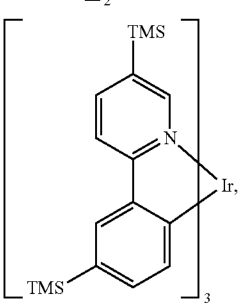
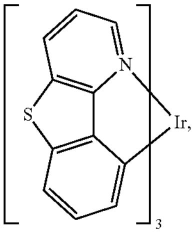
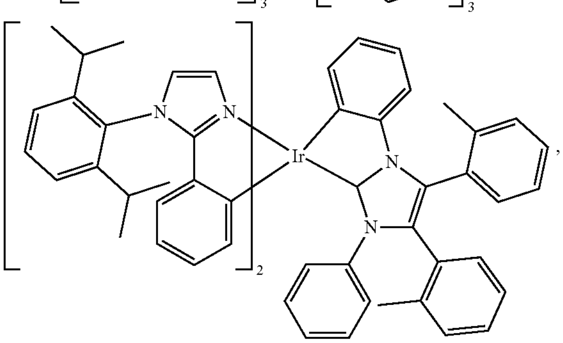
-continued
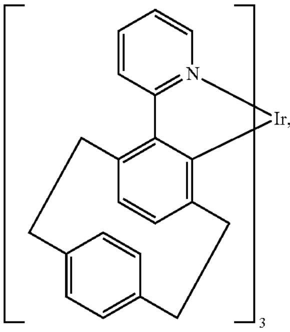
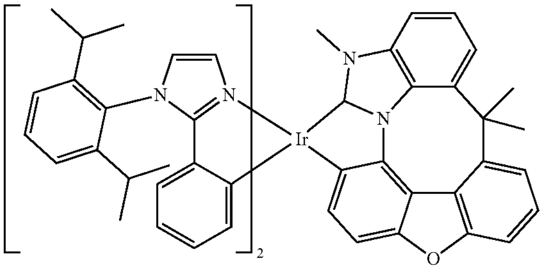
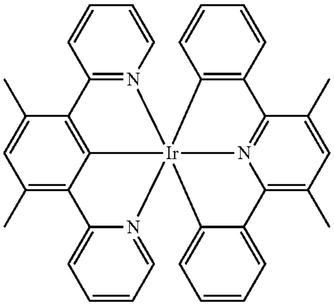
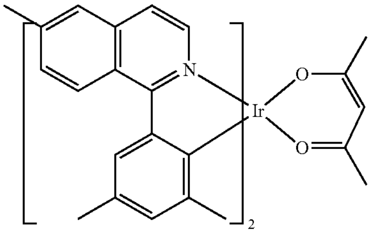
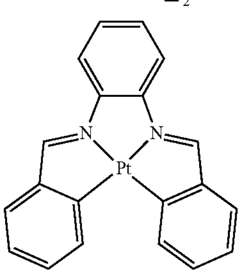
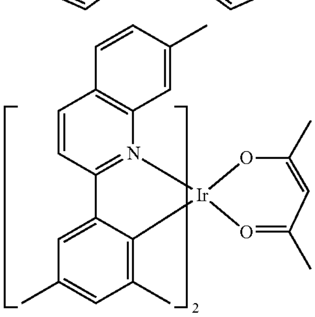

-continued
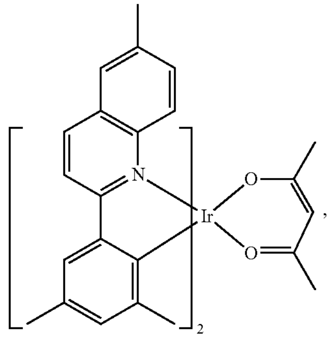
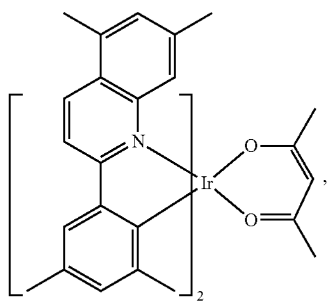
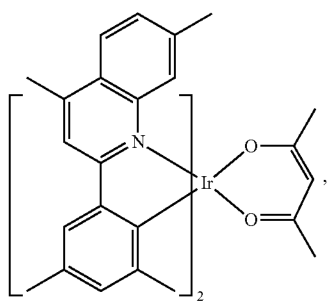
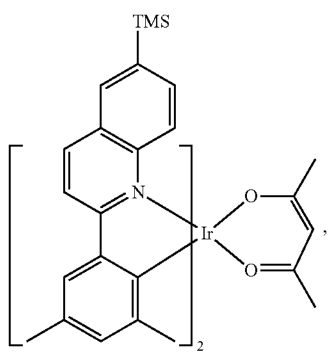
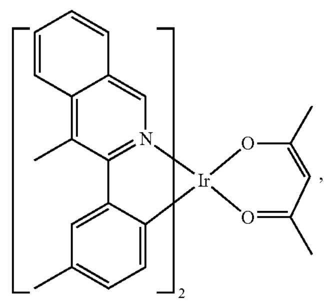
-continued
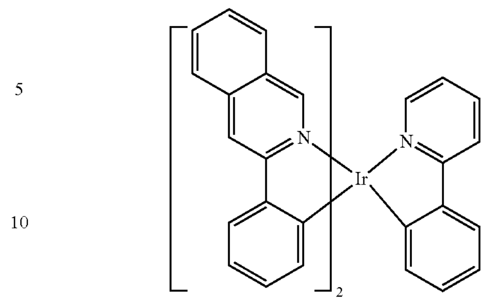
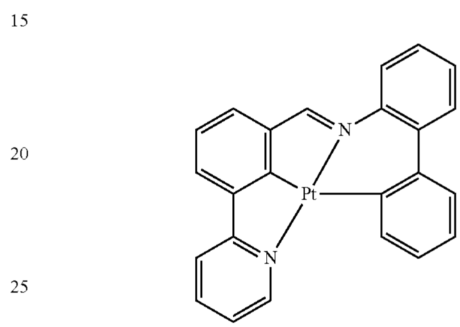
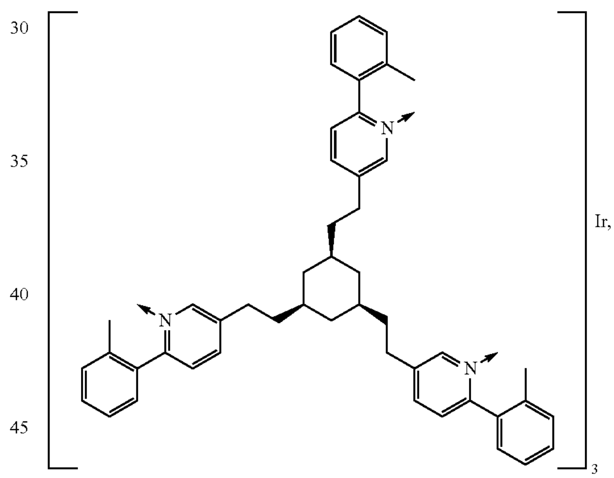
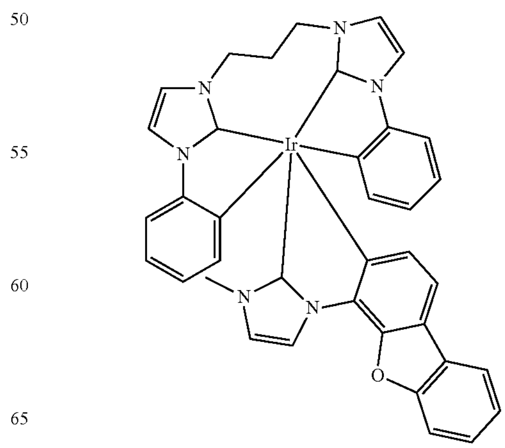

-continued
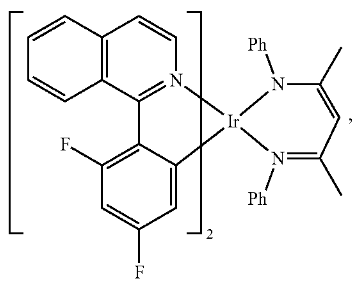
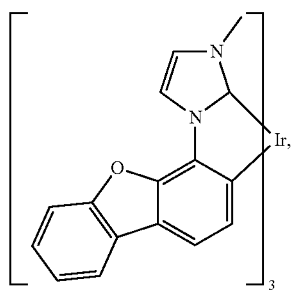
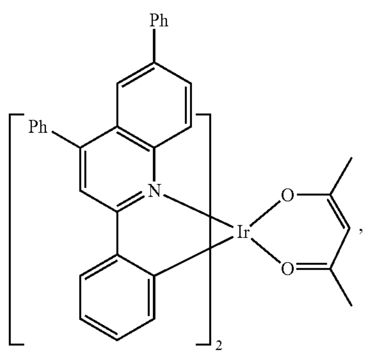
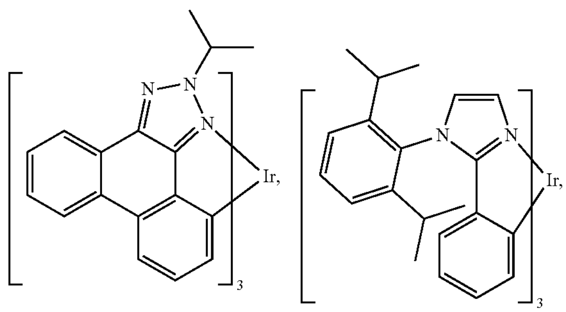
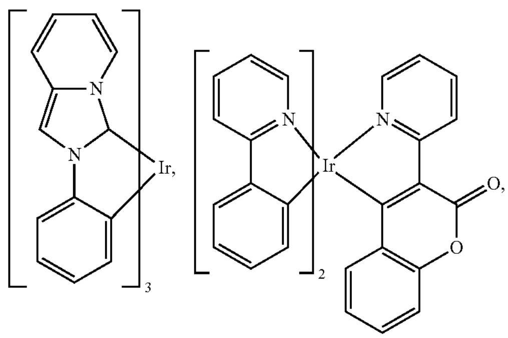
-continued
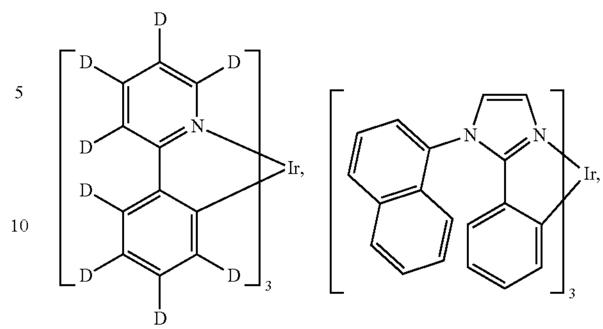
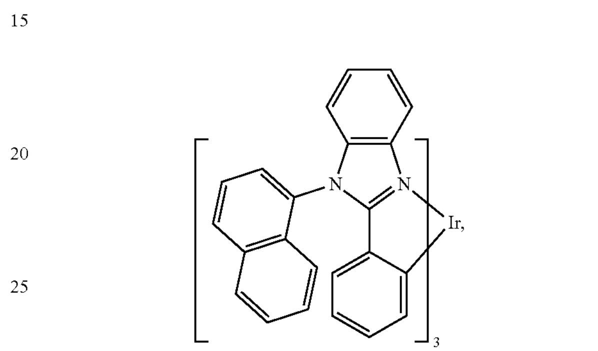
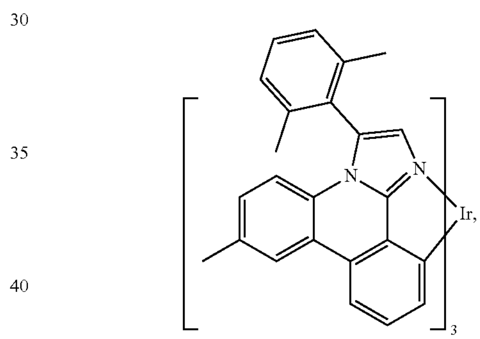
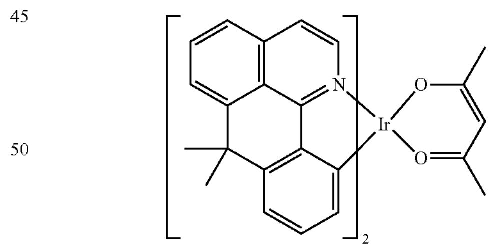
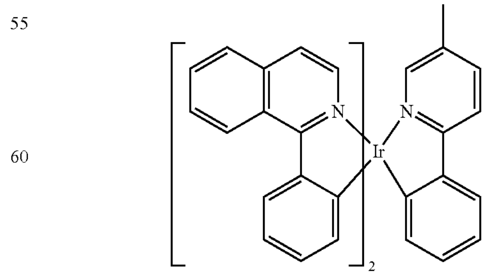

-continued

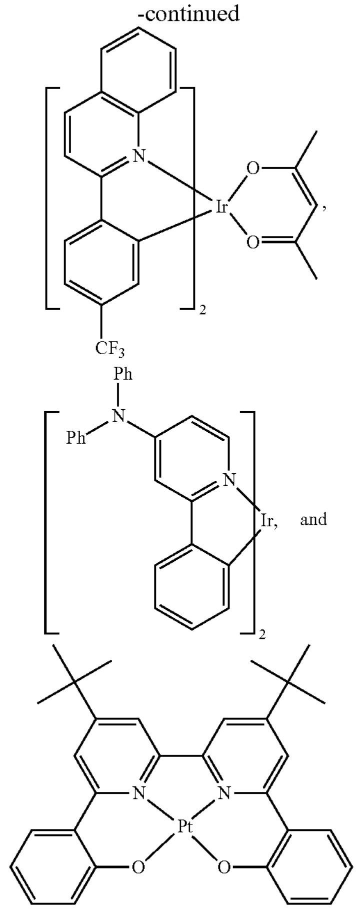

f) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

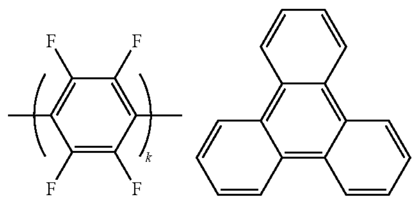

-continued

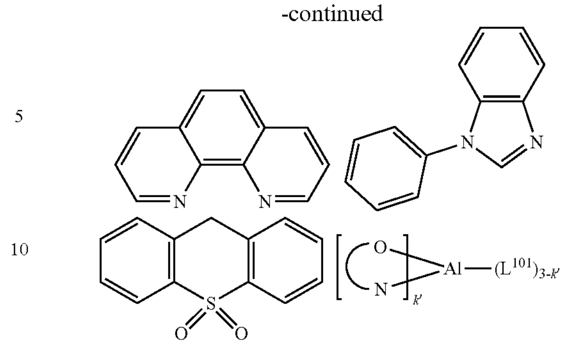

wherein k is an integer from 1 to 20; $L^{101}$ is another ligand, k' is an integer from 1 to 3.

g) ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

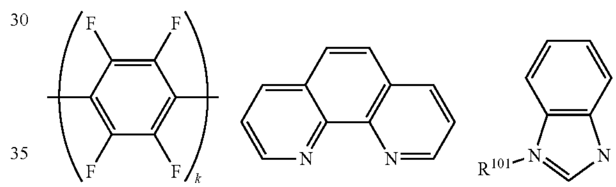

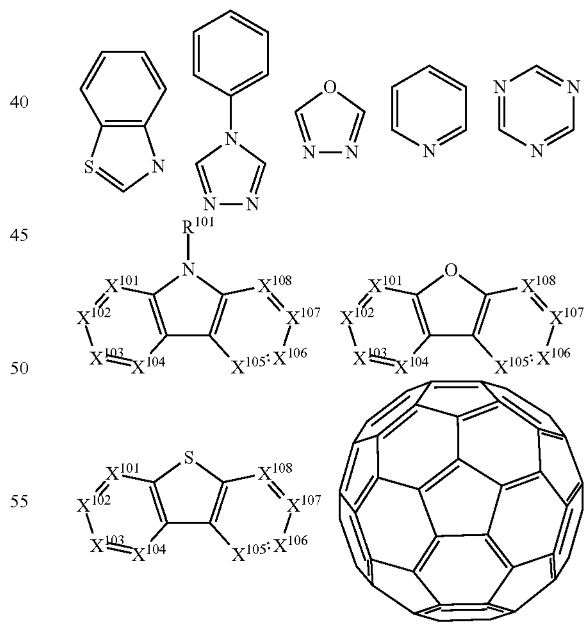

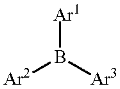

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

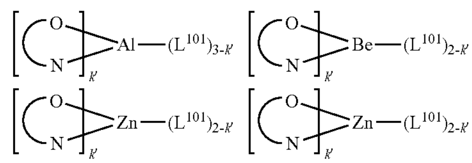

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

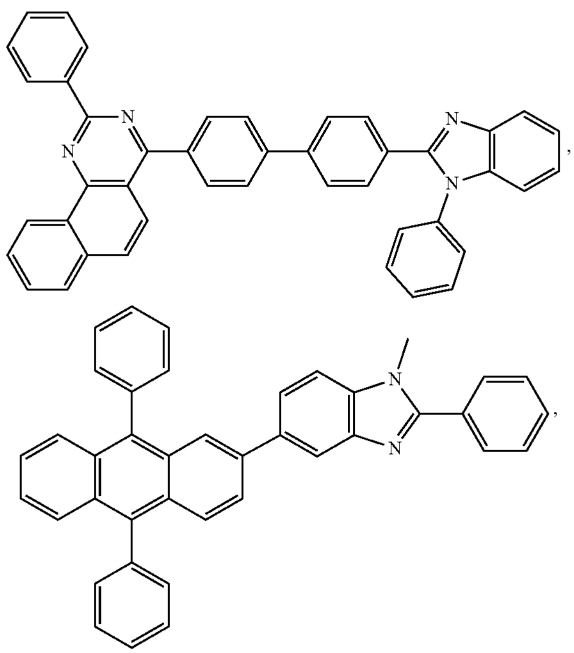

-continued

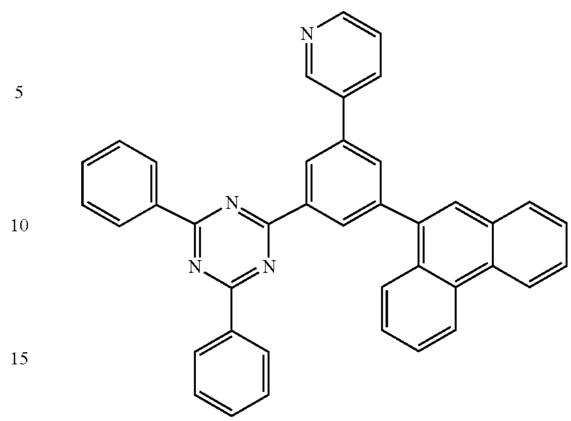

,

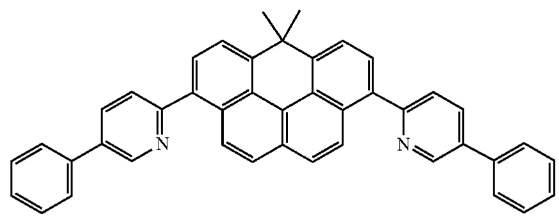

,

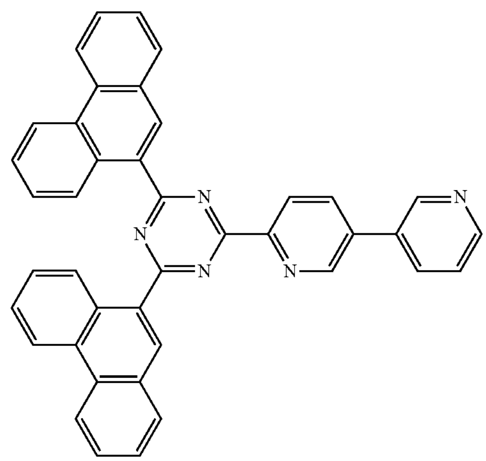

,

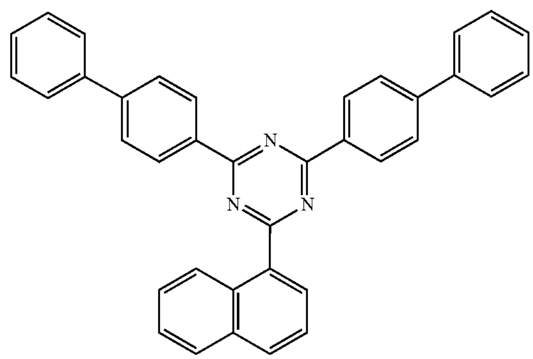

,

-continued
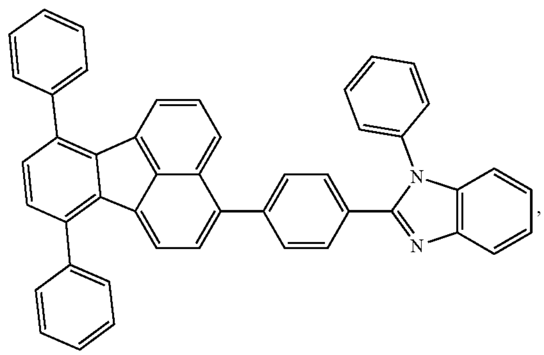,
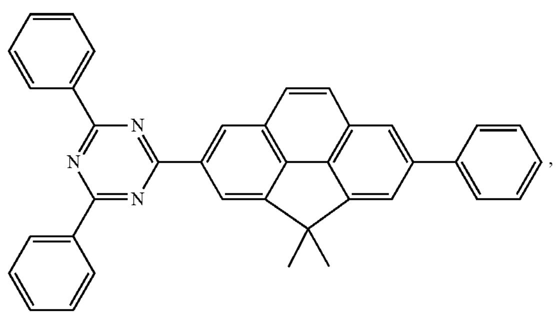,
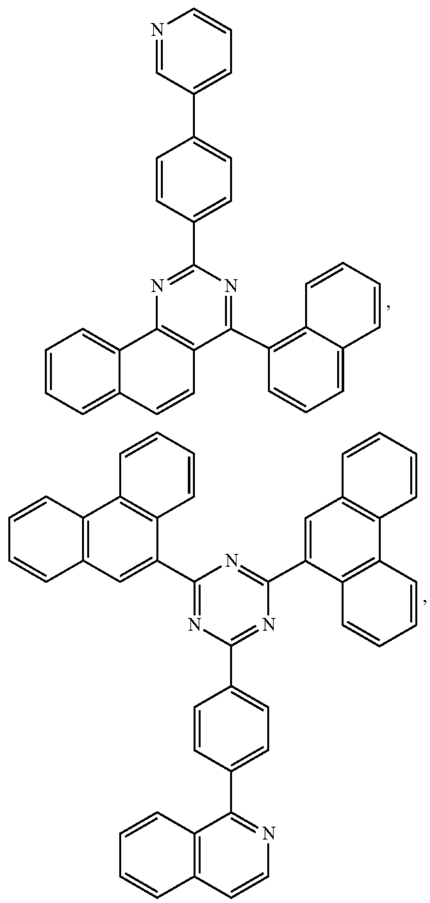,
-continued
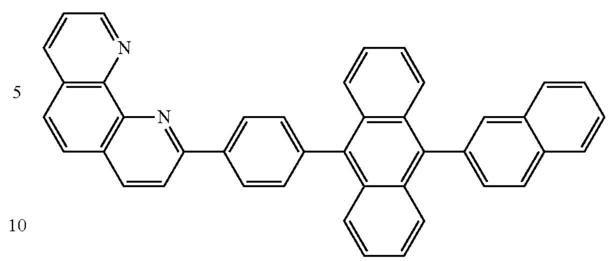,
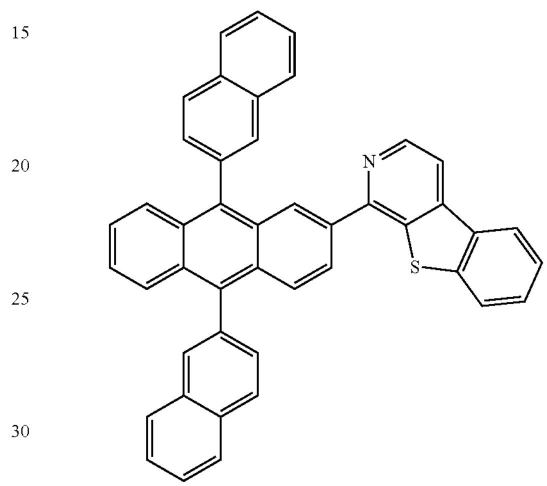,
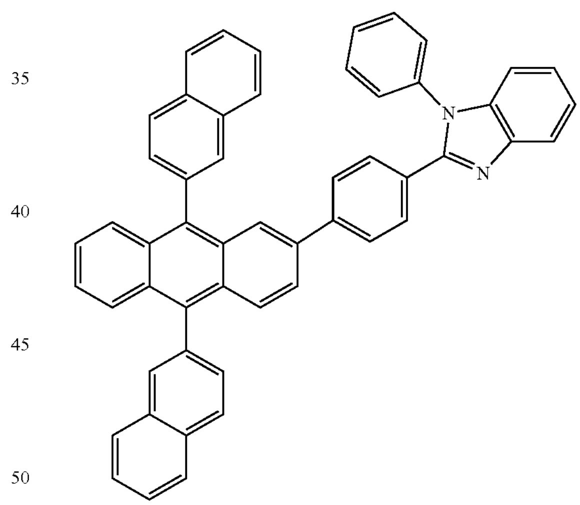,
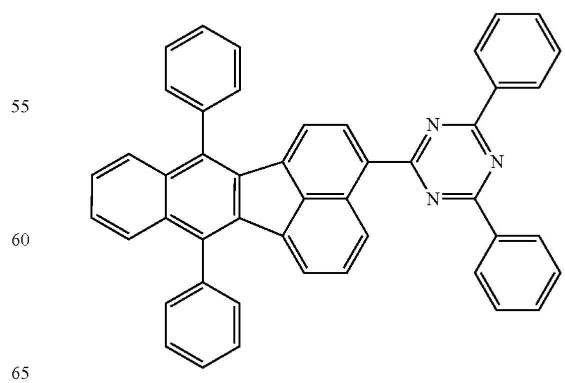, -continued
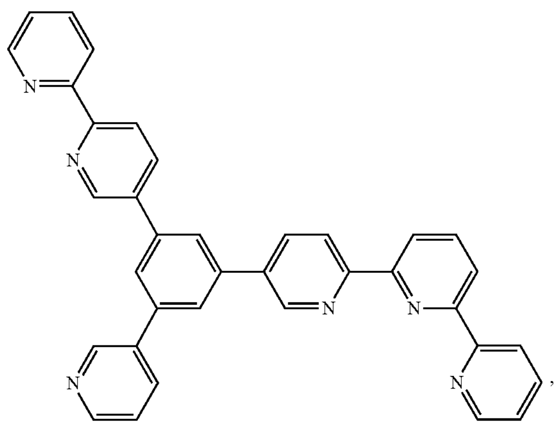
,
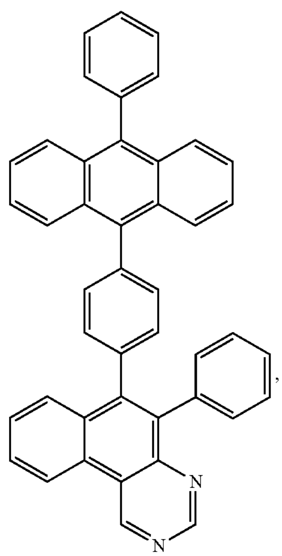
,
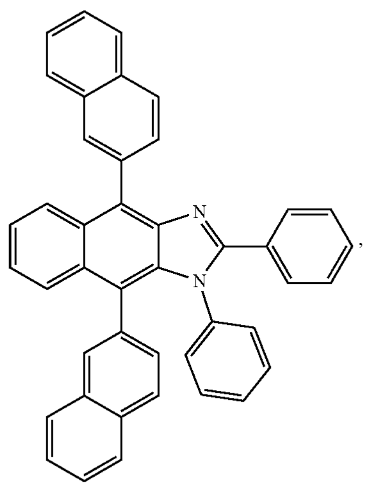
,
-continued
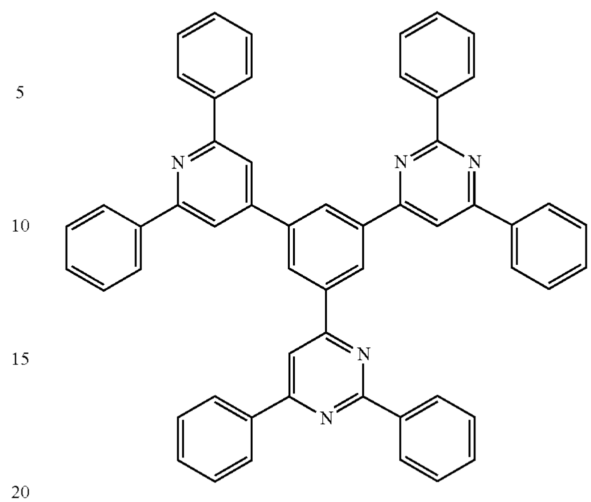
,
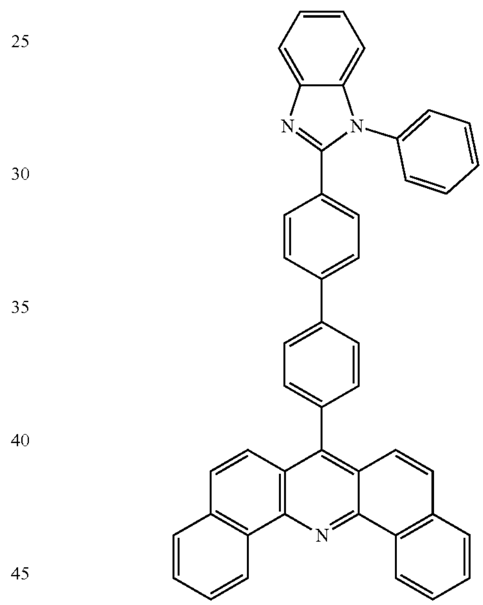
,
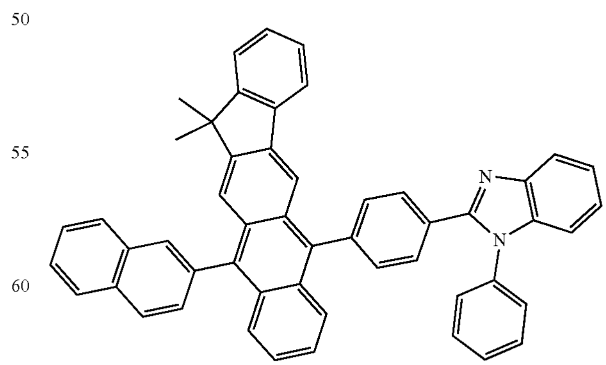
, -continued
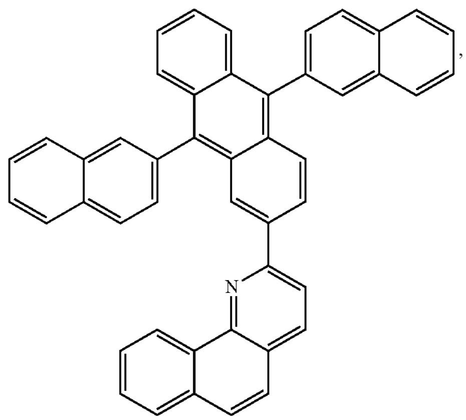
,
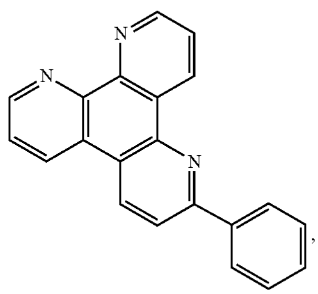
,
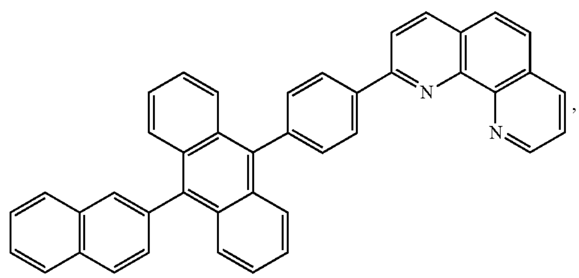
,
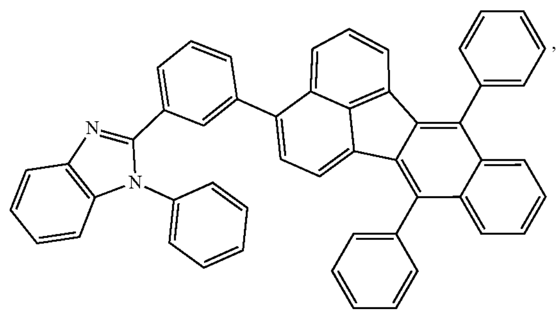
,
-continued
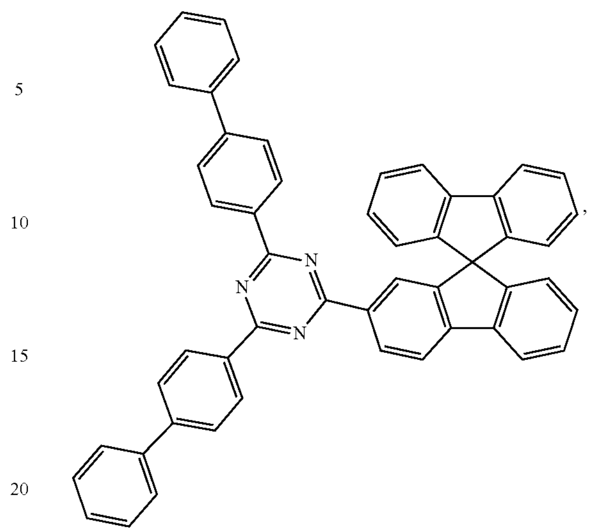
,
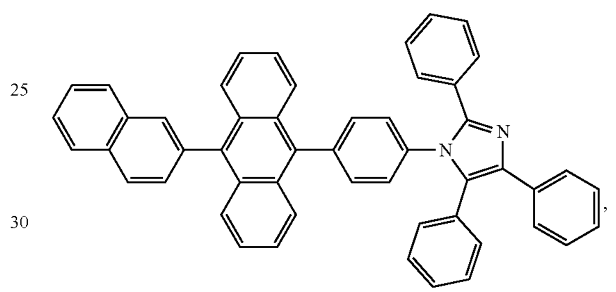
,
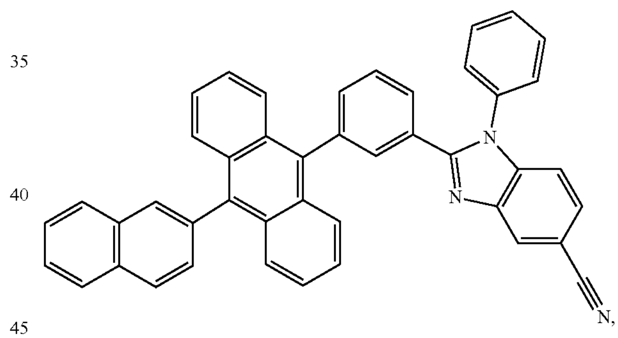
,
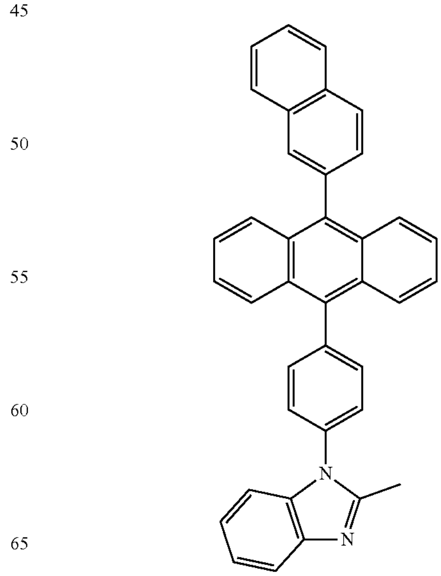
, -continued

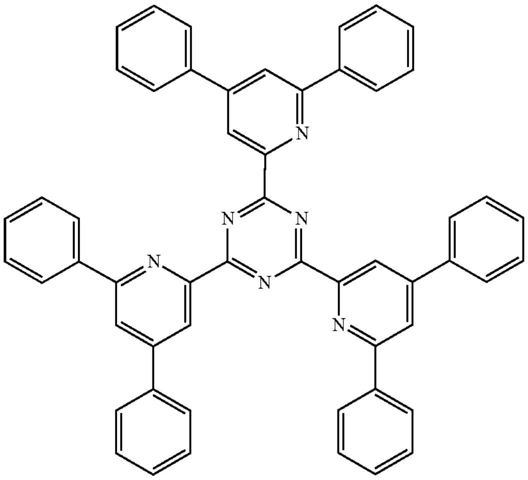

,

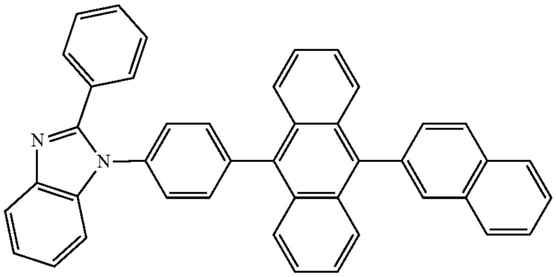

,

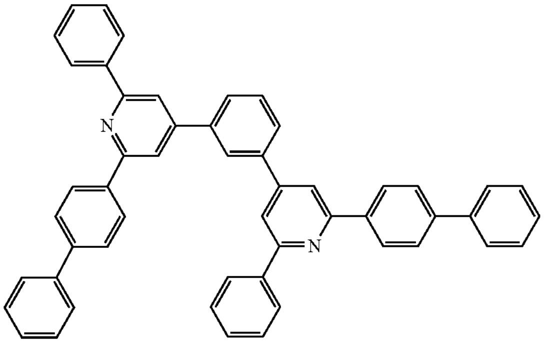

,

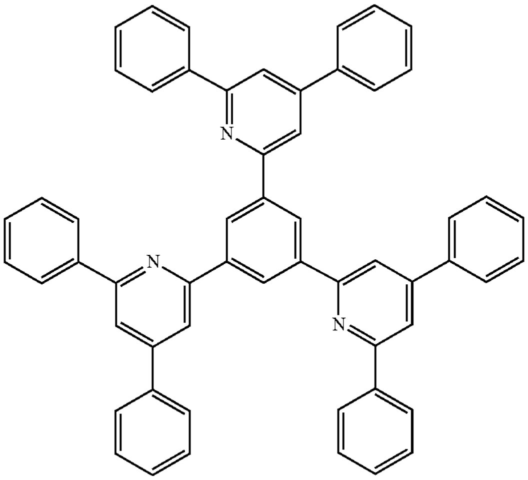

,

-continued

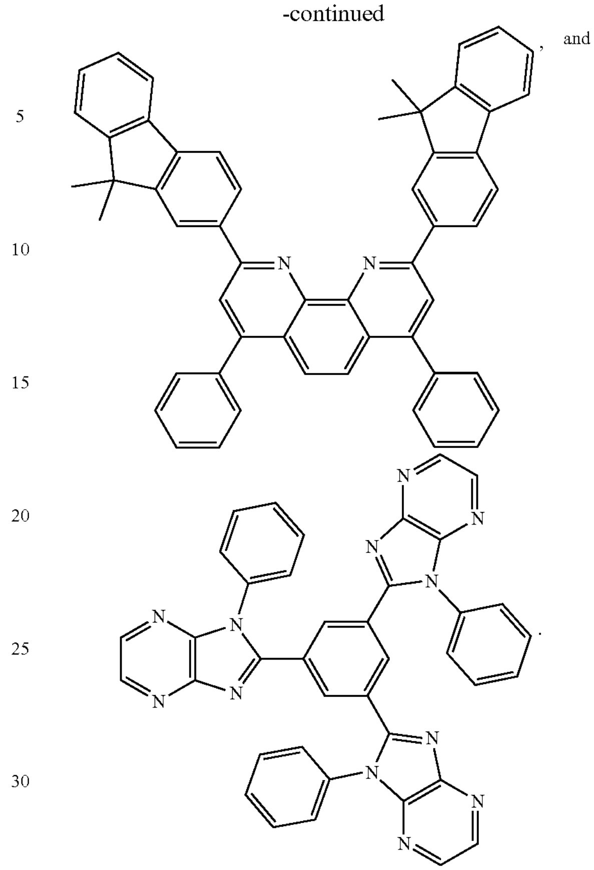

, and

.

h) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

EXAMPLES

(I) Synthetic Examples

Synthesis of 11-(9H-carbazol-9-yl)-14-phenylindolo[1,2-f]phenanthridine

Step 1. Synthesis of 11-chloroindolo[1,2-f]phenanthridine

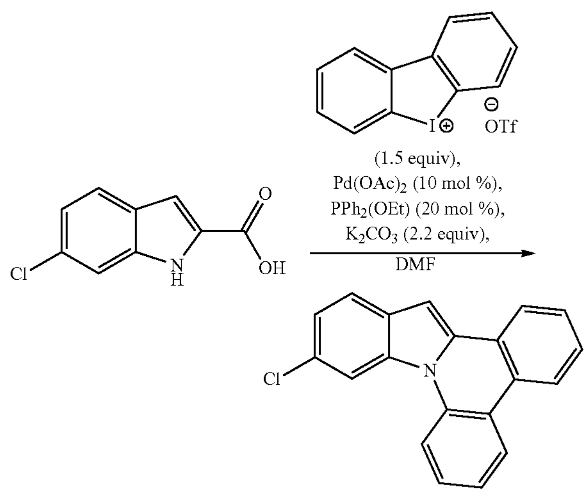

To a 500 ML flask under air was added 6-chloro-1H-indole-2-carboxylic acid (4.57 g, 23.36 mmol), dibenzo[b,d]iodol-5-ium trifluoromethanesulfonate (15.01 g, 35.0 mmol), diacetoxypalladium (0.525 g, 2.336 mmol), ethoxydiphenylphosphane (1.076 g, 4.67 mmol), and DMF (140 ML). The mixture was sparged with nitrogen and kept under nitrogen. Then potassium carbonate (7.10 g, 51.4 mmol) was added and the flask was placed in an oil bath preheated to 145° C. After 22 h the reaction mixture was allowed to cool to RT and diluted with DCM 500 ML. The solution was mixed with water (1 L). A heavy emulsion occurred and was broken up by slowly adding solid LiCl (100 g). The organic layer was separated and the aqueous layer was further extracted with DCM (2×500 mL). The combined organic layers were dried over sodium sulfate, filtered, and concentrated. The residue was dissolved in DCM and absorbed onto celite. The powder was subjected to vacuum chromatography on silica gel eluted with DCM/heptane (0-10%). The fractions containing pure product via TLC analysis were combined and concentrated to give 11-chloroindolo[1,2-f]phenanthridine (2.57 g, 36% yield) as a yellow solid.

Step 2. Synthesis of 14-bromo-11-chloroindolo[1,2-f]phenanthridine

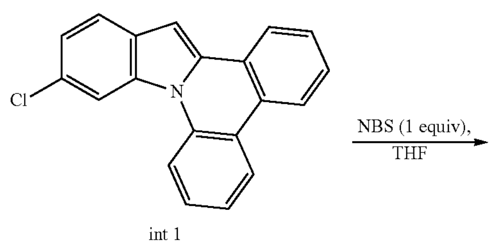

int 1

-continued

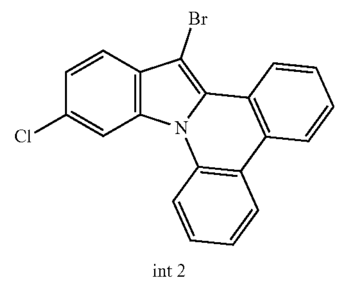

int 2

To a 250 ML RB was added 11-chloroindolo[1,2-f]phenanthridine (0.761 g, 2.52 mmol) and THF (39.5 ML). The solution was stirred at 13° C. To the stirring solution was added 1-bromopyrrolidine-2,5-dione (0.449 g, 2.52 mmol) in THF (11.85 ML). The mixture was stirred for 2.5 h. Then the sol'n was heated and 40 ML THF was added and reheated until all dissolved and the sol'n was clear. Then The THF solution was poured to stirring methanol (1 L), and let stir for 3.5 hr before filtering off the solid. The solids were dried in a vac-oven and 0.807 g (84% yield) of product was obtained.

Step 3. Synthesis of 11-chloro-14-phenylindolo[1,2-f]phenanthridine

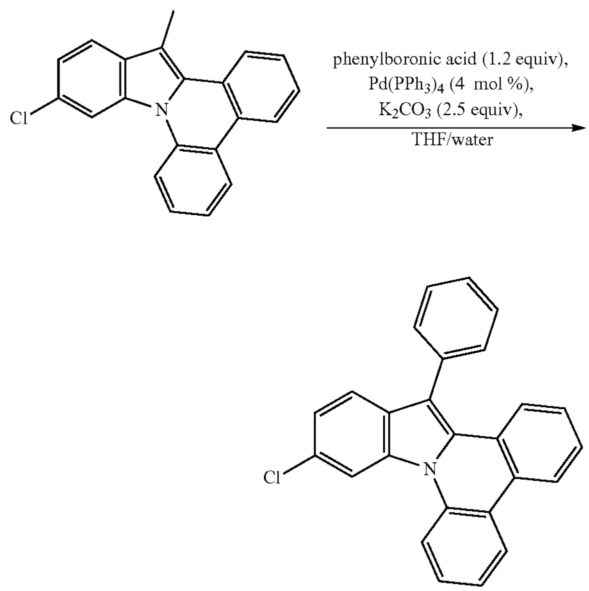

To a 100 ML 3-neck flask under nitrogen was added 14-bromo-11-chloroindolo[1,2-f]phenanthridine (1 g, 2.63 mmol), phenylboronic acid (0.384 g, 3.15 mmol), potassium carbonate (0.908 g, 6.57 mmol), THF (42.0 ML), and water (10.51 ML). The reaction mixture was heated to reflux for 24 hr. After cooling to RT the solution was filtered through a short plug of silica gel, and DCM was used to wash organics through the plug. The filtrate was concentrated, and the resulting solid material was dried under reduced pressure. The semi-crude material was used without further purification assuming quantitative yield.

Step 4. Synthesis of 11-(9H-carbazol-9-yl)-14-phenylindolo[1,2-f]phenanthridine

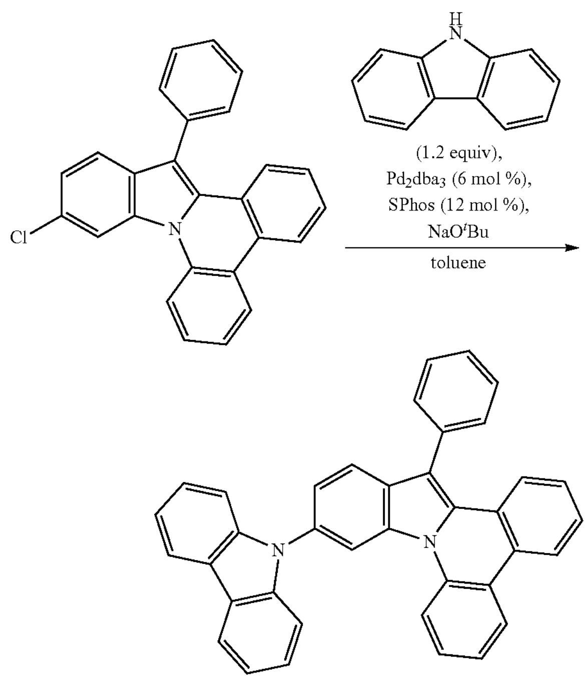

To a dry 0.1 L 3-neck flask under nitrogen, equipped with a water condenser, magnetic stirrer and thermowell, 11-chloro-14-phenylindolo[1,2-f]phenanthridine (1.163 g, 3.08 mmol), sodium 2-methylpropan-2-olate (0.583 g, 6.07 mmol), were added and the mixture was degassed with constant stream of nitrogen. dicyclohexyl(2',6'-dimethoxy-[1,1'-biphenyl]-2-yl)phosphane (0.172 g, 0.419 mmol) and $Pd_2$dba3 (0.172 g, 0.188 mmol) were added followed by Toluene (25.6 ml) and the resulting mixture was further degassed with continuous flow of N2. The reaction mixture was heated to reflux. The reaction mixture was filtered through a plug containing silica gel and basic alumina and eluted with hot toluene providing desired product 1.3 g (83% yield). The product was further processed. The material was dissolved in ~60 ML DCM with heat and slowly poured to 100 mL methanol. The resulting solid was collected via suction filtration. The solid was mixed with product from another batch to give 1.8 g of product and dissolved in 100 mL DCM with some heat and poured to 100 mL methanol, then filtered. The resulting solid was redissolved in 200 mL DCM and poured slowly to 500 ML methanol. The solid was collected via suction filtration to give 11-(9H-carbazol-9-yl)-14-phenylindolo[1,2-f]phenanthridine (1.08 g) as a yellow solid.

(II) Device Examples

All example devices were fabricated by high vacuum (<$10^{-7}$ Torr) thermal evaporation. The anode electrode was 1,150 Å of indium tin oxide (ITO). The cathode consisted of 10 Å of Liq (8-hydroxyquinoline lithium) followed by 1,000 Å of Al. All devices were encapsulated with a glass lid sealed with an epoxy resin in a nitrogen glove box (<1 ppm of $H_2O$ and $O_2$) immediately after fabrication with a moisture getter incorporated inside the package. The organic stack of the device examples consisted of sequentially, from the ITO Surface: 100 of HAT-CN as the hole injection layer (HIL); 450 Å of HTM as a hole transporting layer (HTL); emissive layer (EML) with thickness 400 Å. Emissive layer containing Red Host H1 (inventive compound) and 3 weight % of red emitter RD1. EML was followed by 350 Å of Liq (8-hydroxyquinoline lithium) doped with 40% of ETM as the electron transporting layer (ETL). Device structure is shown in the Table 1.

The chemical structures of the device materials are shown below.

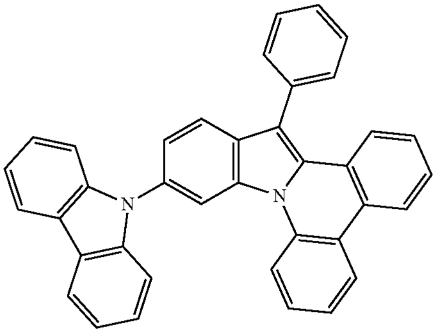

H1

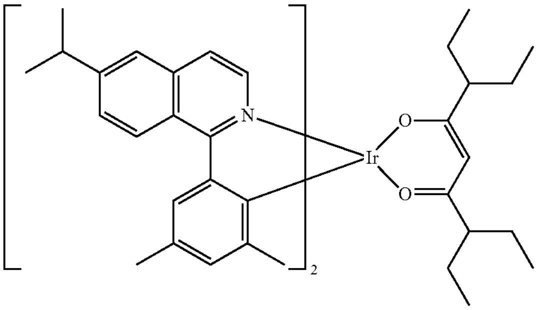

RD1

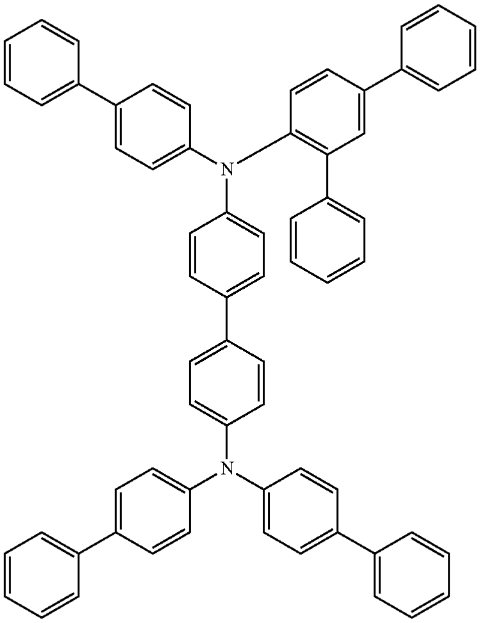

HTM

-continued

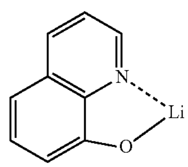

Liq

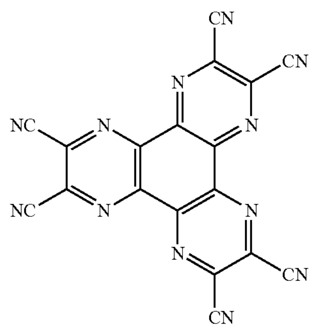

HATCN

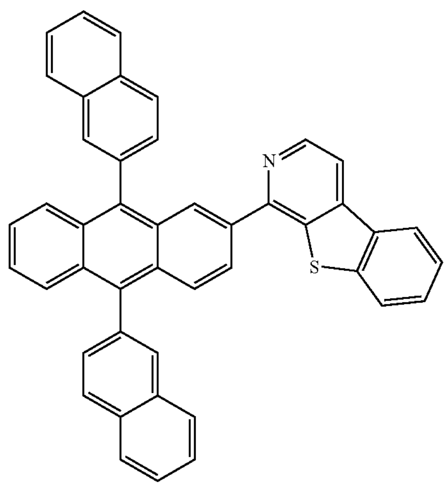

ETM

Upon fabrication the devices EL and JVL performance have been measured. Device Example 1 emitted red emission with maximum wavelength 625 nm defined by red emitter RD1. Device performance is shown in the Table 2.

TABLE 1

| Device example layer structure | | |
|---|---|---|
| [1] Layer | [2] Material | [3] Thickness [Å] |
| [4] Anode | [5] ITO | [6] 1,150 |
| [7] HIL | [8] HAT-CN | [9] 100 |
| [10] HTL | [11] HTM | [12] 450 |
| [13] Red EML | [14] H1: RD1 3% | [15] 400 |
| ]16] ETL | [17] Liq: ETM 40% | [18] 350 |
| [19] EIL | [20] Liq | [21] 10 |
| [22] Cathode | [23] Al | [24] 1,000 |

TABLE 2

| Device performance of Example 1 | | | | | | |
|---|---|---|---|---|---|---|
| | | | | At 1,000 nits | | |
| Example | H-Host | Color | Maximum emission wavelength [nm] | Voltage [V] | LE [cd/A] | EQE [%] |
| Example 1 | H1 | red | 625 | 5.5 | 10.3 | 12.2 |

Based on the device data in Table 2 it is indicated that inventive compound H1 works as red phosphorescence host material with reasonable performance.

What is claimed is:

1. A compound of Formula I:

Formula I

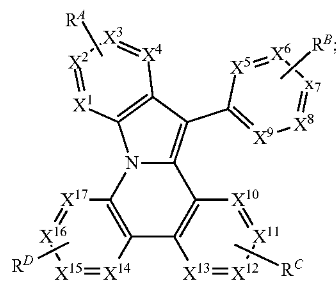

wherein each $X^1$-$X^{17}$ is independently C or N;

$R^A$, $R^B$, $R^C$, and $R^D$ each independently represent mono to the maximum allowable substitution, or no substitution;

each $R^A$, $R^B$, $R^C$, and $R^D$ is independently a hydrogen or a substituent selected from the group consisting of deuterium, halogen, alkyl, cycloalkyl, heteroalkyl, heterocycloalkyl, boryl, germyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof;

wherein at least one of the following conditions (i) or (ii) is true:

(i) at least one of $R^C$ and $R^D$ is joined to its respective ring by a single bond and comprises pyrimidine, triazine, quinazoline, benzene, biphenyl, terphenyl, naphthalene, phenanthrene, anthracene, triphenylene, pyridine, pyrazine, fluorene, dibenzofuran, dibenzothiophene, carbazole, quinoline, isoquinoline, triarylboryl or quinoxaline, which may be further substituted;

(ii) at least one of $R^A$ and $R^B$ is selected from the group consisting of the following structures:

-continued
$R^{A11}$
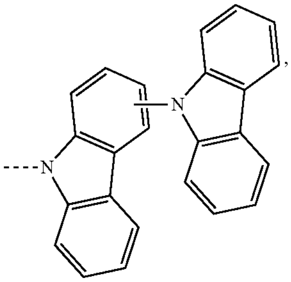
$R^{A12}$
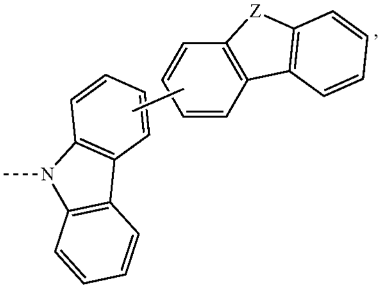
$R^{A13}$
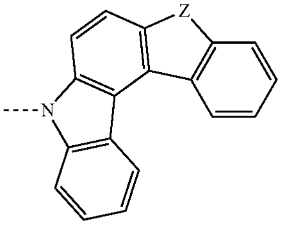
$R^{A14}$
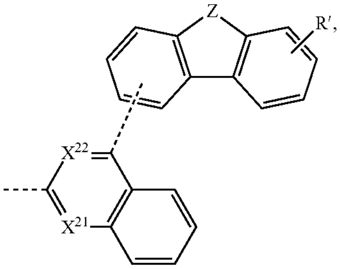
$R^{A15}$
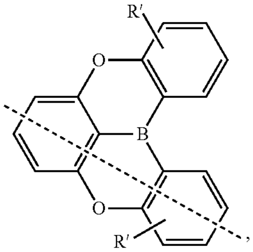
$R^{A16}$
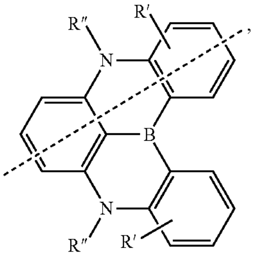
$R^{12}$
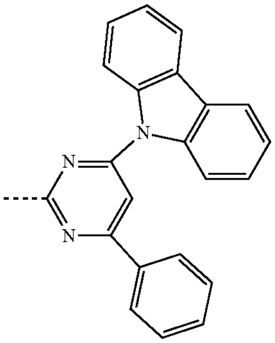
$R^{13}$
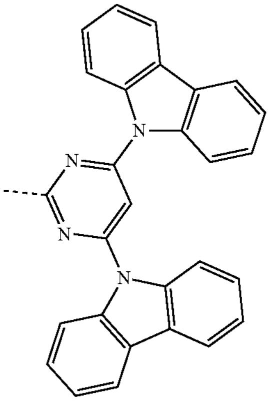
$R^{18}$
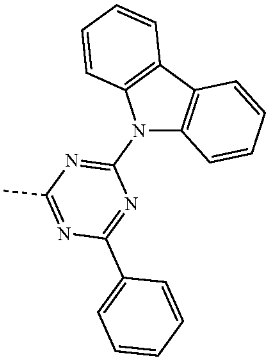
$R^{19}$
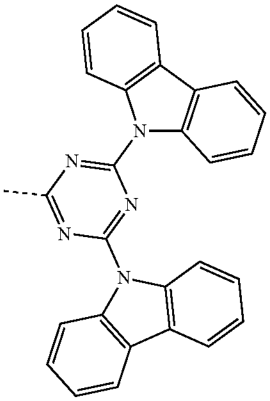

R20
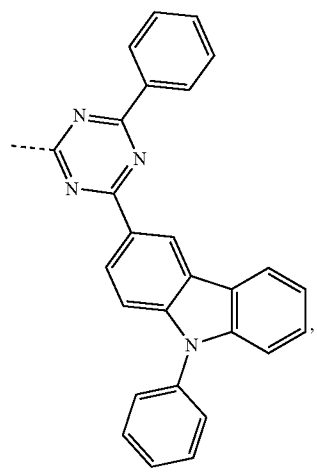
R21
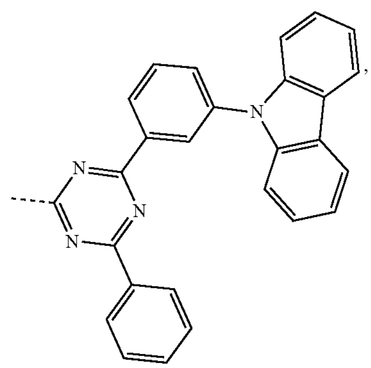
R22
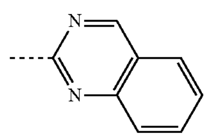
R23
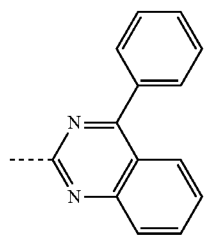
R37
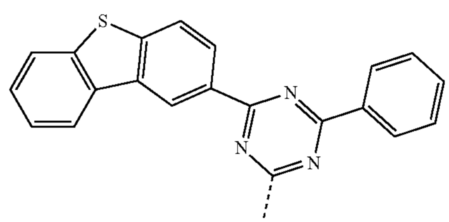
R38
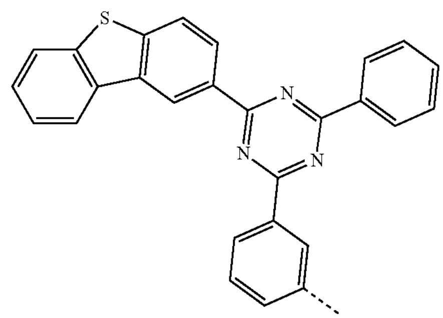
R39
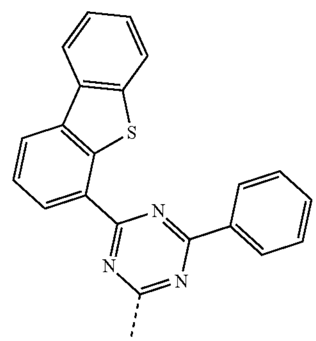
R40
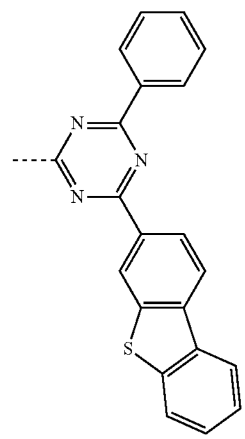
R41
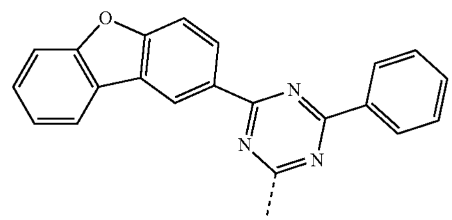
R42
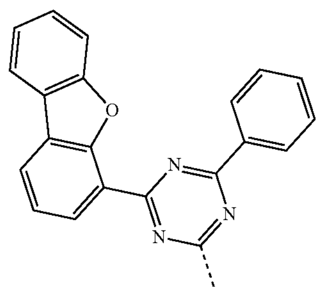

-continued
R43
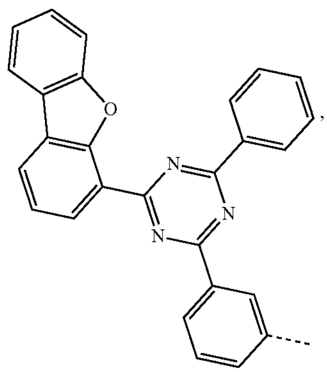
R44
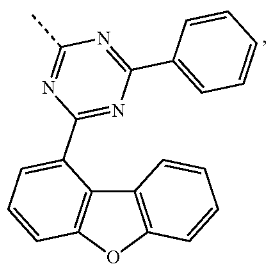
R45
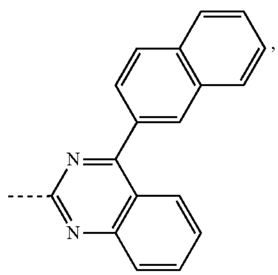
R46
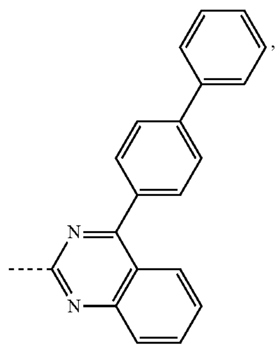
R47
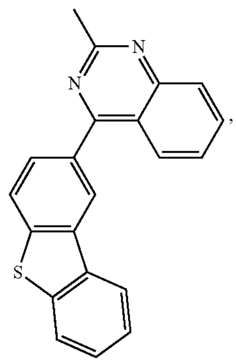
-continued
R48
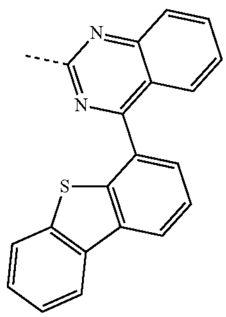
R49
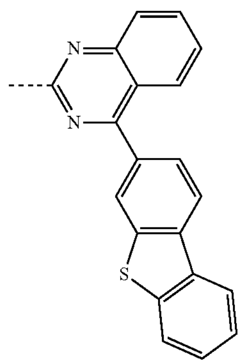
R50
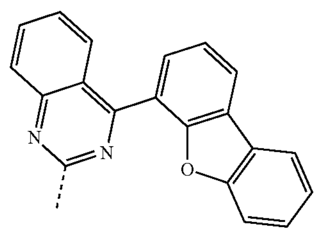
R51
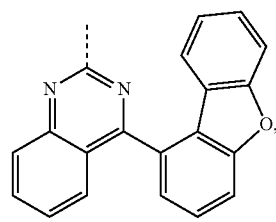
R52
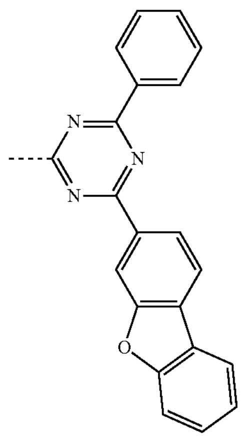

R[55]
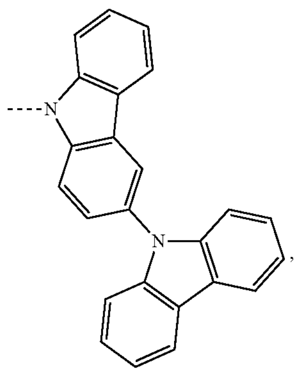
R[56]
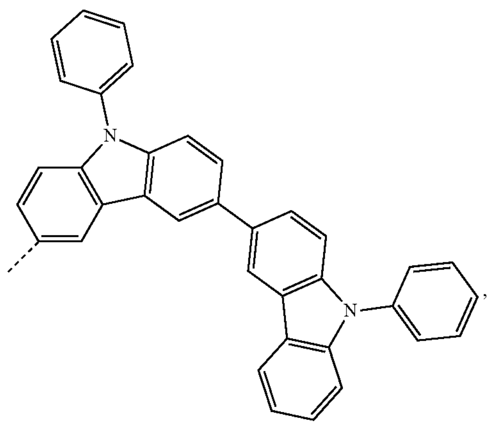
R[57]
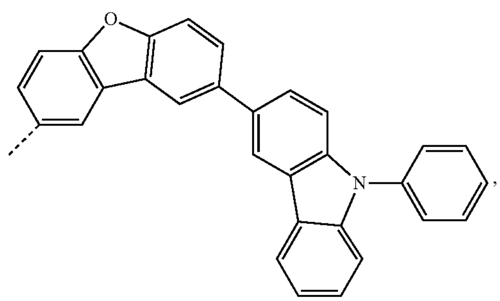
R[58]
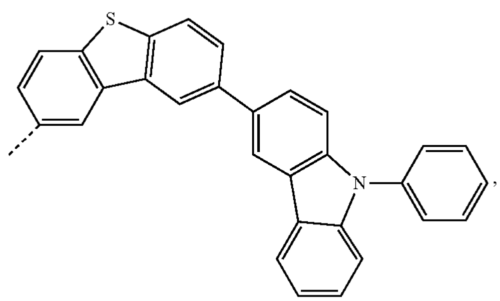
R[59]
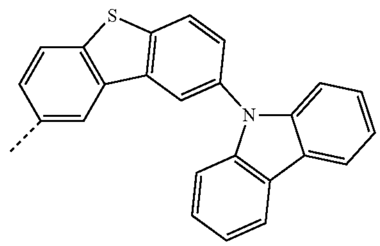
R[60]
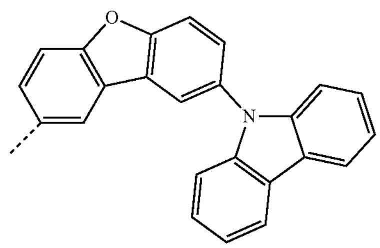
R[61]
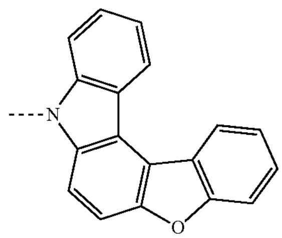
R[62]
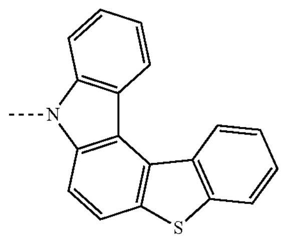
R[63]
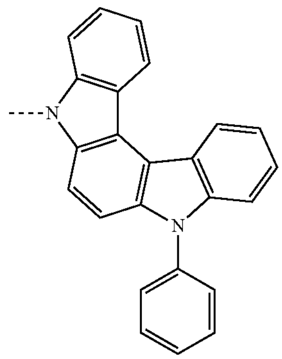
R[64]
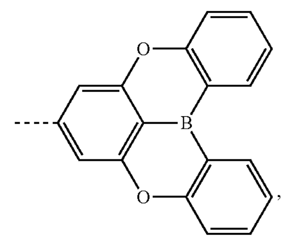

-continued $R^{66}$

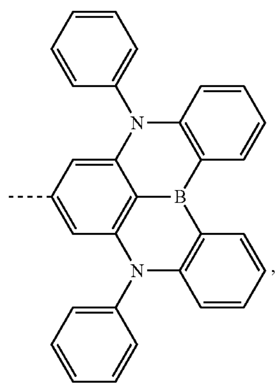

$R^{67}$

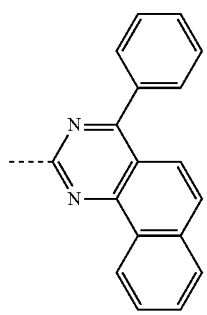

$R^{68}$

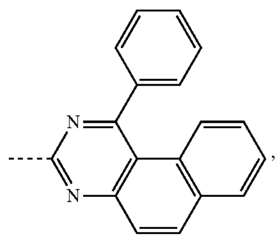

$R^{69}$

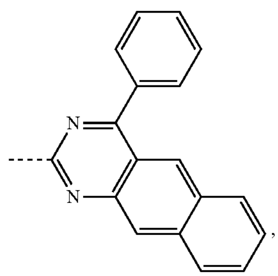

$R^{70}$

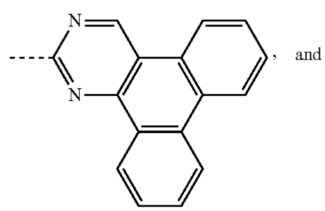

and

-continued $R^{71}$

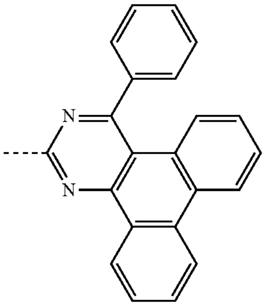

;

wherein R' and R" is independently a hydrogen or a substituent selected from the group consisting of aryl, phenyl, biphenyl, naphthyl, carbazolyl, triazinyl, pyrimidinyl, quinazolinyl and triphenylenyl; $X^{21}$ and $X^{22}$ is independently C or N; and Z represents NR", O, or S, with R" being aryl or heteroaryl.

2. The compound of claim 1, wherein each of $R^A$, $R^B$, $R^C$, and $R^D$ is independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

3. The compound of claim 1, wherein one or two of $R^A$, $R^B$, $R^C$, and $R^D$ comprises pyrimidine, triazine, quinazoline, carbazole, benzene, biphenyl, naphthalene, or triphenyl.

4. The compound of claim 1, wherein $X^1$-$X^{17}$ are C.

5. The compound of claim 1, wherein exact one of $X^1$-$X^{17}$ is N.

6. The compound of claim 1, wherein at least one of $X^1$-$X^4$ is N.

7. The compound of claim 1, wherein at least one of $X^5$-$X^9$ is N.

8. The compound of claim 1, wherein at least one of $X^{10}$-$X^{13}$ is N.

9. The compound of claim 1, wherein at least one of $X^{14}$-$X^{17}$ is N.

10. The compound of claim 1, wherein at least one of $R^A$, $R^B$, $R^C$ and $R^D$ is selected from the group consisting of any one of $R^{A1}$ to $R^{A16}$ as following:

$R^{A1}$

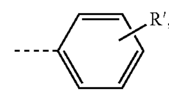

$R^{A2}$

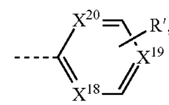

$R^{A3}$

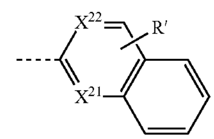

-continued $R^{A4}$

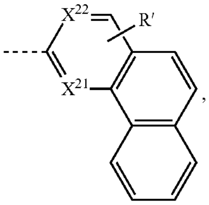

$R^{A5}$

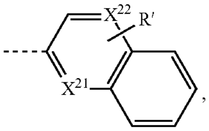

$R^{A6}$

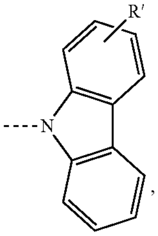

$R^{A7}$

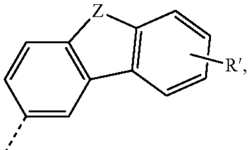

$R^{A8}$

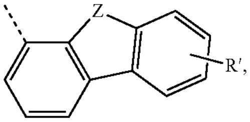

$R^{A9}$

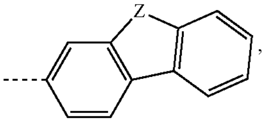

$R^{A10}$

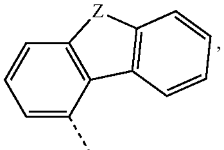

$R^{A11}$

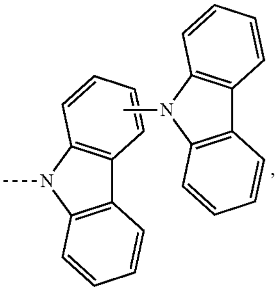

-continued $R^{A12}$

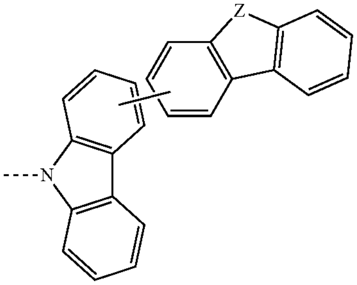

$R^{A13}$

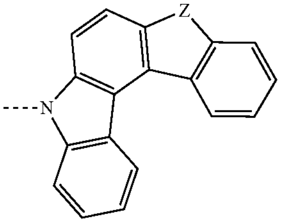

$R^{A14}$

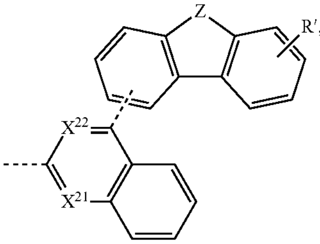

$R^{A15}$

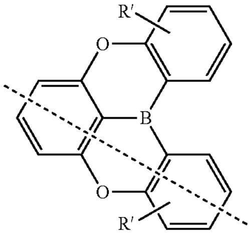

and $R^{A16}$

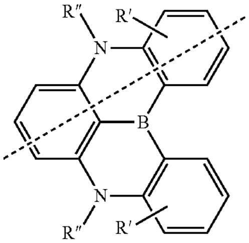

wherein

R' and R" is independently a hydrogen or a substituent selected from the group consisting of aryl, phenyl, biphenyl, naphthyl, carbazolyl, triazinyl, pyrimidinyl, quinazolinyl and triphenylenyl;

$X^{18}$-$X^{22}$ is C or N; and

Z represents NR", O, or S, with R" being aryl or heteroaryl.

11. The compound of claim 1, wherein at least one of $R^A$, $R^B$, $R^C$ and $R^D$ is selected from the group consisting of -continued
$R^1$
$R^2$
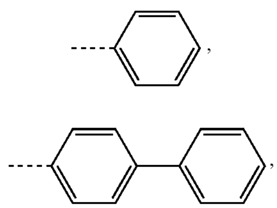
$R^3$
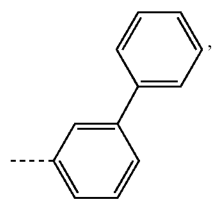
$R^4$
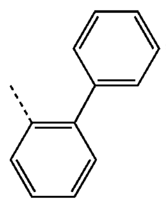
$R^5$
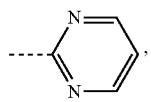
$R^6$
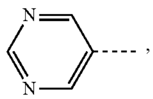
$R^7$
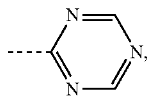
$R^8$
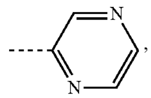
$R^9$
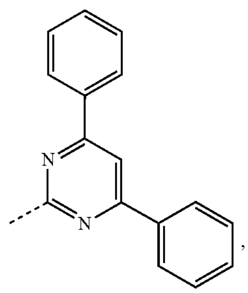
$R^{10}$
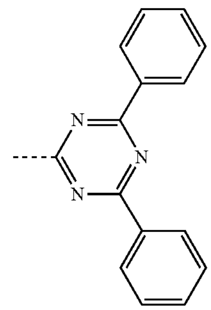
$R^{11}$
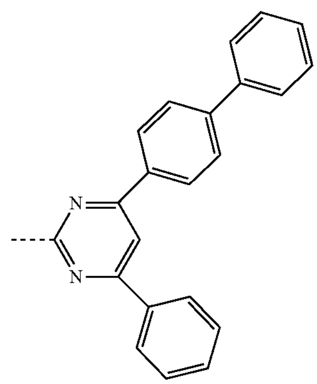
$R^{12}$
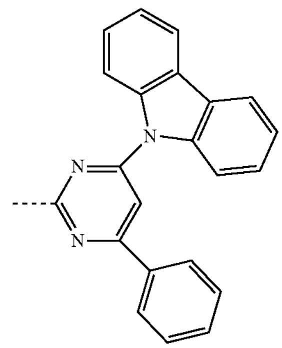
$R^{13}$
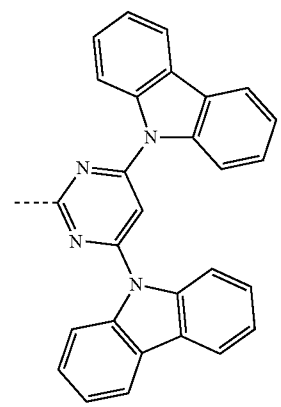

-continued
R[14]
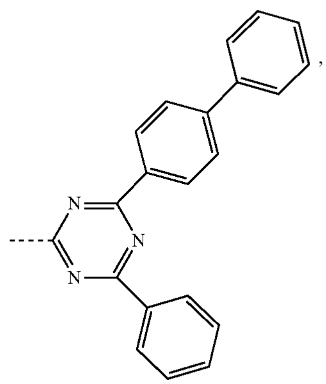
,
R[15]
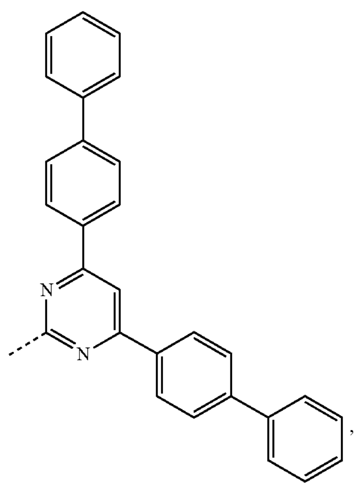
,
R[16]
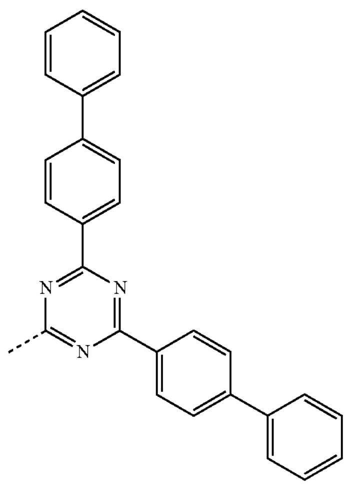
,
-continued
R[17]
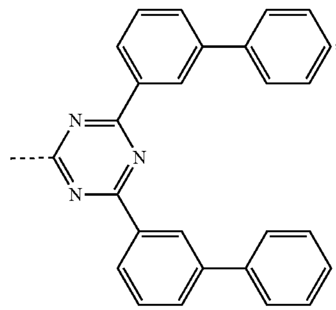
,
R[18]
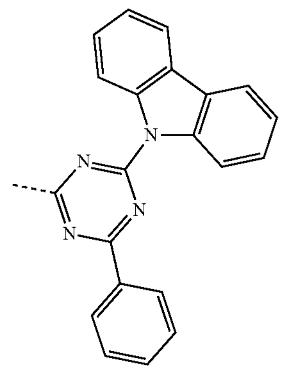
,
R[19]
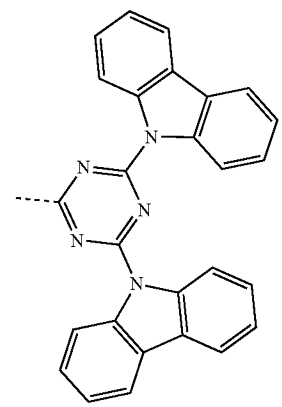
,
R[20]
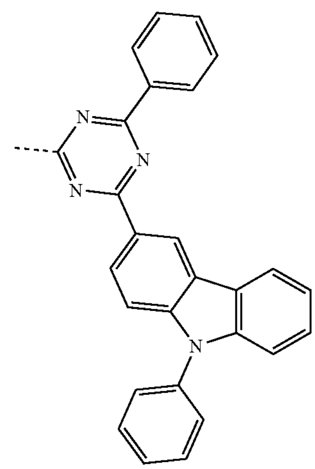
, -continued
$R^{21}$
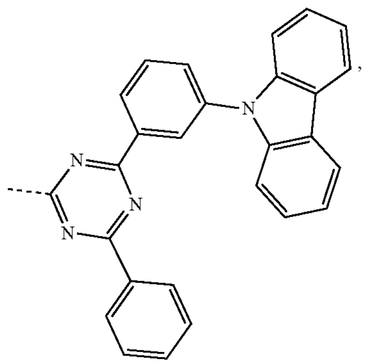,
$R^{22}$
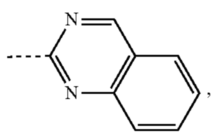,
$R^{23}$
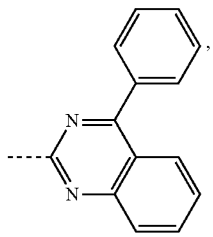,
$R^{24}$
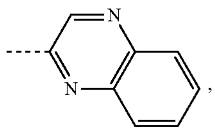,
$R^{25}$
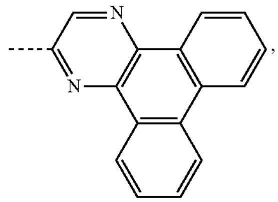,
$R^{26}$
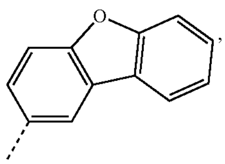,
$R^{27}$
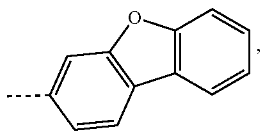,
$R^{28}$
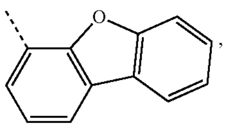,
-continued
$R^{29}$
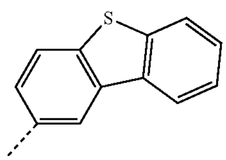,
$R^{30}$
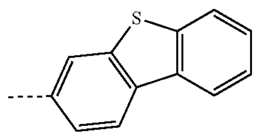,
$R^{31}$
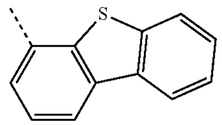,
$R^{32}$
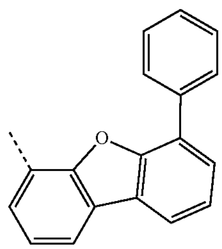,
$R^{33}$
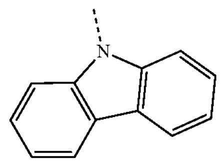,
$R^{34}$
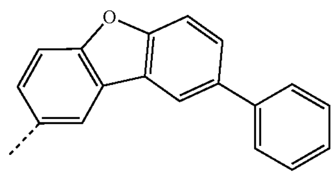,
$R^{35}$
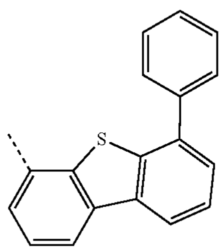,
$R^{36}$
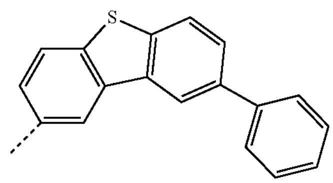, -continued
R[37]
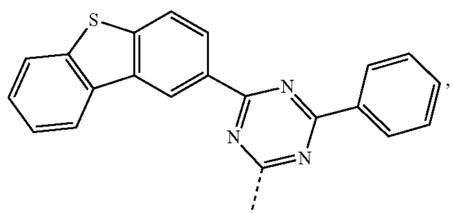
R[38]
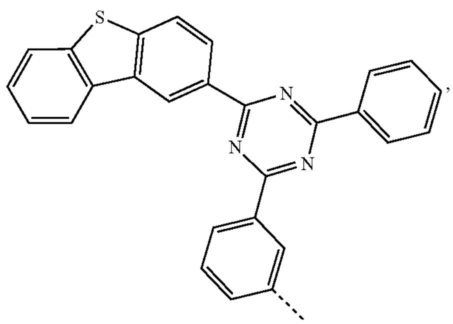
R[39]
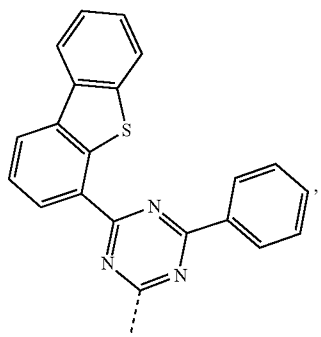
R[40]
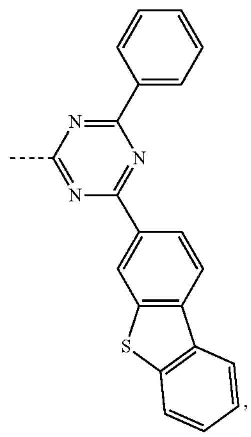
R[41]
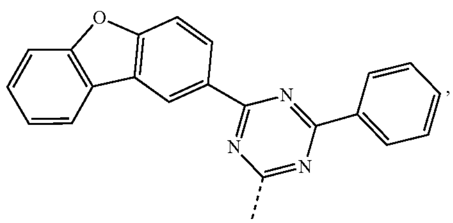
-continued
R[42]
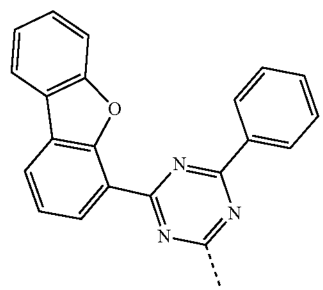
R[43]
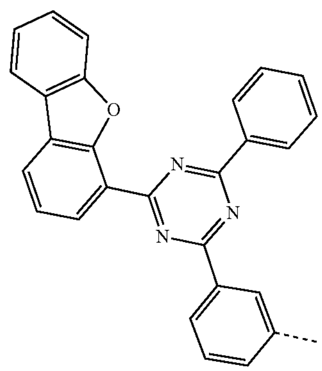
R[44]
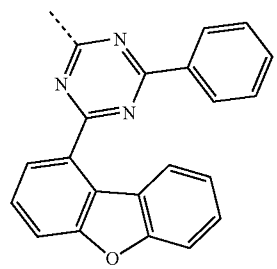
R[45]
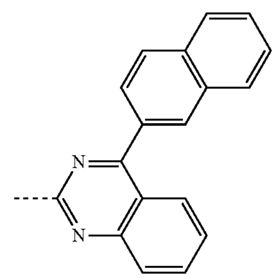
R[46]
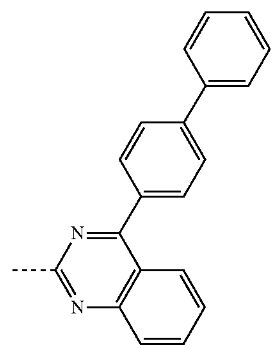

-continued
R47
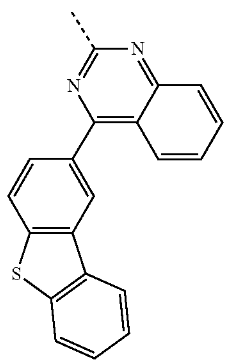
R48
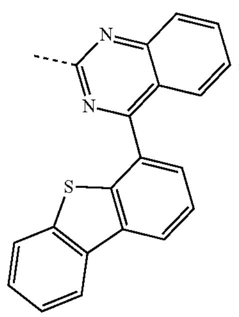
R49
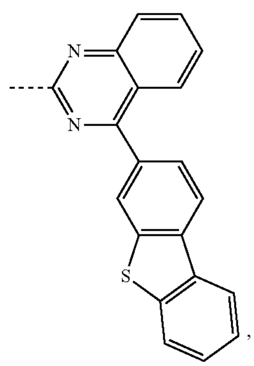
R50
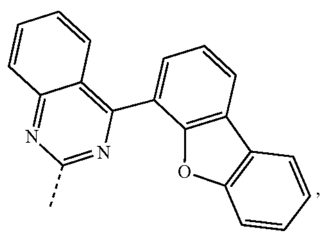
R51
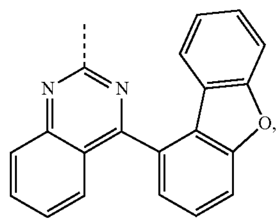
-continued
R52
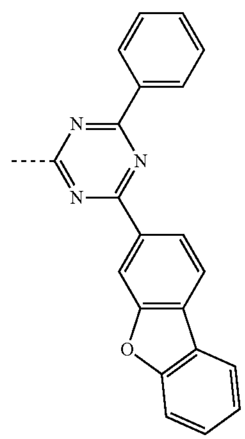
R53
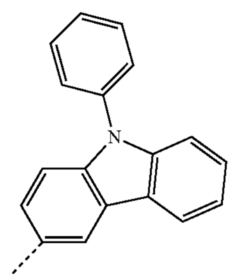
R54
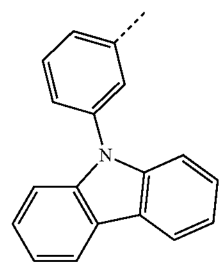
R55
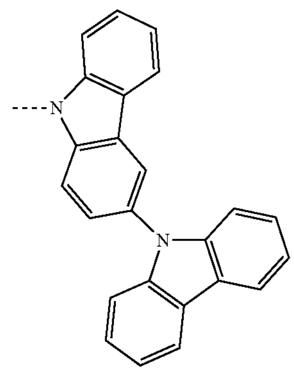

-continued
$R^{56}$
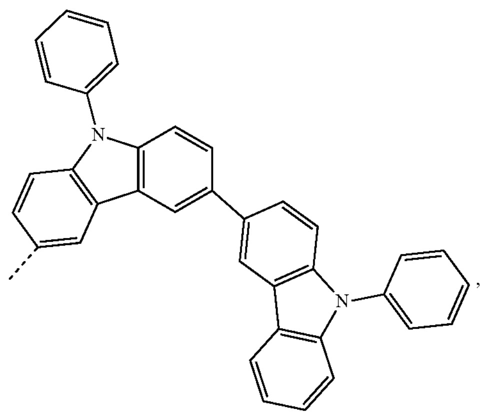
,
$R^{57}$
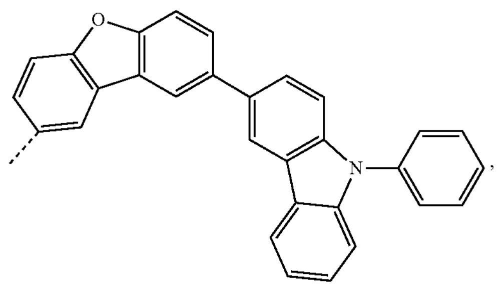
,
$R^{58}$
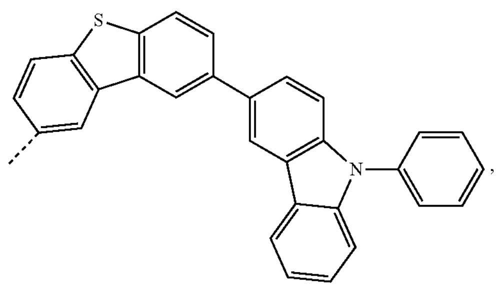
,
$R^{59}$
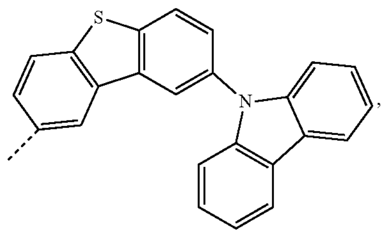
,
$R^{60}$
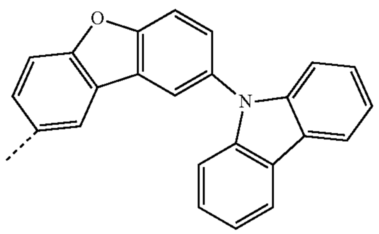
,
$R^{61}$
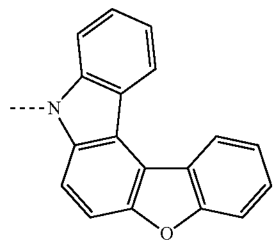
,
$R^{62}$
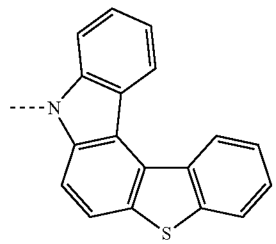
,
$R^{63}$
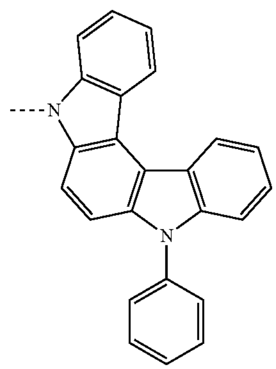
,
$R^{64}$
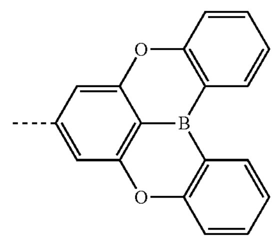
,
$R^{66}$
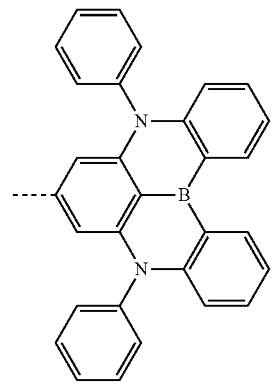
, -continued
$R^{67}$
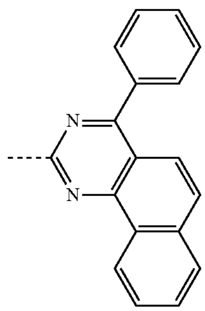
$R^{68}$
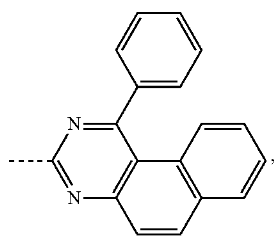
$R^{69}$
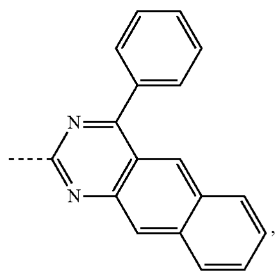
$R^{70}$
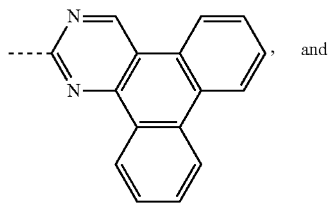
and
$R^{71}$
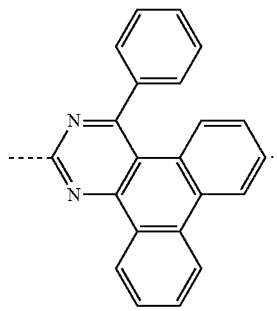
12. The compound of claim 1, wherein the compound is selected from the group consisting of:
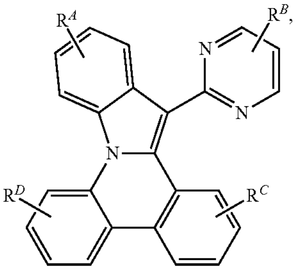
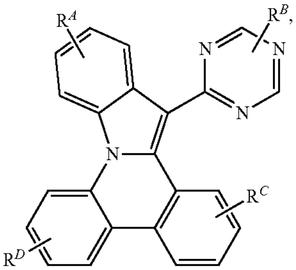
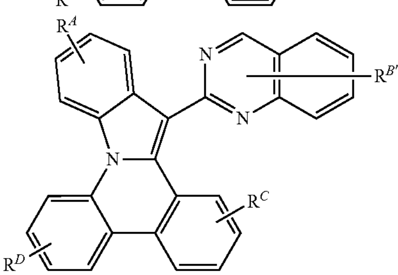
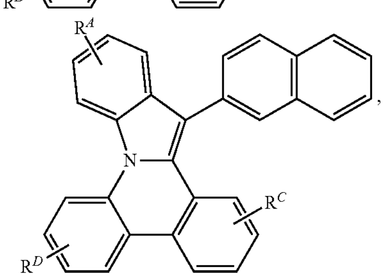
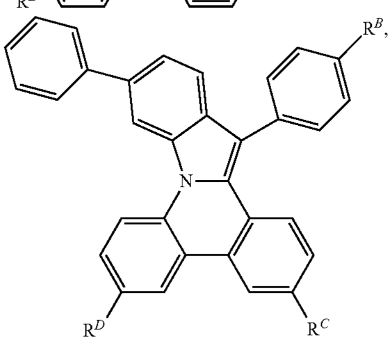
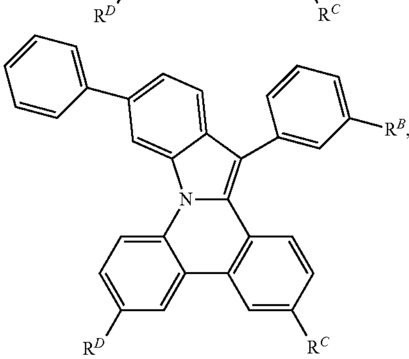

-continued
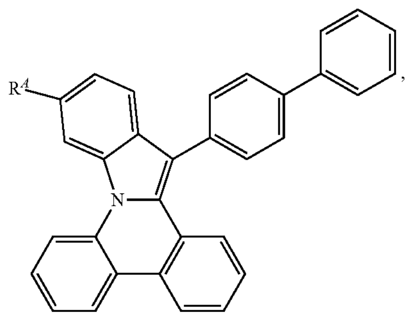
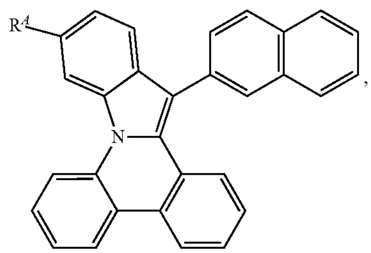
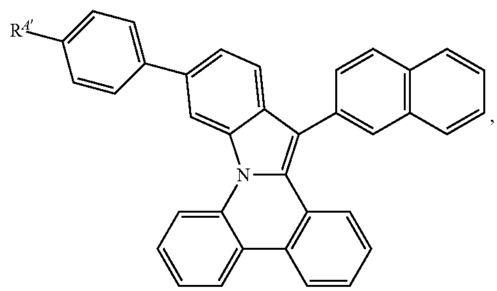
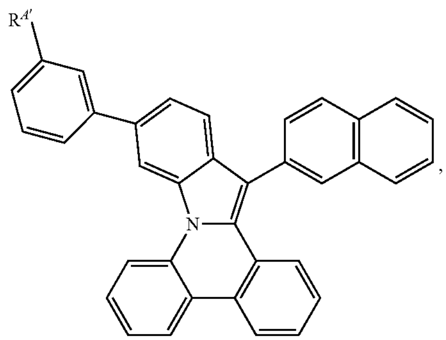
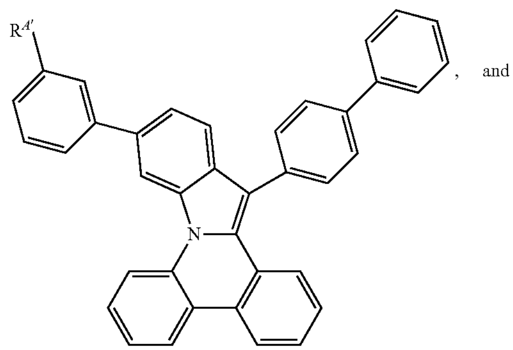
and
-continued
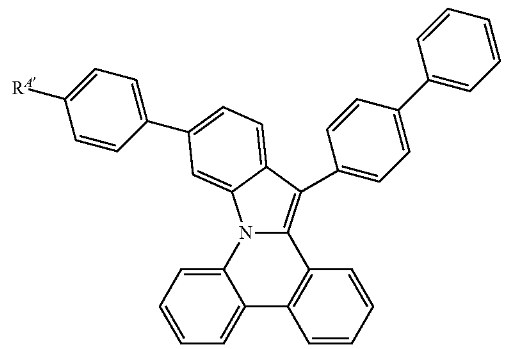
13. The compound of claim 1, wherein the compound is selected from the group consisting of:
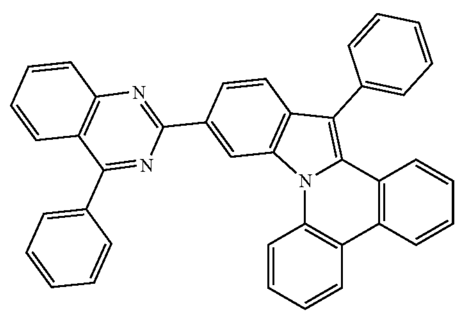
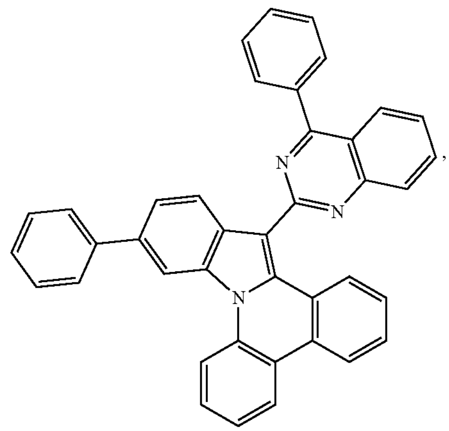
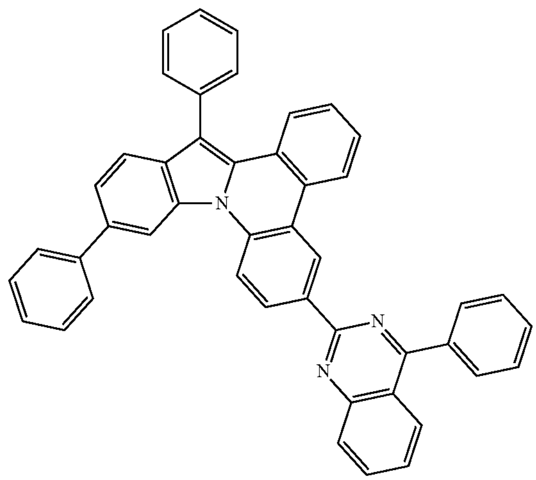

-continued
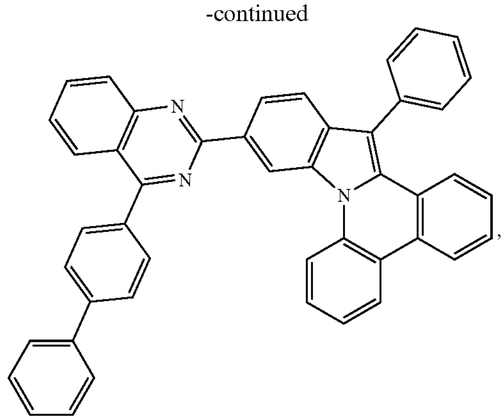
,
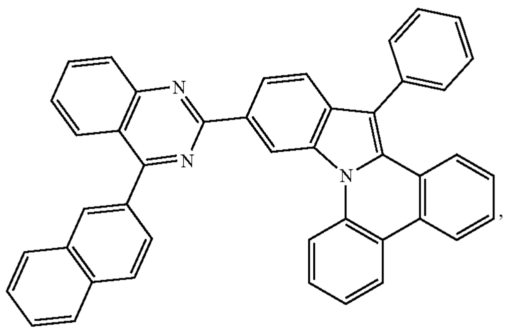
,
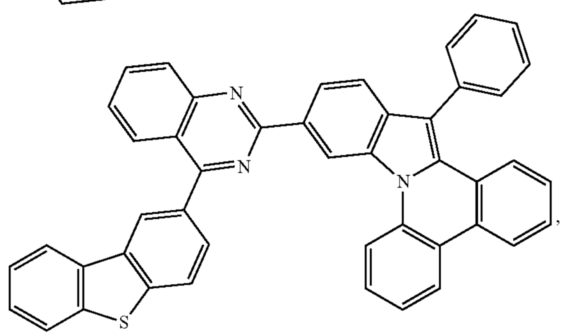
,
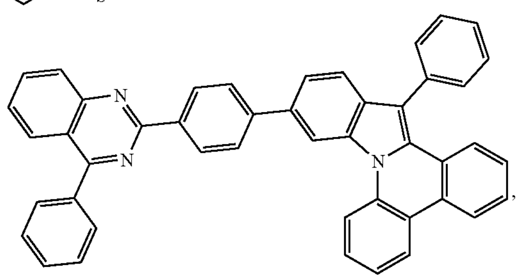
,
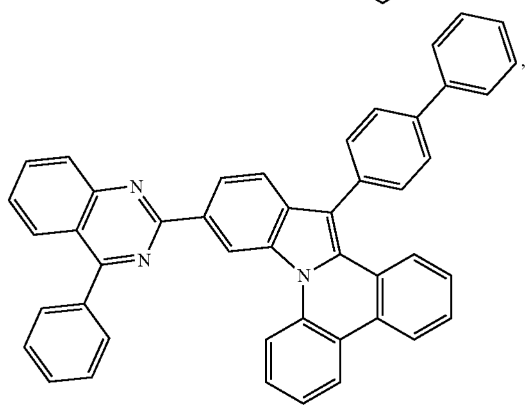
,
-continued
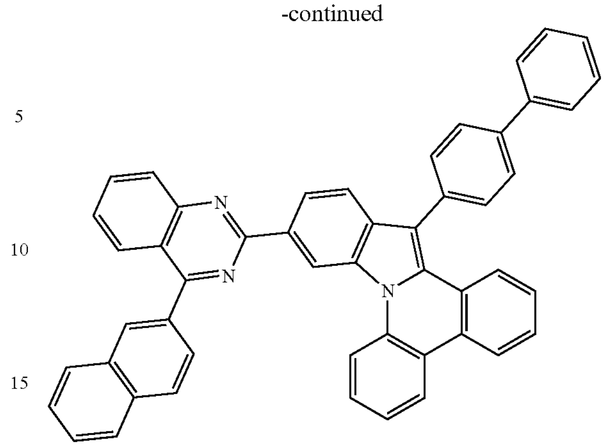
,
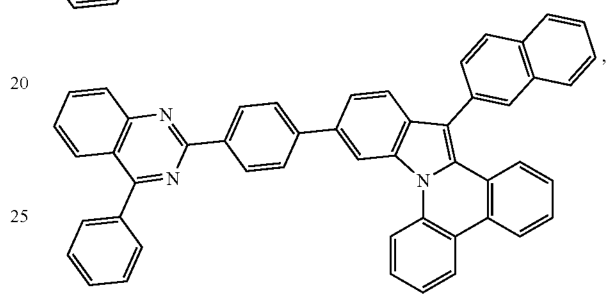
,
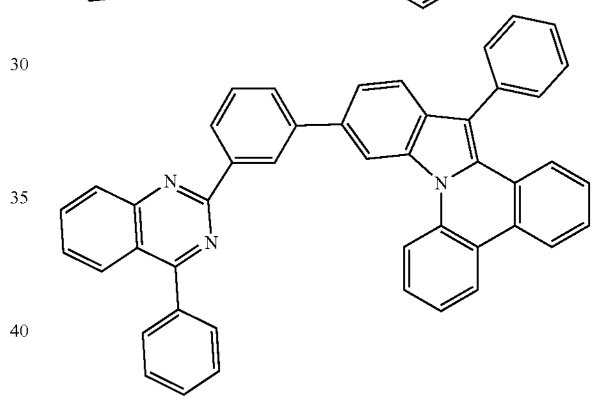
,
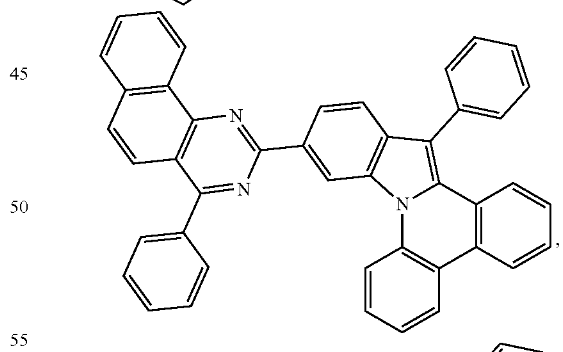
,
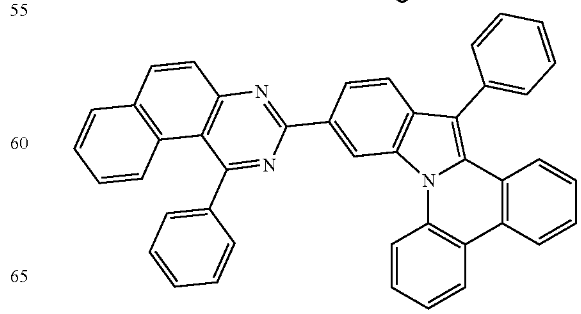
, -continued
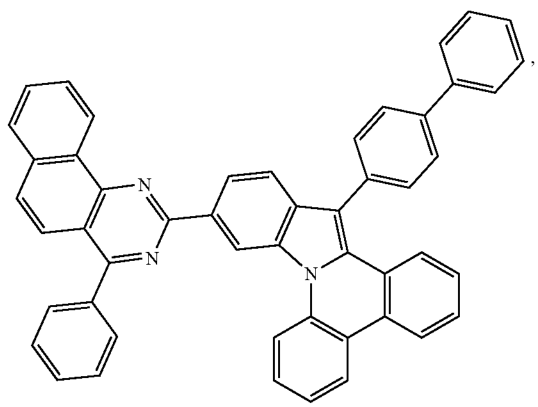
,
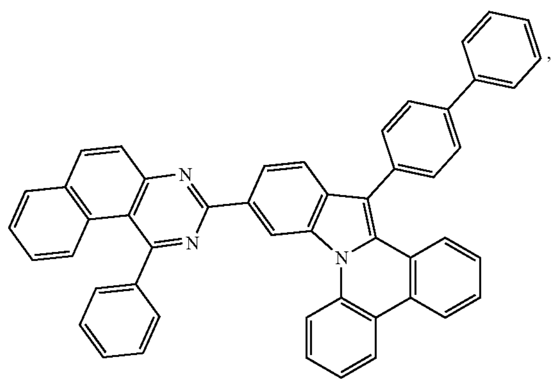
,
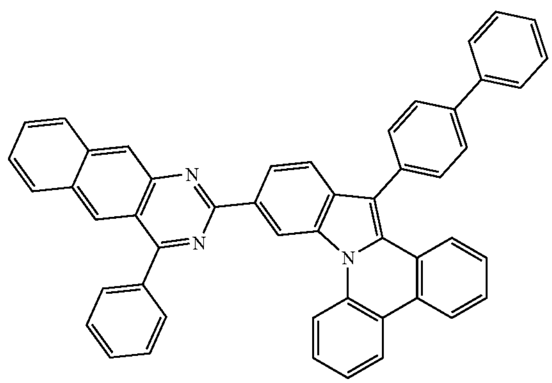
,
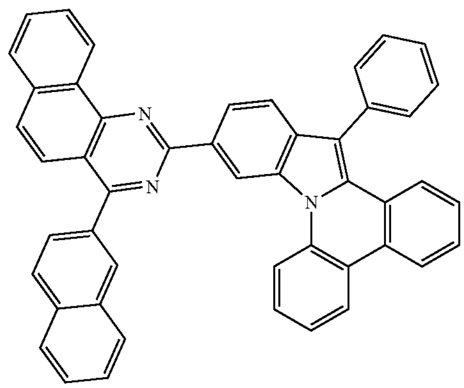
,
-continued
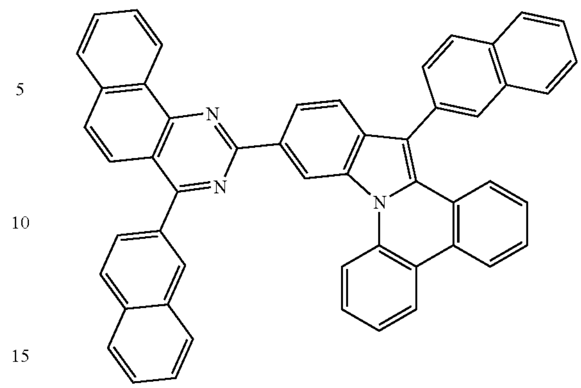
,
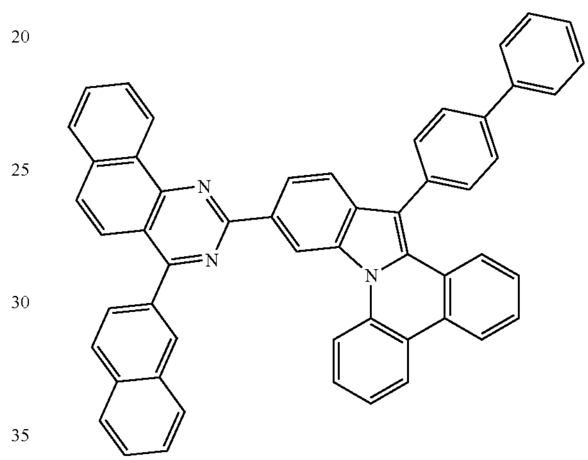
,
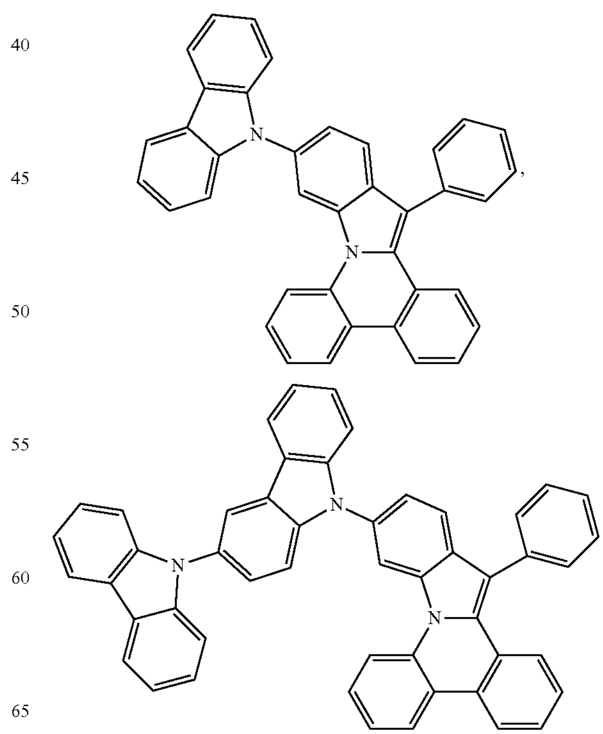
, -continued
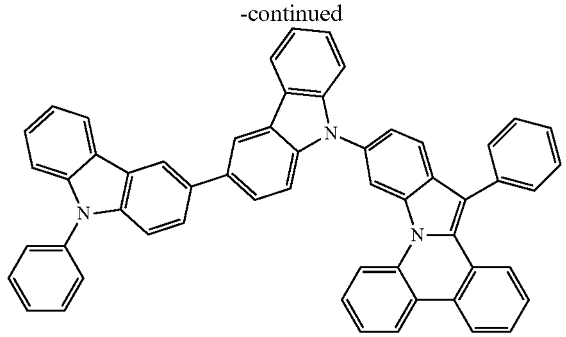
,
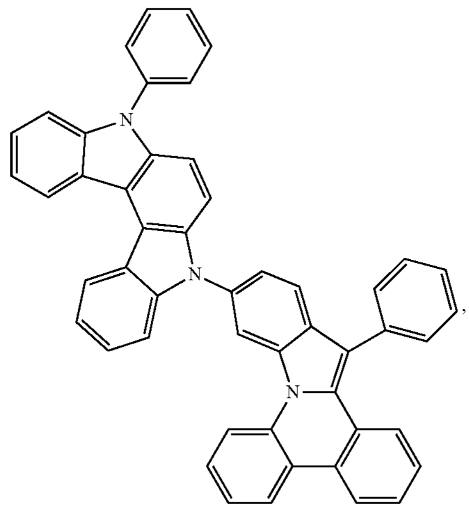
,
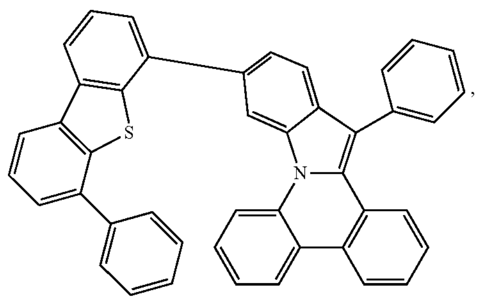
,
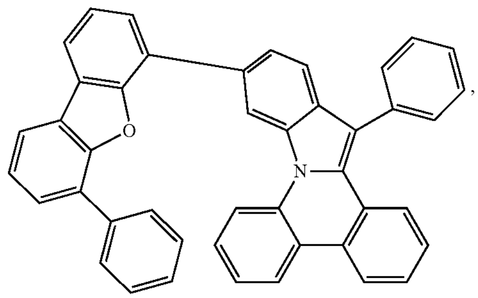
,
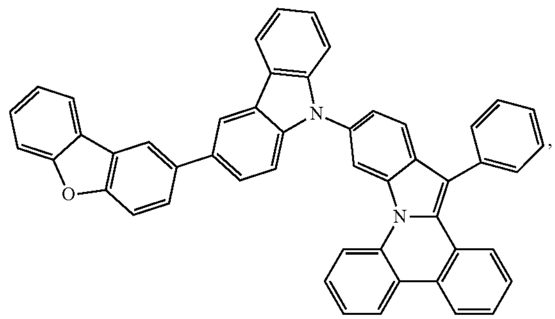
,
-continued
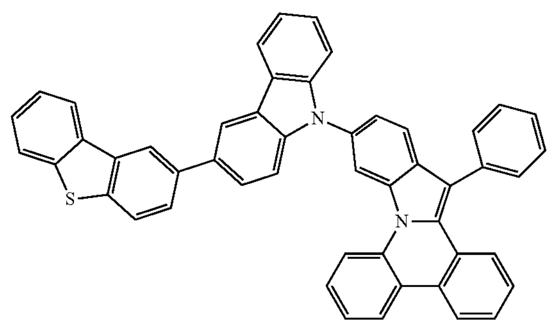
,
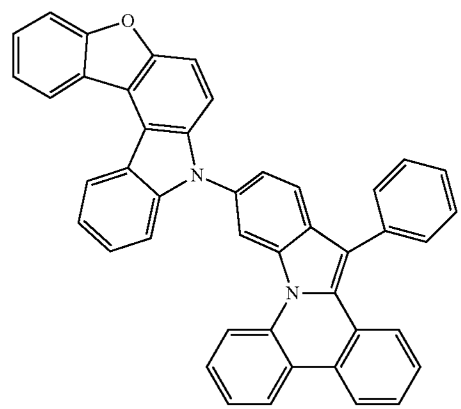
,
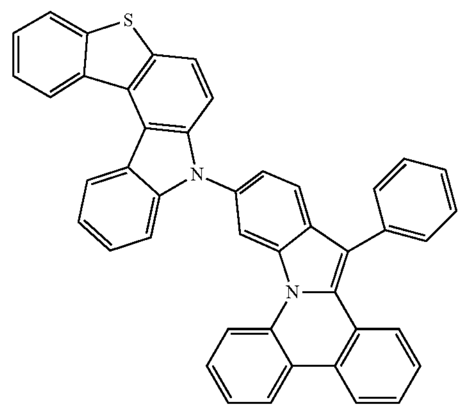
,
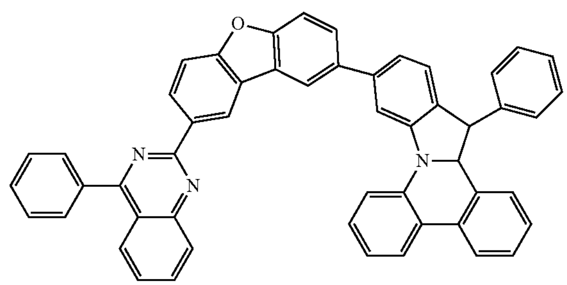
,
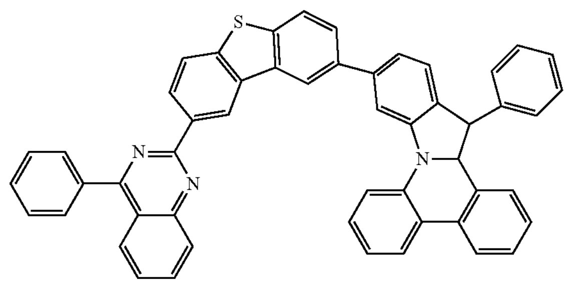
, -continued
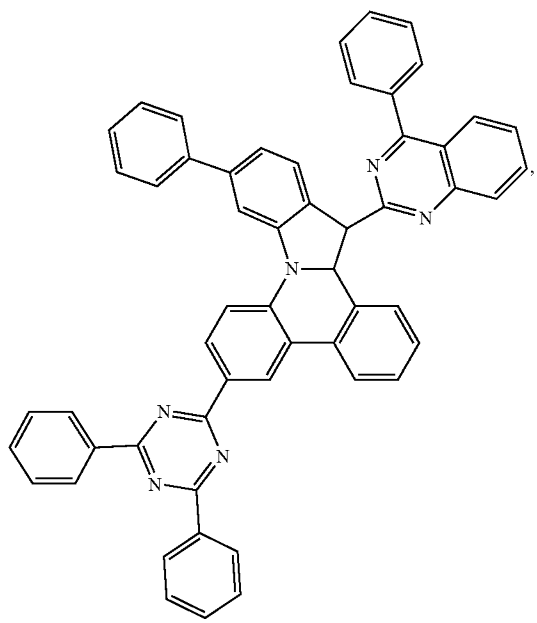
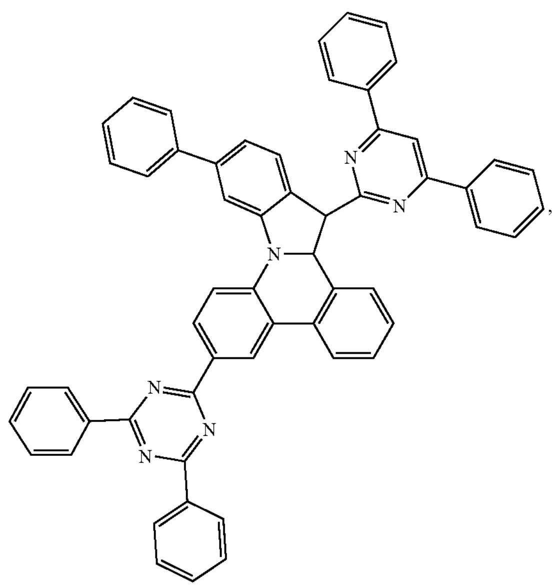
-continued
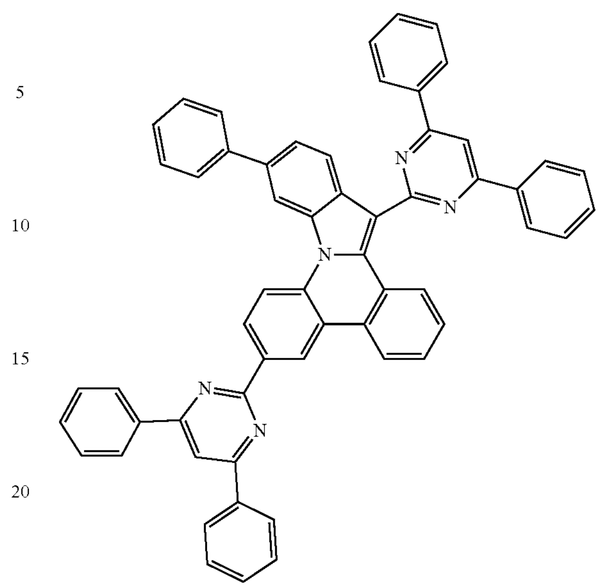
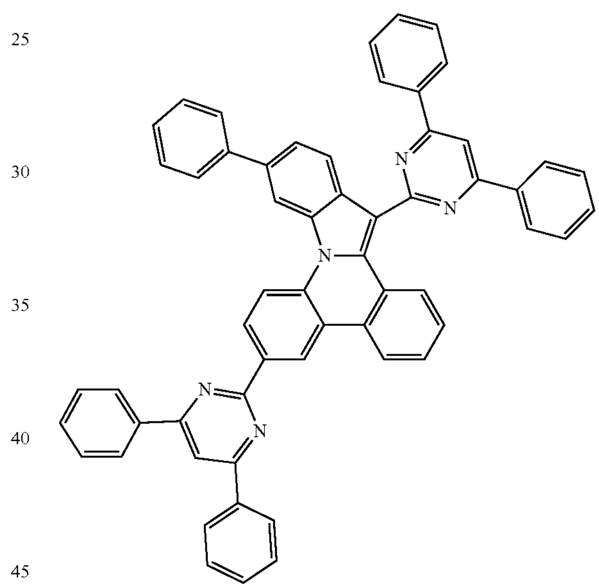
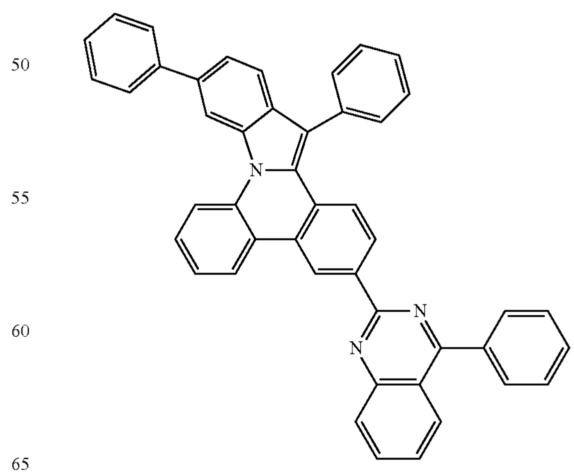

-continued
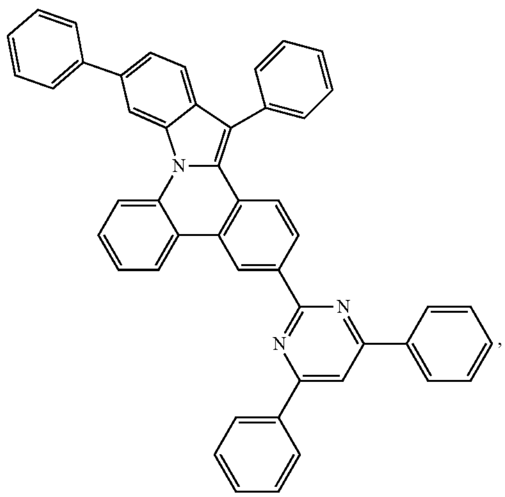
,
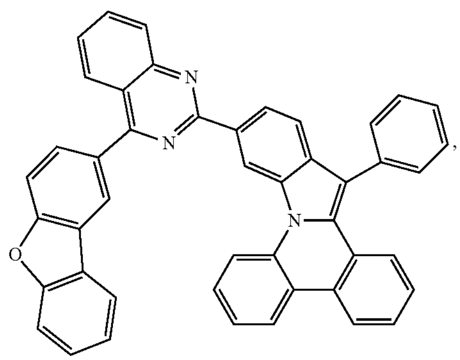
,
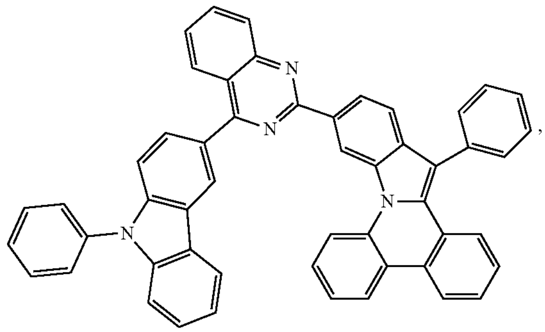
,
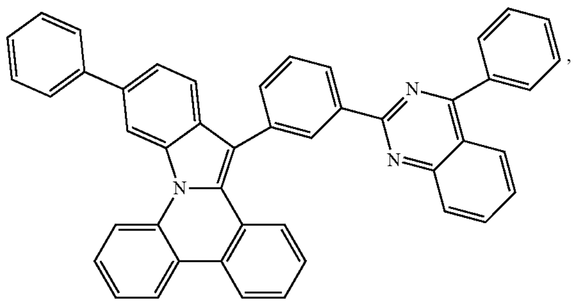
,
-continued
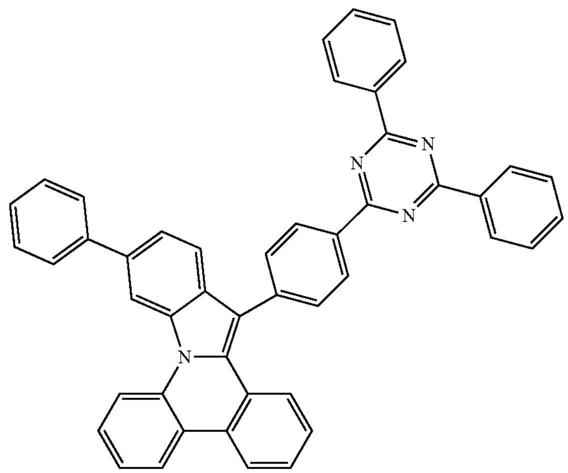
,
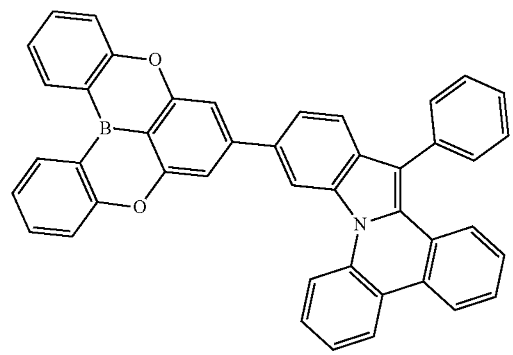
,
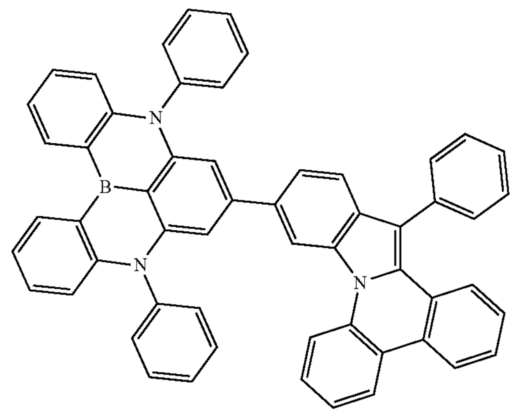
,
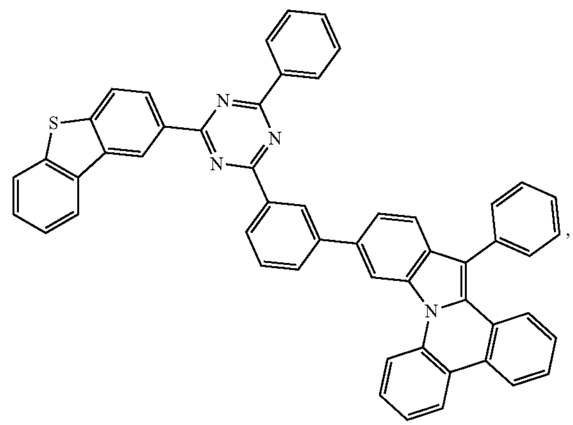
, -continued
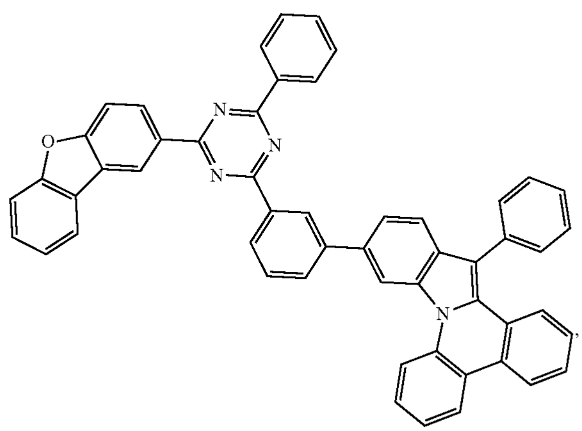
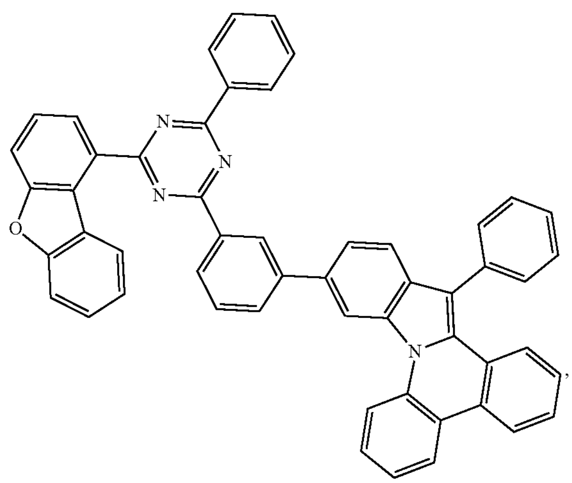
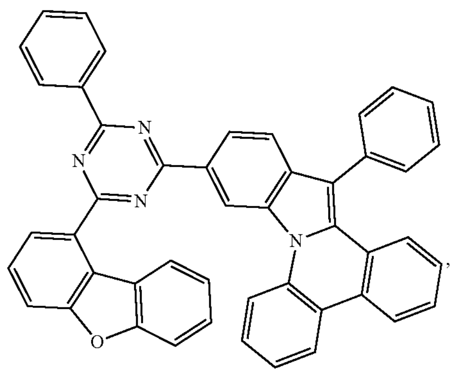
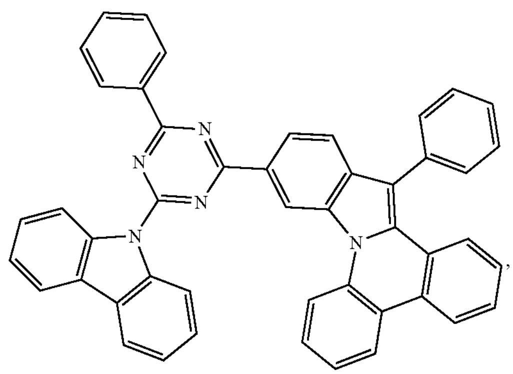
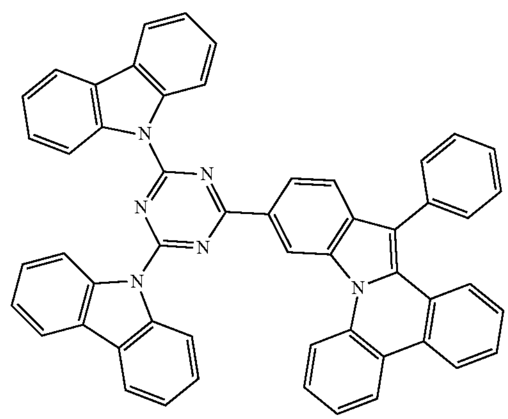
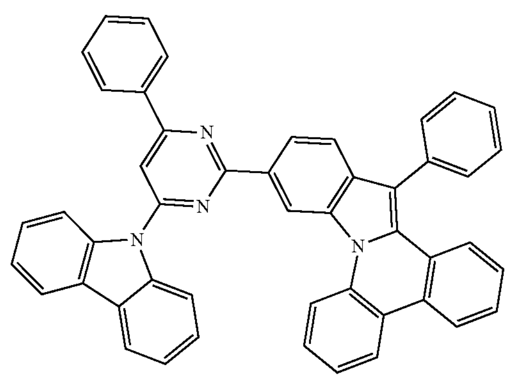
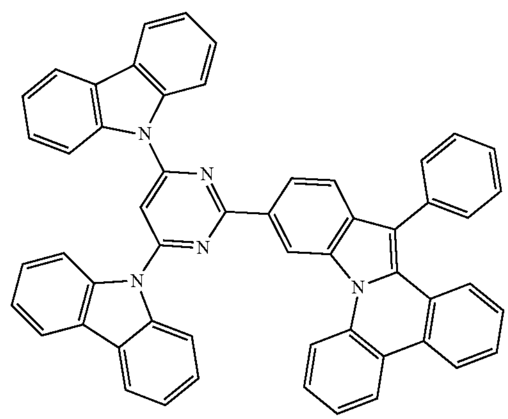
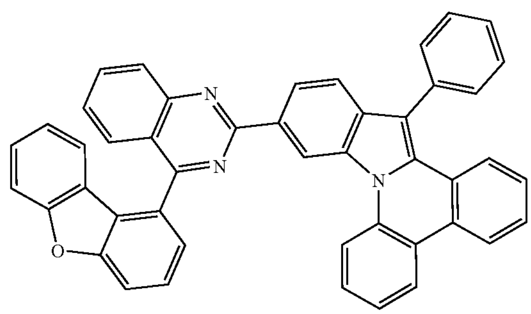

-continued
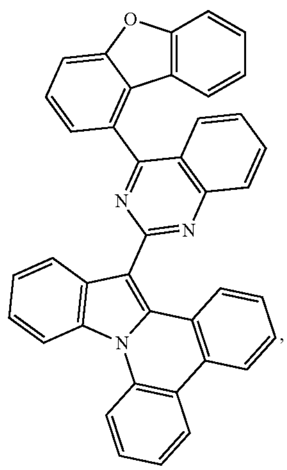
,
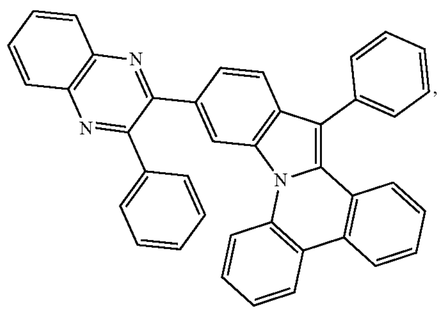
,
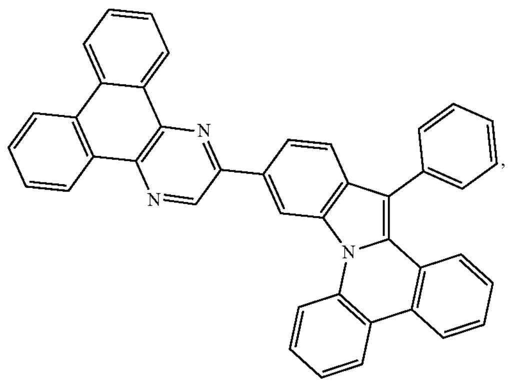
,
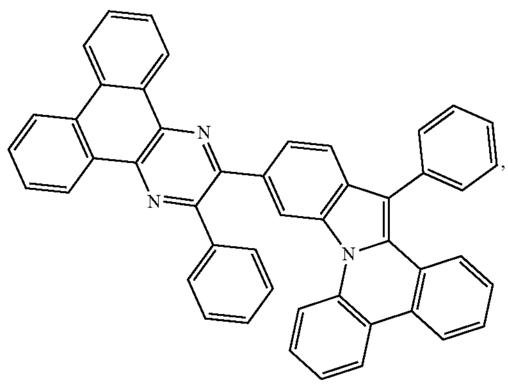
,
-continued
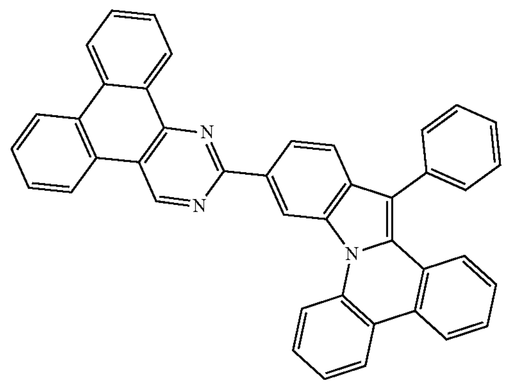
,
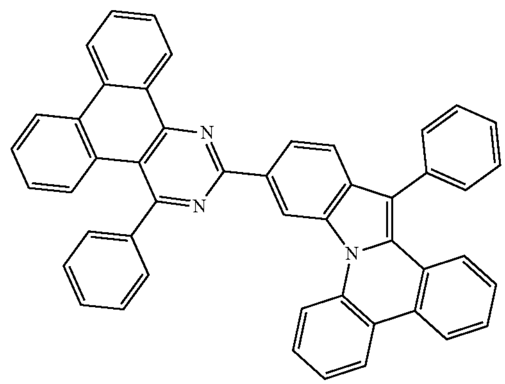
,
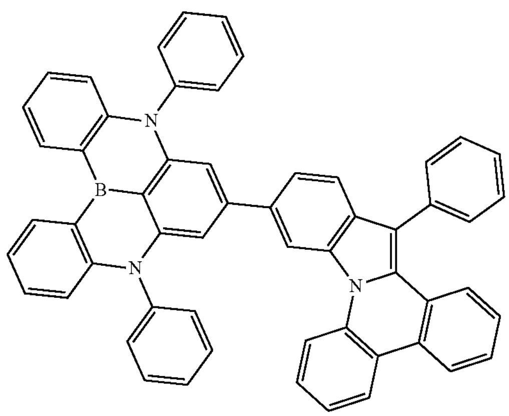
,
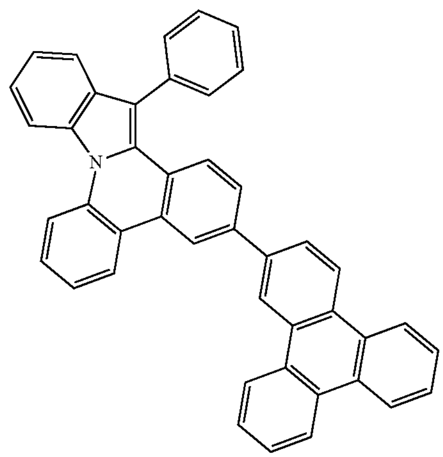
, -continued

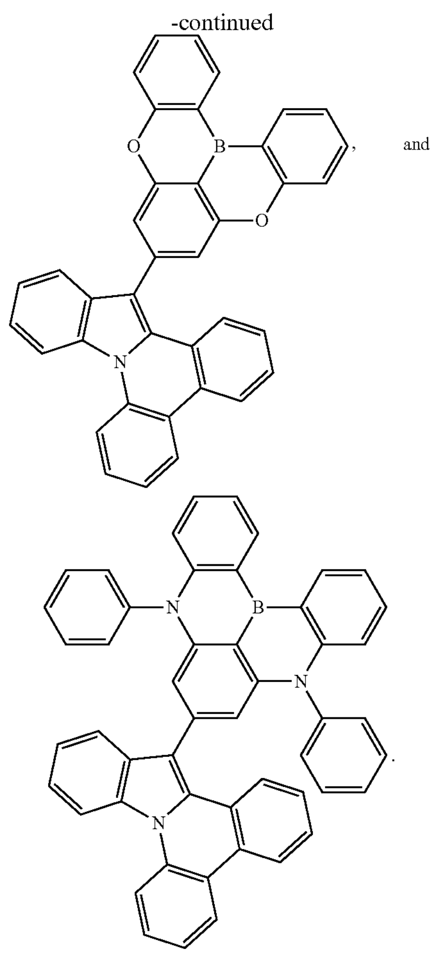

and

14. An organic light emitting device (OLED) comprising:

an anode;

a cathode; and an organic layer disposed between the anode and the cathode, wherein the organic layer comprises a compound of Formula I:

Formula I

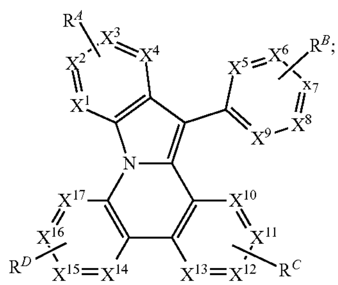

wherein each $X^1$-$X^{17}$ is independently C or N;

$R^A$, $R^B$, $R^C$, and $R^D$ each independently represent mono to the maximum allowable substitution, or no substitution;

each $R^A$, $R^B$, $R^C$, and $R^D$ is independently a hydrogen or a substituent selected from the group consisting of deuterium, halogen, alkyl, cycloalkyl, heteroalkyl, heterocycloalkyl, boryl, germyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof;

wherein at least one of the following conditions (i) or (ii) is true:

(i) at least one of $R^C$ and $R^D$ is joined to its respective ring by a single bond and comprises pyrimidine, triazine, quinazoline, benzene, biphenyl, terphenyl, naphthalene, phenanthrene, anthracene, triphenylene, pyridine, pyrazine, fluorene, dibenzofuran, dibenzothiophene, carbazole, quinoline, isoquinoline, triarylboryl or quinoxaline, which may be further substituted;

(ii) at least one of $R^A$ and $R^B$ is selected from the group consisting of the following structures:

$R^{A11}$

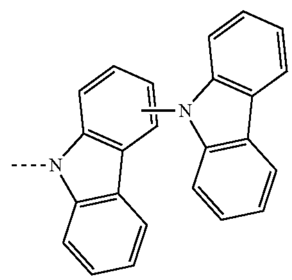

$R^{A12}$

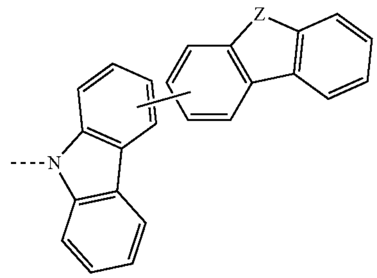

$R^{A13}$

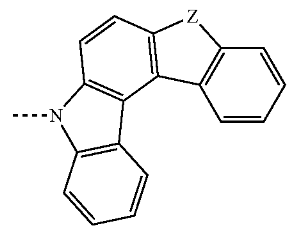

$R^{A14}$

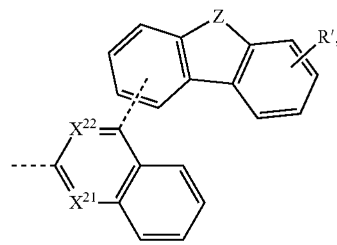

-continued
$R^{A15}$
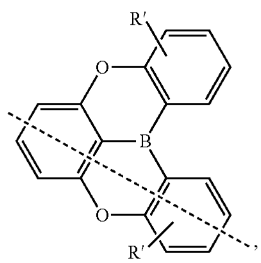
$R^{A16}$
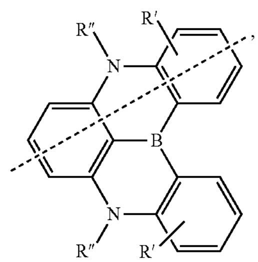
$R^{12}$
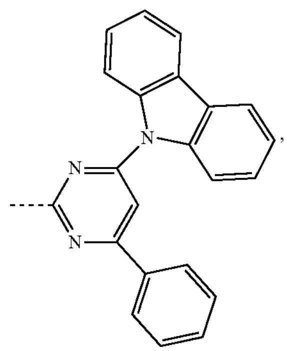
$R^{13}$
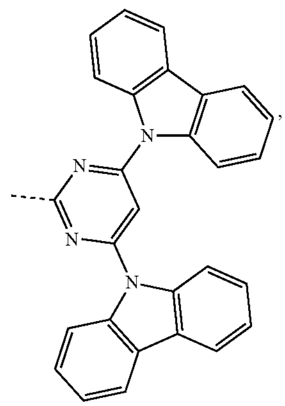
-continued
$R^{18}$
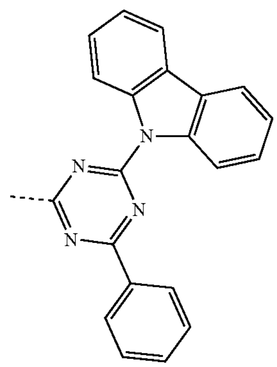
$R^{19}$
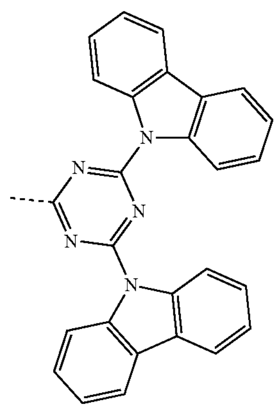
$R^{20}$
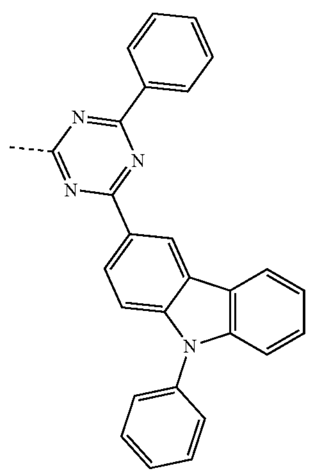
$R^{21}$
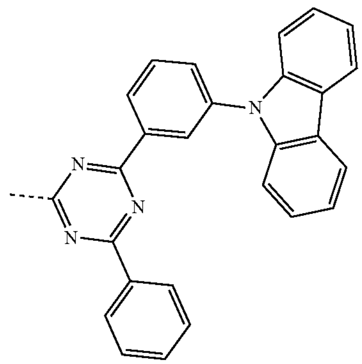

-continued
$R^{22}$
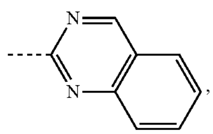
$R^{23}$
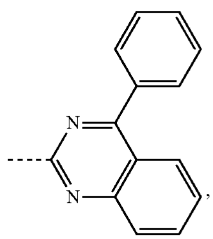
$R^{37}$
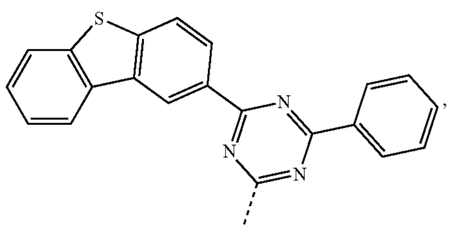
$R^{38}$
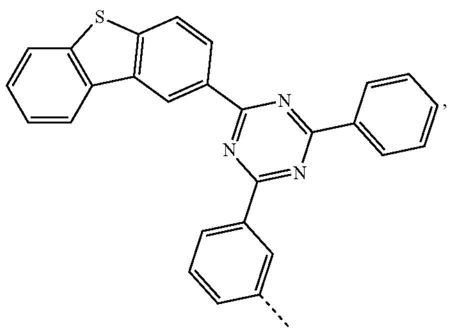
$R^{39}$
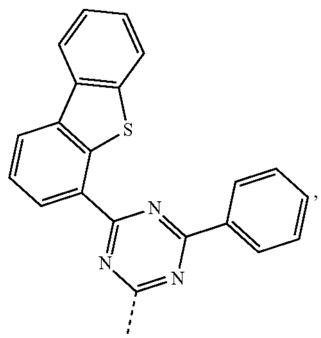
-continued
$R^{40}$
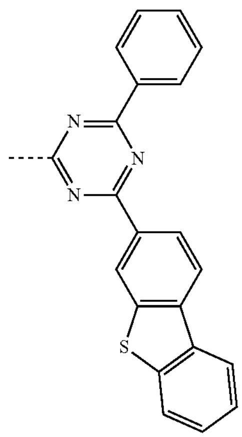
$R^{41}$
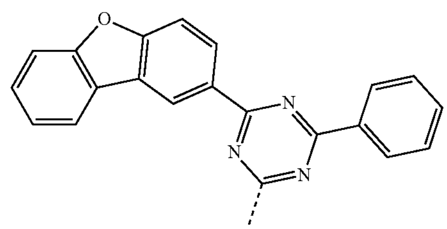
$R^{42}$
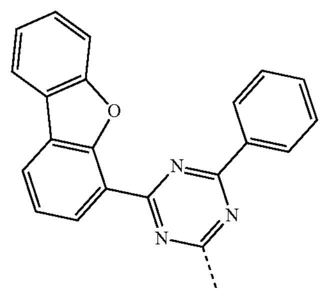
$R^{43}$
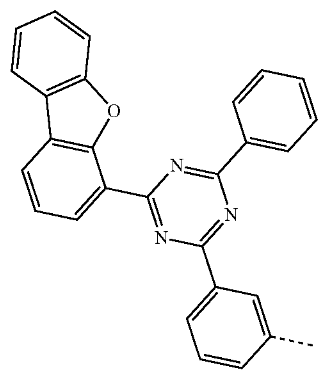
$R^{44}$
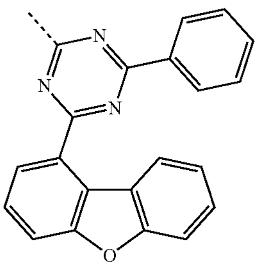

-continued
R[45]
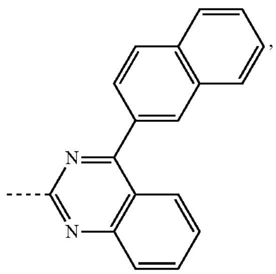
R[46]
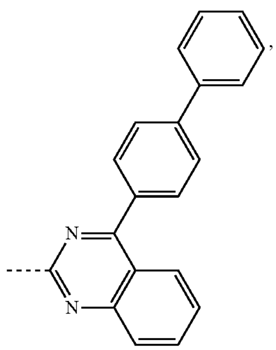
R[47]
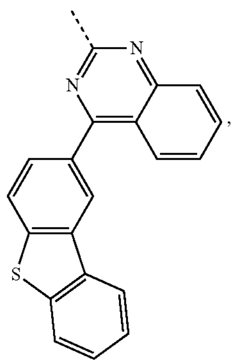
R[48]
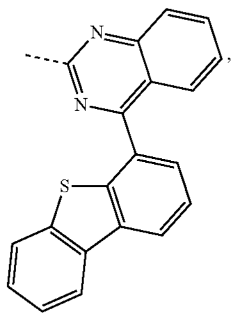
-continued
R[49]
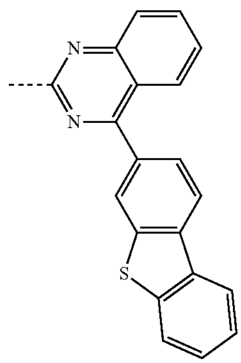
R[50]
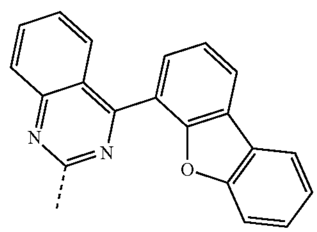
R[51]
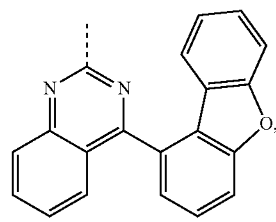
R[52]
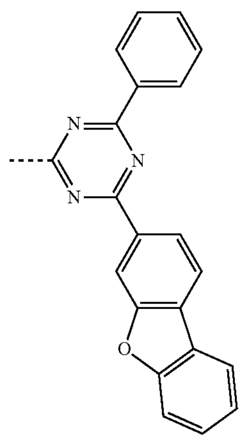
R[55]
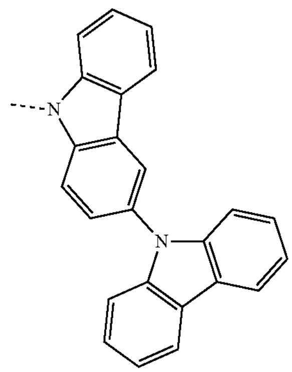

-continued
$R^{56}$
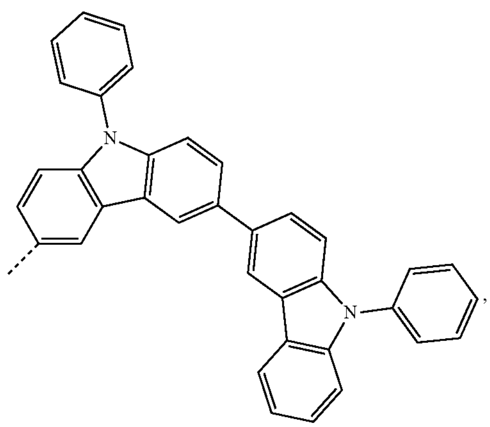
,
$R^{57}$
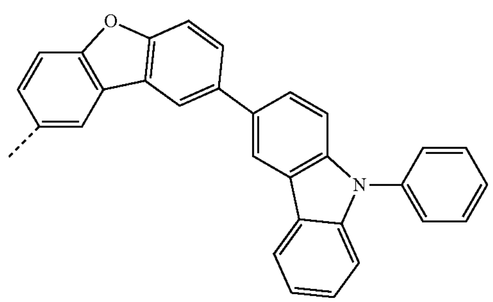
,
$R^{58}$
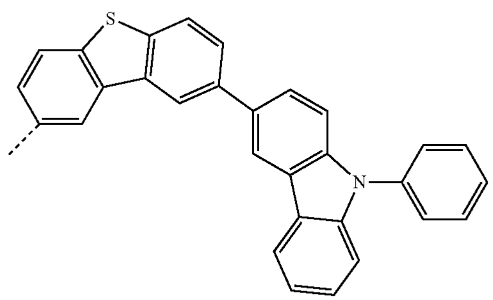
,
$R^{59}$
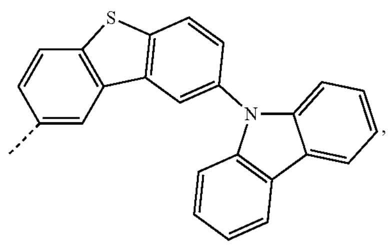
,
$R^{60}$
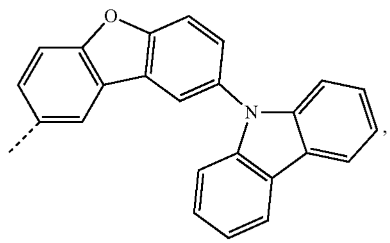
,
-continued
$R^{61}$
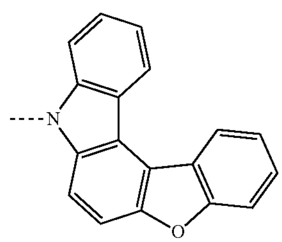
,
$R^{62}$
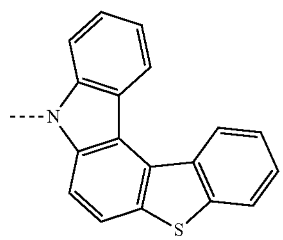
,
$R^{63}$
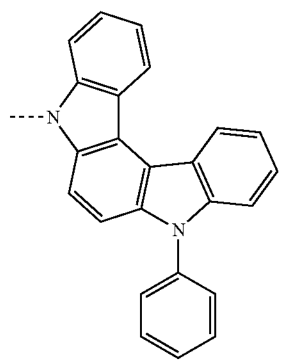
,
$R^{64}$
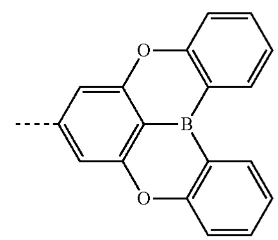
,
$R^{66}$
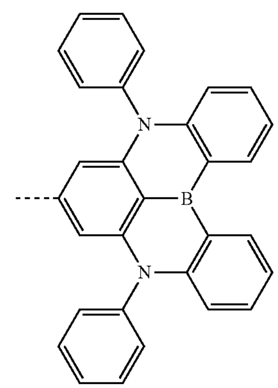
, -continued

R67

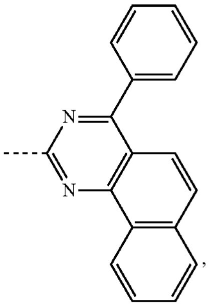

R68

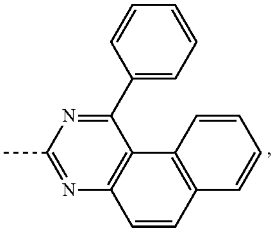

R69

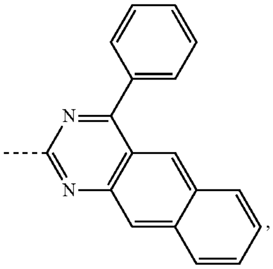

R70

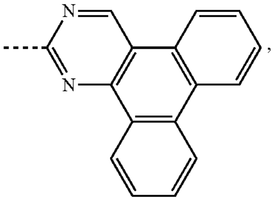

and

R71

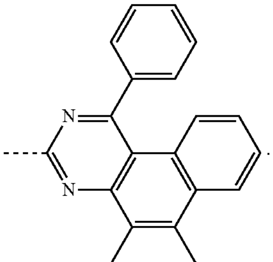

15. The OLED of claim 14, wherein the organic layer is an emissive layer and the compound is an emissive dopant or a non-emissive dopant.

16. The OLED of claim 14, wherein the compound is a host, and the organic layer is an emissive layer that comprises a phosphorescent emitter.

17. The OLED of claim 16, wherein the phosphorescent emitter is a transition metal complex having at least one ligand or part of the ligand if the ligand is more than bidentate selected from the group consisting of:

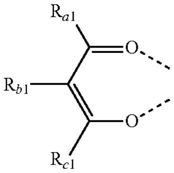

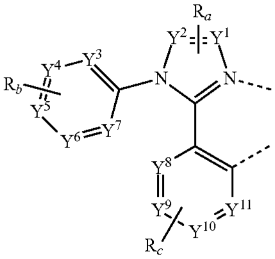

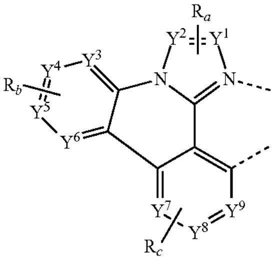

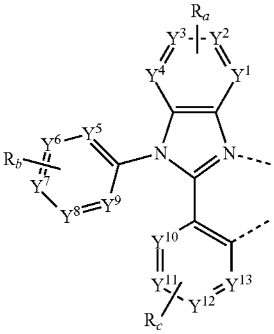

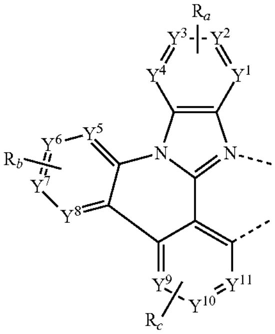

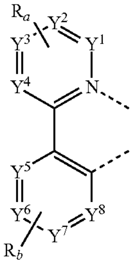

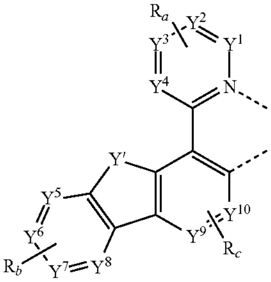

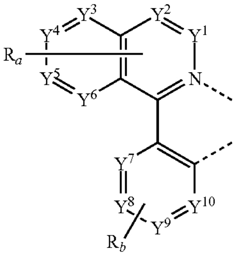

-continued

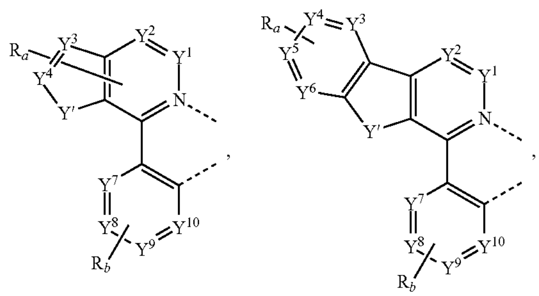

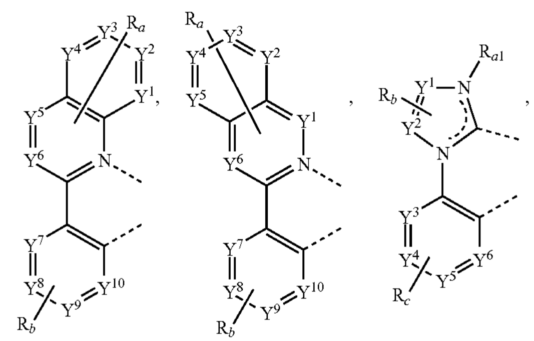

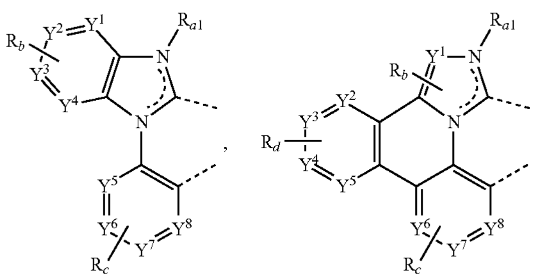

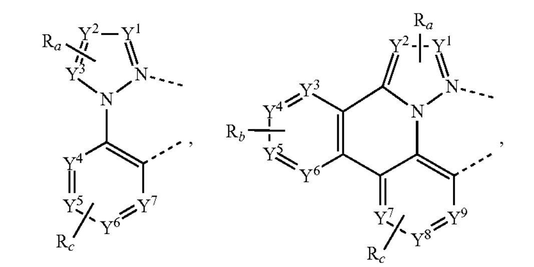

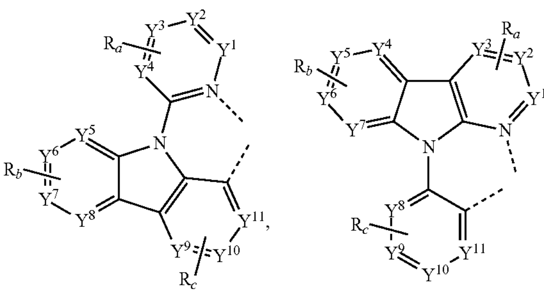

-continued

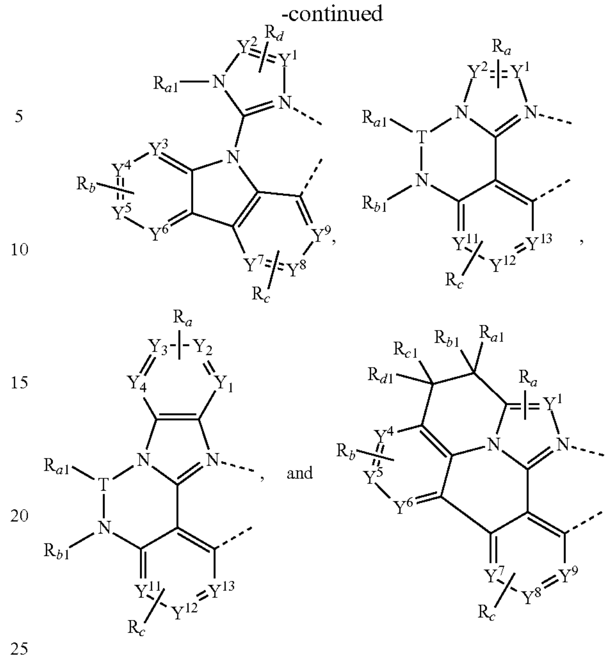

and wherein:

T is selected from the group consisting of B, Al, Ga, and In;

each of $Y^1$ to $Y^{13}$ is independently selected from the group consisting of carbon and nitrogen;

Y' is selected from the group consisting of $BR_e$, $NR_e$, $PR_e$, O, S, Se, C═O, S═O, $SO_2$, $CR_eR_f$, $SiR_eR_f$, and $GeR_eR_f$;

$R_e$ and $R_f$ can be fused or joined to form a ring;

each $R_a$, $R_b$, $R_c$, and $R_d$ independently represent zero, mono, or up to a maximum allowed number of substitutions to its associated ring;

each of $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of deuterium, halide, alkyl, cycloalkyl, heteroalkyl, arylalkyl, alkoxy, aryloxy, amino, silyl, boryl, germyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, selenyl, and combinations thereof; and and any two adjacent substituents of $R_a$, $R_b$, $R_c$, $R_d$, $R_e$ and $R_f$ can be fused or joined to form a ring or form a multidentate ligand.

18. The OLED of claim 14, wherein the compound is an acceptor, and the OLED further comprises a sensitizer selected from the group consisting of a delayed fluorescence emitter, a phosphorescent emitter, and combination thereof.

19. The OLED of claim 14, wherein the compound is a fluorescent emitter, a delayed fluorescence emitter, or a component of an exciplex that is a fluorescent emitter or a delayed fluorescence emitter.

20. A consumer product comprising an organic light-emitting device (OLED) comprising:

an anode;

a cathode; and an organic layer disposed between the anode and the cathode, wherein the organic layer comprises a compound of Formula I:

Formula I

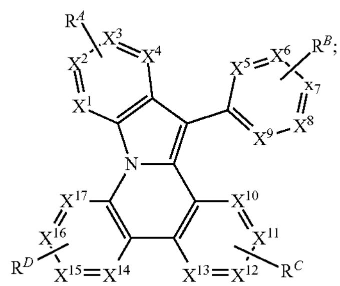

wherein each $X^1$-$X^{17}$ is independently C or N;

$R^A$, $R^B$, $R^C$, and $R^D$ each independently represent mono to the maximum allowable substitution, or no substitution;

each $R^A$, $R^B$, $R^C$, and $R^D$ is independently a hydrogen or a substituent selected from the group consisting of deuterium, halogen, alkyl, cycloalkyl, heteroalkyl, heterocycloalkyl, boryl, germyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof;

wherein at least one of the following conditions (i) or (ii) is true:

(i) at least one of $R^C$ and $R^D$ is joined to its respective ring by a single bond and comprises pyrimidine, triazine, quinazoline, benzene, biphenyl, terphenyl, naphthalene, phenanthrene, anthracene, triphenylene, pyridine, pyrazine, fluorene, dibenzofuran, dibenzothiophene, carbazole, quinoline, isoquinoline, triarylboryl or quinoxaline, which may be further substituted;

(ii) at least one of $R^A$ and $R^B$ is selected from the group consisting of the following structures:

$R^{A11}$

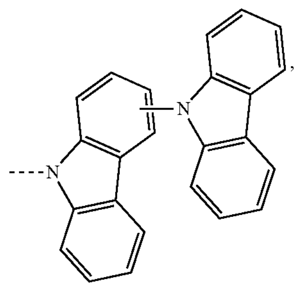

$R^{A12}$

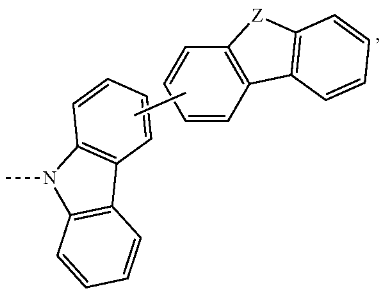

-continued $R^{A13}$

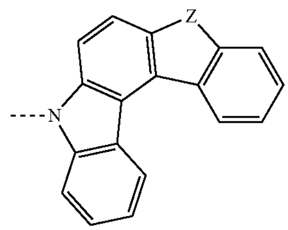

$R^{A14}$

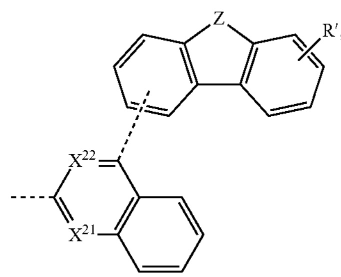

$R^{A15}$

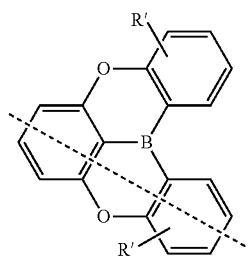

$R^{A16}$

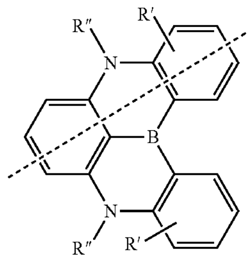

$R^{12}$

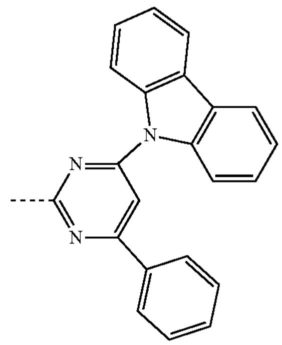

-continued
R13
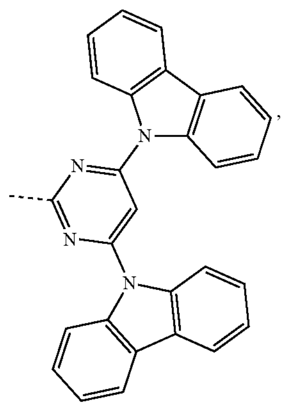
R18
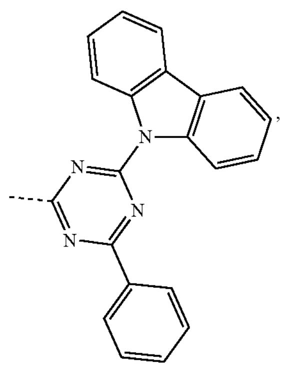
R19
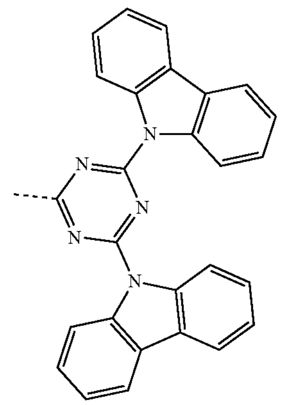
R20
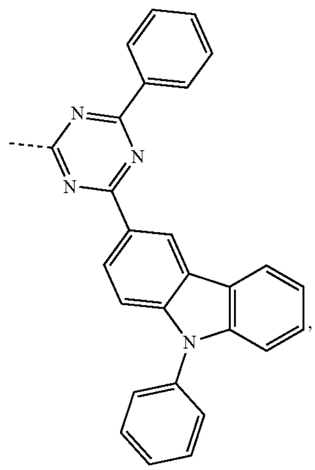
-continued
R21
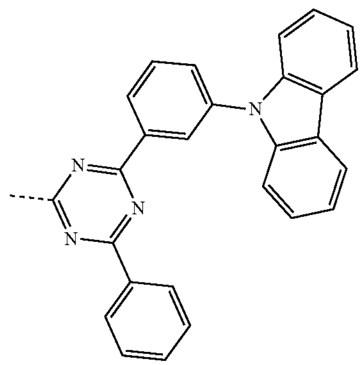
R22
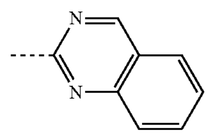
R23
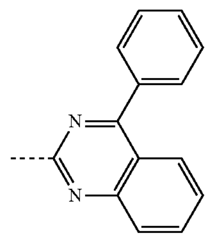
R37
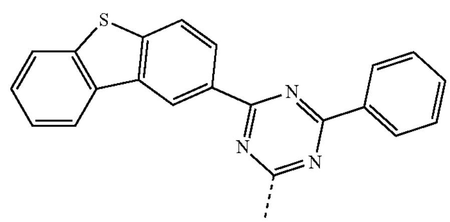
R38
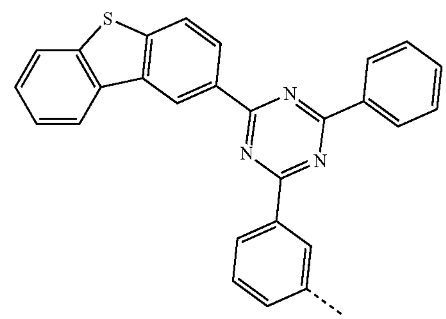
R39
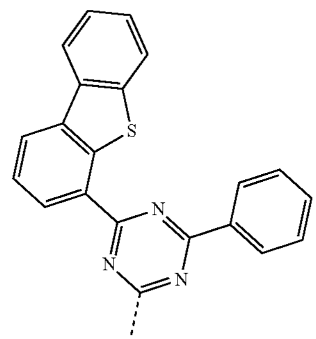

-continued
$R^{40}$
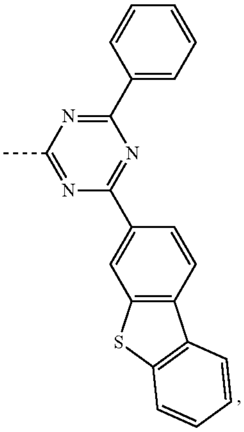,
$R^{41}$
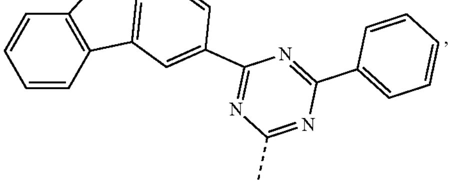,
$R^{42}$
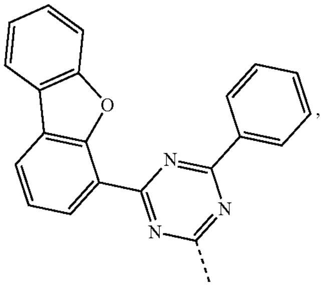,
$R^{43}$
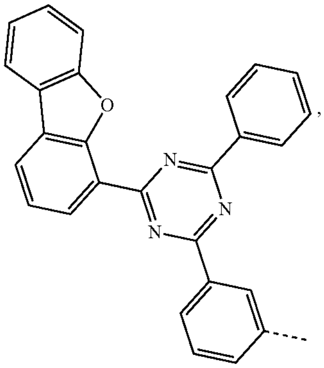
$R^{44}$
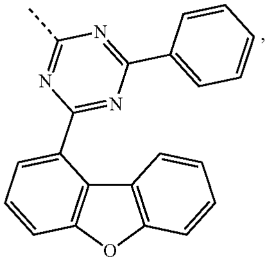,
-continued
$R^{4}$
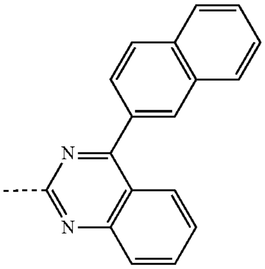,
$R^{46}$
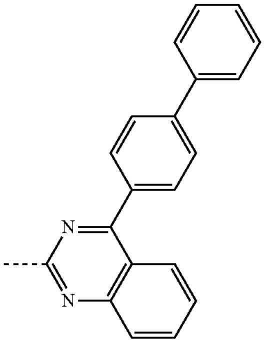,
$R^{47}$
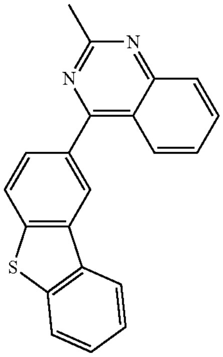,
$R^{48}$
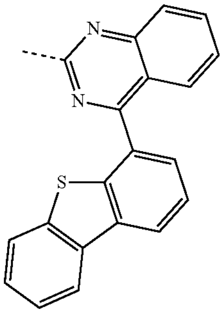, -continued
R[49]
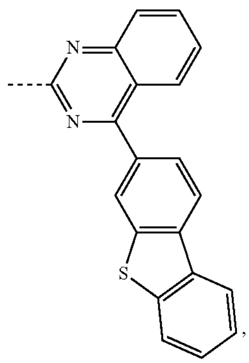
R[50]
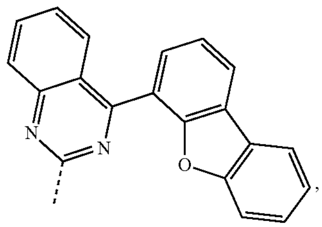
R[51]
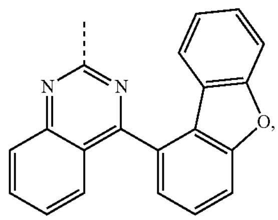
R[52]
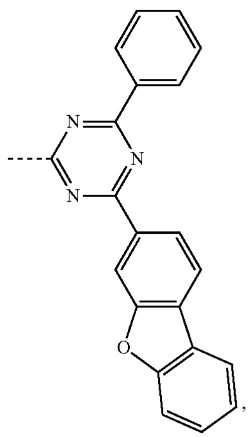
R[55]
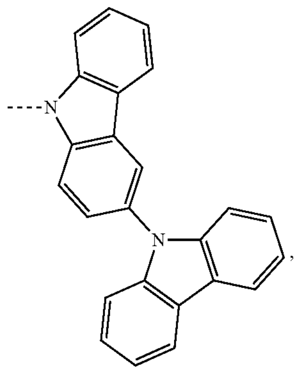
-continued
R[56]
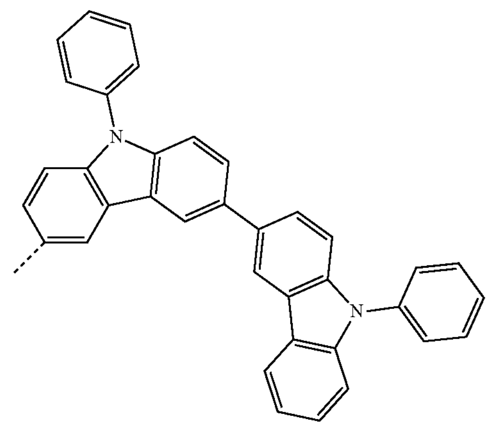
R[57]
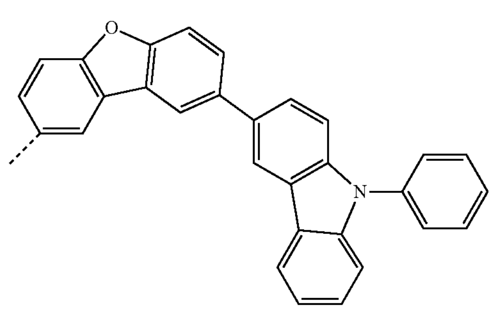
R[58]
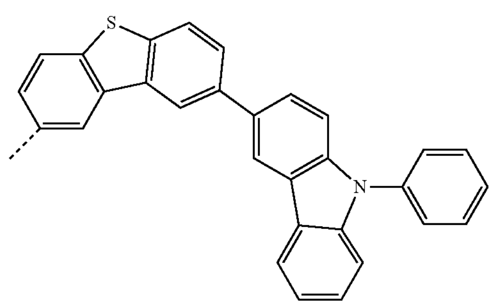
R[59]
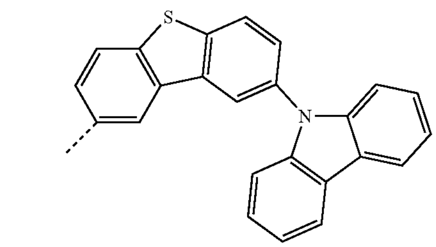
R[60]
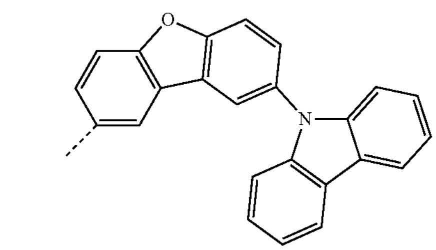

-continued
$R^{61}$
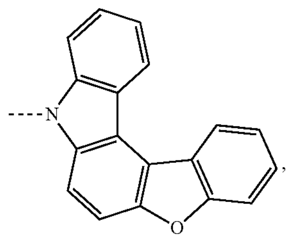
$R^{62}$
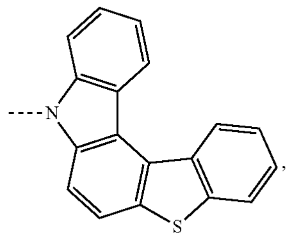
$R^{63}$
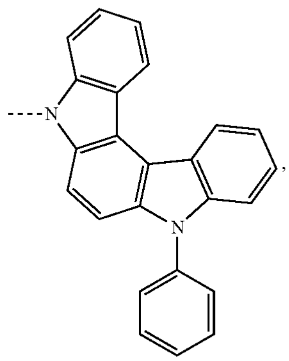
$R^{64}$
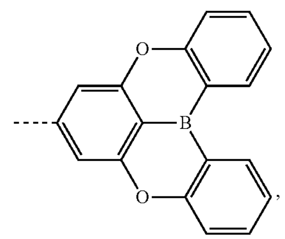
$R^{66}$
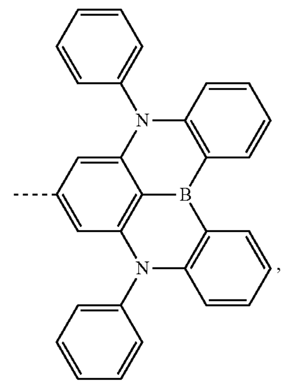
-continued
$R^{67}$
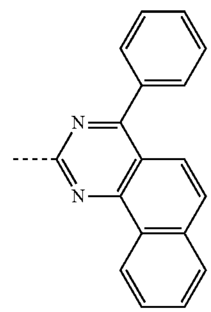
$R^{68}$
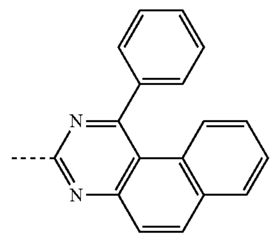
$R^{69}$
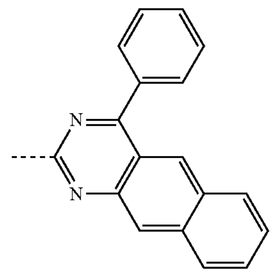
$R^{70}$
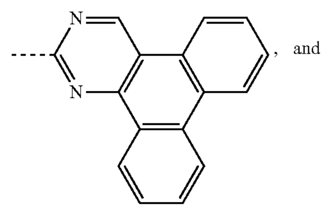
and
$R^{71}$
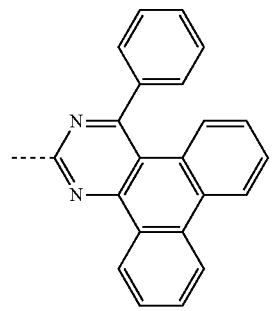
* * * * *